United States Patent [19]

Kleschick et al.

[11] Patent Number: 4,755,212

[45] Date of Patent: Jul. 5, 1988

[54] NOVEL SUBSTITUTED 1,2,4-TRIAZOLO[1,5-A]PYRIMIDINE-2-SULFONAMIDES AND COMPOSITIONS AND METHOD FOR INHIBITING POLLEN FORMATION IN CORN

[75] Inventors: William A. Kleschick, Martinez; Ben C. Gerwick, III, Clayton, both of Calif.; Robert J. Ehr, Eden Prairie, Minn.; William T. Monte, Concord, Calif.; Norman R. Pearson, Walnut Creek, Calif.; Richard W. Meikle, Alamo, Calif.; Mark J. Costales, Walnut Creek, Calif.

[73] Assignee: The Dow Chemical Company, Midland, Mich.

[21] Appl. No.: 934,271

[22] Filed: Nov. 21, 1986

Related U.S. Application Data

[60] Division of Ser. No. 768,393, Aug. 22, 1985, abandoned, and a continuation-in-part of Ser. No. 551,758, Nov. 14, 1983, abandoned.

[51] Int. Cl.⁴ .................... A01N 43/90; C07D 475/00
[52] U.S. Cl. .......................................... 71/92; 544/263
[58] Field of Search ............................. 71/92; 544/263

[56] References Cited

U.S. PATENT DOCUMENTS 3,062,885 11/1962 Kaplan ................................. 260/578

FOREIGN PATENT DOCUMENTS 951652 3/1964 United Kingdom ................ 544/263

OTHER PUBLICATIONS

McRae, D. H. (1985) *Plant Breeding Reviews*, vol. 3; Janick, ed; (AVI Publishing, Wesport CT) pp. 169–191.

*Primary Examiner*—Donald G. Daus
*Assistant Examiner*—Mark W. Noel

[57] ABSTRACT

Novel compounds, e.g., 5,7-dimethyl-N-(2,6-dichlorolphenyl)-1,2,4-triazolo[1,5-a]pyrimidine-2-sulfonamide and their compositions and use in the control of weeds and in the suppression of nitrification of ammonium nitrogen in soil. Other novel compounds and their compositions and use in the inhibition of bolting in sugar beets. Other novel compounds and their compositions and use as plant gametocides.

4 Claims, No Drawings

NOVEL SUBSTITUTED 1,2,4-TRIAZOLO[1,5-A]PYRIMIDINE-2-SULFONAMIDES AND COMPOSITIONS AND METHOD FOR INHIBITING POLLEN FORMATION IN CORN

CROSS-REFERENCE TO RELATED APPLICATION

This is a divisional of application Ser. No. 768,393, filed Aug. 22, 1985 abandoned and a continuation-in-part of application Ser. No. 551,758 filed Nov. 14, 1983 also abandoned.

BACKGROUND OF THE INVENTION

In recent years there has been a great deal of effort directed to the development of sulfonamides having herbicidal activity and several of these compounds have reached the stage of commercialization, i.e., chlorosulfuron and sulfometuron methyl. These compounds exhibit both preemergence and postemergence activity against undesirable vegetation and, in addition, have a low toxicity to mammals. The compounds of the prior art may be depicted as follows:

wherein Ar is usually a benzene derivative and Ar' is usually a pyrimidine or symmetrical triazine derivative.

In addition, there are a number of other sulfonamide herbicides that have been commercialized, for example, methyl sulfanilylcarbamate; O,O-diisopropyl phosphorodithioate-S-ester with N-(2-mercaptoethyl)benzenesulfonamide; 3-isopropyl-1H-2,1,3-benzothiadiazin-4(3H)-one 2,2-dioxide; N-[2,4-dimethyl-5-[[(trifluoromethyl)sulfonyl]amino]phenyl]acetamide and 3,5-dinitro-$N^4,N^4$-dipropylsulfanilamide.

SUMMARY OF THE INVENTION

We have now found that compounds having the formula:

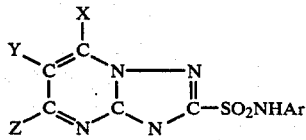

wherein Ar represents an aromatic (substituted or unsubstituted) or heteroaromatic (substituted or unsubstituted) ring system wherein the substituents are electron withdrawing function groups in combination with other organic functional groups are exceptionally active herbicides and are active in the suppression of nitrification of ammonium nitrogen in soil and are effective in beneficially regulating the growth of crops and are readily produced. The aromatic ring may be monocyclic containing six carbon atoms or bicyclic containing ten carbon atoms. The heteroaromatic ring may be monocyclic containing five or six atoms or bicyclic containing nine or ten atoms. The heteroatoms present in the heteroaromatic ring may be one combination of one or more atoms such as nitrogen, oxygen or sulfur.

In addition certain derivatives of compounds of general formula (I) also exhibit herbicidal activity and suppression of nitrification of ammonium nitrogen in soil and are effective in beneficially regulating the growth of crops and have the general formulas:

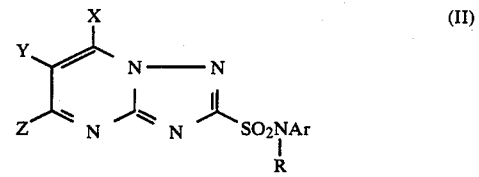

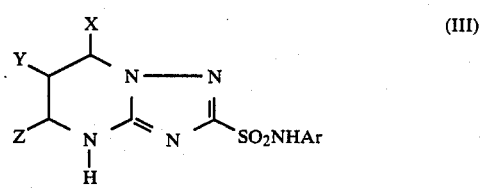

wherein Ar represents an aromatic (substituted or unsubstituted) or heteroaromatic (substituted or unsubstituted) ring system.

DETAILED DESCRIPTION OF THE INVENTION

The aromatic or heteroaromatic ring systems include, for example, phenyl; 1- or 2-napthyl; 2-, 3- or 4-pyridyl; 2- or 3-thienyl; 2- or 3-furyl; 2-, 4- or 5-thiazolyl; 2-, 4- or 5-imidazolyl; 2-, 4- or 5-oxazolyl; 3-, 4- or 5-isothiazolyl; 3-, 4- or 5-isoxazolyl; 3-, 4- or 5-pyrazolyl; 2-benzthiazolyl; 2-benzoxazolyl; 2-benzimidiazolyl and 1-benztriazolyl. Typical examples of substituents found on the aromatic or heteroaromatic ring systems may be one, more than one or a combination of the following: halo (F, Cl, Br, I), $C_1$–$C_4$ alkyl, $C_1$–$C_2$ mono-, di-, tri-, tetra- or perhaloalkyl, phenyl, hydroxy, alkoxy, haloalkoxy, phenoxy, substituted phenoxy, heteroaryloxy, substituted heteroaryloxy, amino, alkylamino, dialkylamino, nitro, alkylthio, haloalkylthio, alkylsulfinyl, haloalkylsulfinyl, alkylsulfonyl, haloalkylsulfonyl, substituted or unsubstituted phenylthio, substituted or unsubstituted phenylsulfinyl, substituted or unsubstituted phenylsulfonyl, cyano, carboxylic acids (and derivatives of carboxylic acids such as esters derived from readily available alcohols and amides derived from ammonia or readily available primary and secondary amines), sulfonic acids (and derivatives of sulfonic acids such as sulfonates derived from readily available alcohols and sulfonamides derived from ammonia or readily available primary or secondary amines), formyl, alkylcarbonyl, haloalkylcarbonyl, phenylcarbonyl, substituted phenylcarbonyl, oximino, oxime ethers, carbinols (and carbinol derivatives such as ethers and esters derived from readily available alkylating agents and carboxylic acids respectively) and mercaptoalkyl (and derivatives of mercaptoalkyl groups such as thioethers and thioesters derived from readily available alkylating agents and carboxylic acids respectively).

The substituents on the triazolopyrimidine fragment of structure I are represented by X, Y and Z. Substituents X, Y and Z may be H, alkyl, haloalkyl, hydroxy, alkoxy, haloalkoxy, phenyl, substituted phenyl, halo (F, Cl, Br, I), alkylthio, phenylthio, amino (including alkyl or aryl substituted amino), carboxylic acids and esters. In addition, two adjacent substituents (i.e., X and Y or Y and Z) may be bonded together in a saturated five, six or seven-membered cyclic structure. Examples of such cyclic structures could be represented by X and Y or Y and Z equal to —(CH₂)ₙ— where n=3, 4 or 5. These cyclic structures may also contain heteroatoms (e.g. N, O or S) as in the case where X and Y or Y and Z is equal to —(CH₂)ₙO— where n=2 or 3. In the above substituents alkyl, alkenyl, alkynyl and alkoxy in each instance have from 1 to 10 carbon atoms.

Preferred compounds of the invention have the general formula:

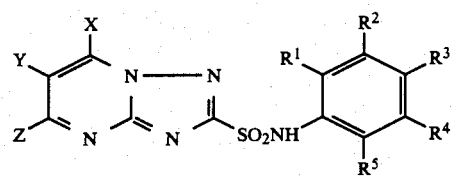

wherein $R^1$ represents halo (F, Cl, Br, I), —NO₂, phenyl, OAr, —CF₃, —OCF₃, —OCF₂CF₂H, —OCF₂CCl₂H, —OCH₂CF₃, —SCF₃, —SCF₂CF₂H, —SCF₂CCl₂H, —SOCF₃, —SOCF₂CF₂H, —SOCF₂CCl₂H, —SO₂CF₃, —SO₂CF₂CF₂H, —SO₂CF₂CCl₂H, —SR⁶, —SOR⁶, —SO₂R⁶, —CN, —COOR⁷, —CONH₂, —CONHR⁸, —CONR⁸(R⁹), —SO₃R⁸ and —SO₃CH₂CF₃; $R^2$ and $R^4$ represent H, halo (F, Cl, Br, I), C₁-C₄ alkyl, COOR⁷ and —OR⁸; $R^3$ is H; and $R^5$ represents H, C₁-C₄ alkyl, C₁-C₄ alkoxy, halo (F, Cl, Br, I), NO₂, CF₃, —OCF₃, —OCF₂CF₂H, —OCF₂CCl₂H, —OCH₂CF₃, —SCF₃, —SCF₂CF₂H, —SCF₂CCl₂H, —SOCF₃, —SOCF₂CF₂H, —SOCF₂CCl₂H, —SO₂CF₃, —SO₂CF₂CF₂H, —SO₂CF₂CCl₂H, —SR⁶, —SOR⁶, —SO₂R⁶, —CN, —COOR⁷, —CONH₂, —CONHR⁸, —CONR⁸(R⁹), —SO₃R⁸, —SO₃CH₂CF₃, —CR⁶R⁶OR⁶ and —CR⁶R⁶SR⁶ wherein Ar represents substituted or unsubstituted aryl or substituted or unsubstituted heteroaryl, $R^6$ represents H, aryl or C₁-C₄ alkyl, $R^7$ represents C₁-C₆ alkyl, alkenyl, alkynyl, aryl, substituted alkyl or substituted aryl and $R^8$ and $R^9$ individually represent C₁-C₄ alkyl; and X, Y and Z represent H, C₁-C₄ alkyl, C₁-C₄ alkoxy halo (F, Cl, Br, I), or X and Y or Y and Z can be joined to form a cycloalkyl ring (i.e., —(CH₂)ₙ— wherein n is 3 or 4) or X and Y or Y and Z can be joined to form a ring containing a heteroatom (i.e., —O(CH₂)ₙ wherein n is 2 or 3).

Preferred compounds of the invention also have the general formula:

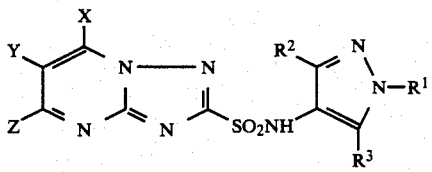

wherein $R^1$ represents H, alkyl or aryl, $R^2$ and $R^3$ represent independently H, C₁-C₄ alkyl, halo (F, Cl, Br, I), —NO₂, phenyl, —CF₃, benzyl, —COOR⁴, —CONH₂, —CONHR⁵, —CONR⁵R⁶, and CN wherein $R^4$ represents C₁-C₆ alkyl, alkenyl, alkynyl, arylalkyl, substituted alkyl or substituted aryl, $R^5$ and $R^6$ individually represent C₁-C₄ alkyl; and X, Y and Z represent H, C₁-C₄ alkyl, C₁-C₄ alkoxy, halo (F, Cl, Br, I), or X and Y or Y and Z can be joined to form a cycloalkyl ring (i.e., —(CH₂)ₙ— wherein n is 3 or 4) or X and Y or Y and Z can be joined to form a ring containing a heteroatom (i.e., —O(CH₂)ₙ— wherein n is 2 or 3.

Most preferred compounds of the invention have the general formula:

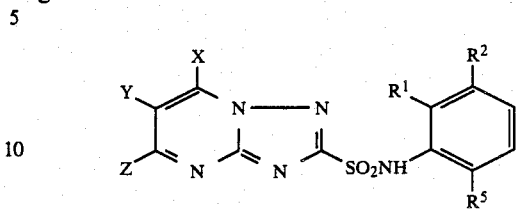

wherein $R^1$ represents C₁-C₄ alkyl, halo (F, Cl, Br, I), —NO₂, —SR⁶, —SOR⁶, SO₂R⁶, —COOR⁷ or CF₃; $R^2$ represents H, halo (F, Cl, Br, I), C₁-C₄ alkyl, and COOR⁷; and $R^5$ represents H, C₁-C₄ alkyl, C₁-C₄ alkoxy, halo (F, Cl, Br, I), CH₂OR⁶, phenyl, NO₂ and COOR⁷ wherein $R^6$ represents C₁-C₄ alkyl and $R^7$ represents C₁-C₄ alkyl, C₁-C₄ alkenyl, C₁-C₄ alkynyl, 2-ethoxyethyl and 2-pyridylmethyl and X, Y and Z independently represent H, halo (F, Cl, Br, I), C₁-C₄ alkyl or C₁-C₄ alkoxy.

Specifically preferred compounds of the invention include:

1. 5,7-Dimethyl-N-)2-trifluoromethylphenyl)-1,2,4-triazolo[1,5-a]pyrimidine-2-sulfonamide.
2. 5,7-Dimethyl-N-(2,6-difluorophenyl)-1,2,4-triazolo[1,5-a]pyrimidine-2-sulfonamide.
3. 5,7-Dimethyl-N-(2,6-dichlorophenyl)-1,2,4-triazolo[1,5-a]pyrimidine-2-sulfonamide.
4. 5,7-Dimethyl-N-(2-chloro-6-fluorophenyl)-1,2,4-triazolo[1,5-a]pyrimidine-2-sulfonamide.
5. 5,7-Dimethyl-N-(2-bromo-6-chlorophenyl)-1,2,4-triazolo[1,5-a]pyrimidine-2-sulfonamide.
6. 5,7-Dimethyl-N-(2-chloro-6-iodophenyl)-1,2,4-triazolo[1,5-a]pyrimidine-2-sulfonamide.
7. 5,7-Dimethyl-N-(2-fluoro-6-methylphenyl)-1,2,4-triazolo[1,5-a]pyrimidine-2-sulfonamide.
8. 5,7-Dimethyl-N-(2-chloro-6-methylphenyl)-1,2,4-triazolo[1,5-a]pyrimidine-2-sulfonamide.
9. 5,7-Dimethyl-N-(2-bromo-6-methylphenyl)-1,2,4-triazolo[1,5-a]pyrimidine-2-sulfonamide.
10. 5,7-Dimethyl-N-(2-methyl-6-nitrophenyl)-1,2,4-triazolo[1,5-a]pyrimidine-2-sulfonamide.
11. 5,7-Dimethyl-N-(2-chloro-6-methoxymethylphenyl)-1,2,4-triazolo[1,5-a]pyrimidine-2-sulfonamide.
12. 5,7-Dimethyl-N-(2-fluoro-6-methoxymethylphenyl)-1,2,4-triazolo[1,5-a]pyrimidine-2-sulfonamide.
13. 5,7-Dimethyl-N-(2-chloro-6-phenylphenyl)-1,2,4-triazolo[1,5-a]pyrimidine-2-sulfonamide.
14. 5,7-Dimethyl-N-(2-methyl-6-trifluoromethylphenyl)-1,2,4-triazolo[1,5-a]pyrimidine-2-sulfonamide.
15. 5,7-Dimethyl-N-(2-fluoro-6-trifluoromethylphenyl)-1,2,4-triazolo[1,5-a]pyrimidine-2-sulfonamide.
16. 5,7-Dimethyl-N-(2,6-dichloro-3-methylphenyl)-1,2,4-triazolo[1,5-a]pyrimidine-2-sulfonamide.
17. 5,7-Dimethyl-N-(2,6-difluoro-3-methylphenyl)-1,2,4-triazolo[1,5-a]pyrimidine-2-sulfonamide.
18. 5,7-Dimethyl-N-(2,3-dimethyl-6-nitrophenyl)-1,2,4-triazolo[1,5-a]pyrimidine-2-sulfonamide.
19. 5,7-Dimethyl-N-(3,6-dimethyl-2-nitrophenyl)-1,2,4-triazolo[1,5-a]pyrimidine-2-sulfonamide.
20. 5,7-Dimethyl-N-(2,3-dichloro-6-methylphenyl)-1,2,4-triazolo[1,5-a]pyrimidine-2-sulfonamide.

21. 5,7-Dimethyl-N-(2-methoxy-6-trifluoromethylphenyl)-1,2,4-triazolo[1,5-a]pyrimidine-2-sulfonamide.
22. Methyl 3-methyl-N-(5,7-dimethyl-1,2,4-triazolo[1,5-a]pyrimidine-2-sulfonyl)anthranilate.
23. Ethyl 3-methyl-N-(5,7-dimethyl-1,2,4-triazolo-[1,5-a]pyrimidine-2-sulfonyl)anthranilate.
24. Isopropyl 3-methyl-N-(5,7-dimethyl-1,2,4-triazolo[1,5-a]pyrimidine-2-sulfonyl)anthranilate.
25. 2-Ethoxyethyl 3-methyl-N-(5,7-dimethyl-1,2,4-triazolo[1,5-a]pyrimidine-2-sulfonyl)anthranilate.
26. 2-Propen-1-yl 3-methyl-N-(5,7-dimethyl-1,2,4-triazolo[1,5-a]pyrimidine-2-sulfonyl)anthranilate.
27. 2-Pyridylmethyl 3-methyl-N-(5,7-dimethyl-1,2,4-triazolo[1,5-a]pyrimidine-2-sulfonyl)anthranilate.
28. Methyl 3-fluoro-N-(5,7-dimethyl-1,2,4-triazolo[1,5-a]pyrimidine-2-sulfonyl)anthranilate.
29. Ethyl 3-fluoro-N-(5,7-dimethyl-1,2,4-triazolo[1,5-a]pyrimidine-2-sulfonyl)anthranilate.
30. Isopropyl 3-fluoro-N-(5,7-dimethyl-1,2,4-triazolo[1,5-a]pyrimidine-2-sulfonyl)anthranilate.
31. Methyl 3-chloro-N-(5,7-dimethyl-1,2,4-triazolo[1,5-a]pyrimidine-2-sulfonyl)anthranilate.
32. Ethyl 3-chloro-N-(5,7-dimethyl-1,2,4-triazolo[1,5-a]pyrimidine-2-sulfonyl)anthranilate.
33. Isopropyl 3-chloro-N-(5,7-dimethyl-1,2,4-triazolo[1,5-a]pyrimidine-2-sulfonyl)anthranilate.
34. Methyl 3-trifluoromethyl-n-(5,7-dimethyl-1,2,4-triazolo[1,5-a]pyrimidine-2-sulfonyl)anthranilate.
35. Ethyl 3-trifluoromethyl-N-(5,7-dimethyl-1,2,4-triazolo[1,5-a]pyrimidine-2-sulfonyl)anthranilate.
36. Isopropyl 3-trifluoromethyl-N-(5,7-dimethyl-1,2,4-triazolo[1,5-a]pyrimidine-2-sulfonyl)anthranilate.
37. Methyl 3,4-dimethyl-N-(5,7-dimethyl-1,2,4-triazolo[1,5-a]pyrimidine-2-sulfonyl)anthranilate.
38. Ethyl 3,4-dimethyl-N-(5,7-dimethyl-1,2,4-triazolo[1,5-a]pyrimidine-2-sulfonyl)anthranilate.
39. Isopropyl 3,4-dimethyl-N-(5,7-dimethyl-1,2,4-triazolo[1,5-a]pyrimidine-2-sulfonyl)anthranilate.
40. Methyl 3,6-dimethyl-N-(5,7-dimethyl-1,2,4-triazolo[1,5-a]pyrimidine-2-sulfonyl)anthranilate.
41. Ethyl 3,6-dimethyl-N-(5,7-dimethyl-1,2,4-triazolo[1,5-a]pyrimidine-2-sulfonyl)anthranilate.
42. Isopropyl 3,6-dimethyl-N-(5,7-dimethyl-1,2,4-triazolo[1,5-a]pyrimidine-2-sulfonyl)anthranilate.
43. Methyl 4-chloro-3-methyl-N-(5,7-dimethyl-1,2,4-triazolo[1,5-a]pyrimidine-2-sulfonyl)anthranilate.
44. Ethyl 4-chloro-3-methyl-N-(5,7-dimethyl-1,2,4-triazolo[1,5-a]pyrimidine-2-sulfonyl)anthranilate.
45. Isopropyl 4-chloro-3-methyl-N-(5,7-dimethyl-1,2,4-triazolo[1,5-a]pyrimidine-2-sulfonyl)anthranilate.
46. Methyl 3-amino-2,4-dichloro-N-(5,7-dimethyl-1,2,4-triazolo[1,5-a]pyrimidine-2-sulfonyl)benzoate.
47. Ethyl 3-amino-2,4-dichloro-N-(5,7-dimethyl-1,2,4-triazolo[1,5-a]pyrimidine-2-sulfonyl)benzoate.
48. Isopropyl 3-amino-2,4-dichloro-N-(5,7-dimethyl-1,2,4-triazolo[1,5-a]pyrimidine-2-sulfonyl)benzoate.
49. Methyl 3-amino-2-bromo-4-methyl-N-(5,7-dimethyl-triazolo[1,5-a]pyrimidine-2-sulfonyl)benzoate.
50. Ethyl 3-amino-2-bromo-4-methyl-N-(5,7-dimethyl-triazolo[1,5-a]pyrimidine-2-sulfonyl)benzoate.
51. Isopropyl 3-amino-2-bromo-4-methyl-N-(5,7-dimethyl-triazolo[1,5-a]pyrimidine-2-sulfonyl)benzoate.
52. 5-Methyl-N-(2-trifluoromethylphenyl)-1,2,4-triazolo[1,5-a]pyrimidine-2-sulfonamide.
53. 5-Methyl-N-(2,6-difluorophenyl)-1,2,4-triazolo[1,5-a]pyrimidine-2-sulfonamide.
54. 5-Methyl-N-(2,6-dichlorophenyl)-1,2,4-triazolo[1,5-a]pyrimidine-2-sulfonamide.
55. 5-Methyl-N-(2-chloro-6-fluorophenyl)-1,2,4-triazolo[1,5-a]pyrimidine-2-sulfonamide.
56. 5-Methyl-N-(2-bromo-6-chlorophenyl)-1,2,4-triazolo[1,5-a]pyrimidine-2-sulfonamide.
57. 5-Methyl-N-(2-chloro-6-iodophenyl)-1,2,4-triazolo[1,5-a]pyrimidine-2-sulfonamide.
58. 5-Methyl-N-(2-fluoro-6-methylphenyl)-1,2,4-triazolo[1,5-a]pyrimidine-2-sulfonamide.
59. 5-Methyl-N-(2-chloro-6-methylphenyl)-1,2,4-triazolo[1,5-a]pyrimidine-2-sulfonamide.
60. 5-Methyl-N-(2-bromo-6-methylphenyl)-1,2,4-triazolo[1,5-a]pyrimidine-2-sulfonamide.
61. 5-Methyl-N-(2-methyl-6-nitrophenyl)-1,2,4-triazolo[1,5-a]pyrimidine-2-sulfonamide.
62. 5-Methyl-N-(2-chloro-6-methoxymethylphenyl)-1,2,4-triazolo[1,5-a]pyrimidine-2-sulfonamide.
63. 5-Methyl-N-(2-fluoro-6-methoxymethylphenyl)-1,2,4-triazolo[1,5-a]pyrimidine-2-sulfonamide.
64. 5-Methyl-N-(2-chloro-6-phenylphenyl)-1,2,4-triazolo[1,5-a]pyrimidine-2-sulfonamide.
65. 5-Methyl-N-(2-methyl-6-trifluoromethylphenyl)-1,2,4-triazolo[1,5-a]pyrimidine-2-sulfonamide.
66. 5-Methyl-N-(2-fluoro-6-trifluoromethylphenyl)-1,2,4-triazolo[1,5-a]pyrimidine-2-sulfonamide.
67. 5-Methyl-N-(2,6-dichloro-3-methylphenyl)-1,2,4-triazolo[1,5-a]pyrimidine-2-sulfonamide.
68. 5-Methyl-N-(2,6-difluoro-3-methylphenyl)-1,2,4-triazolo[1,5-a]pyrimidine-2-sulfonamide.
69. 5-Methyl-N-(2,3-dimethyl-6-nitrophenyl)-1,2,4-triazolo[1,5-a]pyrimidine-2-sulfonamide.
70. 5-Methyl-N-(3,6-dimethyl-2-nitrophenyl)-1,2,4-triazolo[1,5-a]pyrimidine-2-sulfonamide.
71. 5-Methyl-N-(2,3-dichloro-6-methylphenyl)-1,2,4-triazolo[1,5-a]pyrimidine-2-sulfonamide.
72. 5-methyl-N-(2-acetyl-6-methylphenyl)-1,2,4-triazolo[1,5-a]pyrimidine-2-sulfonamide.
73. 5-Methyl-N-(2,6-dichloro-3-methoxyphenyl)-1,2,4-triazolo[1,5-a]pyrimidine-2-sulfonamide.
74. 5-Methyl-N-(2-methylthiomethyl-6-trifluoromethylphenyl)-1,2,4-triazolo[1,5-a]pyrimidine-2-sulfonamide.
75. 5-Methyl-N-(2-methoxy-6-trifluoromethylphenyl)-1,2,4-triazolo[1,5-a]pyrimidine-2-sulfonamide.
76. Methyl 3-methyl-N-(5-methyl-1,2,4-triazolo[1,5-a]pyrimidine-2-sulfonyl)anthranilate.
77. Ethyl 3-methyl-N-(5-methyl-1,2,4-triazolo[1,5-a]pyrimidine-2-sulfonyl)anthranilate.
78. Isopropyl 3-methyl-N-(5-methyl-1,2,4-triazolo[1,5-a]pyrimidine-2-sulfonyl)anthranilate.
79. 2-Ethoxyethyl 3-methyl-N-(5-methyl-1,2,4-triazolo[1,5-a]pyrimidine-2-sulfonyl)anthranilate.
80. 2-Propen-1-yl 3-methyl-N-(5-methyl-1,2,4-triazolo[1,5-a]pyrimidine-2-sulfonyl)anthranilate.
81. 2-Pyridylmethyl 3-methyl-N-(5-methyl-1,2,4-triazolo[1,5-a]pyrimidine-2-sulfonyl)anthranilate.
82. Methyl 3-fluoro-N-(5-methyl-1,2,4-triazolo[1,5-a]pyrimidine-2-sulfonyl)anthranilate.
83. Ethyl 3-fluoro-N-(5-methyl-1,2,4-triazolo[1,5-a]pyrimidine-2-sulfonyl)anthranilate.
84. Isopropyl 3-fluoro-N-(5-methyl-1,2,4-triazolo[1,5-a]pyrimidine-2-sulfonyl)anthranilate.
85. Methyl 3-chloro-N-(5-methyl-1,2,4-triazolo[1,5-a]pyrimidine-2-sulfonyl)anthranilate.
86. Ethyl 3-chloro-N-(5-methyl-1,2,4-triazolo[1,5-a]pyrimidine-2sulfonyl)anthranilate.

87. Isopropyl 3-chloro-N-(5-methyl-1,2,4-triazolo[1,5-a]pyrimidine-2-sulfonyl)anthranilate.
88. Methyl 3-trifluoromethy-N-(5-methyl-1,2,4-triazolo[1,5-a]pyrimidine-2-sulfonyl)anthranilate.
89. Ethyl 3-trifluoromethyl-N-(5-methyl-1,2,4-triazolo[1,5-a]pyrimidine-2-sulfonyl)anthranilate.
90. Isopropyl 3-trifluoromethyl-N-(5-methyl-1,2,4-triazolo[1,5-a]pyrimidine-2-sulfonyl)anthranilate.
91. Methyl 3,4-dimethyl-N-(5-methyl-1,2,4-triazolo[1,5-a]pyrimidine-2-sulfonyl)anthranilate.
92. Ethyl 3,4-dimethyl-N-(5-methyl-1,2,4-triazolo[1,5-a]pyrimidine-2-sulfonyl)anthranilate.
93. Isopropyl 3,4-dimethyl-N-(5-methyl-1,2,4-triazolo[1,5-a]pyrimidine-2-sulfonyl)anthranilate.
94. Methyl 3,6-dimethyl-N-(5-methyl-1,2,4-triazolo[1,5-a]pyrimidine-2-sulfonyl)anthranilate.
95. Ethyl 3,6-dimethyl-N-(5-methyl-1,2,4-triazolo[1,5-a]pyrimidine-2-sulfonyl)anthranilate.
96. Isopropyl 3,6-dimethyl-N-(5-methyl-1,2,4-triazolo[1,5-a]pyrimidine-2-sulfonyl)anthranilate.
97. Methyl 4-chloro-3-methyl-N-(5-methyl-1,2,4-triazolo[1,5-a]pyrimidine-2-sulfonyl)anthranilate.
98. Ethyl 4-chloro-3-methyl-N-(5-methyl-1,2,4-triazolo[1,5-a]pyrimidine-2-sulfonyl)anthranilate.
99. Isopropyl 4-chloro-3-methyl-N-(5-methyl-1,2,4-triazolo[1,5-a]pyrimidine-2-sulfonyl)anthranilate.
100. Methyl 3-amino-2,4-dichloro-N-(5-methyl-1,2,4-triazolo[1,5-a]pyrimidine-2-sulfonyl)benzoate.
101. Ethyl 3-amino-2,4-dichloro-N-(5-methyl-1,2,4-triazolo[1,5-a]pyrimidine-2-sulfonyl)benzoate.
102. Isopropyl 3-amino-2,4-dichloro-N-(5-methyl-1,2,4-triazolo[1,5-a]pyrimidine-2-sulfonyl)benzoate.
103. Methyl 3-amino-2-bromo-4-methyl-N-(5-methyl-1,2,4-triazolo[1,5-a]pyrimidine-2-sulfonyl)benzoate.
104. Ethyl 3-amino-2-bromo-4-methyl-N(5-methyl-1,2,4-triazolo[1,5-a]pyrimidine-2-sulfonyl)benzoate.
105. Isopropyl 3-amino-2-bromo-4-methyl-N-(5-methyl-1,2,4-triazolo[1,5-a]pyrimidine-2-sulfonyl)benzoate.
106. 6-Methyl-N-(2-trifluoromethylphenyl)-1,2,4-triazolo[1,5-a]pyrimidine-2-sulfonamide.
107. 6-Methyl-N-(2,6-difluorophenyl)-1,2,4-triazolo[1,5-a]pyrimidine-2-sulfonamide.
108. 6-Methyl-N-(2,6-dichlorophenyl)-1,2,4-triazolo[1,5-a]pyrimidine-2-sulfonamide.
109. 6-Methyl-N-(2-chloro-6-fluorophenyl)-1,2,4-triazolo[1,5-]pyrimidine-2-sulfonamide.
110. 6-Methyl-N-(2-bromo-6-chlorophenyl)-1,2,4-triazolo[1,5-a]pyrimidine-2-sulfonamide.
111. 6-Methyl-N-(2-chloro-6-iodophenyl)-1,2,4-triazolo[1,5-a]pyrimidine-2-sulfonamide.
112. 6-Methyl-N-(2-fluoro-6-methylphenyl)-1,2,4-triazolo[1,5-a]pyrimidine-2-sulfonamide.
113. 6-Methyl-N-(2-chloro-6-methylphenyl)-1,2,4-triazolo[1,5-a]pyrimidine-2-sulfonamide.
114. 6-Methyl-N-(2-bromo-6-methylphenyl)-1,2,4-triazolo[1,5-a]pyrimidine-2-sulfonamide.
115. 6-Methyl-N-(2-methyl-6-nitrophenyl)-1,2,4-triazolo[1,5-a]pyrimidine-2-sulfonamide.
116. 6-Methyl-N-(2-chloro-6-methoxymethylphenyl)-1,2,4-triazolo[1,5-a]pyrimidine-2-sulfonamide.
117. 6-Methyl-N-(2-fluoro-6-methoxymethylphenyl)-1,2,4-triazolo[1,5-a]pyrimidine-2-sulfonamide.
118. 6-Methyl-N-(2-chloro-6-phenylphenyl)-1,2,4-triazolo[1,5-a]pyrimidine-2-sulfonamide.
119. 6-Methyl-N-(2-methyl-6-trifluoromethylphenyl)-1,2,4-triazolo[1,5-a]pyrimidine-2-sulfonamide.
120. 6-Methyl-N-(2-fluoro-6-trifluoromethylphenyl)-1,2,4-triazolo[1,5-a]pyrimidine-2-sulfonamide.
121. 6-Methyl-N-(2,6-dichloro-3-methylphenyl)-1,2,4-triazolo[1,5-a]pyrimidine-2-sulfonamide.
122. 6-Methyl-N-(2,6-difluoro-3-methylphenyl)-1,2,4-triazolo[1,5-a]pyrimidine-2-sulfonamide.
123. 6-Methyl-N-(2,3-dimethyl-6-nitrophenyl)-1,2,4-triazolo[1,5-a]pyrimidine-2-sulfonamide.
124. 6-Methyl-N-(3,6-dimethyl-2-nitrophenyl)-1,2,4-triazolo[1,5-a]pyrimidine-2-sulfonamide.
125. 6-Methyl-N-(2,3-dichloro-6-methylphenyl)-1,2,4-triazolo[1,5-a]pyrimidine-2-sulfonamide.
126. 6-Methyl-N-(2-methoxy-6-trifluoromethylphenyl)-1,2,4-triazolo[1,5-a]pyrimidine-2-sulfonamide.
127. Methyl 3-methyl-N-(6-methyl-1,2,4-triazolo[1,5-a]pyrimidine-2-sulfonyl)anthranilate.
128. Ethyl 3-methyl-N-(6-methyl-1,2,4-triazolo[1,5-a]pyrimidine-2-sulfonyl)anthranilate.
129. Isopropyl 3-methyl-N-(6-methyl-1,2,4-triazolo[1,5-a]pyrimidine-2-sulfonyl)anthranilate.
130. 2-Ethoxyethyl 3-methyl-N-(6-methyl-1,2,4-triazolo[1,5-a]pyrimidine-2-sulfonyl)anthranilate.
131. 2-Propen-1-yl 3-methyl-N-(6-methyl-1,2,4-triazolo[1,5-a]pyrimidine-2-sulfonyl)anthranilate.
132. 2-Pyridylmethyl 3-methyl-N-(6-methyl-1,2,4-triazolo[1,5-a]pyrimidine-2-sulfonyl)anthranilate.
133. Methyl 3-fluoro-N-(6-methyl-1,2,4-triazolo[1,5-a]pyrimidine-2-sulfonyl)anthranilate.
134. Ethyl 3-fluoro-N-(6-methyl-1,2,4-triazolo[1,5-a]pyrimidine-2-sulfonyl)anthranilate.
135. Isopropyl 3-fluoro-N-(6-methyl-1,2,4-triazolo[1,5-a]pyrimidine-2-sulfonyl)anthranilate.
136. Methyl 3-chloro-N-(6-methyl-1,2,4-triazolo[1,5-a]pyrimidine-2-sulfonyl)anthranilate.
137. Ethyl 3-chloro-N-(6-methyl-1,2,4-triazolo[1,5-a]pyrimidine-2-sulfonyl)anthranilate.
138. Isopropyl 3-chloro-N-(6-methyl-1,2,4-triazolo[1,5-a]pyrimidine-2-sulfonyl)anthranilate.
139. Methyl 3-trifluoromethyl-N-(6-methyl-1,2,4-triazolo[1,5-a]pyrimidine-2-sulfonyl)anthranilate.
140. Ethyl 3-trifluoromethyl-N-(6-methyl-1,2,4-triazolo[1,5-a]pyrimidine-2-sulfonyl)anthranilate.
141. Isopropyl 3-trifluoromethyl-N-(6-methyl-1,2,4-triazolo[1,5-a]pyrimidine-2-sulfonyl)anthranilate.
142. Methyl 3,4-dimethyl-N-(6-methyl-1,2,4-triazolo[1,5-a]pyrimidine-2-sulfonyl)anthranilate.
143. Ethyl 3,4-dimethyl-N-(6-methyl-1,2,4-triazolo[1,5-a]pyrimidine-2-sulfonyl)anthranilate.
144. Isopropyl 3,4-dimethyl-N-(6-methyl-1,2,4-triazolo[1,5-a]pyrimidine-2-sulfonyl)anthranilate.
145. Methyl 3,6-dimethyl-N-(6-methyl-1,2,4-triazolo[1,5-a]pyrimidine-2-sulfonyl)anthranilate.
146. Ethyl 3,6-dimethyl-N-(6-methyl-1,2,4-triazolo[1,5-a]pyrimidine-2-sulfonyl)anthranilate.
147. Isopropyl 3,6-dimethyl-N-(6-methyl-1,2,4-triazolo[1,5-a]pyrimidine-2-sulfonyl)anthranilate.
148. Methyl 4-chloro-3-methyl-N-(6-methyl-1,2,4-triazolo[1,5-a]pyrimidine-2-sulfonyl)anthranilate.
149. Ethyl 4-chloro-3-methyl-N-(6-methyl-1,2,4-triazolo[1,5-a]pyrimidine-2-sulfonyl)anthranilate.
150. Ispropyl 4-chloro-3-methyl-N-(6-methyl-1,2,4-triazolo[1,5-a]pyrimidine-2-sulfonyl)anthranilate.
151. Methyl 3-amino-2,4-dichloro-N-(6-methyl-1,2,4-triazolo[1,5-a]pyrimidine-2-sulfonyl)benzoate.
152. Ethyl 3-amino-2,4-dichloro-N-(6-methyl-1,2,4-triazolo[1,5-a]pyrimidine-2-sulfonyl)benzoate.
153. Isopropyl 3-amino-2,4-dichloro-N-(6-methyl-1,2,4-triazolo[1,5-a]pyrimidine-2-sulfonyl)benzoate.

154. Methyl 3-amino-2-bromo-4-methyl-N-(6-methyl-1,2,4-triazolo[1,5-a]pyrimidine-2-sulfonyl)benzoate.
155. Ethyl 3-amino-2-bromo-4-methyl-N-(6-methyl-1,2,4-triazolo[1,5-a]pyrimidine-2-sulfonyl)benzoate.
156. Isopropyl 3-amino-2-bromo-4-methyl-N-(6-methyl-1,2,4-triazolo[1,5-a]pyrimidine-2-sulfonyl)benzoate.
157. 7-Methyl-N-(2-trifluoromethylphenyl)-1,2,4-triazolo[1,5-a]pyrimidine-2-sulfonamide.
158. 7-Methyl-N-(2,6-difluorophenyl)-1,2,4-triazolo[1,5-a]pyrimidine-2-sulfonamide.
159. 7-Methyl-N-(2,6-dichlorophenyl)-1,2,4-triazolo[1,5-a]pyrimidine-2-sulfonamide.
160. 7-Methyl-N-(2-chloro-6-fluorophenyl)-1,2,4-triazolo[1,5-a]pyrimidine-2-sulfonamide.
161. 7-Methyl-N-(2-bromo-6-chlorophenyl)-1,2,4-triazolo[1,5-a]pyrimidine-2-sulfonamide.
162. 7-Methyl-N-(2-chloro-6-iodophenyl)-1,2,4-triazolo[1,5-a]pyrimidine-2-sulfonamide.
163. 7-Methyl-N-(2-fluoro-6-methylphenyl)-1,2,4-triazolo[1,5-a]pyrimidine-2-sulfonamide.
164. 7-Methyl-N-(2-chloro-6-methylphenyl)-1,2,4-triazolo[1,5-a]pyrimidine-2-sulfonamide.
165. 7-Methyl-N-(2-bromo-6-methylphenyl)-1,2,4-triazolo[1,5-a]pyrimidine-2-sulfonamide.
166. 7-Methyl-N-(2-methyl-6-nitrophenyl)-1,2,4-triazolo[1,5-a]pyrimidine-2-sulfonamide.
167. 7-Methyl-N-(2-chloro-6-methoxymethylphenyl)-1,2,4-triazolo[1,5-a]pyrimidine-2-sulfonamide.
168. 7-Methyl-N-(2-fluoro-6-methoxymethylphenyl)-1,2,4-triazolo[1,5-a]pyrimidine-2-sulfonamide.
169. 7-Methyl-N-(2-chloro-6-phenylphenyl)-1,2,4-triazolo[1,5-a]pyrimidine-2-sulfonamide.
170. 7-Methyl-N-(2-methyl-6-trifluoromethylphenyl)-1,2,4-triazolo[1,5-a]pyrimidine-2-sulfonamide.
171. 7-Methyl-N-(2-fluoro-6-trifluoromethylphenyl)-1,2,4-triazolo[1,5-a]pyrimidine-2-sulfonamide.
172. 7-Methyl-N-(2,6-dichloro-3-methylphenyl)-1,2,4-triazolo[1,5-a]pyrimidine-2-sulfonamide.
173. 7-Methyl-N-(2,6-difluoro-3-methylphenyl)-1,2,4-triazolo[1,5-a]pyrimidine-2-sulfonamide.
174. 7-Methyl-N-(2,3-dimethyl-6-nitrophenyl)-1,2,4-triazolo[1,5-a]pyrimidine-2-sulfonamide.
175. 7-Methyl-N-(3,6-dimethyl-2-nitrophenyl)-1,2,4-triazolo[1,5-a]pyrimidine-2-sulfonamide.
176. 7-Methyl-N-(2,3-dichloro-6-methylphenyl)-1,2,4-triazolo[1,5-a]pyrimidine-2-sulfonamide.
177. 7-Methyl-N-(2-methoxy-6-trifluoromethylphenyl)-1,2,4-triazolo[1,5-a]pyrimidine-2-sulfonamide.
178. Methyl 3-methyl-N-(7-methyl-1,2,4-triazolo[1,5-a]pyrimidine-2-sulfonyl)anthranilate.
179. Ethyl 3-methyl-N-(7-methyl-1,2,4-triazolo[1,5-a]pyrimidine-2-sulfonyl)anthranilate.
180. Isopropyl 3-methyl-N-(7-methyl-1,2,4-triazolo[1,5-a]pyrimidine-2-sulfonyl)anthranilate.
181. 2-Ethoxyethyl 3-methyl-N-(7-methyl-1,2,4-triazolo[1,5-a]pyrimidine-2-sulfonyl)anthranilate.
182. 2-Propen-1-yl 3-methyl-N-(7-methyl-1,2,4-triazolo[1,5-a]pyrimidine-2-sulfonyl)anthranilate.
183. 2-Pyridylmethyl 3-methyl-N-(7-methyl-1,2,4-triazolo[1,5-a]pyrimidine-2-sulfonyl)anthranilate.
184. Methyl 3-fluoro-N-(7-methyl-1,2,4-triazolo[1,5-a]pyrimidine-2-sulfonyl)anthranilate.
185. Ethyl 3-fluoro-N-(7-methyl-1,2,4-triazolo[1,5-a]pyrimidine-2-sulfonyl)anthranilate.
186. Isopropyl 3-fluoro-N-(7-methyl-1,2,4-triazolo[1,5-a]pyrimidine-2-sulfonyl)anthranilate.
187. Methyl 3-chloro-N-(7-methyl-1,2,4-triazolo[1,5-a]pyrimidine-2-sulfonyl)anthranilate.
188. Ethyl 3-chloro-N-(7-methyl-1,2,4-triazolo[1,5-a]pyrimidine-2-sulfonyl)anthranilate.
189. Isopropyl 3-chloro-N-(7-methyl-1,2,4-triazolo[1,5-a]pyrimidine-2-sulfonyl)anthranilate.
190. Methyl 3-trifluoromethyl-N-(7-methyl-1,2,4-triazolo[1,5-a]pyrimidine-2-sulfonyl)anthranilate.
191. Ethyl 3-trifluoromethyl-N-(7-methyl-1,2,4-triazolo[1,5-a]pyrimidine-2-sulfonyl)anthranilate.
192. Isopropyl 3-trifluoromethyl-N-(7-methyl-1,2,4-triazolo[1,5-a]pyrimidine-2-sulfonyl)anthranilate.
193. Methyl 3,4-dimethyl-N-(7-methyl-1,2,4-triazolo[1,5-a]pyrimidine-2-sulfonyl)anthranilate.
194. Ethyl 3,4-dimethyl-N-(7-methyl-1,2,4-triazolo[1,5-a]pyrimidine-2-sulfonyl)anthranilate. 195. Isopropyl 3,4-dimethyl-N-(7-methyl-1,2,4-triazolo[1,5-a]pyrimidine-2-sulfonyl)anthranilate.
196. Methyl 3,6-dimethyl-N-(7-methyl-1,2,4-triazolo[1,5-a]pyrimidine-2-sulfonyl)anthranilate.
197. Ethyl 3,6-dimethyl-N-(7-methyl-1,2,4-triazolo[1,5-a]pyrimidine-2-sulfonyl)anthranilate.
198. Isopropyl 3,6-dimethyl-N-(7-methyl-1,2,4-triazolo[1,5-a]pyrimidine-2-sulfonyl)anthranilate.
199. Methyl 4-chloro-3-methyl-N-(7-methyl-1,2,4-triazolo[1,5-a]pyrimidine-2-sulfonyl)anthranilate.
200. Ethyl 4-chloro-3-methyl-N-(7-methyl-1,2,4-triazolo[1,5-a]pyrimidine-2-sulfonyl)anthranilate.
201. Isopropyl 4-chloro-3-methyl-N-(7-methyl-1,2,4-triazolo[1,5-a]pyrimidine-2-sulfonyl)anthranilate.
202. Methyl 3-amino-2,4-dichloro-N-(7-methyl-1,2,4-triazolo[1,5-a]pyrimidine-2-sulfonyl)benzoate.
203. Ethyl 3-amino-2,4-dichloro-N-(7-methyl-1,2,4-triazolo[1,5-a]pyrimidine-2-sulfonyl)benzoate.
204. Isopropyl 3-amino-2,4-dichloro-N-(7-methyl-1,2,4-triazolo[1,5-a]pyrimidine-2-sulfonyl)benzoate.
205. Methyl 3-amino-2-bromo-4-methyl-N-(7-methyl-1,2,4-triazolo[1,5-a]pyrimidine-2-sulfonyl)benzoate.
206. Ethyl 3-amino-2-bromo-4-methyl-N-(7-methyl-1,2,4-triazolo[1,5-a]pyrimidine-2-sulfonyl)benzoate.
207. Isopropyl 3-amino-2-bromo-4-methyl-N-(7-methyl-1,2,4-triazolo[1,5-a]pyrimidine-2-sulfonyl)benzoate.
208. 6-Chloro-N-(2,6-dichlorophenyl)-1,2,4-triazolo[1,5-a]pyrimidine-2-sulfonamide.
209. 6-Chloro-N-(2,6-difluorophenyl)-1,2,4-triazolo[1,5-a]pyrimidine-2-sulfonamide.
210. 6-Chloro-N-(2-chloro-6-methylphenyl)-1,2,4-triazolo[1,5-a]pyrimidine-2-sulfonamide.
211. 6-Chloro-N-(2-methyl-6-nitrophenyl)-1,2,4-triazolo[1,5-a]pyrimidine-2-sulfonamide.
212. 6-Chloro-N-(2,6-dichloro-3-methylphenyl)-1,2,4-triazolo[1,5-a]pyrimidine-2-sulfonamide.
213. 6-Chloro-N-(2,3-dimethyl-6-nitrophenyl)-1,2,4-triazolo[1,5-a]pyrimidine-2-sulfonamide.
214. 6-Chloro-N-(2-methoxy-6-trifluoromethylphenyl)-1,2,4-triazolo[1,5-a]pyrimidine-2-sulfonamide.
215. Methyl 3-methyl-N-(6-chloro-1,2,4-triazolo[1,5-a]pyrimidine-2-sulfonyl)anthranilate.
216. Methyl 3-fluoro-N-(6-chloro-1,2,4-triazolo[1,5-a]pyrimidine-2-sulfonyl)anthranilate.
217. 5-Methoxy-N-(2,6-dichlorophenyl)-1,2,4-triazolo[1,5-a]pyrimidine-2-sulfonamide.
218. 5-Methoxy-N-(2,methoxy-6-trifluoromethylphenyl)-1,2,4-triazolo[1,5-a]pyrimidine-2-sulfonamide.
219. 5-Methoxy-6-methyl-N-(2,6-dichlorophenyl)-1,2,4-triazolo[1,5-a]pyrimidine-2-sulfonamide.

220. 5-Methoxy-6-methyl-N-(2,5-difluorophenyl)-1,2,4-triazolo[1,5-a]pyrimidine-2-sulfonamide.
221. 5-Methoxy-6-methyl-N-(2-chloro-6-fluorophenyl)-1,2,4-triazolo[1,5-a]pyrimidine-2-sulfonamide.
222. 5-Methoxy-6-methyl-N-(2-bromo-6-chlorophenyl)-1,2,4-triazolo[1,5-a]pyrimidine-2-sulfonamide.
223. 5-Methoxy-6methyl-N-(2-chloro-6-iodophenyl)-1,2,4-triazolo[1,5-a]pyrimidine-2-sulfonamide.
224. 5-Methoxy-6-methyl-N-(2-trifluoromethylphenyl)-1,2,4-triazolo[1,5-a]pyrimidine-2-sulfonamide.
225. 5-Methoxy-6-methyl-N-(2-fluoro-6-methylphenyl)-1,2,4-triazolo[1,5-a]pyrimidine-2-sulfonamide.
226. 5-Methoxy-6-methyl-N-(2-chloro-6-methylphenyl)-1,2,4-triazolo[1,5-a]pyrimidine-2-sulfonamide.
227. 5-Methoxy-6-methyl-N-(2-bromo-6-methylphenyl)-1,2,4-triazolo[1,5-a]pyrimidine-2-sulfonamide.
228. 5-Methoxy-6-methyl-N-(2-methyl-6-nitrophenyl)-1,2,4-triazolo[1,5-a]pyrimidine-2-sulfonamide.
229. 5-Methoxy-6-methyl-N-(2-chloro-6-methoxyphenyl)-1,2,4-triazolo[1,5-a]pyrimidine-2-sulfonamide.
230. 5-Methoxy-6-methyl-N-(2-fluoro-6-methoxyphenyl)-1,2,4-triazolo[1,5-a]pyrimidine-2-sulfonamide.
231. 5-Methoxy-6-methyl-N-(2-chloro-6-phenylphenyl)-1,2,4-triazolo[1,5-a]pyrimidine-2-sulfonamide.
232. 5-Methoxy-6-methyl-N-(2-methyl-6-trifluoromethyl-phenyl)-1,2,4-triazolo[1,5-a]pyrimidine-2-sulfonamide.
233. 5-Methoxy-6-methyl-N-(2-fluoro-6-trifluoromethyl-phenyl)-1,2,4-triazolo[1,5-a]pyrimidine-2-sulfonamide.
234. 5-Methoxy-6-methyl-N-(2,6-dichloro-3-methylphenyl)-1,2,4-triazolo[1,5-a]pyrimidine-2-sulfonamide.
235. 5-Methoxy-6-methyl-N-(2,6-diflouro-3-methylphenyl)-1,2,4-triazolo[1,5-a]pyrimidine-2-sulfonamide.
236. 5-Methoxy-6-methyl-N-(2,3-dimethyl-6-nitrophenyl)-1,2,4-triazolo[1,5-a]pyrimidine-2-sulfonamide.
237. 5-Methoxy-6-methyl-N-(3,6-dimethyl-2-nitrophenyl)-1,2,4-triazolo[1,5-a]pyrimidine-2-sulfonamide.
238. 5-Methoxy-6-methyl-N-(2,3-dichloro-6-methylphenyl)-1,2,4-triazolo[1,5-a]pyrimidine-2-sulfonamide.
239. Methyl 3-methyl-N-(5-methoxy-6-methyl-1,2,4-triazolo[1,5-a]pyrimidine-2-sulfonyl)anthranilate.
240. Ethyl 3-methyl-N-(5-methyoxy-6-methyl-1,2,4-triazolo[1,5-a]pyrimidine-2-sulfonyl)anthranilate.
241. Isopropyl 3-methyl-N-(5-methoxy-6-methyl-1,2,4-triazolo[1,5-a]pyrimidine-2-sulfonyl)anthranilate.
242. 2-Ethoxyethyl 3-methyl-N-(5-methoxy-6-methyl-1,2,4-triazolo[1,5-a]pyrimidine-2-sulfonyl)anthranilate.
243. 2-Propen-1-yl 3-methyl-N-(5-methoxy-6-methyl-1,2,4-triazolo[1,5-a]pyrimidine-2-sulfonyl)anthranilate.
244. 2-Pyridylmethyl 3-methyl-N-(5-methoxy-6-methyl-1,2,4-triazolo[1,5-a]pyrimidine-2-sulfonyl)anthranilate.
245. Methyl 3-fluoro-N-(5-methoxy-6-methyl-1,2,4-triazolo[1,5-a]pyrimidine-2-sulfonyl)anthranilate.
246. Ethyl 3-fluoro-N-(5-methoxy-6-methyl-1,2,4-triazolo[1,5-a]pyrimidine-2-sulfonyl)anthranilate.
247. Isopropyl 3-fluoro-N-(5-methoxy-6-methyl-1,2,4-triazolo[1,5-a]pyrimidine-2-sulfonyl)anthranilate.
248. Methyl 3-chloro-N-(5-methoxy-6-methyl-1,2,4-triazolo[1,5-a]pyrimidine-2-sulfonyl)anthranilate.
249. Ethyl 3-chloro-N-(5-methoxy-6-methyl-1,2,4-triazolo[1,5-a]pyrimidine-2-sulfonyl)anthranilate.
250. Isopropyl 3-chloro-N-(5-methoxy-6-methyl-1,2,4-triazolo[1,5-a]pyrimidine-2-sulfonyl)anthranilate.
251. Methyl 3-trifluoromethyl-N-(5-methoxy-6-methyl-1,2,4-triazolo[1,5-a]pyrimidine-2-sulfonyl)anthranilate.
252. Ethyl 3-trifluoromethyl-N-(5-methoxy-6-methyl-1,2,4-triazolo[1,5-a]pyrimidine-2-sulfonyl)anthranilate.
253. Isopropyl 3-trifluoromethyl-N-(5-methoxy-6-methyl-1,2,4-triazolo[1,5-a]pyrimidine-2-sulfonyl)anthranilate.
254. Methyl 3,4-dimethyl-N-(5-methoxy-6-methyl-1,2,4-triazolo[1,5-a]pyrimidine-2-sulfonyl)anthranilate.
255. Ethyl 3,4-dimethyl-N-(5-methoxy-6-methyl-1,2,4-triazolo[1,5-a]pyrimidine-2-sulfonyl)anthranilate.
256. Isopropyl 3,4-dimethyl-N-(5-methoxy-6-methyl-1,2,4-triazolo[1,5-a]pyrimidine-2-sulfonyl)anthranilate.
257. Methyl 3,6-dimethyl-N-(5-methoxy-6-methyl-1,2,4-triazolo[1,5-a]pyrimidine-2-sulfonyl)anthranilate.
258. Ethyl 3,6-dimethyl-N-(5-methoxy-6-methyl-1,2,4-triazolo[1,5-a]pyrimidine-2-sulfonyl)anthranilate.
259. Isopropyl 3,6-dimethyl-N-(5-methoxy-6-methyl-1,2,4-triazolo[1,5-a]pyrimidine-2-sulfonyl)anthranilate.
260. Methyl 4-chloro-3-methyl-N-(5-methoxy-6-methyl-1,2,4-triazolo[1,5-a]pyrimidine-2-sulfonyl)anthranilate.
261. Ethyl 4-chloro-3-methyl-N-(5-methoxy-6-methyl-1,2,4-triazolo[1,5-a]pyrimidine-2-sulfonyl)anthranilate.
262. Isopropyl 4-chloro-3-methyl-N-(5-methoxy-6-methyl-1,2,4-triazolo[1,5-a]pyrimidine-2-sulfonyl)anthranilate.
263. Methyl 3-amino-2,4-dichloro-N-(5-methoxy-6-methyl-1,2,4-triazolo[1,5-a]pyrimidine-2-sulfonyl)benzoate.
264. Ethyl 3-amino-2,4-dichloro-N-(5-methoxy-6-methyl-1,2,4-triazolo[1,5-a]pyrimidine-2-sulfonyl)benzoate.
265. Isopropyl 3-amino-2,4-dichloro-N-(5-methoxy-6-methyl-1,2,4-triazolo[1,5-a]pyrimidine-2-sulfonyl)benzoate.
266. Methyl 3-amino-2,4-dichloro-N-(5-methoxy-6-methyl-1,2,4-triazolo[1,5-a]pyrimidine-2-sulfonyl)benzoate.
267. Ethyl 3-amino-2-bromo-4-methyl-N-(5-methoxy-6-methyl-1,2,4-triazolo[1,5-a]pyrimidine-2-sulfonyl)benzoate.
268. Isopropyl 3-amino-2-bromo-4-methyl-N-(5-methoxy-6-methyl-1,2,4-triazolo[1,5-a]pyrimidine-2-sulfonyl)benzoate.
269. 5-Methyl-7-trifluoromethyl-N-(2-trifluoromethylphenyl)-1,2,4-triazolo[1,5-a]pyrimidine-2-sulfonamide.
270. 5-Methyl-7-trifluoromethyl-N-(2,6-dichlorophenyl)-1,2,4-triazolo[1,5-a]pyrimidine-2-sulfonamide.

271. 5-Methyl-7-trifluoromethyl-N-(2,6-difluorophenyl)-1,2,4-triazolo[1,5-a]pyrimidine-2-sulfonamide.
272. 5-Methyl-7-trifluoromethyl-N-(2-chloro-6-fluorophenyl)-1,2,4-triazolo[1,5-a]pyrimidine-2-sulfonamide.
273. 5-Methyl-7-trifluoromethyl-N-(2-bromo-6-chlorophenyl)-1,2,4-triazolo[1,5-a]pyrimidine-2-sulfonamide.
274. 5-Methyl-7-trifluoromethyl-N-(2-chloro-6-iodophenyl)-1,2,4-triazolo[1,5-a]pyrimidine-2-sulfonamide.
275. 5-Methyl-7-trifluoromethyl-N-(2-fluoro-6-methylphenyl)-1,2,4-triazolo[1,5-a]pyrimidine-2-sulfonamide.
276. 5-Methyl-7-trifluoromethyl-N-(2-chloro-6-methylphenyl)-1,2,4-triazolo[1,5-a]pyrimidine-2-sulfonamide.
277. 5-Methyl-7-trifluoromethyl-N-(2-bromo-6-methylphenyl)-1,2,4-triazolo[1,5-a]pyrimidine-2-sulfonamide.
278. 5-Methyl-7-trifluoromethyl-N-(2-methyl-6-nitrophenyl)-1,2,4-triazolo[1,5-a]pyrimidine-2-sulfonamide.
279. 5-Methyl-7-trifluoromethyl-N-(2-chloro-6-methoxymethylphenyl)-1,2,4-triazolo[1,5-a]pyrimidine-2-sulfonamide.
280. 5-Methyl-7-trifluoromethyl-N-(2-fluoro-6-methoxymethylphenyl)-1,2,4-triazolo[1,5-a]pyrimidine-2-sulfonamide.
281. 5-Methyl-7-trifluoromethyl-N-(2-chloro-6-phenylphenyl)-1,2,4-triazolo[1,5-a]pyrimidine-2-sulfonamide.
282. 5-Methyl-7-trifluoromethyl-N-(2-methyl-6-trifluoromethylphenyl)-1,2,4-triazolo[1,5-a]pyrimidine-2-sulfonamide.
283. 5-Methyl-7-trifluoromethyl-N-(2-fluoro-6-trifluoromethylphenyl)-1,2,4-triazolo[1,5-a]pyrimidine-2-sulfonamide.
284. 5-Methyl-7-trifluoromethyl-N-(2,6-dichloro-3-methylphenyl)-1,2,4-triazolo[1,5-a]pyrimidine-2-sulfonamide.
285. 5-Methyl-7-trifluoromethyl-N-(2,6-difluoro-3-methylphenyl)-1,2,4-triazolo[1,5-a]pyrimidine-2-sulfonamide.
286. 5-Methyl-7-trifluoromethyl-N-(2,3-dimethyl-6-nitrophenyl)-1,2,4-triazolo[1,5-a]pyrimidine-2-sulfonamide.
287. 5-Methyl-7-trifluoromethyl-N-(3,6-dimethyl-2-nitrophenyl)-1,2,4-triazolo[1,5-a]pyrimidine-2-sulfonamide.
288. 5-Methyl-7-trifluoromethyl-N-(2,3-dichloro-6-methylphenyl)-1,2,4-triazolo[1,5-a]pyrimidine-2-sulfonamide.
289. Methyl 3-methyl-N-(5-methyl-7-trifluoromethyl-1,2,4-triazolo[1,5-a]pyrimidine-2-sulfonyl)anthranilate.
290. Ethyl 3-methyl-N-(5-methyl-7-trifluoromethyl-1,2,4-triazolo[1,5-a]pyrimidine-2-sulfonyl)anthranilate.
291. Isopropyl 3-methyl-N-(5-methyl-7-trifluoromethyl-1,2,4-triazolo[1,5-a]pyrimidine-2-sulfonyl)anthranilate.
292. 2-Ethoxyethyl 3-methyl-N-(5-methyl-7-trifluoromethyl-1,2,4-triazolo[1,5-a]pyrimidine-2-sulfonyl)anthranilate.
293. 2-Propen-1-yl 3-methyl-N-(5-methyl-7-trifluoromethyl-1,2,4-triazolo[1,5-a]pyrimidine-2-sulfonyl)anthranilate.
294. 2-Pyridylmethyl 3-methyl-N-(5-methyl-7-trifluoromethyl-1,2,4-triazolo[1,5-a]pyrimidine-2-sulfonyl)anthranilate.
295. Methyl 3-fluoro-N-(5-methyl-7-trifluoromethyl-1,2,4-triazolo[1,5-a]pyrimidine-2-sulfonyl)anthranilate.
296. Ethyl 3-fluoro-N-(5-methyl-7-trifluoromethyl-1,2,4-triazolo[1,5-a]pyrimidine-2-sulfonyl)anthranilate.
297. Isopropyl 3-fluoro-N-(5-methyl-7-trifluoromethyl-1,2,4-triazolo[1,5-a]pyrimidine-2-sulfonyl)anthranilate.
298. Methyl 3-chloro-N-(5-methyl-7-trifluoromethyl-1,2,4-triazolo[1,5-a]pyrimidine-2-sulfonyl)anthranilate.
299. Ethyl 3-chloro-N-(5-methyl-7-trifluoromethyl-1,2,4-triazolo[1,5-a]pyrimidine-2-sulfonyl)anthranilate.
300. Isopropyl 3-chloro-N-(5-methyl-7-trifluoromethyl-1,2,4-triazolo[1,5-a]pyrimidine-2-sulfonyl)anthranilate.
301. Methyl 3-trifluoromethyl-N-(5-methyl-7-trifluoromethyl-1,2,4-triazolo[1,5-a]pyrimidine-2-sulfonyl)anthranilate.
302. Ethyl 3-trifluoromethyl-N-(5-methyl-7-trifluoromethyl-1,2,4-triazolo[1,5-a]pyrimidine-2-sulfonyl)anthranilate.
303. Isopropyl 3-trifluoromethyl-N-(5-methyl-7-trifluoromethyl-1,2,4-triazolo[1,5-a]pyrimidine-2-sulfonyl)anthranilate.
304. Methyl 3,4-dimethyl-N-(5-methyl-7-trifluoromethyl-1,2,4-triazolo[1,5-a]pyrimidine-2-sulfonyl)anthranilate.
305. Ethyl 3,4-dimethyl-N-(5-methyl-7-trifluoromethyl-1,2,4-triazolo[1,5-a]pyrimidine-2-sulfonyl)anthranilate.
306. Isopropyl 3,4-dimethyl-N-(5-methyl-7-trifluoromethyl-1,2,4-triazolo[1,5-a]pyrimidine-2-sulfonyl)anthranilate.
307. Methyl 3,6-dimethyl-N-(5-methyl-7-trifluoromethyl-1,2,4-triazolo[1,5-a]pyrimidine-2-sulfonyl)anthranilate.
308. Ethyl 3,6-dimethyl-N-(5-methyl-7-trifluoromethyl-1,2,4-triazolo[1,5-a]pyrimidine-2-sulfonyl)anthranilate.
309. Isopropyl 3,6-dimethyl-N-(5-methyl-7-trifluoromethyl-1,2,4-triazolo[1,5-a]pyrimidine-2-sulfonyl)anthranilate.
310. Methyl 4-chloro-3-methyl-N-(5-methyl-y-trifluoromethyl-1,2,4-triazolo[1,5-a]pyrimidine-2-sulfonyl)anthranilate.
311. Ethyl 4-chloro-3-methyl-N-(5-methyl-y-trifluoromethyl-1,2,4-triazolo[1,5-a]pyrimidine-2-sulfonyl)anthranilate.
312. Isopropyl 4-chloro-3-methyl-N-(5-methyl-y-trifluoromethyl-1,2,4-triazolo[1,5-a]pyrimidine-2-sulfonyl)anthranilate.
313. Methyl 3-amino-2,4-dichloro-N-(5-methyl-7-trifluoromethyl-1,2,4-triazolo[1,5-a]pyrimidine-2-sulfonyl)benzoate.
314. Ethyl 3-amino-2,4-dichloro-N-(5-methyl-7-trifluoromethyl-1,2,4-triazolo[1,5-a]pyrimidine-2-sulfonyl)benzoate.

315. Isopropyl 3-amino-2,4-dichloro-N-(5-methyl-7-trifluoromethyl-1,2,4-triazolo[1,5-a]pyrimidine-2-sulfonyl)benzoate.
316. Methyl 3-amino-2,bromo-4-methyl-N-(5-methyl-7-trifluoromethyl-1,2,4-triazolo[1,5-a]pyrimidine-2-sulfonyl)benzoate.
317. Ethyl 3-amino-2,bromo-4-methyl-N-(5-methyl-7-trifluoromethyl-1,2,4-triazolo[1,5-a]pyrimidine-2-sulfonyl)benzoate.
318. Isopropyl 3-amino-2,bromo-4-methyl-N-(5-methyl-7-trifluoromethyl-1,2,4-triazolo[1,5-a]pyrimidine-2-sulfonyl)benzoate.
319. N-(2-Trifluoromethylphenyl-1,2,4-triazolo[1,5-a]pyrimidine-2-sulfonamide.
320. N-(2,6-Dichlorophenyl)-1,2,4-triazolo[1,5-a]pyrimidine-2-sulfonamide.
321. N-(2-6-Difluorophenyl)-1,2,4-triazolo[1,5-a]pyrimidine-2-sulfonamide.
322. N-(2-Chloro-6-fluorophenyl)-1,2,4-triazolo[1,5-a]pyrimidine-2-sulfonamide.
323. N-(2-Bromo-6-chlorophenyl)-1,2,4-triazolo[1,5-a]pyrimidine-2-sulfonamide.
324. N-(2-Chloro-6-iodophenyl)-1,2,4-triazolo[1,5-a]pyrimidine-2-sulfonamide.
325. N-(2-Fluoro-6-methylphenyl)-1,2,4-triazolo[1,5-a]pyrimidine-2-sulfonamide.
326. N-(2-Chloro-6-methylphenyl)-1,2,4-triazolo[1,5-a]pyrimidine-2-sulfonamide.
327. N-(2-Bromo-6-methylphenyl)-1,2,4-triazolo[1,5-a]pyrimidine-2-sulfonamide.
328. N-(2-Methyl-6-nitrophenyl)-1,2,4-triazolo[1,5-a]pyrimidine-2-sulfonamide.
329. N-(2-Chloro-6-methyloxymethylphenyl)-1,2,4-triazolo-[1,5-a]pyrimidine-2-sulfonamide.
330. N-(2-Fluoro-6-methyloxymethylphenyl)-1,2,4-triazolo-[1,5-a]pyrimidine-2-sulfonamide.
331. N-(2-Chloro-6-phenylphenyl)-1,2,4-triazolo[1,5-a]pyrimidine-2-sulfonamide.
332. N-(2-Methyl-6-trifluoromethylphenyl)-1,2,4-triazolo-[1,5-a]pyrimidine-2-sulfonamide.
333. N-(2-Fluoro-6-trifluoromethylphenyl)-1,2,4-triazolo[1,5-a]pyrimidine-2-sulfonamide.
334. N-(2,6-Dichloro-3-methylphenyl)-1,2,4-triazolo-[1,5-a]pyrimidine-2-sulfonamide.
335. N-(2,6-Difluoro-3-methylphenyl)-1,2,4-triazolo-[1,5-a]pyrimidine-2-sulfonamide.
336. N-(2,3-dimethyl-6-nitrophenyl)-1,2,4-triazolo[1,5-a]pyrimidine-2-sulfonamide.
337. N-(3,6-dimethyl-2-nitrophenyl)-1,2,4-triazolo-[1,5-a]pyrimidine-2-sulfonamide.
338. N-(2,3-dichloro-6-methylphenyl)-1,2,4-triazolo-[1,5-a]pyrimidine-2-sulfonamide.
339. Methyl 3-methyl-N-(1,2,4-triazolo[1,5-a]pyrimidine-2-sulfonyl)anthranilate.
340. Ethyl 3-methyl-N-(1,2,4-triazolo[1,5-a]pyrimidine-2-sulfonyl)anthranilate.
341. Isopropyl 3-methyl-N-(1,2,4-triazolo[1,5-a]pyrimidine-2-sulfonyl)anthranilate.
342. 2-Ethoxyethyl 3-methyl-N-(1,2,4-triazolo[1,5-a]pyrimidine-2-sulfonyl)anthranilate.
343. 2-Propen-1-yl 3-methyl-N-(1,2,4-triazolo[1,5-a]pyrimidine-2-sulfonyl)anthranilate.
344. 2-Pyridylmethyl 3-methyl-N-(1,2,4-triazolo[1,5-a]pyrimidine-2-sulfonyl)anthranilate.
345. Methyl 3-fluoro-N-(1,2,4-triazolo[1,5-a]pyrimidine-2-sulfonyl)-anthranilate.
346. Ethyl 3-fluoro-N-(1,2,4-triazolo[1,5-a]pyrimidine-2-sulfonyl)-anthranilate.
347. Isopropyl 3-fluoro-N-(1,2,4-triazolo[1,5-a]pyrimidine-2-sulfonyl)-anthranilate.
348. Methyl 3-chloro-N-(1,2,4-triazolo[1,5-a]pyrimidine-2-sulfonyl)-anthranilate.
349. Ethyl 3-chloro-N-(1,2,4-triazolo[1,5-a]-pyrimidine-2-sulfonyl)-anthranilate.
350. Isopropyl 3-chloro-N-(1,2,4-triazolo[1,5-a]pyrimidine-2-sulfonyl)-anthranilate.
351. Methyl 3-trifluoromethyl-N-(1,2,4-triazolo[1,5-a]-pyrimidine-2-sulfonyl)anthranilate.
352. Ethyl 3-trifluoromethyl-N-(1,2,4-triazolo[1,5-a]-pyrimidine-2-sulfonyl)anthranilate.
353. Isopropyl 3-trifluoromethyl-N-(1,2,4-triazolo[1,5-a]-pyrimidine-2-sulfonyl)anthranilate.
354. Methyl 3,4-dimethyl-N-(1,2,4-triazolo[1,5-a]-pyrimidine-2-sulfonyl)anthranilate.
355. Ethyl 3,4-dimethyl-N-(1,2,4-triazolo[1,5-a]-pyrimidine-2-sulfonyl)anthranilate.
356. Isopropyl 3,4-dimethyl-N-(1,2,4-triazolo[1,5-a]-pyrimidine-2-sulfonyl)anthranilate.
357. Methyl 3,6-dimethyl-N-(1,2,4-triazolo[1,5-a]-pyrimidine-2-sulfonyl)anthranilate.
358. Ethyl 3,6-dimethyl-N-(1,2,4-triazolo[1,5-a]-pyrimidine-2-sulfonyl)anthranilate.
359. Isopropyl 3,6-dimethyl-N-(1,2,4-triazolo[1,5-a]-pyrimidine-2-sulfonyl)anthranilate.
360. Methyl 4-chloro-3-methyl-N-(1,2,4-triazolo[1,5-a]-pyrimidine-2-sulfonyl)anthranilate.
361. Ethyl 4-chloro-3-methyl-N-(1,2,4-triazolo[1,5-a]-pyrimidine-2-sulfonyl)anthranilate.
362. Isopropyl 4-chloro-3-methyl-N-(1,2,4-triazolo[1,5-a]-pyrimidine-2-sulfonyl)anthranilate.
363. Methyl 3-amino-2,4-dichloro-N-(1,2,4-triazolo[1,5-a]-pyrimidine-2-sulfonyl)anthranilate.
364. Ethyl 3-amino-2,4-dichloro-N-(1,2,4-triazolo[1,5-a]-pyrimidine-2-sulfonyl)anthranilate.
365. Isopropyl 3-amino-2,4-dichloro-N-(1,2,4-triazolo[1,5-a]-pyrimidine-2-sulfonyl)anthranilate.
366. Methyl 3-amino-2-bromo-4-methyl-N-(1,2,4-triazolo-[1,5-a]pyrimidine-2-sulfonyl)benzoate.
367. Ethyl 3-amino-2-bromo-4-methyl-N-(1,2,4-triazolo-[1,5-a]pyrimidine-2-sulfonyl)benzoate.
368. Isopropyl 3-amino-2-bromo-4-methyl-N-(1,2,4-triazolo-[1,5-a]pyrimidine-2-sulfonyl)benzoate.
369. 5-Methyl-7-trifluoromethyl-N(2-methoxy-6-trifluoromethylphenyl)-1,2,4-triazolo[1,5-a]-pyrimidine-2-sulfonamide.
370. N(2-methoxy-6-trifluoromethylphenyl)-1,2,4-triazolo[1,5-a]pyrimidine-2-sulfonamide.

In addition, the following compounds are preferred due to their high levels of herbicidal activity and selectivity to crop species:
1. 5,7-Dimethyl-N-(2-chloro-1-napthyl)-1,2,4-triazolo[1,5-a]pyrimidine-2-sulfonamide.
2. 5-Methyl-N-(2-chloro-1-napthyl)-1,2,4-triazolo[1,5-a]pyrimidine-2-sulfonamide.
3. 5-Methyl-N-(1,3-dimethyl-5-trifluoromethyl-4-pyrazolyl)-1,2,4-triazolo[1,5-a]pyrimidine-2-sulfonamide.

In addition, certain derivatives of compounds corresponding to I also exhibit herbicidal activity and nitrification inhibition activity in soil. For example, compounds having the formula:

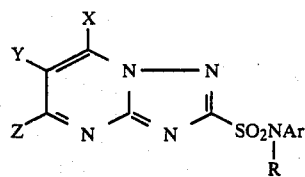

(II)

wherein Ar and X, Y and Z are as described above for compound I and R represents alkyl, alkenyl, alkynyl, phenylalkyl, substituted phenylalkyl, acyl, alkoxycarbonyl, phenoxycarbonyl, dialkylaminocarbonyl, alkylsulfonyl, phenylsulfonyl, alkylthiocarbonyl or phenylthiocarbonyl wherein alkyl, alkenyl and alkynyl are as above defined.

Preferred derivatives of the invention have the general formula:

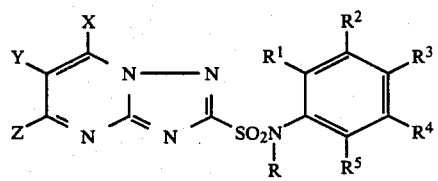

wherein X, Y, Z, $R^1$, $R^2$, $R^3$, $R^4$ and $R^5$ are as described above for I and R represents $C_1$–$C_4$ alkyl, allyl, benzyl, —$COR^{10}$, —$CO_2R^{10}$, —$CONR_2^{10}$, —$COSR^{10}$, and —$SO_2R^{10}$ wherein $R^{10}$ is $C_1$–$C_6$ alkyl, phenyl, substituted phenyl or $C_1$–$C_2$ haloalkyl.

Most preferred derivatives of the invention have the general formula:

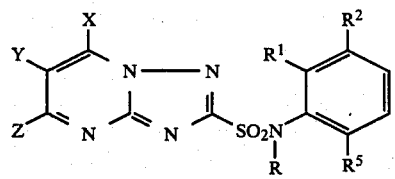

wherein X, Y, Z, $R^1$, $R^2$ and $R^5$ are as described above for I and R is $COR^{10}$ wherein $R^{10}$ is $C_1$–$C_4$ alkyl.

Specifically preferred derivatives of this embodiment of the invention include all of the specifically preferred compounds listed previously in other embodiments of the invention wherein the hydrogen of the sulfonamide portion of their structures ($SO_2NH$) has been replaced with any of the following groups:

1. $COCH_3$.
2. $COCH_2CH_3$.
3. $COCH_2CH_2CH_3$.
4. $COCH(CH_3)_2$.
5. $COCH_2CH_2CH_2CH_3$.
6. $COCH_2CH(CH_3)_2$.
7. $COCH_2C(CH_3)_3$.
8. $COCH_2C_6H_5$.
9. COcyclo—$C_6H_{11}$.
10. $COCH=CHC_6H_5$.
11. $COC_6H_5$.
12. $COCH_2Cl$.
13. $COCH_2CH_2Cl$.
14. $COCH_2CH_2COOCH_3$.
15. $COCH_2CH_2COOCH_2CH_3$.
16. $COOCH_3$.
17. $COOCH_2CH_3$.
18. $CON(CH_3)_2$.
19. $C(O)SCH_3$.
20. $C(O)SCH_2CH_3$.
21. $SO_2CH_3$.
22. $SO_2C_6H_5$.

Another series of derivatives of compounds of type I also possess herbicidal activity. These compounds are represented by the general formula:

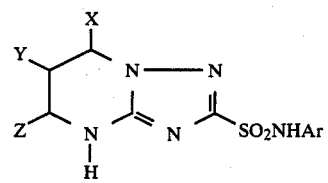

(III)

wherein X, Y, Z and Ar are as described above for compounds of type I.

Preferred derivatives of this invention have the general formula:

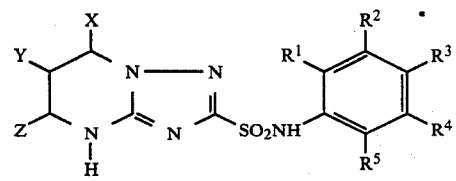

wherein X, Y, Z, $R^1$, $R^2$, $R^3$, $R^4$, and $R^5$ are as described above for I.

Most preferred derivatives of this invention have the general formula:

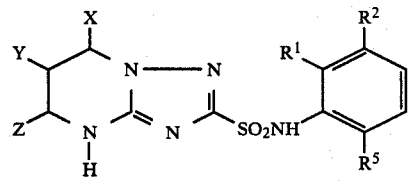

wherein X, Y, Z, $R^1$, $R^2$ and $R^5$ are as described above for I.

Specifically preferred derivatives of this invention include:

1. 5,7-Dimethyl-N-(2,6-dichlorophenyl)-4,5,6,7-tetrahydro-1,2,4-triazolo[1,5-a]pyrimidine-2-sulfonamide.
2. 5-Methyl-N-(2,6-dichlorophenyl)-4,5,6,7-tetrahydro-1,2,4-triazolo[1,5-a]pyrimidine-2-sulfonamide.
3. 5,7-Dimethyl-N-(2-trifluoromethylphenyl)-4,5,6,7-tetrahydro-1,2,5-triazolo[1,5-a]pyrimidine-2-sulfonamide.

Furthermore, in the above invention corresponding to general formula III the existence of stereoisomerism is possible. For example stereoiosmeric relationships exist when at least one of substituents X, Y and Z does not equal hydrogen. When only one of substituents X, Y and Z does not equal hydrogen the compound of type III may exist as a mixture of enantiomers. One enantiomer will be designated as having the R-configuration and the other will be designated as having the S-configuration. Each enantiomer may exhibit different levels of herbicidal activity. When two or more of substituents X, Y or Z in structure III do not equal hydrogen, the material may exist as a mixture of diastereomers. For example when two substituents among X, Y and Z do not equal hydrogen, the compound may exist as two diastereomers. When all three of substituents X, Y and Z do not equal hydrogen the compound may exist as four diastereomers. In addition all of the diastereomers described above exist as a mixture of two enantiomers. All of the stereoisomers described above, diastereomers and their enantiomeric pairs, may exhibit different levels of herbicidal activity.

The synthesis of compounds of general structure I can be carried out in a straightforward manner as illustrated in Scheme I. Reaction of sulfonyl chloride IV with the appropriate aromatic (substituted or unsubstituted) or heteroaromatic (substituted or unsubstituted) amino compound (ArNH$_2$) under basic conditions yields the desired product I. A wide range of solvents may be employed (i.e., CH$_2$Cl$_2$, CH$_3$CN or pyridine) at temperatures ranging from 0° C. to reflux. Bases which serve as catalysts include pyridine, 4-dimethylaminopyridine ad tertiary alkylamines such as triethylamine or N-methylmorpholine. Generally the amino compound serves as the limiting reagent. Molar ratios of between 1.1 and 1.0 for the sulfonylchloride to amino compound and molar ratios of between 5.0 and 1.1 for the base to amino compound are used most often. A wide range of concentrations may be employed (i.e., 0.1–5M). Generally concentrations in the range of 0.5–2M are used to give a homogeneous reaction which proceeds at a convenient rate. In addition it is sometimes advantageous to use a combination of pyridine derived base catalysts and tertiary amine bases. The use of pyridine as a solvent is convenient as the pyridine can serve both as a solvent and catalyst in the transformation.

nucleophic) is it advantageous to prepare a metal derivative of the amino compound by treatment with a strong base. The corresponding amide bases are generally prepared in ether solvents (i.e., THF) using strong bases such as alkali metal alkyls (i.e., n-BuLi) or alkali metal hydrides (i.e., NaH or KH) at temperatures ranging from −80° C. to 0° C. The amide thus generated in situ can be reacted with sulfonylchloride IV to yield the desired product I. Generally, molar ratios of the starting amino compound to sulfonyl chloride of 2 to 3 are used to ensure complete reaction.

Sulfonyl chlorides IV are new and represent key intermediates in the synthesis of sulfonamides I. Sulfonyl chlorides IV may be prepared according to routes outlined in Scheme II. Mercaptan IV may be converted to sulfonyl chloride IV by treatment with Cl$_2$ in an aqueous acidic medium. Generally the medium would be aqueous acetic acid or aqueous HCl. The temperature of the reaction mixture is generally maintained between −20° C. and 25° C. during the course of the chlorine addition. Most preferably, temperature ranges between −20° C. and 0° C. are employed to minimize unwanted side reactions such as hydrolysis of IV to the corresponding sulfonic acid. Alternatively, the mercaptan IV may be suspended in a two phase system of aqueous acid (i.e., HCl) and an organic solvent (i.e., CH$_2$Cl$_2$) and treated with sodium hypochlorite. This serves to convert IV to the sulfonyl chloride IV in a reproducibly good yield. The solubility of the product in the organic phase serves to protect it from hydrolysis to the sulfonic acid. Again, temperatures in the range of −20° C. to 25° C. are employed with temperatures in the range of −5° C. to 5° C. being most generally used.

SCHEME II.

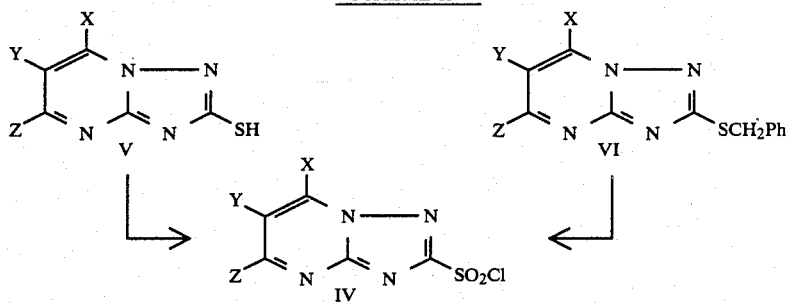

As an alternative, it is sometimes preferred to prepare sulfonyl chloride IV from benzyl sulfide VI (Scheme

SCHEME I.

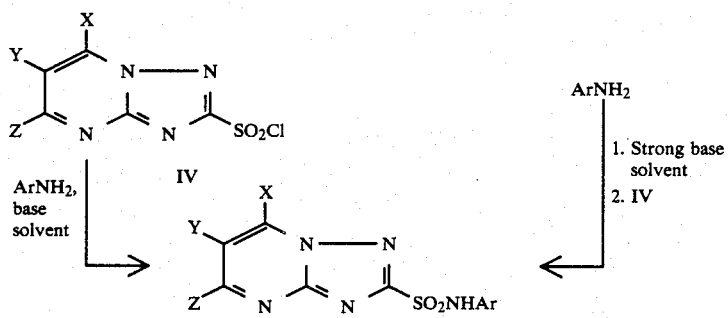

An additional alternative route to compounds of general formula I is illustrative in Scheme I. In cases where the amino compound (ArNH$_2$) is less reactive (less II). Reaction conditions as described above for the conversion of V to IV are operable. This procedure yields by-products containing benzyl residues which are generally removed by washing the product with water and/or an appropriate organic solvent and drying in vacuo.

Compounds of general structure V or VI may be prepared by routes illustrated in Scheme III. Some derivatives of structures V and VI are known materials (i.e., V X=Z=Me, Y=H and VI X=Z=Me, Y=H) prepared by methods described in *J. Med. Chem.*, 25, 420 (1982). Compound IV is prepared directly by reaction of a 1,3-diketone with commercially available 3-amino-5-mercapto-1,2,4-triazole VII in glacial acetic acid as a solvent. Generally the reaction is performed at reflux. Alternatively, VII may be benzylated with benzyl chloride using an alkali earth metal alkoxide (i.e., NaOH) as a base to yield known benzyl sulfide VIII (*J. Heterocycl. Chem.*, 12, 1187 (1975)). Benzyl sulfide VIII can be condensed with not only 1,3-diketones but also β-keto esters, malonic esters, malonaldehyde, β-ketoaldehydes or α-formyl esters or derivatives thereof (i.e., acetals or enol ethers) to yield products of type VI as illustrated in Table A. Generally these reactions can be carried out under acidic conditions (i.e., glacial acetic acid as a solvent) or basic conditions (i.e., NaOR in ROH wherein R is $C_1$ to $C_4$ alkyl). In cases where the X, Y and Z substituents in VI are derived from a 1,3-diketone, compound VI may be prepared by benzylation of IV using an appropriate base (i.e., NaOH) and benzyl chloride in a variety of solvents (i.e., $H_2O$, $CH_3OH$, EtOH, THF, dioxane, $CH_3CN$, DMF or DMSO or combinations of the aforementioned).

TABLE A

| 1,3-Dicarbonyl Compound or Derivative | Reaction Conditions | Compound of Formula V or VI | | |
|---|---|---|---|---|
| | | X | Y | Z |
| R-CO-CHR'-CO-R'' | acid | R | R' | R'' |
| R-CO-CHR'-CH(OR)(OR) | acid | H | R' | R |
| R-CO-CHR'-COOR | acid | OH* | R' | R |
| RO-CH(OR)-CHR'-CH(OR)(OR) (RO,RO,OR,OR) | acid | H | H | H |
| $RO_2C$-CHR'-$CO_2R$ | base | OH | R' | OH |

*In this structural representation, as well as others bearing OH groups at 5- or 7-positions of the 1,2,4-triazolo[1,5-a]pyrimidine, the enol form has been depicted. Clearly this is the equilibrium with the various keto forms.

In instances where the 1,3-dicarbonyl compound is unsymmetrical, the possibility of obtaining two different isomers from condensation with VIII exists. In general, under acidic conditions the exocyclic nitrogen in VIII is the first to condense with the 1,3-dicarbonyl compound. Under basic conditions the endocyclic nitrogen in VIII is sometimes more reactive. Consequently, in situations where a clear difference in reactivity of the two carbonyl functionalities in the 1,3-dicar-

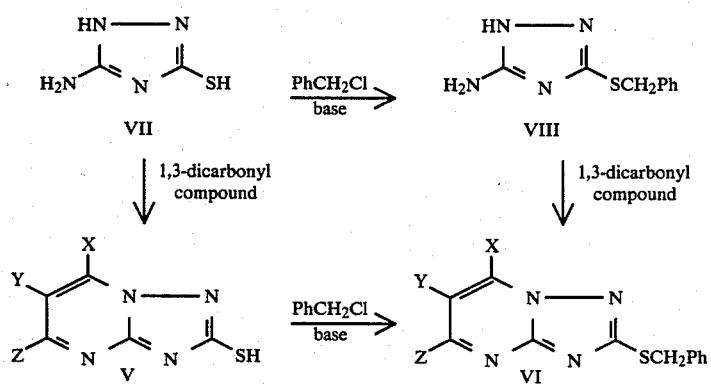

SCHEME III.

bonyl compound exists, some measures of regiochemical control may be achieved by choice of reaction conditions (i.e., entries 2 and 3 in Table I).

To prepare the alternative regioisomer to that depicted in entry 4 in Table A (i.e., VI X=R, Y=R' and Z=OH) a route illustrated in Scheme IV was followed. Compound VIII was condensed with 2,3-dibromocarboxylic acid esters to yield VI (X=R, Y=R', Z=OH). The reaction is generally carried out in refluxing pyridine.

SCHEME IV.

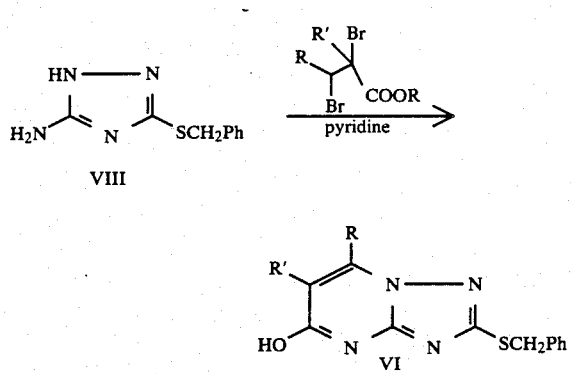

An additional route to compounds of type VI involves condensation of compound VIII with methanaminium compounds of type VII as illustrated in Scheme V. The condensation is usually carried out by reaction in refluxing glacial acetic acid and is useful in the synthesis of a number of 6-substituted 1,2,4-triazolo[1,5-a]pyrimidines.

SCHEME V.

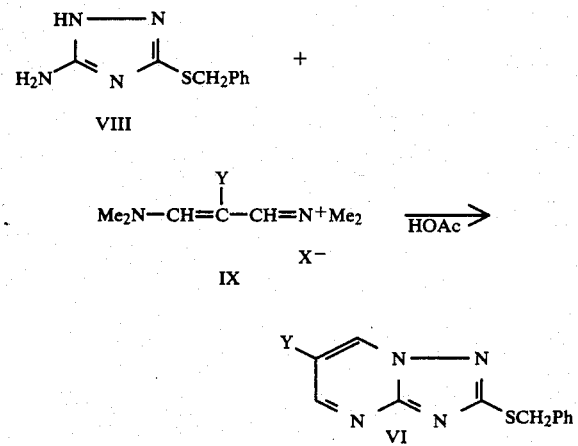

In the synthetic routes listed above, compounds of type VI where X and/or Z is OH are capable of undergoing further transformation (Scheme VI). For example, treatment of compound VI (X and/or Z=OH) with phosphorus oxychloride yields VI (X and/or Z=Cl). The reaction is generally carried out at reflux in neat phosphorus oxychloride or with phosphorous oxychloride in a solvent (i e CH$_3$CN). Compound VI (X and/or Z=Cl) can be further reacted with nucelophiles (i.e., NaOCH$_3$, MeMgBr) to yield VI (X and/or Z=OCH$_3$ or CH$_3$, respectively). In addition compound VI (X and/or Z=Cl) may be reduced to affort VI (X and/or Z=H). An effective reducing agent for this type of transformation is zinc-copper couple in the pressure of acid.

SCHEME VI.

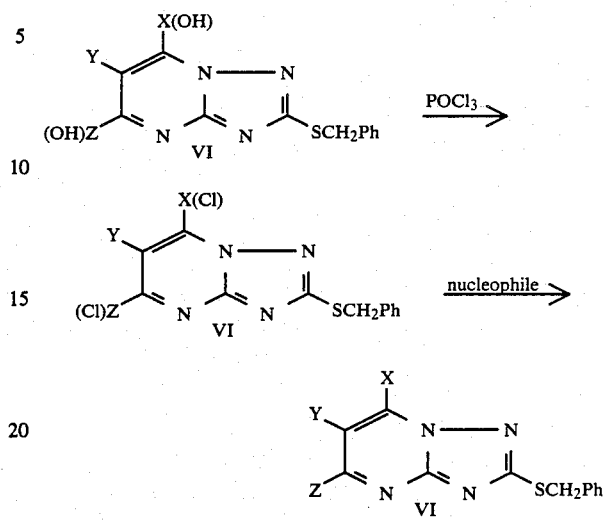

Other compounds of the present invention are best prepared in a manner illustrated in Scheme VII. Compounds such as is represented by structure XI wherein X$^1$ and Z$^1$ are independently represented by hydrogen, C$_1$–C$_4$ alkyl, thioalkyl, thioaryl, amino (including mono- and disubstituted alkylamino, mono- and disubstituted arylamino and arylalkylamino) can be prepared by this method. The method involves the reaction of compound X wherein X and Z independently represents hydrogen, C$_1$–C$_4$ alkyl or an appropriate leaving group, with a nucleophile in a suitable solvent. This procedure affects the substitution of the leaving group by the nucleophilic unit. A representative leaving group that is effective in this process is trifluoroethoxide (–OCH$_2$CF$_3$). Representative nucleophiles for this process include alkali metal salts of alkyl mercaptans, alkali metal salts of aryl mercaptans, ammonia, primary and secondary alkylamines, primary and secondary arylamines, secondary arylalkylamines, and alkali metal salts of hydroxides. These nucleophiles result in the displacement of the leaving group (X and/or Z) in compound V to produce compound XI containing X$^1$ and/or Z$^1$ represented as alkylthio, arylthio, amino, mono- and disubstituted alkylamino, mono- and disubstituted arylamino, arylalkylamino or hydroxyl respectively. Suitable solvents for this transformation include polar aprotic solvents (i.c., DMSO, DMF), alcohols and water. Suitable reaction temperatures range from 0° C. to 100° C. although the temperature of the reaction is usually not critical. Reaction temperatures of 20° C. to 30° C. are most frequently employed.

SCHEME VII.

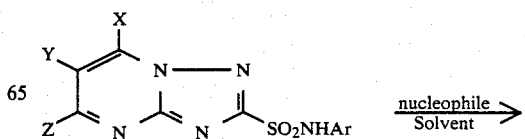

-continued
SCHEME VII.

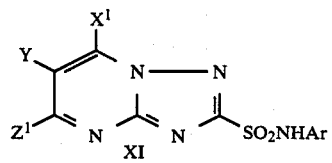

In addition certain compounds of the present invention containg a halogen in the 6-position on the 1,2,4-triazolo[1,5-a]pyrimidine ring system may be prepared by halogenation of the corresponding 6-unsubstituted compound. This is illustrated in Scheme VIII. In general N-halo-succinimide derivatives are the halogenating agents of choice. Reactions are often performed in acid solvents at temperatures ranging from room temperature to 150° C.

SCHEME VIII

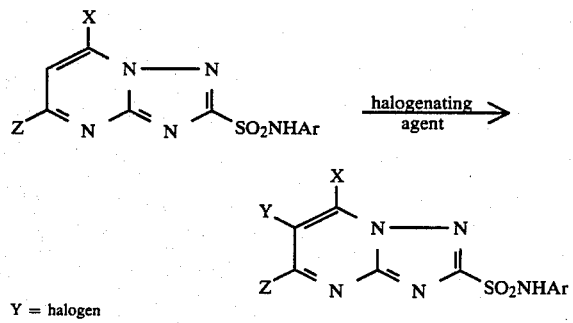

Y = halogen

Another method to prepare the compounds of the present invention is illustrated in Scheme IX. Compounds of general structure I can be oxidized to yield compounds of structure XII. Oxidizing agents capable of this transformation include various transition metal oxidants such as derivatives of hexavalent chromium ($Cr^{VI}$) or heptavalent manganese ($Mn^{VII}$), organic peracids or peroxides. Oxidizing agents such as potassium permanganate, chromium trioxide, peracetic acid and hydrogen peroxide are frequently employed. Preferred conditions for the conversion of I to XII involve reaction of I with two to five molar equivalents of potassium permanganate in 0.1N to 1.0N aqueous alkali metal hydroxide (i.e., NaOH or KOH) as a solvent. The reaction may be run at temperatures ranging from ambient temperature to reflux. Most commonly the reaction is run at 50° C. to 60° C. The product of this reaction (XII) can be hydrolyzed to compound XIII by treatment with aqueous acid in an organic co-solvent. Typical acids include hydrochloric acid, sulfuric acid, acetic acid, trifluoroacetic acid or methane sulfonic acid. Appropriate organic co-solvents include acetone, methyl ethyl ketone, ethanol, acetonitrile or tetrahydrofuran. Lastly, compound XIII can be reconverted to a compound of general structure I by cyclization with a 1,3-dicarbonyl compound or an equivalent of a 1,3-dicarbonyl compound. The conditions for this cyclization, the structural requirements for the 1,3 dicarbonyl compound or an equivalent and structural considerations for the product are as described previously for the conversion of VII and V and VIII to VI.

SCHEME IX

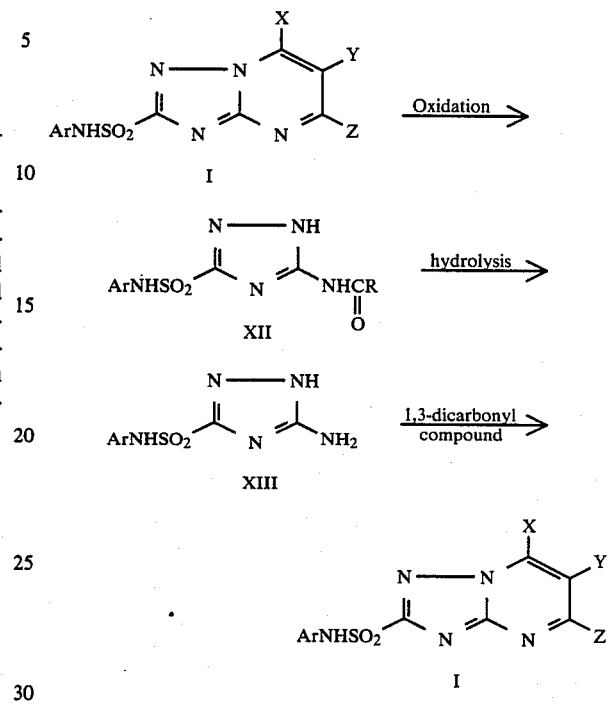

The method for the preparation of compounds of structure I as illustrated in Scheme IX is employed advantageously in certain situations. Various functional groups present on the 1,2,4-triazolo-[1,5-a]pyrimidine ring system (X, Y and Z) of I which impart useful herbicidal, nitrification inhibitory or plant growth regulatory activity can only be produced in low yield by previously described routes. The primary cause for the low yield in the previously described routes is the incompatability of the function group or the ring system which bears the functional group to the conditions required to form the required sulfonyl chlorides IV. Examples of substituents (X, Y and Z) present in compounds of structure I which are advantageously prepared by the method outlined in Scheme IX include H, halo (F, Cl, Br and I), hydroxy, $C_1$-$C_4$ alkyl, $C_1$-$C_4$ alkoxy, $C_1$-$C_4$ alkylthio, $C_1$-$C_4$ alkysulfinyl, $C_1$-$C_4$ alkylsulfonyl, $C_1$-$C_4$ mono- or polyhaloalkyl, $C_1$-$C_4$ mono- or polyhaloakoxy, $C_1$-$C_4$ mono- or polyhaloalkylthio, $C_1$-$C_4$ mono- or polyhaloalkylsulfinyl, $C_1$-$C_4$ mono- or polyhaloalkylsulfonyl, amino, $C_1$-$C_4$ mono- or dialkylamino, phenyl, substituted phenyl, phenoxy, substituted phenoxy, thiophenyl, phenylsulfinyl, phenylsulfonyl, substituted thiophenyl, substituted phenylsulfinyl, substituted phenylsulfonyl, carboxyl, and carboxyl derivatives such as esters derived from $C_1$-$C_4$ alcohols. The substituents X and Y or Y and Z can also be joined to form a ring containing a total of five to seven atoms. This ring may contain heteroatoms (i.e., nitrogen, oxygen or sulfur), unsaturation (i.e., —CO— or —C=C—) or a halogen substituent.

The compounds of structure I which are most advantageously prepared by the method outlined in Scheme IX contain substituents (X, Y and Z) which are one or more of the following: H, halo (F, Cl, Br and I), $C_1$-$C_4$ alkyl, $C_1$-$C_4$ alkoxy, $C_1$-$C_4$ alkylthio, $C_1$-$C_4$ alkylsulfinyl, $C_1$-$C_4$ alkylsulfonyl, $C_1$-$C_4$ mono- or polyhaloalkyl, $C_1$-$C_4$ mono- or polyhaloalkoxy, $C_1$-$C_4$ mono- or polyhaloalkylthio, $C_1$-$C_4$ mono- or polyhaloalkylsulfinyl, $C_1$-$C_4$ mono- or polyhaloalkylsulfonyl, amino and $C_1$-$C_4$ mono- or dialkylamino.

Specifically preferred substituent patterns of structure I which may be prepared by the method outlined in Scheme IX are the following:

1. X=Y=Z=H
2. X=$CF_3$, Y=H and Z=$CH_3$
3. X=Z=$CF_3$ and Y=H
4. X=Cl, Y=H and Z=$CH_3$
5. X=$OCH_3$, Y=H and Z=$CH_3$
6. X=$OCH_2CF_3$, Y=H and Z=$CH_3$
7. X=$SCH_3$, Y=H and Z=$CH_3$
8. X=$N(CH_3)_2$, Y=H and Z=$CH_3$ The starting material of structure I in the reaction sequence of Scheme IX may contain one or more of the following substituents: H, halo (F, Cl, Br and I) and $C_1$-$C_4$ alkyl. The intermediates (XII and XIII) are new compounds. The aromatic ring in the starting material I and intermediates XII and XIII is as described previously for structure I. The R group in intermediates XII may be H or $CH_3$.

Compounds of the present invention represented by structure II are derived from compounds represented by structure I as illustrated in Scheme X. The derivatization procedure involves treatment of compound I with a base in a suitable solvent followed by the introduction of an appropriate electrophilic derivatizing reagent. From this process compounds of general structure II can be isolated in good yields. Suitable bases include tertiary alkylamines (i.e., triethylamine), pyridine, 4-dimethylaminopyridine, alkali metal carbonate (i.e, $Na_2CO_3$ or $K_2CO_3$) and alkali metal alkoxides (i.e, sodium ethoxide or potassium t-butoxide). Suitable solvents include ethers (i.e., tetrahydrofuran), pyridine, acetone, acetonitrile, alcohols (i.e., methanol, ethanol, isopropanol and t-butanol) and polar aprotic solvents (i.e., DMSO and DMF). Suitable electrophilic reagents include alkyl halides, arylalkyl halides (i.e., benzyl chloride), carboxylic acid chlorides, alkyl chloro formates, aryl chloro formates, N,N-dialkyl carbamoyl chlorides, alkyl sulfonyl chlorides, aryl sulfonyl chlorides, alkyl chloro thioformates

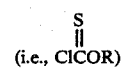

and aryl chlorothioformates

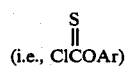

SCHEME X

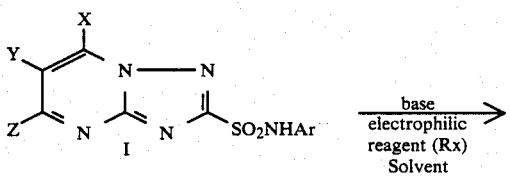

-continued
SCHEME X

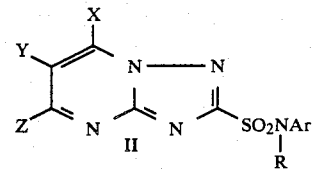

Compounds of the present invention represented by structure III are also derived from compounds represented by structure I as illustrated in Scheme XI. The general process involves the reduction of compounds of general structure I with an appropriate reducing agent in a suitable solvent to yield compounds of general structure III. Reducing agents which are effective include metal hydrides (i.e., sodium borohydride) in the presence of acids (i.e., methane sulfonic acid) and hydrogen in the presence of a normal hydrogenation catalyst (i.e., palladium on carbon). For reductions with metal hydrides polar aprotic solvents (i.e., DMSO) are most frequently used. For reductions using hydrogen and a catalyst alcohols (i.e, ethanol) are most frequently employed as solvents.

SCHEME XI

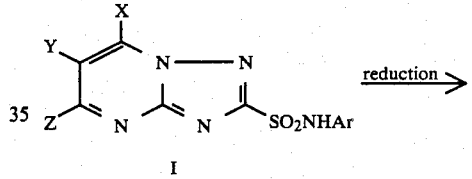

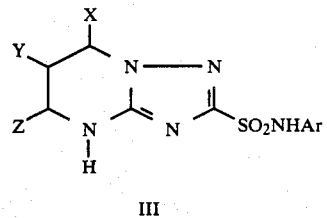

The majority of the amino compounds ($ArNH_2$) utilized to prepare the compounds of the present invention (see structure I) as illustrated in Scheme I were obtained from commercial sources or prepared by known literature procedures or minor modifications of literature procedures.

A number of the amino compounds ($ArNH_2$) used to prepare the compounds of the present invention are derivatives of anthranilic acid. Many of these compounds can be prepared according to conventional methods described by S. J. Holt et al., Royal Soc. Proc. Sec. B, 148, 481 (1958), P. W. Sadler et al., J. Am. Chem. Soc., 78, 1251 (1956), and G. Reissenweber et al., U.S. Pat. No. 4,310,677 (1982). Other anthranilic acid derivatives can be prepared by standard derivatizations (i.e., conversion to esters and amides) of known substituted or unsubstituted 2-nitrobenzoic acids followed by reduction of the nitro group as represented in Scheme XII.

SCHEME XII

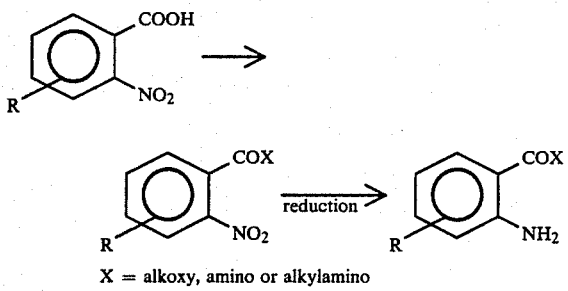

X = alkoxy, amino or alkylamino

A number of the amino compounds are prepared by reduction of anthranilic acids or esters and subsequent derivatization of the reduction product. This is outlined in Scheme XIII. The carbinol reduction products may be derivatized by reaction with base and various electrophiles (i.e., alkyl halides and carboxylic acid chlorides).

SCHEME XIII

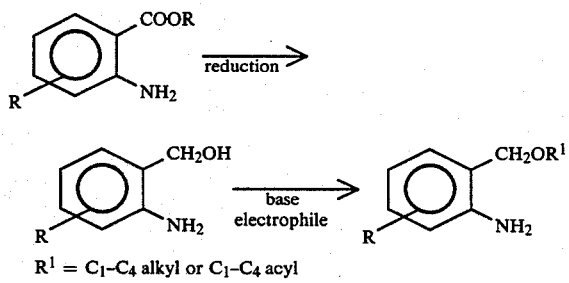

$R^1$ = $C_1$-$C_4$ alkyl or $C_1$-$C_4$ acyl

A large number of the amino compounds utilized in the preparation of the compounds of this invention contain halogen substituents ortho to the amino group. Many of these compounds were prepared by halogenation of the corresponding material bearing no substituent in the ortho position according to a general procedure described by R. S. Neale et al., *J. Org. Chem.*, 29, 3390 (1964). The starting materials for these halogenations were commercially available or known in the literature (i.e., British Patent No. 695,164 (1953); D. S. Noyce et al., *J. Org. Chem.* 26, 1732 (1961) and U.S. Pat. No. 3,813,234 (1974)). In certain instances to facilitate the transformation and insure ortho selectivity in the halogenation process the starting materials for the halogenation were acetamide derivatives (ArNHCOCH$_3$) or derivatives containing groups (i.e., Br) which would block halogenation at other positions in the molecule (i.e., para to the amino group). Following halogenation the acetamide derivatives were hydrolized back to the desired amino compound and the blocking groups were removed (i.e., Br in the para position was selectively removed by reduction in the presence of —Cl in the ortho position). Other chlorine and bromine substituted amino compounds were prepared by known procedures (i.e., U.S. Pat. No. 4,188,342 (1980); C. R. Rasmussen et al. *J. Med. Chem.*, 21, 1044 (1978); H. E. Dadswell et al. *J. Chem. Soc.*, 1102 (1927); U.S. Pat. No. 3,813,234 (1974) and P. B. D. DeLaMare and J. H. Ridd, "Aromatic Substitution, Nitration and Halogenation", Academic Press, New York (1959), P. 106.

A number of the amino compounds used as starting materials for the compounds of this invention contain sulfur substituents in the ortho position. These were prepared using known procedures (i.e., R. R. Gupta et al *Heterocycles*, 16, 1527 (1981) and J. P. Chupp et. al., *J. Org. Chem.*, 49, 4711 (1984)). In some cases alkylthio groups were present and these were synthesized by alkylation of the corresponding mercaptan. Compounds having alkyl or aryl sulfinyl or sulfonyl groups were synthesized by oxidation of the appropriate alkyl or arylthio groups.

Some starting amino compounds containing amino, alkylamino, aryloxy or pyridyloxy groups were prepared by catalytic reduction of the corresponding nitro compounds. The amino, alkylamino, aryloxy or pyridyloxy group were usually introduced via displacement of a leaving group ortho to the nitro group in the requisite nitrobenzene.

Other starting amino compounds were prepared by procedures involving metalation of the aromatic ring of N-substituted derivatives (i.e., t-butoxycarbonyl derivatives) of an aromatic amino compound followed by the resulting organometallic reagent with an electrophile. This general procedure is described in H. Gschwend, *Org. Reactions*, Vol. 20, 1–360 (1979) and is outlined in Scheme XIV. Suitable metalating agents are organolithium reagents (i.e., n-butyllithium or t-butyllithium). Typical electrophiles include alkyl halides (i.e., methyl iodide, ethyl iodide), aldehydes (i.e., formaldehyde, acetaldehyde), ketones (i.e., acetone), alkyl or aryl sulfonyl halides (i.e., methyl sulfenyl chloride), and dialkyl or diaryldisulfides (i.e., dimethyldisulfide). These electrophiles are useful for the introduction of alkyl, hydroxy alkyl and arylthio or arylthio groups to the position ortho to the amino group. After the reaction of the organometallic intermediate with the electrophile the nitrogen substituent is removed by hydrolysis.

SCHEME XIV

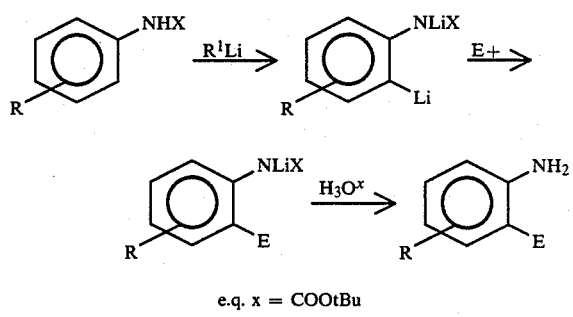

e.q. x = COOtBu

Other aromatic amino compounds used to prepare compounds of the present invention are prepared by conversion of carboxylic acid groups or derivatives of carboxylic acid groups to amino groups by standard methodology. Such a transformation is illustrated in Scheme XV and described in *J. Royal Netherlands Chem. Soc.*, 97, 53 (1978)

Scheme XV

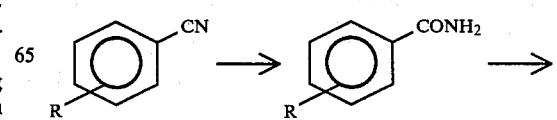

-continued
Scheme XV

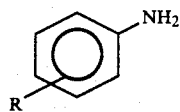

Other amino compounds such as those which are heteroaromatic amino compounds are prepared by known procedures such as those described in *Rec. Trav. Chim.*, 69, 673 (1950), T. Talik et al., *Chem. Abstracts*, 59: 869a (1963) and L. C. Behr and R. Fusco in "*Heterocyclic Compounds*", A. Weissberger, Ed. Vol 22, Interscience Publishers, New York (1967), p 3–174 or straightforward modification of the art described above.

Other amino compounds used to prepare compounds of the present invention are prepared by direct metalation of the aromatic ring. This is illustrated schematically in Scheme XVI. An aromatic ring bearing one to three substituents on the ring may be metalated with an alkyl lithium reagent (i.e. n-butyl lithium, s-butyl lithium or t-butyl lithium) to form an aryl lithium intermediate. This reaction is most frequently carried out in an etherial solvent (i.e. diethyl ether, tetrahydrofuran or 1,2-dimethoxyethane) at temperature ranging from $-78°$ C. to ambient temperature. It is sometimes advantageous to perform the metalation reaction in the presence of additives such as tetramethylethylenediamine. The aryl lithium reagent is generated in situ and is reacted with carbon dioxide followed by protonation of the resultant carboxylate to form the carboxylic acid. The carboxylic acid can then be converted to the corresponding amino compound by standard methodology of the Hoffman, Curtius, Lossen and Schmidt reactions.

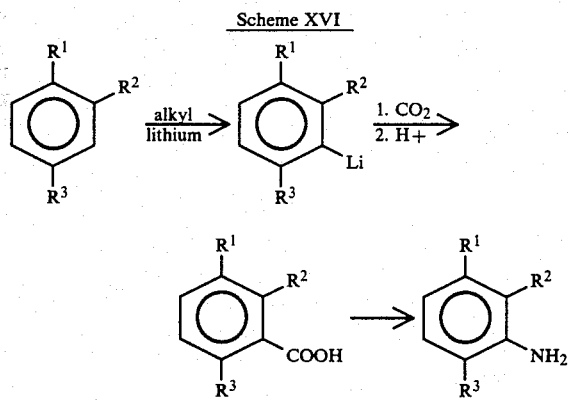

Scheme XVI

The substituents ($R^1$, $R^2$, and $R^3$), which are operable in the process illustrated in Scheme XVI are as follows: $R^1$, $R^2$, and $R^3$ may be chosen from among H, halogen (F, Cl, Br and I), $C_1$–$C_4$ alkyl, $C_1$–$C_4$ mono- or polyhaloalkyl or $C_1$–$C_4$ alkoxy. Most preferred substituents are $R^1$ is equal to H or $C_1$–$C_4$ alkyl; $R^2$ and $R^3$ are equal to halo (F or Cl), $C_1$–$C_4$ mono- or polyhaloalkyl or $C_1$–$C_4$ alkoxy.

The intermediate carboxylic acid formed as illustrated in Scheme XVI or derivatives of the carboxylic acid (i.e. esters and amides) can be utilized to prepare other amino compounds which are useful in the preparation of compounds I of the present invention. This process is illustrated in Scheme XVII. When the carboxylic acid product contains a leaving group such as a halogen atom (i.e. F, Cl or Br) at an adjacent position, the carboxylic acid may be converted to a suitable derivative and the halogen may then be replaced by displacement with a suitable nucleophile. Nucleophiles which are useful in this case include ammonia, $C_1$–$C_4$ monoalkyl amines, $C_1$–$C_4$ dialkylamines, $C_1$–$C_4$ alkali metal alkoxides, $C_1$–$C_4$ alkali metal mono- or polyhaloxides or $C_1$–$C_4$ alkali metal mercaptides. The use of these nucleophiles serves to replace the halogen substituent with amino, $C_1$–$C_4$ monoalkylamino, $C_1$–$C_4$ dialkylamino, $C_1$–$C_4$ alkoxy, $C_1$–$C_4$ mono- or polyhaloalkoxy or $C_1$–$C_4$ alkylthio respectively. The resultant products of the nucleophilic displacement can be converted to the corresponding amino compound by standard methodology of the Hoffman, Curtius, Lossen and Schmidt reactions.

Scheme XVII

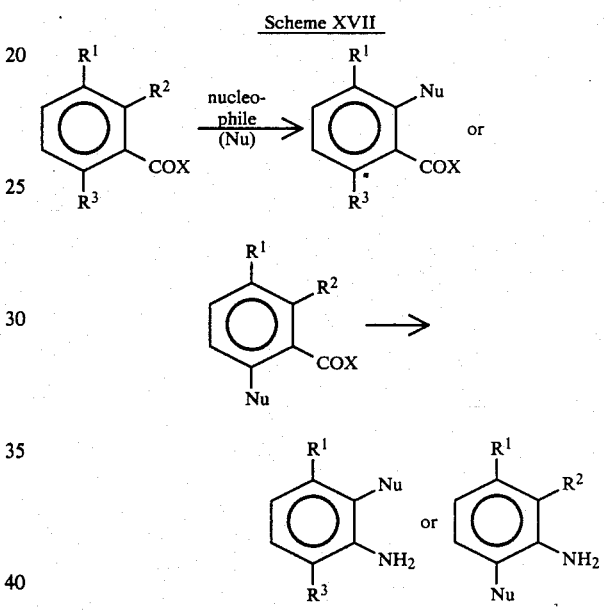

$R^2$ or $R^3$ = halogen
X=OH, $OR^4$ $N(R^4)_2$ where $R^4$=H or $C_1$–$C_4$ alkyl.

Other amino compounds which are sueful in the preparation of compounds I of the present invention can be prepared as illustrated in Scheme XVIII. The starting material for this procedure is 2,6-difluoroaniline. The amino group of the aniline is protected with a silyl protecting group according to a general procedure described by Magnus et. al in *Tetrahedron Lett.*, 1787 (1981) ad Guggenheim et. al. in *Tetrahedron Lett.*, 1253 (1984). The protected aniline can then be metalated with an alkyl lithium reagent (i.e. n-butyl lithium, s-butyl lithium or t-butyl lithium) to form the corresponding aryl lithium reagent. The metalation is best carried out in etherial solvents such as diethyl ether, tetrahydrofuran or dimethoxyethane at temperatures ranging from $-78°$ C. to ambient temperature. It is sometimes advantageous to carry out the metalation in the presence of additives such tetramethylethylenediamine. The aryl lithium reagent is formed in situ and can be reacted with a variety of electrophilic reagents such as $C_1$–$C_4$ alkyl halides, $C_1$–$C_4$ dialkyldisulfides or $C_1$–$C_4$ alkyl sulfenyl halides, dimethylformamide, $C_1$–$C_4$ acyl halides or $C_1$–$C_4$ N-methyl-O-methyl alkylhydroxamates, $C_1$–$C_4$ alkyl chloroformates and carbon dioxide. These electrophilic reagents serve to introduce $C_1$–$C_4$ alkyl, $C_1$–$C_4$ alkylthio, formyl, $C_1$–$C_4$ acyl, $C_1$–$C_4$ alkoxycarbonyl and carboxyl groups respectively directly into the 3-position of the aromatic ring. The product from electrophilic substitution can be protected using standard methodology as described in the literature to form the desired amino compound.

Scheme XVIII

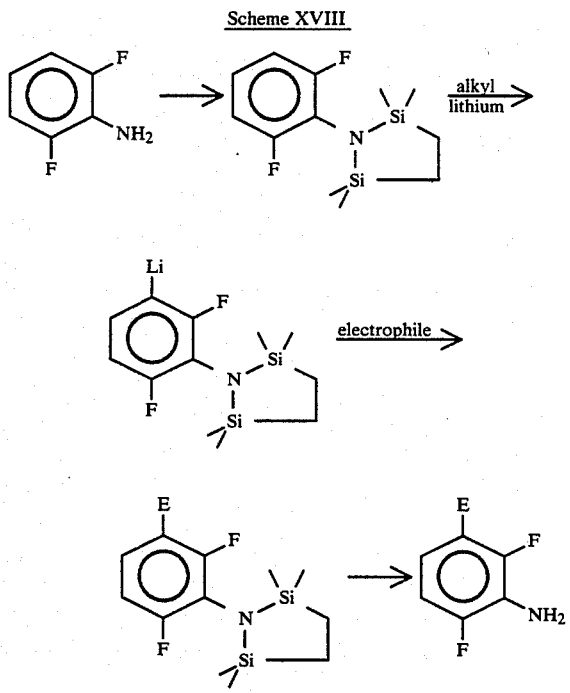

The table which follows contains a listing of aromatic amino compounds prepared by methods described above and not previously described in known art which are useful in the preparation of the biologically active compounds of this invention.

| Compound | $R^1$ | $R^2$ | $R^3$ | $R^4$ | $R^5$ |
|---|---|---|---|---|---|
| A | Cl | COOCH$_3$ | H | H | Cl |
| B | Br | COOCH$_3$ | H | H | CH$_3$ |
| C | CH$_3$ | Cl | H | H | COOCH$_3$ |
| D | Cl | CF$_3$ | H | H | Cl |
| E | Cl | Cl | Br | H | CH$_3$ |
| F | Cl | Cl | H | H | CH$_3$ |
| G | Cl | H | H | H | CH$_2$COH$_3$ |
| H | Cl | H | H | H | CH$_2$OAC |
| I | Cl | H | H | H | CH$_2$OCH$_2$Ph |
| J | 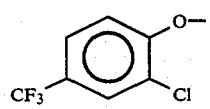 | H | H | H | H |

-continued

| Compound | $R^1$ | $R^2$ | $R^3$ | $R^4$ | $R^5$ |
|---|---|---|---|---|---|
| K | 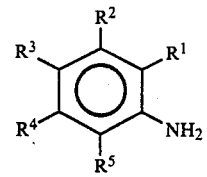 | H | H | H | H |
| L | (same group, CF$_3$/Cl phenoxy) | H | H | H | F |
| M | F | H | H | H | SCH$_3$ |
| N | CF$_3$ | H | H | H | OCH$_3$ |
| O | CF$_3$ | H | H | H | N(CH$_3$)$_2$ |

Using the routes illustrated above or minor variations based on the principles illustrated above the novel compounds of this invention can be prepared.

The invention is further illustrated by the following examples.

EXAMPLE 1

Preparation of 5,7-dimethyl-2-mercapto-1,2,4-triazolo[1,5-a]pyrimidine

A solution of 10.1 g (0.0870 mol) of 3-amino-5-mercapto-1,2,4 triazole, 8.71 g (0.0870 mol) of 2,4-pentandione and 0.8 ml of piperidine in 300 ml of HOAc was heated at reflux for 21.5 hours. After cooling to room temperature, the solid which separated was collected by filtration and dried in vacuo to yield 13.4 g of pale yellow needles, m.p. 245°–246° C. (decomposition); $^1$H NMR (DMSO-d$_6$—CDCl$_3$) $\delta$13.9 (1H, broad, SH), 7.19 (1H, broad s, H in 6-position) 2.63 and 2.51 (3H each, s, CH$_3$ groups in 5- and 7-positions), IR (KBr) ~2680, 1628, 1560, 1400 and 1170 cm$^{-1}$. An analytical sample was prepared by recrystallization from acetic acid to yield colorless plates, m.p. 243.5°–244.5° C. (decomposition).

Analysis: Calculated for C$_7$H$_8$N$_4$S: C, 46.65; H, 4.47; N, 31.09; Found: C, 46.34; H, 4.41; N, 30.82.

EXAMPLE 2

Preparation of 2-benzylthio-5,7-dimethyl-1,2,4-triazolo[1,5-a]pyrimidine

Twenty percent NaOH (14.0 g, 70 mmol) was added dropwise to a suspension of 11.5 g (64.0 mmol) of the mercaptan prepared in Example 4 in 125 ml of H$_2$O over about 5 minutes. Benzyl chloride (7.4 ml, 8.1 g, 64 mmol) in 20 ml of CH$_3$OH was added and the resulting mixture was vigorously stirred at room temperature for 24 hours. The solid which began separating shortly after the addition of benzyl chloride was collected by filtration and dried in vacuo to afford 16.1 g of white solid, m.p. 134°–135° C. (lit m.p. 132°–134° C., T. Novinson et al, *J. Med. Chem.*, 25, 420 (1982)): $^1$H NMR (CDCl$_3$) δ7.1–7.6 (5H, m. Ph), 6.63 (1H, s, H in 6-position), 4.50 (2H, s, —CH$_2$S—), 2.67 and 2.58 (3H each, s, CH$_3$ groups in 5- and 7-positions); IR (CHCl$_3$) 1620, 1447, 1339 and 1295 cm$^{-1}$. 93% yield.

Analysis: Calculated for C$_{14}$H$_{14}$N$_4$S: C, 62.20; H, 5.22; N, 20.72; Found: C, 62.21; H, 5.14; N, 20.89.

EXAMPLE 3

Preparation of
2-benzylthio-6,7-cyclopentano-5-methyl-1,2,4-triazolo[1,5-a]pyrimidine A solution of 51.6 g (0.250 mol) of 3-amino-5-benzylthio-1,2,4-triazole and 31.5 g (0.250 mol) of 2-acetylcyclopentanone in 600 ml of HOAC was heated at reflux for 9.5 hours. The solvent was removed by evaporation, and the brown solid residue was recrystallized from EtOH to yield a light brown solid. A second recrystallization from EtOH gave 45.4 g (61 percent) of the desired product as a light brown solid, m.p. 157°–158.5° C.: $^1$H NMR (CDCl$_3$) δ7.0–7.6 (5H, m), 4.51 (2H, s), 3.29 (2H, t), 2.97 (2H, t), 2.0–2.7 (5H, m including s at 2.52); IR (CHCl$_3$) 1621, 1343 and 1290 cm$^{-1}$.

Analysis: Calculated for C$_{16}$H$_{16}$N$_4$S: C, 64.84; H, 5.44, N, 18.90; S, 10.82. Found: C, 64.88; H, 5.47; N, 18.98; S, 10.72.

EXAMPLE 4

Preparation of
2-benzylthio-5,6,7-trimethyl-1,2,4-triazolo[1,5-a]pyrimidine

A solution of 51.6 g (0.250 mol) of 3-amino-5-benzylthio-1,2,4-triazole and 28.5 g (0.250 mol) of 3-methyl-2,4-pentanedione in 350 ml of glacial acetic acid was heated at reflux for 17 hours. Upon cooling to room temperature, the reaction mixture was poured onto ice. The pale yellow solid which separated was collected by filtration, washed with water and dried in vacuo to yield 67.1 g (94%) of the desired product as a pale yellow solid, m.p. 133.5°–135° C. The IR and $^1$H NMR spectra were consistent with the assigned structure.

Analysis: Calculated for C$_{15}$H$_{15}$N$_4$S: C, 63.35; H, 5.67; N, 19.70; S, 11.27; Found: C, 63.07; H, 5.48; N, 19.71; S, 11.09.

EXAMPLE 5

Preparation of
2-benzylthio-6-chloro-1,2,4-triazolo[1,5-a]pyrimidine

A solution of 6.52 g (31.6 mmol) of 3-amino-5-benzylthio-1,2,4-triazole and 9.09 g (31.6 mmol) of 1,3-bis(-dimethylamino)-2-chlorotrimethinium perchlorate in 100 ml of glacial acetic acid was heated at reflux for 19 hours. After cooling to room temperature, the solution was poured into 300 ml of water. The solid which separated was collected by filtration, washed with water and dried in vacuo to yield 4.12 g (48%) fo the desired product as a brown solid, m.p. 119.5°–135° C. (decomposition). IR and $^1$H NMR spectra were consistent with the assigned structure.

Analysis: Calculated for C$_{12}$H$_9$ClN$_4$S: C, 51.90; H, 3.20; N, 20.24; Found: C, 51.87; H, 3.42; N, 19.81.

EXAMPLE 6

Preparation of
2-benzylthio-1,2,4-triazolo[1,5-a]pyrimidine

A solution of 2.0 g (9.6 mmol) of 3-amino-5-benzylthio-1,2,4-triazole and 2.3 ml (9.6 mmol) of malonaldehyde bis(diethylacetal) in 20 ml of glacial acetic acid was heated at reflux for 17 hours. After cooling to room temperature, the solvent was removed by evaporation at reduced pressure. The brown solid residue was recrystallized from isopropyl alcohol to afford 0.4 g (17%) of the desired product as a light brown crystalline solid, m.p. 104°–106° C. IR and $^1$H NMR spectra were consistent with the assigned structure.

Analysis: Calculated for C$_{10}$H$_{12}$N$_4$S: C, 59.52; H, 4.13; N, 23.13. Found: C, 59.19; H, 4.09; N, 22.73.

EXAMPLE 7

Preparation of
2-benzylthio-5-methyl-1,2,4-triazolo[1,5-a]pyrimidine

A solution of sodium ethoxide in EtOH was prepared by dissolving 0.54 g (24 mg-atoms) of sodium metal in 120 ml of anhydrous EtOH, and 10.0 g (48 mmol) of 3-amino-5-benzylthio-1,2,4-triazole was added. After stirring for 15 minutes at room temperature, 6.4 ml (6.35 g, 48.4 mmol) of acetylacetaldehyde dimethyl acetal dissolved in 100 ml of absolute EtOH was added dropwise. After the addition was complete the reaction mixture was stirred at room temperature for 68 hours. The product which separated from solution was collected by filtration and dried to give 10.1 g (83%) of tan solid, m.p. 128.5°–130° C. IR and $^1$H NMR spectra were in agreement with the assigned structure.

Analysis: Calculated for C$_{13}$H$_{12}$N$_4$S: C, 60.94; H, 4.68; N, 21.86. Found: C, 60.69; H, 4.61; N, 21.85.

EXAMPLE 8

Preparation of
2-benzylthio-5-hydroxy-7-methyl-1,2,4-triazolo[1,5-a]pyrimidine

Ethyl 2,3-dibromobutyrate (1.33 g, 48.5 mmol) was added dropwise over 15 minutes to a solution of 10 g (49 mmol) of 3-amino-5 -benzylthio-1,2,4-triazole in 20 ml of pyridine heated to 65° C. After the addition was complete, the reaction mixture was heated at 65° C. for 20 hours, cooled to room temperature and filtered. The filtrate was concentrated by evaporation at reduced pressure. The residue was triturated with methanol to separate 1.64 g (13%) of the desired product as a colorless crystalline solid, m.p. 219°–220° C. IR and $^1$H NMR spectra were in agreement with the assigned structure.

Analysis: Calculated for C$_{13}$H$_{12}$N$_4$OS: C, 57.37; H, 4.41; N, 20.60; Found: C, 56.86; H, 4.41; N, 20.72.

EXAMPLE 9

Preparation of
2-benzylthio-5-methoxy-7-methyl-1,2,4-triazolo[1,5-a]pyrimidine

A solution of 2.67 g (9.80 mmol) of 2-benzylthio-5-hydroxy-7-methyl-1,2,4-triazolo[1,5-a]pyrimidine in 50 ml of phosphorous oxychloride was heated at reflux for 3 hours. The excess phosphorous oxychloride was removed by evaporation at reduced pressure. The residue was partitioned between CH$_2$Cl$_2$ and cold water. The organic phase was separated, dried (MgSO$_4$) and concentrated by evaporation at reduced pressure. The resulting solid was added to 50 ml (0.22 mol) of a 25 weight percent solution of sodium methoxide in methanol. The resulting suspension was stirred at room temperature for 30 minutes, diluted with 50 ml of water and filtered. The solid collected was dried in vacuo to yield 1.41 g (41%) of the desired product as a light brown solid, m.p. 112.5°-115° C. IR and ¹H NMR spectra were consistent with the assigned structure.

EXAMPLE 10

Preparation of 2-benzylthio-7-methyl-1,2,4-triazolo[1,5-a]pyrimidine

A solution of 50 g (0.24 mol) of 3-amino-5-benzylthio-1,2,4-triazole in 500 ml of glacial acetic acid was added dropwise over 3-4 hours to a solution of 34.0 g (0.25 mol) of acetylacetaldehyde dimethyl acetal in 500 ml of glacial acetic acid heated at 100° C. After the addition was complete the reaction mixture was heated at reflux overnight, cooled to room temperature and poured into an ice-water mixture. The solid which separated was collected by filtration and recrystallized from ethanol to yield 27 g (41%) of the desired product as a solid, m.p. 102°-104° C. IR and ¹H NMR spectra were in agreement with the assigned structure.

Analysis: Calculated for $C_{13}H_{12}N_4S$: C, 60.94; H, 4.68; N, 21.85; Found: C, 60.81; H, 4.68; N, 21.74.

EXAMPLE 11

Preparation of 2-benzylthio-6-methyl-1,2,4-triazolo[1,5-a]pyrimidine

A suspension of 14.4 g (0.124 mol) of 3-amino-5-benzyl-1,2,4-triazole and 30.0 g (0.124 mol) of 1,3-bis(dimethylamino)-2-methyltrimethinium perchlorate in 500 ml of glacial acetic acid was heated at reflux for 63 hours. The reaction mixture was subjected to the work-up described in Example 5 to yield 13.9 g (68%) of the desired product as a brown solid, m.p. 254°-256° C. IR and ¹H NMR spectra were in agreement with the assigned structure.

Analysis: Calculated for $C_6H_6N_4S$: C, 43.35; H, 3.61; N, 33.72; Found: C, 42.71; H, 3.49; N, 33.26.

EXAMPLE 12

Preparation of 2-benzylthio-6-chloro-5,7-dimethyl-1,2,4-triazolo[1,5-a]pyrimidine To a suspension of 153 g (0.74 mol) 3-amino-5-benzylthio-1,2,4-triazole in 250 ml of glacial acetic acid was added to 100 g (0.74 mol) of 3-chloro-2,4-pentanedione in a dropwise manner. The reaction mixture was heated at reflux for 18 hours and cooled to room temperature. The reaction mixture was poured over ice and the oil which separated solidified upon stirring. The solid was collected by filtration and recrystallized from methanol to yield 116 g (79%) of the desired product as an off white solid, m.p. 164°-166° C. IR and ¹H NMR spectra were in agreement with the assigned structure.

Analysis: Calculated for $C_{14}H_{13}ClN_4S$: C, 55.16; H, 4.30; N, 18.38; Found: C, 55.11; H, 4.30; N, 18.34.

EXAMPLE 13

Preparation of 2-benzylthio-6-ethoxy-1,2,4-triazolo[1,5-a]pyrimidine

This material was prepared in 28% yield from 3-amino-5-benzylthio-1,2,4-triazole and 1,3-bis(dimethylamino)-2-ethoxytrimethinium perchlorate following the general procedure described in Example 5. The desired product was isolated as a solid, m.p. 139°-140° C. IR and ¹H NMR spectra were in agreement with the assigned structure.

Analysis: Calculated for $C_{14}H_{14}N_4OS$: C, 58.73; H, 4.89; N, 19.57; Found: C, 58.68; H, 4.64; N, 19.58.

EXAMPLE 14

Preparation of 2-benzylthio-5-isopropyl-1,2,4-triazolo[1,5-a]pyrimidine

This material was prepared in 96% yield from 3-amino-5-benzylthio-1,2,4-triazole and 4-methyl-3-oxopentanal following the general procedure described in Example 7. The desired product was isolated as a solid, m.p. 65°-66° C. IR and ¹H NMR were in agreement with the assigned structure.

Analysis: Calculated for $C_{15}H_{16}N_4S$: C, 63.36; H, 5.63; N, 19.71; Found: C, 63.00; H, 5.62; N, 19.62.

EXAMPLE 15

Preparation of 2-benzylthio-5,6-dimethyl-1,2,4-triazolo[1,5-a]pyrimidine

A solution of 5.0 g (24 mmol) of 3-amino-5-benzylthio-1,2,4-triazole and 5.0 g (41 mmol) of the sodium salt of 2-methyl-3-oxobutanal in 200 ml of glacial acetic acid was heated at reflux overnight. The solution was cooled to room temperature and the reaction mixture was concentrated by evaporation at reduced pressure. The residue was combined with ice and $H_2O$ to separate a tan solid. The solid was collected by filtration, dried and carefully recrystallized from ethyl acetate to yield 3.53 g (54%) of the desired product as a crystalline solid, m.p. 147°-149° C. IR and ¹H NMR spectra were in agreement with the assigned structure.

Analysis: Calculated for $C_{14}H_{14}N_4S$: C, 62.10; H, 5.18; N, 20.72; Found: C, 61.58; H, 5.18; N, 20.45.

EXAMPLE 16

Preparation of 2-benzylthio-6-chloro-7-hydroxy-5-methyl-1,2,4-triazolo[1,5-a]pyrimidine A solution of 16 g (77 mmol) of 3-amino-5-benzylthio-1,2,4-triazole and 10.6 g (77 mmol) of ethyl 2-chloroacetoacetate in 150 ml of glacial acetic acid was heated at 100° C. for 17 hours. Upon cooling to room temperature the solid which separated was collected by filtration. The filtrate was diluted with ice water to separate an additional quantity of solid. The solids were combined and dried to yield 14.0 g (60%) of the desired product as a solid, m.p. 258°-260° C. IR and ¹H NMR were in agreement with the assigned structure.

Analysis: Calculated for $C_{13}H_{11}ClN_4OS$: C, 50.89; H, 3.58; N, 18.27; Found: C, 50.51; H, 3.36; N, 18.67.

EXAMPLE 17

Preparation of 2-benzylthio-6,7-dichloro-5-methyl-1,2,4-triazolo[1,5-a]pyrimidine This material was prepared in 68% yield from 2-benzylthio-6-chloro-7-hydroxy-5-methyl-1,2,4-triazolo[1,5-a]pyrimidine and phosphorus oxychloride following the general procedure described in Example 20. The desired product was isolated as a solid, m.p. 103°-105° C. IR and ¹H NMR spectra were in agreement with the assigned structure.

Analysis: Calculated for $C_{13}H_{10}Cl_2N_4S$: C, 48.00; H, 3.07; N, 17.23; Found: C, 47.40; H, 3.00; N, 17.43.

EXAMPLE 18

Preparation of
2-benzylthio-6-chloro-5-methyl-1,2,4-triazolo[1,5-a]pyrimidine

This material was prepared by reduction of 2-benzylthio-6,7-dichloro-5-methyl-1,2,4-triazolo[1,5-a]pyrimidine with zinc-copper couple following the general procedure described in Example 21. The desired product was isolated in 88% yield as a solid, m.p. 160°–161° C. IR and $^1$H NMR spectra were in agreement with the assigned structure.

Analysis: Calculated for $C_{13}H_{11}ClN_4S$: C, 53.56; H, 3.56; N, 19.27; Found: C, 53.30; H, 3.79; N, 19.28.

EXAMPLE 19

Preparation of
2-benzylthio-5,7-dihydroxy-1,2,4-triazolo[1,5-a]pyrimidine

A solution of 125 g (0.58 mol) of a 25% solution of sodium methoxide in methanol dissolved in 100 ml of absolute ethanol was treated with 66.3 ml (0.29 mol) of dimethyl malonate followed by 60.0 g (0.20 mol) of 3-amino-5-benzylthio-1,2,4-triazole. The resulting solution was heated at reflux for 5 days. On cooling to room temperature the solid which had separated was collected by filtration, washed with cold ethanol and dissolved in 1000 ml of water. The resulting yellow solution was acidified with concentrated HCl to precipitate a solid. The solid was collected by filtration and dried to yield 70.1 g (82%) of the desired product as a white solid, m.p. 199°–210° C. (decompostion). IR and $^1$H NMR spectra were in agreement with the assigned structure.

Analysis: Calculated for $C_{12}H_{10}N_4O_2S \cdot H_2O$: C, 49.30; H, 4.14, N. 19.16; Found: C, 48.70; H, 3.89; N. 18.83.

EXAMPLE 20

Preparation of
2-benzylthio-5,7-dichloro-1,2,4-triazolo[1,5-a]pyrimidine

A suspension of 70.0 g (0.24 mol) of 2-benzylthio-5,7-dihydroxyl-1,2,4-triazolo[1,5-a]pyrimidine and 67.0 ml (0.72 mol) of phosphorous oxychloride in 600 ml of acetonitrile was heated at reflux for 3 hours. The resulting orange solution was stirred at room temperature overnight (17 hours). The solution was filtered and the filtrate was concentrated by evaporation at reduced pressure. The residue was partitioned between cold water and methylene chloride, and the organic phase was separated and dried (MgSO$_4$). The organic phase was concentrated to induce crystallization. The desired product was collected by filtration to yield 98.0 g (81%) of solid, m.p. 97°–100° C. IR and $^1$H NMR spectra were in agreement with the assigned structure.

Analysis: Calculated for $C_{12}H_8Cl_2N_4S$: C, 46.32; H, 2.59; N, 18.00; Found: C, 46.43; H, 2.57; N, 18.08.

EXAMPLE 21

Preparation of
2-benzylthio-5-chloro-1,2,4-triazolo[1,5-a]pyrimidine

A zinc-copper couple was prepared following the procedure of Bradley (*J. Org. Chem.* 31, 626 (1966)) by stirring 1.0 g of copper sulfate in 20 ml of water with 15.0 g of zinc dust for 2 hours. The couple was collected by filtration, washed with acetone and dried overnight under vacuum at 100° C. To a solution of 33.0 g (106 mmol) of 2-benzylthio-5,7-dichloro-1,2,4-triazolo[1,5-a]pyrimidine in 12.5 ml (213 mmol) of acetic acid, 50 ml of methanol and 300 ml of tetrahydrofuran was added 20.5 g of Zn—Cu couple. The mixture was stirred overnight at 22°–23° C. When the reaction was complete (TLC analysis) the reaction mixture was filtered through celite and the filtrate was concentrated by evaporation at reduced pressure. The residue was triturated with hexane to separate a solid. The solid was collected by filtration to yield the desired product as 26.5 g (92%) of orange solid, m.p. 125°–127° C. IR and $^1$H NMR spectra were in agreement with the assigned structure.

Analysis: Calculated for $C_{12}H_9ClN_4S$: C, 52.08; H, 3.25; N, 20.25; Found: C, 51.76; H, 3.00; N, 20.27.

EXAMPLE 22

Preparation of
2-benzylthio-5-methoxy-1,2,4-triazolo[1,5-a]pyrimidine

A mixture of 6.0 g (22 mmol) of 2-benzylthio-5-chloro-1,2,4-triazolo[1,5-a]pyrimidine in 25 ml of methanol was treated with 5.0 g (23.8 mmol) of a 25% solution of sodium methoxide in methanol. After stirring for 1.5 hours the reaction mixture was diluted with 100 ml of water and neutralized with 3N HCL (aq). The solid which separated was collected by filtration, washed with water and dried to afford 5.0 g (84%) of the desired product as a white solid, m.p. 126°–128° C. IR and $^1$H NMR spectra were in agreement with the assigned structure.

Analysis: Calculated for $C_{13}H_{12}N_4OS$: C, 57.34; H, 4.41; N, 20.58; Found: C, 57.21; H, 4.42; N, 20.13.

EXAMPLE 23

Preparation of
2-benzylthio-5-(2,2,2-trifluoroethoxy)-1,2,4-triazolo[1,5-]pyrimidine A solution of sodium 2,2,2-trifluoroethoxide in tetrahydrofuran was prepared by the addition of 1.1 g (48 mg-atom) of sodium metal to a solution of 3.5 ml (48 mmol) of 2,2,2-trifluoroethanol in 100 ml of tetrahydrofuran. To this solution was added 7.0 g (25 mmol) of 2-benzylthio-5-chloro-1,2,4-triazolo[1,5-a]pyrimidine, and the reaction mixture was stirred for 30 minutes and concentrated by evaporation at reduced pressure to approximately one quarter of the original volume. Pentane (200 ml) was added to induce crystallization. The solid which separated was collected by filtration to yield 6.42 g (75%) of the desired product as a light yellow wolid, m.p. 114°–118° C. IR and $^1$H NMR spectra were in agreement with the assigned structure.

Analysis: Calculated for $C_{14}H_{11}F_3N_4OS$: C, 49.40; H, 3.23; N, 16.46; Found: C, 49.63; H, 3.09; N, 16.70.

EXAMPLE 24

Preparation of
2-benzylthio-5-ethoxy-1,2,4-triazolo[1,5-a]pyrimidine

This material was prepared by heating 2-benzylthio-5-(2,2,2-trifluoroethoxy)-1,2,4-triazolo[1,5-a]pyrimidine in boiling ethanol. The hot mixture was filtered and the filtrate was concentrated. The crude product was recrystallized from isopropanol to yield the desired product as a solid, m.p. 115°–117° C. IR and $^1$HNMR spectra were in agreement with the assigned structure.

Analysis: Calculated for $C_{14}H_{14}N_4OS$: C, 58.73; H, 4.89; N, 19.31; S, 11.20; Found: C, 57.90; H, 4.69; N, 19.30; S, 10.79.

EXAMPLE 25

Preparation of 2-benzylthio-5,7-dihydroxy-6-methyl-1,2,4-triazolo[1,5-a]pyrimidine This material was prepared in 80% yield from 3-amino-5-benzylthio-1,2,4-triazole and dimethyl 2-methyl malonate following the general procedure described in Example 19. The product was isolated as a solid, m.p. 260°–272° C. (decomposition). IR and $^1H$ NMR spectra were in agreement with the assigned structure.

Analysis: Calculated for $C_{13}H_{12}N_4O_2S$: C, 54.15; H, 4.16; N, 19.44; Found: C, 53.48; H, 4.07; N, 19.53.

EXAMPLE 26

Preparation of 2-benzylthio-5,7-dichloro-6-methyl-1,2,4-triazolo[1,5-a]pyrimidine This material was prepared in 97% yield from the reaction of 2-benzylthio-5,7-dihydroxy-6-methyl-1,2,4-triazolo[1,5-a]pyrimidine and phosphorous oxychloride following the general procedure described in Example 20. The product was isolated as a solid, m.p. 121°–123° C. IR and $^1H$ NMR spectra were in agreement with the assigned structure.

Analysis: Calculated for $C_{13}H_{10}Cl_2N_4S$: C, 48.01; H, 3.08; N, 17.23; Found: C, 47.65; H, 3.11; N, 17.70.

EXAMPLE 27

Preparation of 2-benzylthio-5-chloro-6-methyl-1,2,4-triazolo[1,5-a]pyrimidine This material was prepared in 32% yield by reduction of 2-benzylthio-5,7-dichloro-6-methyl-1,2,4-triazolo[1,5-a]pyrimidine with zinc-copper couple following the general procedure described in Example 21. The desired product was isolated as a solid, m.p. 179°–181° C. IR and $^1H$ NMR spectra were in agreement with the assigned structure.

Analysis: Calculated for $C_{13}H_{11}ClN_4S$: C, 53.70; H, 3.79; N, 19.28; Found: C, 53.33; H, 3.73; N, 19.53.

EXAMPLE 28

Preparation of 2-benzylthio-5-methoxy-6-methyl-1,2,4-triazolo[1,5-a]pyrimidine This material was prepared in 64% yield by reaction of 2-benzylthio-5-chloro-6-methyl-1,2,4-triazolo[1,5-a]pyrimidine with sodium methoxide following the general procedure described in Example 22. The desired product was isolated as a solid, m.p. 145°–146° C. IR and $^1H$ NMR spectra were in agreement with the assigned structure.

Analysis: Calculated for $C_{14}H_{14}N_4OS$: C, 58.73; H, 4.89; N, 19.58; Found: C, 58.34; H, 4.84; N, 19.67.

EXAMPLE 29

Preparation of 2-benzylthio-6-ethoxycarbonyl-7-methyl-1,2,4-triazolo[1,5-a]pyrimidine A solution of 15 g (73 mmol) of 3-amino-5-benzylthio-1,2,4-triazole and 15.0 g (80.0 mmol) of ethyl ethoxymethyleneacetoacetate in 250 ml of glacial acetic acid was heated at reflux for 60 hours. After cooling the volume of the reaction was reduced to approximately one quarter of the oroginal volume by evaporation at reduced pressure. The resulting residue was poured into water, and the solid which separated was collected by filtration, washed with water and dried to yield 7.88 g (33%) of the desired product as a solid, m.p. 98°–99° C. IR and $^1H$ NMR spectra were in agreement with the assigned structure.

Analysis: Calculated for $C_{16}H_{16}N_4O_2S$: C, 58.52; H, 4.87; N, 17.07; Found: C, 58.81; H, 4.89; N. 17.03.

EXAMPLE 30

Preparation of 2-benzylthio-6-(4-nitrophenyl)-1,2,4-triazolo[1,5-a]pyrimidine This material was prepared from 3-amino-5-benzylthio-1,2,4-triazole and 1,3-bis(dimethylamino)-2-(4-nitrophenyl)-trimethinium perchlorate following the general procedure described in Example 5. The desired product was isolated as a solid, m.p. 195°–199° C. IR and $^1H$ NMR spectra were in agreement with the assigned structure.

EXAMPLE 31

Preparation of 2-benzylthio-5,6-cyclopentano-7-hydroxy-1,2,4-triazolo[1,5-a]pyrimidine A solution of 20.6 g (100 mmol) of 3-amino-5-benzylthio-1,2,4-triazole and 15 ml (16 g, 0.10 mol) of 2-carboethoxycyclopentanone in 110 ml of glacial acetic acid was heated at reflux for 23 hours. After cooling to room temperature the solid which separated from the reaction mixture was collected by filtration, washed with acetic acid and dried in vacuo to yield 22.4 g (75%) of the desired product as a colorless crystalline solid, m.p. 241°–243° C. IR and $^1H$ NMR spectra were in agreement with the assigned structure.

Analysis: Calculated for $C_{15}H_{14}N_4OS$: C, 60.38; H, 4.73; N, 18.78; S, 10.75; Found: C, 60.10; H, 4.66; N, 18.91; S, 10.72.

EXAMPLE 32

Preparation of 2-benzylthio-7-chloro-5,6-cyclopentano-1,2,4-triazolo[1,5-a]pyrimidine A solution of 5.97 g (20.0 mmol) of 2-benzylthio-5,6-cyclopentano-7-hydroxy-1,2,4-triazolo[1,5-a]pyrimidine in 250 ml of phosphorus oxychloride was heated at reflux for 50 minutes. After cooling to room temperature the excess phosphorus oxychloride was removed by distillation at aspirator pressure. The residue was partitioned between ice cold water and methylene chloride. The organic phase was dried ($Na_2SO_4$) and evaporated at reduced pressure. The residue was chromatographed on silica gel eluting with EtOAc-hexane (1:1, v/v) to yield 3.72 g (59%) of the desired product as a yellow solid, m.p. 119°–120° C. IR and $^1H$ NMR spectra were in agreement with the assigned structure.

Analysis: Calculated for $C_{15}H_{13}ClN_4S$: C, 56.87; H, 4.14; N, 17.68; Cl, 11.19; S, 10.12; Found: C, 56.91; H, 4.06; N, 17.83; Cl, 10.68; S; 9.65.

EXAMPLE 33

Preparation of
2-benzylthio-5,6-cyclopentano-7-methyl-1,2,4-triazolo[1,5-a]pyrimidine A solution of 2.47 g (7.80 mmol) of 2-benzylthio-7-chloro-5,6-cyclopentano-1,2,4-triazolo[1,5-a]pyrimidine in 40 ml of dry tetrahydrofuran was cooled to 5° C. and 5.9 ml (17 mmol) of 2.9M methyl magnesium bromide in ether was added over 5 minutes. After the addition was complete the reaction mixture was warmed to room temperature and stirred overnight (17 hours). The reaction was quenched by addition of 10 ml of saturated aqueous ammonium chloride. The organic phase was separated, dried ($Na_2SO_4$) and evaporated at reduced pressure. The red oil residue was chromatographed on silica gel (HPLC) eluting with EtOAc-hexane (1:1, v/v) to yield 1.12 g (48%) of the desired product as a pale red solid, m.p. 109°-111° C. IR and $^1$H NMR spectra were in agreement with the assigned structure.

Analysis: Calculated for $C_{16}H_{16}N_4S$: C, 64.84; H, 5.44; N, 18.90; S, 10.82; Found: C, 64.99; H, 5.41; N. 18.16; S, 10.42.

EXAMPLE 34

Preparation of
2-benzylthio-5,7-bis-(trifluoromethyl)-1,2,4-triazolo[1,5-a]pyrimidine A solution of 20.8 g (0.100 mol) of 1,1,1,5,5,5-hexafluoro-2,4-pentanedione and 20.6 g (0.100 mol) of 3-amino-5-benzylthio-1,2,4-triazole in 150 ml of glacial acetic acid was heated at reflux for 14 hours. The solution was cooled to room temperature and poured over ice. The solid which separated was collected by filtration, washed with water and dried in vacuo to yield 35.5 g (94%) of the desired product as a pale yellow solid, m.p. 78.5°-80.5° C. IR, $^1$H NMR and $^{19}$F NMR spectra were in agreement with the assigned structure.

Analysis: Calculated for $C_{14}H_8F_6N_4S$: C, 44.45; H, 2.13; N, 14.81; S, 8.48; Found: C, 44.53; H, 2.15; N, 14.97; S, 8.39.

EXAMPLE 35

Preparation of
2-benzylthio-5-methyl-7-trifluoromethyl-1,2,4-triazolo[1,5-a]pyrimidine This material was prepared in 84% yield from 3-amino-5-benzylthio-1,2,4-triazole and 1,1,1-trifluoro-2,4-pentanedione following the general procedure described in Example 34. The product was purified by recrystallization from benzene-hexane to yield a tan solid, m.p. 83.5°-84.5° C. IR, $^1$H NMR and $^{19}$F NMR spectra were in agreement with the assigned structure.

Analysis: Calculated for $C_{14}H_{11}F_3N_4S$: C, 51.85; H, 3.42; N, 17.27; S, 9.89; Found: C, 51.73; H, 3.44; N, 18.01; S, 10.08.

EXAMPLE 36

Preparation of
2-benzylthio-5,7-diphenyl-1,2,4-triazolo[1,5-a]pyrimidine

A solution of 8.40 g (37.5 mmol) of dibenzoylmethane and 7.73 g (37.5 mmol) of 3-amino-5-benzylthio-1,2,4-triazole in 50 ml of glacial acetic acid was heated at reflux for 24 hours. Upon cooling to room temperature the solid which separated was collected by filtration and dried. The product was chromatographed on silica gel (HPLC) eluting with EtOAc-hexane (3:7, v/v) to afford 5.08 g (34%) of the desired product as a colorless solid, m.p. 122.5°-123.5° C. IR and $^1$H NMR spectra were in agreement with the assigned structure.

Analysis: Calculated for $C_{24}H_{18}N_4S$: C, 73.07; H, 4.60; N, 14.20; S, 8.13; Found: C, 73.48; H, 4.54; N, 14.17; S, 7.97.

EXAMPLE 37

Preparation of
2-benzylthio-5-methyl-7-phenyl-1,2,4-triazolo[1,5-a]pyrimidine and
2-benzylthio-7-methyl-5-phenyl-1,2,4-triazolo[1,5-a]pyrimidine A solution of 20.6 g (100 mmol) of 3-amino-5-benzylthio-1,2,4-triazole and 16.2 g (100 mmol) of benzoyl acetone in 100 ml of glacial acetic acid was heated at reflux for 14 hours. The solvent was removed by evaporation at reduced pressure and the residue was chromatographed on silica gel (HPLC) eluting with EtOAc-hexane (3:7, v/v) to afford 4.81 g (14%) of 2-benzylthio-7-methyl-5-phenyl-1,2,4-triazolo[1,5-a]pyrimidine as a pale yellow wolid, m.p. 154°-155° C. IR and $^1$H NMR spectra were in agreement with the assigned structure.

Analysis: Calculated for $C_{19}H_{16}N_4S$: C, 68.65; H, 4.85; N, 16.85; S, 9.65; Found: C, 68.76; H, 4.82; N, 16.98; S, 9.93.

Further elution afforded 22.8 g (69%) of 2-benzylthio-5-methyl-7-phenyl-1,2,4-triazolo[1,5-a]pyrimidine as a pale yellow solid, m.p. 110°-111° C. IR and $^1$H NMR spectra were in agreement with the assigned structure.

Analysis: Calculated for $C_{19}H_{16}N_4S$: C, 68.65; H, 4.85; N, 16.85; S, 9.65; Found: C, 68.52; H, 4.75; N. 16.93; S, 9.61.

EXAMPLE 38

Preparation of
5,7-dimethyl-1,2,4-triazolo[1,5-a]pyrimidine-2-sulfonyl chloride

Chlorine was bubbled into a suspension of 99.0 g (0.366 mol) of 2-benzylthio-5,7-dimethyl-1,2,4-triazolo[1,5-a]pyrimidine in 700 ml of HOAc—$H_2O$ (1:1, v/v) cooled to $-1°$ C. During the course of the addition the temperature of the reaction mixture was maintained below 5° C. After 2.5 hours the chlorine addition was ceased and the reaction mixture was filtered to collect a tan solid. The filtrate was diluted with $H_2O$ to separate an additional quantity of solid which was collected by filtration. The combined solid products were dried in vacuo to yield 70.4 g (78%) of crude sulfonyl chloride III (X=Z=Me, Y=H) as a tan solid. IR and $^1$HNMR spectra confirmed the structure.

Recrystallization from EtOAc produced an analytical sample as an off-white solid, m.p. 128.5°-130.5° C.

Analysis: Calculated for $C_7H_7ClN_4O_2S$: C, 34.09; H, 2.86; N, 20.73; S, 13.00; Found: C, 34.34; H, 2.80; N, 22.64; S, 12.85.

EXAMPLE 39

Preparation of
6,7-cyclopentano-5-methyl-1,2,4-triazolo[1,5-a]pyrimidine-2-sulfonyl chloride Chlorine gas was bubbled into a suspension of 4.45 g (15.0 mmol) of 2-benzylthio-6,7-cyclopentano-5-methyl-1,2,4-triazolo[1,5-a]pyrimidine in 30 ml of HOA- C—H$_2$O (1:1, v/v) cooled to $-4°$ C. After 30 minutes the addition was stopped and the reaction mixture was stirred for 30 minutes maintaining the temperature below 5° C. The reaction mixture was filtered and the collected solid was dried under vacuum to yield 3.46 g (85 percent) of the desired sulfonyl chloride as a cream colored solid which was used directly without further purification: IR (CHCl$_3$) 1627, 1551, 1398 and 1170 cm$^{-1}$; $^1$H NMR (CDCl$_3$) δ3.50 (2H, broad t), 3.18 (2H, broad t) and 2.2–2.8 (5H, m including s at 2.68).

EXAMPLE 40

Preparation of 5,6,7-trimethyl-1,2,4-triazolo[1,5-a]pyrimidine-2-sulfonyl chloride Chlorine was bubbled into a suspension of 28.4 g (0.100 mol) of 2-benzylthio-5,6,7-trimethyl-1,2,4-triazolo[1,5-a]pyrimidine in 200 ml of glacial acetic acid—H$_2$O (1:1, v/v) and cooled to $-5°$ C. The chlorine addition continued over 35 minutes and the temperature of the reaction mixture never exceeded 5° C. After the addition was complete, the reaction mixture was stirred for 5 minutes and filtered. The solid collected was washed twice with H$_2$O and dried in vacuo to yield 24.3 g (93%) of the crude sulfonyl chloride as a pale yellow solid. The IR and $^1$H NMR were consistent with the assigned structure. The crude sulfonyl chloride was used in subsequent transformations without further purification.

EXAMPLE 41

Preparation of 6-chloro-1,2,4-triazolo[1,5-a]pyrimidine-2-sulfonyl chloride

A suspension of 3.75 g (13.5 mmol) of 2-benzylthio-6-chloro-1,2,4-triazolo[1,5-a]pyrimidine in 40 ml of AcOH—H$_2$O (1:1, v/v) was cooled to $-10°$ C. and chlorine gas was bubbled into the reaction mixture for 10 minutes. After the addition was complete, the reaction mixture was stirred for 10 minutes and diluted with 25 ml of H$_2$O. The mixture was filtered and the filtrate was extracted with CH$_2$Cl$_2$. The organic phase was evaporated at reduced pressure to afford 2.14 g of the crude sulfonyl chloride as a liquid. IR and $^1$H NMR spectra were in agreement with the assigned structure.

EXAMPLE 42

Preparation of 1,2,4-triazolo[1,5-a]pyrimidine-2-sulfonyl chloride

A suspension of 8.0 g (33 mmol) of 2-benzylthio-1,2,4-triazolo[1,5-a]pyrimidine in 60 ml of HOAc—H$_2$O (1:1, v/v) was cooled below 0° C. and chlorine gas was bubbled into the reaction mixture for 15 minutes. The temperature of the reaction mixture was maintained below 10° C. during the course of the addition. After the addition was complete, the reaction mixture was stirred for 15 minutes, diluted with H$_2$O and extracted with CH$_2$Cl$_2$. The organic phase was dried (MgSO$_4$) and evaporated at reduced pressure to yield 5.74 g of the desired crude product as a brown oil. IR and $^1$H NMR were in agreement with the assigned structure.

Recrystallization from EtOAc gave an analytical sample, m.p. 105°–109° C.

Analysis: Calculated for C$_5$H$_3$ClN$_4$O$_2$S: C, 27,45; H, 1.32; N, 25.62; Found: C, 28.91; H, 1.52; N, 25.79.

EXAMPLE 43

Preparation of 5-methyl-1,2,4-triazolo[1,5-a]pyrimidine-2-sulfonyl chloride

A suspension of 2.77 g (10.8 mmol) of 2-benzylthio-5-methyl-1,2,4-triazolo[1,5-a]pyrimidine in 40 ml of AcOH—H$_2$O (1:1, v/v) was cooled to $-10°$ C. and chlorine gas was bubbled into the solution for 10 minutes. After the addition was complete, the reaction mixture was stirred for 5 minutes, diluted with H$_2$O (25 ml) and filtered. The solid collected was dried in vacuo to yield 1.17 g of the desired sulfonyl chloride. IR and $^1$H NMR were in agreement with the assigned structure.

An additional quantity of the product contaminated with by-products containing benzyl residues was obtained by extraction of the filtrate with CH$_2$Cl$_2$ and evaporation of the organic phase at reduced pressure.

EXAMPLE 44

Preparation of 5-methoxy-7-methyl-1,2,4-triazolo[1,5-a]pyrimidine-2-sulfonyl chloride A suspension of 1.41 g (4.93 mmol) of 2-benzylthio-5-methoxy-7-methyl-1,2,4-triazolo[1,5-a]pyrimidine in 40 ml of AcOH—H$_2$O (1:1, v/v) was cooled to $-20°$ C., and chlorine gas was bubbled into the reaction mixture for 5 minutes. After the addition was complete, the reaction mixture was stirred for 10 minutes, diluted with H$_2$O (20 ml) and filtered. The solid collected was dried in vacuo to yield 0.63 g of the desired crude sulfonyl chloride as a colorless solid. IR and $^1$H NMR were in agreement with the assigned structure.

EXAMPLE 45

Preparation of 7-methyl-1,2,4-triazolo[1,5-a]pyrimidine-2-sulfonyl chloride

A suspension of 3.52 g (13.7 mmol) of 2-benzylthio-5-methyl-1,2,4-triazolo[1,5-a]pyrimidine in 40 ml of AcOH—H$_2$O (1:1, v/v) was cooled to $-10°$ C., and chlorine gas was bubbled into the reaction mixture for 10 minutes. After the addition was complete, the reaction mixture was stirred for 10 minutes, diluted with H$_2$O and filtered. The solid collected was dried in vacuo to yield 0.46 g of the desired sulfonyl chloride as a tan solid. IR and $^1$H NMR spectra were in agreement with the assigned structure.

An additional quantity (2.2 g) of crude sulfonyl chloride contaminated with by-products containing benzyl residues was obtained by extraction of the filtrate with CH$_2$Cl$_2$ and evaporation at reduced pressure.

EXAMPLE 46

Preparation of 6-methyl-1,2,4-triazolo[1,5-a]pyrimidine-2-sulfonyl chloride

A suspension of 10.0 (60 mmol) of 2-benzylthio-6-methyl-1,2,4-triazolo[1,5-a]pyrimidine in 260 ml of methylene chloride, 100 ml of water and 17 ml of concentrated HCl was cooled to $-5°$ C. and treated with 284 ml (197 mmol) of 5.25% aqueous sodium hypochlorite (commercial bleach) by dropwise addition. After the addition was complete the reaction mixture was stirred for 20 minutes at 0° C. and filtered. The organic layer was separated and the aqueous layer was extracted twice with methylene chloride. The combined organic phases were dried (MgSO$_4$) and evaporated at reduced pressure to yield 7.0 g (50%) of the desired product as a solid, m.p. -106°–108° C. IR and $^1$H NMR spectra were in agreement with the assigned structure.

Analysis: Calculated for C$_6$H$_5$ClN$_4$O$_2$S: C, 30.96; H, 2.15; N, 24.08; Found: C, 31.00; H, 2.23; N, 23.91

EXAMPLE 47

Preparation of 6-chloro-5,7-dimethyl-1,2,4-triazol[1,5-a]pyrimidine-2-sulfonyl chloride This material was prepared in 50% yield from 2-benzylthio-6-chloro-5,7-dimethyl-1,2,4-triazolo[1,5-a]pyrimidine following the general procedure described in Examples 38–45. The product was isolated as a pale yellow solid, m.p. 131°–133° C. IR and $^1$H NMR spectra were in agreement with the assigned structure.

EXAMPLE 48

Preparation of 6-ethoxy-1,2,4-triazolo[1,5-a]pyrimidine-2-sulfonyl chloride

This material was prepared in 82% yield from 2-benzylthio-6-ethoxy-1,2,4-triazolo[1,5-a]pyrimidine following the general procedure described in Examples 38–45. The product was isolated as a solid m.p. 134°–137° C. IR and $^1$H NMR spectra were in agreement with the assigned structure.

Analysis: Calculated for C$_7$H$_7$ClN$_4$O$_3$S: C, 31.96; H, 2.66; n, 21.31; Found: C, 32.64; H, 2.36; N, 21.30.

EXAMPLE 49

Preparation of 5-isopropyl-1,2,4-triazolo[1,5-a]pyrimidine-2-sulfonyl chloride

This material was prepared in 56% yield from 2-benzylthio-5-isopropyl-1,2,4-triazolo[1,5-a]pyrimidine following the general procedure described in Example 46. The product was isolated as a solid, m.p. 60°–62° C. IR and 1$^1$HNMR spectra were in agreement with the assigned structure.

Analysis: Calculated for C$_8$H$_9$ClN$_4$O$_2$S: C, 36.85; H, 3.45; N, 21.49; Found: C, 37.02; H, 3.49; N, 21.71.

EXAMPLE 50

Preparation of 5,6-dimethyl-1,2,4-triazolo[1,5-a]pyrimidine-2-sulfonyl chloride

This material was prepared in 80% yield from 2-benzylthio-5,6-dimethyl-1,2,4-triazolo[1,5-a]pyrimidine following the general procedure described in Example 46. The product was isolated as a solid, m.p. 116°–120° C. IR and $^1$H NMR spectra were in agreement with the assigned structure.

Exact mass calculated for C$_7$H$_7$ClN$_4$O$_2$S: 245.9984; Found: 245.9981.

EXAMPLE 51

Preparation of 6-chloro-5-methyl-1,2,4-triazolo[1,5-a]pyrimidine-2-sulfonyl chloride This material was prepared in 60% yield from 2-benzylthio-6-chloro-5-methyl-1,2,4-triazolo[1,5-a]pyrimidine following the general procedure described in Examples 38–45. The product was isolated as a solid, m.p. 99°–101° C. IR and $^1$H NMR spectra were in agreement with the assigned structure.

EXAMPLE 52

Preparation of 5-methoxy-1,2,4-triazolo[1,5-a]pyrimidine-2-sulfonyl chloride

This material was prepared in 57% yield from 2-benzylthio-5-methoxy-1,2,4-triazolo[1,5-a]pyrimidine following the general procedure described in Examples 38–45. The product was isolated as a solid, m.p. 110°–112° C. IR and $^1$H NMR spectra were in agreement with the assigned structure.

Analysis: Calculated for C$_6$H$_5$ClN$_4$O$_3$S: C, 28.97; H, 2.01: N, 22.53; Found: C, 29.90; H, 2.23; N, 22.76.

EXAMPLE 53

Preparation of 5-(2,2,2-trifluoroethoxy)-1,2,4-triazolo[1,5-a]pyrimidine-2-sulfonyl chloride This material was prepared in 74% yield from 2-benzylthio-5-(2,2,2-trifluoroethoxy)-1,2,4-triazolo[1,5-a]pyrimidine following the general procedure described in Examples 38–45. The product was isolated as a solid, m.p. 91°–96° C. IR and $^1$H NMR spectra were in agreement with the assigned structure.

Exact mass calculated for C$_7$H$_4$ClF$_3$N$_4$O$_3$S: 315.9655; Found: 315.9650.

EXAMPLE 54

Preparation of 5-ethoxy-1,2,4-triazolo[1,5-a]pyrimidine-2-sulfonyl chloride

This material was prepared in 74% yield from 2-benzylthio-5-ethoxy-1,2,4-triazolo[1,5-a]pyrimidine following the general procedure described in Examples 38–45. The product was isolated as a solid, m.p. 91°–96° C. IR and $^1$H NMR spectra were in agreement with the assigned structure.

EXAMPLE 55

Preparation of 5-methoxy-6-methyl-1,2,4triazolo[1,5-a]pyrimidine-2-sulfonyl chloride This material was prepared in 80% yield from 2-benzylthio-5-methoxy-6-methyl-1,2,4-triazolo[1,5-a]pyrimidine following the general procedure outlined in Examples 38–45. The product was isolated as a solid, m.p. 154°–157° C. IR and $^1$H NMR spectra were in agreement with the assigned structure.

Analysis: Calculated for C$_7$H$_7$ClN$_4$O$_3$S: C, 32.00; H, 2.67; N, 21.33; Found: C, 32.35; H, 2.61; N, 21.45.

EXAMPLE 56

Preparation of 6-ethoxycarbonyl-7-methyl-1,2,4-triazolo[1,5-a]pyrimidine-2-sulfonyl chloride This material was prepared in 82% yield from 2-benzylthio-6-ethoxycarbonyl-7-methyl-1,2,4-triazolo[1,5-a]pyrimidine following the general procedure described in Example 46. The product was isolated as a solid, m.p. 65°–69° C. IR and $^1$H NMR spectra were in agreement with the assigned structure.

Analysis: Calculated for C$_9$H$_9$ClN$_4$O$_4$S: C, 35.47; H, 2.95; N, 18.39; Found: C, 36.04; H, 3.02; N, 18.27.

EXAMPLE 57

Preparation of 6-(4-nitrophenyl)-1,2,4-triazolo[1,5-a]pyrimidine-2-sulfonyl chloride This material was prepared in 71% yield from 2-benzylthio-6-(4-nitrophenyl)-1,2,4-triazolo[1,5-a]pyrimidine following the general procedure described in Examples 38-45. The product was isolated as a solid, m.p. 159°-167° C. IR and $^1$H NMR spectra were in agreement with the assigned structure.

EXAMPLE 58

Preparation of 5,7-dimethyl-N-(2-chlorophenyl)-1,2,4-triazolo[1,5-a]pyrimidine-2-sulfonamide To a solution of 0.74 ml (0.90 g, 7.0 mmol) of o-chloroaniline in 10 ml of dry pyridine was added 1.89 g (7.66 mmol) of the sulfonyl chloride prepared in Example 1. The resulting dark solution was stirred at ambient temperature for 18 hours and evaporated to dryness. The residue was treated with 15 ml of 1N NaOH and charcoal stirred for 15 minutes. The mixture was filtered through celite and the filtrate was acidified with 3N HCl to precipitate the product. Filtration and drying in vacuo gave the desired product (2.01 g, 85%) as a light brown solid, m.p. 188°-189.5° C. IR and $^1$H NMR spectra were in agreement with the desired structure I (Ar=o-chlorophenyl, X=Z=Me, Y=H).

Analysis: Calculated for $C_{13}H_{12}ClN_5O_2S$: C, 46.23; H, 3.58; N, 20.73; Cl, 10.50; S, 9.49; Found: C, 46.09; H, 3.58; N, 20.89; Cl, 10.34; S, 9.37.

EXAMPLE 59

Preparation of methyl N-(5,7-dimethyl-1,2,4-triazolo[1,5-a]pyrimidine-2-sulfonyl)anthranilate To a solution of 0.91 ml (1.1 g, 7.0 mmol) of methyl anthranilate in 10 ml of dry pyridine was added 1.89 g (7.66 mmol) of the sulfonyl chloride prepared in Example 1. The resulting dark solution was stirred at room temperature for 18 hours and evaporated to dryness. The residue was treated with 15 ml of 1N NaOH and charcoal and stirred for 15 minutes. The mixture was filtered through celite, and the filtrate was acidified with 3N HCl to precipitate the product. The product was collected by filtration and dried in vacuo to yield 2.27 g (90%) of the desired product I (X=Z=Me, Y=H, Ar=o-carbomethoxyphenyl) as a cream colored solid, m.p. 169.5°-170.5° C. IR and $^1$H NMR spectra confirmed the structure of the product.

Analysis: Calculated for $C_{15}H_{15}N_5O_4S$: C, 49.86; H, 4.18; N, 19.38; S, 8.87; Found: C, 49.68; H, 4.13; N, 19.35; S, 8.69.

EXAMPLE 60

Preparation of 5,7-dimethyl-N-(2,6-dimethylphenyl)-1,2,4-triazolo[1,5-a]pyrimidine-2-sulfonamide A solution of 2.2. g (8.9 mmol) of 5,7-dimethyl-1,2,4-triazolo[1,5-a]pyrimidine-2-sulfonyl chloride, 1.01 ml (8.4 mmol) of 2,6-dimethylaniline, 0.7 ml (8.4 mmol) of dry pyridine and 4 mg of DMAP in 20 ml of $CH_2Cl_2$ was stirred at room temperature for 17 hours. The solvent was removed by evaporation and the residue was taken up in 0.5M NaOH. The solution was extracted with diethyl ether and the aqueous phase was acidified with 3N HCl to precipitate a solid. The solid was collected by filtration and dried in vacuo to yield 2.72 g (97 percent) of the desired product as a white solid, m.p. 263°-266° C. (decomp.): $^1$H NMR (DMSO-$d_6$) $\delta$10.4 (1H, broad S), 7.55 (1H, s), 7.2 (3H, s), 2.7 and 2.8 (3H each, s) and 2.1 (6H, s); IR (KBr) 3100, 2980-2780, 1628, 1540 and 1355 cm$^{-1}$.

Analysis: Calculated for $C_{15}H_{17}N_5O_2S$: C, 54,31; H, 5.23; N, 21.23; Found: C, 53.59; H, 5.07; N, 20.65.

EXAMPLE 61

Preparation of 6,7-cyclopentano-5-methyl-N-(2,6-dichlorophenyl)-1,2,4-triazolo[1,5-a]pyrimidine-2-sulfonamide A solution of 3.31 g (12.1 mmol) of crude 6,7-cyclopentano-5-methyl-1,2,4-triazolo[1,5-a]pyrimidine-2-sulfonyl chloride and 1.87 g (11.6 mmol) of 2,6-dichloroaniline in 15 ml of dry pyridine was stirred at 45°-50° C. for 23 hours. The majority of the pyridine was removed by evaporation at reduced pressure, and the residue was treated with 25 ml of 1N NaOH and ice. After stirring for 15 minutes, the mixture was filtered and the filtrate was acidified with 3N HCl to precipitate a light brown solid. The solid was taken up in 0.5N NaOH and filtered. The filtrate was acidified with 3N HCl to precipitate a solid. The solid was collected by filtration and dried in vacuo to yield 1.19 g (26 percent) of the desired sulfonamide as a light brown solid, m.p. 264°-266° C.: $^1$H NMR (DMSO-$d_6$) $\delta$10.83 (1H, broad s), 7.1-7.6 (3H, m) and 2.0-3.6 (9H, m including s at 2.57); IR (KBr) 3410, 1620, 1549, 1442, 1399, 1358 and 1167$^{-1}$.

Analysis: Calculated for $C_{15}H_{13}Cl_2N_5O_2S$: C, 45.24; H, 3.29; N, 17.58; Found: C, 45.47; H, 3.18; N, 17.41.

EXAMPLE 62

Preparation of 5,7-dimethyl-N-(2,4,6-trichlorophynyl)-1,2,4-trizaolo[1,5-a]pyrimidine-2-sulfonamide A solution (10.7 ml, 17.1 mmol) of 1.60M N-butyllithium in hexane was added to a solution of 3.20 g (16.3 mmol) of 2,4,6-trichloroaniline in 20 ml of dry THF cooled to $-78°$ C. The resultant solution was then allowed to warm to room temperature. This solution was added to a solution of 2.00 g (8.11 mmol) of 5,7-dimethyl-1,2,4-triazolo[1,4-a]pyrimidine-2-sulfonyl chloride in 30 ml of dry THF cooled to $-10°$ C. The temperature of the reaction mixture was maintained between $-13°$ C. and $-9°$ C. during to course of the addition. After the addition was complete, the reaction mixture was stirred for 30 minutes and warmed to room temperature. After 1 hour at room temperature, THF was removed from the reaction mixture by evaporation. The residue was triturated with $H_2O$ and filtered. The filtrate was treated with charcoal and filtered through celite. The filtrate was washed with $Et_2O$, and the aqueous phase was separated and acidified with 3N HCl to precipitqte a solid. The solid was collected by filtration, washed with water and dried in vacuo to yield 0.70 g (21%) of the desired product as a tan solid, m.p. >200° C. (decomp.) $^1$H NMR and IR spectra were consistent with the assigned structure.

Analysis: Calculated for $C_{13}H_{10}N_5O_2S$: C, 38.40; H, 2.48; N, 17.22; Found: C, 38.36; H, 2.48; N, 17.14.

EXAMPLE 63

Preparation of 6-chloro-N-(2,6-difluorophenyl)-1,2,4-triazolo[1,5-a]pyrimidine-2-sulfonamide The starting 2,6-difluoroaniline (1.7 g, 13 mmol) was dissolved in 3.5 ml of pyridine and 3.5 g (14 mmol) of 6-chloro-1,2,4-triazolo[1,5-a]pyrimidine-2-sulfonyl chloride was added. After an exothermic reaction subsided the reaction mixture was heated at 60°–70° C. overnight. The solvent was removed by evaporation at reduced pressure and the residue was taken up in aqueous sodium bicarbonate. The aqueous solution was washed with ether, and acidified with acqueous HCl. The solid which separated upon acidification was collected by filtration, dried and recrystallized from methanol to afford 2.5 g (55%) of the desired product as a crystalline solid, m.p. 224°–226° C. IR and $^1$H NMR spectra were in agreement with the assigned structure.

Analysis: Calculated for $C_{11}H_6ClF_2N_5O_2S$: C, 38.21; H, 1.75; N, 20.26; Found: C, 38.32; H, 1.44; N, 20.18.

EXAMPLE 64

Preparation of methyl 3-methyl-N-(6-methyl-1,2,4-triazolo[1,5-a]pyrimidine-2-sulfonyl)anthranilate Methyl 3-methylanthranilate (2.1 g, 13 mmol) was dissolved in 4 ml pyridine and 6-methyl-1,2,4-triazolo[1,5-a]pyrimidine-2-sulfonyl chloride was added. After a mild exothermic reaction subsided the reaction mixture was stirred at 50° C. for 24 hours. The pyridine was removed by evaporation at reduced pressure and the residue was treated with in 10% aqueous sodium bicarbonate. Insouble material was collected by filtration, washed with ether and dried to yield 2.9 (63%) of the desired product as a solid, m.p. 198.5°–205° C. An analytical sample was prepared by recrystallization from ethanol to yield a crystalline solid, m.p. 208.5°–210.5° C. IR and $^1$H NMR spectra were in agreement with the assigned structure.

Analysis: Calculated for $C_{15}H_{15}N_5O_4S$: C, 49.85; H, 4.18; N, 19.38; Found: C, 49.96; H, 4.14; N, 19.75.

EXAMPLE 65

Preparation of 5-methyl-N-(2,6-difluorophenyl)-1,2,4-triazolo[1,5-a]pyrimidine-2-sulfonamide The starting 2,6-difluoroaniline (18.1 g, 0.140 mol) was dissolved in 45 ml of pyridine and 36.1 g (0.155 mol) of 5-methyl-1,2,4-triazolo[1,5-a]pyrimidine-2-sulfonyl chloride was added. After an exothermic reaction subsided the reaction mixture was stirred at room temperature for 15.5 hours. The pyridine was removed by evaporation at reduced pressure, and the residue was treated with 600 ml of 0.5N naOH. After stirring to dissolve all soluble material the mixture was filtered through celite and the filtrate was acifified with 3N HCl. The precipitate which separated upon acidification was collected by filtration and dried to yield 33.0 g (73%) of the desired product as a pale red solid, m.p. 245°–247° C. IR and $^1$H NMR spectra were in agreement with the assigned structure.

Analysis: Calculated for $C_{12}H_9F_2N_5O_2S$: C, 44.31; H, 2.79; N, 21.53; Found: C, 44.69; H, 2.80; N, 21.85.

EXAMPLE 66

Preparation of 5,7-dimethyl-N-(2-acetoxymethyl-6-chlorophenyl)-1,2,4-triazolo[1,5-a]pyrimidine-2-sulfonamide A solution of 1.30 gm (6.50 mmol) of 2-amino-3-chlorobenzyl acetate, 4.11 gm (52.0 mmol) of pyridine and 5.0 ml of acetonitrile was treated with 1.61 gm (6.50 mmol) of 5,7-dimethyl-1,2,4-triazolo[1,5-a]pyrimidine-2-sulfonyl chloride and the resulting mixture stirred at 25° C. for 120 hours. An additional 0.53 gm (2.2 mmol) of the sulfonyl chloride was added and stirring at 25° C. continued for an additional 24 hours. The mixture was filtered and the filtrate evaporated to provide a brown oil. The oil was then dissolved in 40 ml of m ethylene chloride and stirred with 25 ml of 0.5M NaOH. After 5 minutes, the aqueous phase was separated, washed with ether and acidified with 3N HCl. A light brown solid was collected, washed with water, dried and recrystallized from acetonitrile to provide 0.35 gm (13%) of the desired product as a solid, m.p. 214°–217° C., containing approximately 10% of an impurity. IR and $^1$H NMR spectra were in agreement with the assigned structure.

Analysis: Calculated for $C_{16}H_{16}ClN_5O_4S$: C, 46.89; H, 3.94; N, 17.08; Found: C, 46.60; H, 3.80, N, 17.73.

EXAMPLE 67

Preparation of methyl 3-amino-2-bromo-4-methyl-N-(5,7-dimethyl-1,2,4-triazolo[1,5-a]pyrimidine-2-sulfonyl)benzoate A solution of 1.50 g (6.15 mmol) of methyl 2-bromo-3-amino-4-methylbenzoate in 7 ml of pyridine was treated with 1.67 g (6.76 mmol) of 5,7-dimethyl-1,2,4-triazolo[1,5-a]-pyrimidine-2-sulfonyl chloride. After stirring at 25° C. for 18 hours an additional 0.46 g (1.9 mmol) of the sulfonyl chloride was added and the reaction mixture was heated at 52°–55° C. for 3 hours. The solvent was removed by evaporation and the residue was partitioned between methylene chloride and dilute aqueous HCl. The organic phase was washed with water, dried and evaporated at reduced pressure to yield 1.85 g (66%) of the desired product as a yellow solid upon trituration with ethyl acetate. An analytical sample was prepared by recrystallization from acetonitrile-DMF to afford a crystalline solid, m.p. 229°–231° C. IR and $^1$H NMR spectra were in agreement with the assigned structure.

Analysis: Calculated for $C_{16}H_{16}BrN_5O_4S$: C, 42.30; H, 3.55; N, 15.41; Found: C, 42.29; H, 3.45; N, 15.68.

EXAMPLE 68

Preparation of 3-amino-2-bromo-4-methyl-N-(5,7-dimethyl-1,2,4-triazolo[1,5-a]pyrimidine-2-sulfonyl)benzoic acids A solution of 2.78 g (6.12 mmol) of methyl 3-amino-2-bromo-4-methyl-N-(5,7-dimethyl-1,2,4-triazolo[1,5-a]pyrimidine-2-sulfonyl)benzoate and 30 ml of 5% aqueous NaOH in 30 ml of water was stirred at 25° C. for 2.5 hours. The reaction mixture was filtered and the filtrate was cooled in ice and acidified to approximately pH 2 with 3N HCl. The solid which separated was collected by filtration, washed with water and dried in vacuo to yield 2.10 g (78%) of the desired product as a gold solid, m.p. 290° C. (decomposition). IR and $^1$H NMR spectra were in agreement with the assigned structure.

Analysis: Calculated for $C_{15}H_{14}BrN_5O_4S$: C, 40.92; H, 3.21; N, 15.90; Found: C, 40.51; H, 3.11; N, 16.01.

EXAMPLE 69

Preparation of 5-methylthio-N-(2,6-dichlorophenyl)-1,2,4-triazolo[1,5-a]pyrimidine-2-sulfonamide To 25 ml (13 mmol) of a 0.52M solution of sodium methyl mercaptide in DMSO prepared by bubbling methyl mercaptan into a suspension of sodium hydride in DMSO, was added 2.6 g (5.9 mmol) of 5-(2,2,2-trifluoroethoxy)-N-(2,6-dichlorophenyl)-1,2,4-triazolo[1,5-a]-pyrimidine-2-sulfonamide. The solution was stirred at room temperature for 25 hours, diluted with 100 ml of ice water and neutralized with 3N aqueous HCl. The gummy solid which separated was collected and taken up in 0.5N aqueous NaOH. The mixture was filtered to remove insoluble material, and the filtrate was acidified with 6N aqueous HCl. The solid which separated was collected by filtration and dried to yield 1.5 g (66%) of the desired product as a pale yellow solid, m.p. 239°–243° C. IR and $^1H$ NMR spectra were in agreement with the assigned structure.

Analysis: Calculated for $C_{12}H_9Cl_2N_2O_2S_2$: C, 36.92; H, 2.31; N, 17.95; Found: C, 36.51; H, 2.41; N, 17.68.

EXAMPLE 70

Preparation of 5-dimethylamino-N-(2,6-dichlorophenyl)-1,2,4-triazolo[1,5-a]pyrimidine-2-sulfon-amide The starting 5-(2,2,2-trifluoroethoxy)-N-(2,6-dichlorophenyl)-1,2,4-triazolo[1,5-a]pyrimidine-2-sulfonamide (1.5 g, 3.4 mmol) was dissolved in 5 ml (44 mmol) of 50% aqueous dimethylamine. After stirring for 48 hours at room temperature the solution was diluted with water and acidified with 6N aqueous HCl. The solid which separated was collected by filtration and treated with 0.5N aqueous NaOH and filtered to remove insoluble material. The filtrate was acidified to precipitate a solid. The solid was collected and dried to yield 1.0 g (60%) of the desired product as a solid, m.p. >310° C. IR and $^1H$ NMR spectra were in agreement with the assigned structure.

Analysis: Calculated for $C_{13}H_{12}Cl_2H_6O_2S$: C, 40.31; H, 3.10; N, 21.71; S, 8.28; Found: C, 40.08; H, 3.05; N, 22.33 S, 7.99.

EXAMPLE 71

Preparation of 6-bromo-5-methyl-N-(2,6-dichlorophenyl)-1,2,4-triazolo[1,5-a]pyrimidine-2-sulfonamide A suspension of 4.0 g (11 mmol) of 5-methyl-N-(2,6-dichlorophenyl)-1,2,4-triazolo[1,5-a]pyrimidine-2-sulfonamide in 50 ml of glacial acetic acid and 10 ml of acetic anhydride was stirred at 90° C. for 30 minutes. N-Bromosuccinimide (2.4 g, 13 mmol) was added to this hot solution, and the reaction mixture was stirred at 90° C. for 60 minutes. The solution was cooled and poured into 200 ml of ice water. A solid which separated was collected and dried. This crude product was purified by dissolving the sample in methylene chloride, filtering the solution through silica gel and triturating the fitrate with pentane. The desired product was obtained as a solid, m.p. 215°–216° C. IR and $^1H$ NMR spectra were in agreement with the assigned structure.

Exact mass calculated for $C_{12}H_8BrCl_2N_5O_2S$: 438.8898; Found: 438.8899.

EXAMPLE 72

Preparation of 5,7,N-trimethyl-N-(2,6-dichlorophenyl)-1,2,4-triazolo[1,5-a]pyrimidine-2-sulfonamide A mixture of 3.00 g (8.06 mmol) of 5,7-dimethyl-1,N-(2,6-dichlorophenyl)-2,4-triazolo[1,5-a]pyrimidine-2-sulfonamide and 0.90 g (8.1 mmol) of potassium t-butoxide in 30 ml of acetonitrile was heated at reflux for 40 minutes. After cooling to room temperature 1.14 g (8.06 mmol) of methyl iodide were added, and the reaction was heated at reflux for 1 hour. After cooling to room temperature, the reaction mixture was diluted with methylene chloride and washed with 1% aqueous NaOH. The organic phase was spearated, dried ($MgSO_4$) and evaporated at reduced pressure. The brown solid residue was recrystallized from acetone to give 1.60 g (51%) of the desire product as a tan solid, m.p. 220°–222° C. IR and $^1H$ NMR spectra were in agreement with the assigned structure.

Analysis: Calculated for $C_{14}H_{13}Cl_2N_5O_2S$: C, 43.54; H, 3.39; N, 18.13; Found: C, 43.55; H, 3.32; N, 18.03.

EXAMPLE 73

Preparation of 5-methyl-N-benzoly-N-(2,6-dichlorophenyl)-1,2,4-triazolo[1,5-a]pyrimidine-2-sulfonamide A mixture of 3.00 g (8.37 mmol) of 5-methyl-N-(2,6-dichlorophenyl)-1,2,4-triazolo[1,5-a]pyrimidine-2-sulfonamide and 1.16 g (8.37 mmol) of anhydrous powdered $K_2CO_3$ in 100 ml of acetone was heated at reflux for 30 minutes. A solution of 1.18 g (8.37 mmol) of benzoyl chloride in 10 ml of acetone was added, and the reaction was heated at reflux for 115 min. The reaction was filtered, and the filtrate was evaporated at reduced pressure. The solid residue was collected by filtration, washed thoroughly with aqueous $NaHCO_3$ and $H_2O$ and dried to yield 2.75 g (72%) of the desired product as a solid, m.p. 187°–189° C. IR and $^1H$ NMR spectra were in agreement with the assigned structure.

Analysis: Calculated for $C_{19}H_{13}Cl_2N_5O_3S$: C, 49.36; H, 2.83; N, 15.15; Found: C, 48.97; H, 2,84; N, 15.16.

EXAMPLE 74

Preparation of 5-methyl-N-(2,6-dichlorophenyl)-4,5,6,7-tetrahydro-1,2,4-triazolo[1,5-a]pyrimidine-2-sulfonamide Sodium borohydride (0.6 g, 16 mmol) was added to a solution of 3.0 g (8.3 mmol) of 5-methyl-N-(2,6-dichlorophenyl)-1,2,4-triazolo[1,5-a]pyrimidine-2-sulfonamide in 25 ml of dry DMSO. An exothermic reaction occured and 2.0 ml (31 mmol) of methane sulfonic acid in 5 ml of DMSO was added at a rate to maintain the temperature of the reaction mixture at 60° C. After the addition was complete the reaction mixture was stirred for 10 minutes and carefully quenched with 0.5N aqueous NaOH. The clear yellow solution was filtered, and the filtrate was acidified with 3N aqueous HCl. The resulting precipitate was treated with dilute aqueous NaOH and filtered to remove insoluble material. The filtrate was acidified with aqueous HCl to precipitate a solid. The solid was collected by filtration and dried to yield 1.11 g (37%) of the desired product as a solid, m.p.

230°–235° C. IR and $^1$H NMR spectra were in agreement with the assigned structure.

Analysis: Calculated for $C_{12}H_{12}Cl_2N_5O_2S$: C, 39.89; H, 3.32; N, 19.39; Found: C, 39.72; H, 3.42; N, 19.19.

EXAMPLE 75

Preparation of methyl 3-amino-2,4-dichlorobenzoate

This material was prepared by chlorination of methyl 3-amino-4-chlorobenzoate with N-chlorosuccinimide. The product was isolated as a solid, m.p. 50°–52° C. The product was characterized by IR and $^1$H NMR spectroscopy and combustion analysis.

EXAMPLE 76

Preparation of methyl 3-amino-2-bromo-4-methylbenzoate

A mixture of 16.5 g (100 mmol) of methyl 3-amino-4-methylbenzoate and 300 ml of $CCl_4$ was treated with 18.6 g (105 mmol) of N-bromosuccinimide and stirred at ambient temperature for 4 hours. The reaction mixture was filtered, and the filtrate was evaporated at reduced pressure to afford an amber oil. To remove material resulting from bromination at the 6-position, the crude product was taken up in 100 ml of hexane and 60 ml of ether and treated with 3.96 g (50.0 mmol) of pyridine and 3.06 g (30.0 mmol) of acetic anhydride. After stirring for 3 hours at 25° C., the precipitate was removed by filtration. The filtrate was evaporated at reduced pressure to yield an amber oil. The crude product was purified by HPLC to afford 14.5 g (59%) of the desired product as an amber oil. IR and $^1$H NMR spectra were in agreement with the assigned structure.

Analysis: Calculated for $C_9H_{10}BrNO_2$: C, 44.29; H, 4.13; N, 5.74; Found: C, 44.14; H, 3.96; N, 5.72.

EXAMPLE 77

Preparation of methyl 3-methyl-4-chloro-anthranilate

This material was prepared by esterification of the corresponding anthranilic acid with HCl in methanol. The product was isolated as a solid, m.p. 72°–74° C.

EXAMPLE 78

Preparation of 2,6-dichloro-3-trifluoromethyl aniline

This material was prepared by chlorination of 2-chloro-5-trifluoromethyl aniline with N-chlorosuccinimide followed by chromatographic purification. The product was isolated as a yellow oil which was characterized by IR and $^1$H NMR spectroscopy and combustion analysis.

EXAMPLE 79

Preparation of 4-bromo-2,3-dichloro-6-methyl aniline

This material was prepared from 4-bromo-5-chloro-2-methyl aniline by chlorination with N-chlorosuccinimide. The product was isolated as a solid, m.p. 66°–68° C. The product was characterized by IR and $^1$H NMR spectroscopy and combustion analysis.

EXAMPLE 80

Preparation of 2,3-dichloro-6-methyl aniline

A slurry of 6.50 g (25.5 mmol) of 2,3-dichloro-4-bromo-6-methyl aniline and 8.37 g (102 mmol) of sodium acetate in 120 ml of acetic acid-ethanol (1:1, v/v) was treated with 0.65 g of 5% palladium on carbon. The mixture was hydrogenated in a Parr hydrogenation apparatus at an initial pressure of 50 psi for 10 minutes. The reaction mixture was filtered, and the filtrate was concentrated by evaporation at reduced pressure. The residue was partitioned between ether and water, and the organic layer was washed with 5% aqueous sodium hydroxide, dried and evaporated at reduced pressure. The residue was purified by Kugelrohr distillation to afford 4.00 g (89%) of the desired product as a colorless oil, b.p. 60°–70° C. (0.15 mm). IR and $^1$H NMR spectra were in agreement with the assigned structure.

Analysis: Calculated for $C_7H_7Cl_2N$: C, 47.76; H, 4.01; N, 7.95; Found: C, 48.11; H, 4.04; N, 8.19.

EXAMPLE 81

Preparation of 2-amino-3-chlorobenzyl alcohol

A solution of 28.9 g (155 mmol) of methyl 3-chloroanthranilate in 100 ml of ether was added dropwise to a stirred suspension of 7.67 g (202 mmol) of lithium aluminum hydride in 400 ml of ether. After stirring for 5 hours at room temperature, the grey mixture was treated sequentially with 7.7 ml of water, 7.7 ml of 15% sodium hydroxide and 23 ml of water. The reaction mixture was filtered, and the filtrate was evaporated at reduced pressure. The oily residue was dissolved in ether, and precipitation of the product was induced by addition of hexane. The product was collected by filtration to yield a tan solid in 67% yield, m.p. 56°–68° C. IR and $^1$H NMR spectra were in agreement with the assigned structure.

Analysis: Calculated for $C_7H_8ClNO$: C, 53.35; H, 5.12; N, 8.88; Found: C, 53.16; H, 4.84; N, 9.28.

EXAMPLE 82

Preparation of 2-chloro-6-methoxymethylaniline

A solution of 4.00 g (25.4 mmol) of 2-amino-3-chlorobenzyl alcohol in 30 ml of dry THF was cooled to −78° C., treated with 16.7 ml (26.7 mmol) of 1.60M n-butyllithium in hexane, warmed to 0°–5° C., treated with 3.61 g (25.4 mmol) of methyl iodide and heated at reflux for 5.5 hours. The solvent was removed by evaporation at reduced pressure. The residue was partitioned between 175 ml of ether and water, and the organic phase was separated and dried ($MgSO_4$). The solvent was removed by evaporation at reduced pressure, and the residue was purified by HPLC eluting with ETOAc (5:95, v/v) to afford 1.1 g of the desired product as a pale brown oil. IR and $^1$H NMR spectra were in agreement with the assigned structure.

Analysis: Calculated for $C_8H_{10}ClNO$: C, 56.00; H, 5.87; N, 8.16; Found: C, 56.25; H, 5.98; N, 8.28.

EXAMPLE 83

Preparation of 2-acetoxymethyl-6-chloro aniline

This material was prepared from 2-amino-3-chlorobenzyl alcohol and acetyl chloride by the general procedure outlined in Example 82. The product was isolated as an amber oil and was characterized by IR and $^1$H NMR spectroscopy and combustion analysis.

EXAMPLE 84

Preparation of 2-benzyloxymethyl-6-chloro aniline

This material was prepared from 2-amino-3-chlorobenzyl alcohol and benzyl bromide by the general procedure outlined in Example 82. The product was purified by Kugelrohr distillation to yield an oil, bp 118°–125° C. (0.1 mm). The product was characterized by IR and $^1$H NMR spectroscopy.

EXAMPLE 85

Preparation of N-v butoxycarbony-2-fluoro aniline

A solution of 2-fluoroaniline (30.0 g, 0.27 mol) and di-t-butylcarbonate (66.5 g, 0.30 mol) in 100 ml of THF was heated at reflux for 4 hours. The solvent was removed by evaporation at reduced pressure, and the residue was partitioned between 1M aqueous citric acid and ethyl acetate. The organic phase was washed with saturated aqueous NaCl. The solvent was removed to afford the desired product with was used without further purification. IR and $^1$H NMR spectra were in agreement with the assigned structure.

Analysis: Calculated for $C_{11}H_{14}FNO_2$: C, 62.55; H, 6.68; N, 6.63; Found: C, 62.45; H, 6.39; N, 6.21.

EXAMPLE 86

Preparation of 2-fluoro-6-methylaniline

A solution of 8.15 g (38.5 mmol) of N-t-butoxycarbonyl-2-fluoroaniline in 30 ml of dry THF was cooled to −70° C., and 46.3 ml (93 mmol) of 2.0M t-butyllithium in pentane was added dropwise at a rate sufficient to maintain the temperature below −65° C. When the addition was complete the reaction mixture was stirred at −70° C. for 15 minutes, warmed to −20° C. and stirred for 2.5 hours. A solution of 6.8 g (30 mmol) of methyl iodide in THF was added and the reaction was allowed to warm to room temperature. The reaction mixture was partitioned between ether and water, and the organic layer was washed with saturated aqueous NaCl and dried (MgSO$_4$). Evaporation at reduced pressure gave a yellow solid which was added to 25 ml of 3N HCl and heated at reflux for 3 hours. After cooling to room the pH of the solution was adjusted to pH 7, and the solution was extracted twice with methylene chloride. The combined organic phases were washed with water and dried (MgSO$_4$). Evaporation at reduced pressure gave a yellow oil which was Kugelrohr distilled to yield 3.8 g (80%) of the desired product as a liquid, bp 91°–93° C. (0.1 mm). IR and $^1$H NMR spectra were in agreement with the assigned structure.

Analysis: Calculated for $C_7H_8FN$: C, 67.20; H, 6.45; N, 11.20; Found: C, 67.61; H, 6.09; N, 11.53.

EXAMPLE 87

Preparation of 2-fluoro-6-methylthioaniline

This material was prepared for N-t-butoxycarbonyl-2-fluoroaniline and dimethyl disulfide following the general procedure outlined in Example 86. IR and $^1$H NMR spectra of the product were consistent with the assigned structure.

EXAMPLE 88

Preparation of 2-(2-chloro-4-trifluoromethylphenoxy)nitrobenzene

A mixture of 29.4 g (0.200 mol) of 2-fluoro nitrobenzene, 41.0 g (0.200 mol) of 2-chloro-4-trifluoromethylphenol and 30.0 g (0.220 mol) of $K_2CO_3$ in 150 ml of DMSO was heated at 100° C. for 6 hours. The reaction mixture was poured over ice and extracted with ether. The organic phase was washed with water and saturated aqueous NaCl and dried (MgSO$_4$). The solvent was removed by evaporation at reduced pressure to yield 56.1 g (88%) of the desired product as a yellow oil. IR and $^1$H NMR spectra were in agreement with the assigned structure.

Analysis: Calculated for $C_{13}H_7ClF_3NO_3$: C, 49.15; H, 2.22; N, 4.41; Found: C, 49.47; H, 2.07; N, 4.13.

EXAMPLE 89

Preparation of 2-(2-chloro-4-trifluoromethylphenoxy)aniline

Raney Nickel (4.0 g) was washed with water and added to 250 ml of ethanol. To this mixture under a nitrogen blanket was added 56 g (0.18 mol) of 2-(2-chloro-4-trifluoromethyl)phenoxy nitrobenzene. This mixture was hydrogenated in a Parr hydrogenation apparatus at an initial pressure of 50 psi. The catalyst was removed by filtration through celite and the filtrate was evaporated at reduced pressure to yeild 49.9 g (100%) of the desired product as an amber oil. IR and $^1$H NMR spectra were in agreement with the assigned structure.

Analysis: Calculated for $C_{13}H_9ClF_3NO$: C, 54.27; H, 3.15; N, 4.87; Found: C, 54.72; H, 3.01; N, 4.61.

EXAMPLE 90

Preparation of 2-(3-chloro-5-trifluoromethyl-2-pyridyloxy)nitrobenzene

This material was prepared in 63% yield from 3-chloro-2-fluoro-5-trifluoromethylpyridine and 2-nitrophenol following the general procedure outlined in Example 88. The product was isolated as an amber oil which was characterized by IR and $^1$H NMR spectroscopy.

EXAMPLE 91

Preparation of 2-(3-chloro-5-trifluoromethyl-2-pyridyloxy)aniline

This material was prepared in 61% yield by hydrogenation of 2-(3-chloro-5-trifluoromethyl-2-pyridyloxy)-nitrobenzene following the general procedure outlined in Example 89. The crude product was recrystallized from hexane to yield the desired product as white needles, m.p. 133°–135° C. IR and $^1$H NMR spectra were in agreement with the assigned structure.

Analysis: Calculated for $C_{12}H_8ClF_3N_2O$: C, 49.94; H, 2.79; N, 30.50; Found: C, 49.93; H, 2.91; N, 30.27.

EXAMPLE 92

Preparation of 2-(2-chloro-4-trifluoromethylphenoxy)-6-fluoro nitrobenzene

This material was prepared in 47% yeild from 2,6-difluoronitrobenzene and 2-chloro-4-trifluoromethylphenol following the general procedure outlined in Example 88. The product was isolated as an oil which was characterized by IR and $^1$H NMR spectroscopy.

EXAMPLE 93

Preparation of 2-(2-chloro-4-trifluoromethylphenoxy)-6-fluoroaniline

This material was prepared in 72% yield by hydrogenation of 2-(2-chloro-4-trifluoromethylphenoxy)-6-fluoro nitrobenzene following the general procedure outlined in Example 89. The crude product was Kugelrohr distilled to yield the desired product as a liquid, bp. 102°–103° C. (10 mm). IR and $^1$H NMR spectra were in agreement with the assigned structure.

Analysis: Calculated for $C_{13}H_8ClF_4NO$: C, 51.09; H, 2.64; H, 9.17; Found: C, 51.34; H, 2.41; H, 9.16.

The compounds prepared employing the above general procedures and the appropriate starting materials are tabulated in the following Tables I through XLV.

TABLE I

Structure: pyrimidine with CH₃ groups connected via N=N to C(SO₂NH-Ar)=N, where Ar is phenyl with R¹, R², R³, R⁴, R⁵ substituents.

| Compound | R¹ | R² | R³ | R⁴ | R⁵ | Melting Point | Elemental Analysis | C | H | N | Cl | S |
|---|---|---|---|---|---|---|---|---|---|---|---|---|
| 1 | H | H | H | H | H | 195°–198° C. | Calcd. for $C_{13}H_{13}N_5O_2S$: | 51.48 | 4.32 | 23.08 | | |
| | | | | | | | Found: | 50.86 | 4.26 | 23.12 | | |
| 2 | —CH₃ | H | H | H | H | 222°–224° C. | Calcd. for $C_{14}H_{15}N_5O_2S$: | 52.99 | 4.76 | 22.06 | | |
| | | | | | | | Found: | 52.75 | 4.79 | 22.25 | | |
| 3 | —OH | H | H | H | H | >150° C. (decomp.) | Calcd. for $C_{13}H_{13}N_5O_3S$: | 48.90 | 4.10 | 21.92 | | |
| | | | | | | | Found: | 48.45 | 4.15 | 21.77 | | |
| 4 | —OCH₃ | H | H | H | H | 208°–210.5° C. | Calcd. for $C_{14}H_{15}N_5O_3S$: | 50.44 | 4.54 | 21.00 | | |
| | | | | | | | Found: | 50.17 | 4.54 | 21.12 | | |
| 5 | —NHCH₃ | H | H | H | H | 227°–228° C. | Calcd. for $C_{14}H_{16}N_6O_2S$: | 50.59 | 4.85 | 25.28 | | |
| | | | | | | | Found: | 49.70 | 4.87 | 25.12 | | |
| 6 | —I | H | H | H | H | 189°–192° C. | Calcd. for $C_{13}H_{12}IN_5O_2S$: | 36.38 | 2.82 | 16.31 | | |
| | | | | | | | Found: | 36.61 | 2.81 | 16.15 | | |
| 7 | —Cl | H | H | H | H | 188°–189.5° C. | Calcd. for $C_{13}H_{12}ClN_5O_2S$: | 46.23 | 3.58 | 20.73 | 10.50 | 9.49 |
| | | | | | | | Found: | 46.09 | 3.58 | 20.89 | 10.34 | 9.37 |
| 8 | —F | H | H | H | H | 189°–190° C. | Calcd. for $C_{13}H_{12}FN_5O_2S$: | 48.59 | 3.76 | 21.79 | | 9.98 |
| | | | | | | | Found: | 48.79 | 3.74 | 21.88 | | 9.86 |
| 9 | —SCH₃ | H | H | H | H | 142°–144° C. | Calcd. for $C_{14}H_{15}N_5O_2S_2$: | 48.13 | 4.33 | 20.04 | | |
| | | | | | | | Found: | 47.99 | 4.28 | 20.40 | | |
| 10 | —COOCH₃ | H | H | H | H | 169.5°–170.5° C. | Calcd. for $C_{15}H_{15}N_5O_4S$: | 49.86 | 4.18 | 19.38 | | 8.87 |
| | | | | | | | Found: | 49.68 | 4.13 | 19.35 | | 8.69 |
| 11 | —COOH | H | H | H | H | 247°–248° C. | Calcd. for $C_{14}H_{13}N_5O_4S$: | 48.41 | 3.77 | 20.16 | | 9.23 |
| | | | | | | | Found: | 47.87 | 3.66 | 20.27 | | 8.87 |
| 12 | —NO₂ | H | H | H | H | 140° C. | Calcd. for $C_{13}H_{12}N_6O_4S$: | 44.83 | 3.47 | 24.13 | | 9.21 |
| | | | | | | | Found: | 44.91 | 3.48 | 24.11 | | 9.11 |
| 13 | —CF₃ | H | H | H | H | 198.5–200.5° C. | Calcd. for $C_{14}H_{12}F_3N_5O_2S$: | 45.28 | 3.26 | 18.86 | | 8.63 |
| | | | | | | | Found: | 45.39 | 3.16 | 18.74 | | 8.87 |
| 14 | —CN | H | H | H | H | 237.5–239° C. | Exact mass calcd for $C_{14}H_{12}N_6O_2S$: | | | 328.0742 | | |
| | | | | | | | Found: | | | 328.0748 | | |
| | | | | | | | Analysis | C | H | N | Cl | S |
| 15 | —SO₂NMe₂ | H | H | H | H | 91° C. | Calcd. for $C_{15}H_{18}N_6O_4S_2$: | 43.89 | 4.42 | 20.47 | | 15.62 |
| | | | | | | | Found: | 44.25 | 4.37 | 20.21 | | 15.23 |
| 16 | —SO₂N(Me)Et | H | H | H | H | 80° C. | Calcd. for $C_{16}H_{20}N_6O_4S_2$: | 45.27 | 4.75 | 19.80 | 15.11 | 14.77 |
| | | | | | | | Found: | 45.07 | 4.64 | 19.60 | | |
| 17 | H | —Cl | H | H | H | 231°–232.5° C. | Exact mass calcd. for $C_{13}H_{12}ClN_5O_2S$: | | | 337.0400 | | |
| | | | | | | | Found: | | | 337.0415 | | |
| 18 | H | H | —Cl | H | H | 237°–239° C. | Exact mass calcd. for $C_{13}H_{12}ClN_5O_2S$: | | | 337.0400 | | |
| | | | | | | | Found: | | | 337.0411 | | |
| | | | | | | | Analysis | C | H | N | Cl | S |
| 19 | —Cl | —Cl | H | H | H | 214.5–216.5° C. | Calcd. for $C_{13}H_{11}Cl_2N_5O_2S$: | 41.95 | 2.98 | 18.81 | 19.05 | 8.61 |
| | | | | | | | Found: | 42.02 | 3.03 | 18.99 | 18.24 | 8.30 |
| 20 | —Cl | H | —Cl | H | H | 176°–177.5° C. | Calcd. for $C_{13}H_{11}Cl_2N_5O_2S$: | 41.95 | 2.98 | 18.81 | 19.05 | 8.61 |

TABLE I-continued

[Structure: pyrimidine ring with CH3 groups bonded to N-N=C(SO2NH-phenyl) where phenyl has substituents R1, R2, R3, R4, R5]

| Compound | R1 | R2 | R3 | R4 | R5 | Melting Point | Elemental Analysis | | | | | |
|---|---|---|---|---|---|---|---|---|---|---|---|---|
| | | | | | | | | C | H | N | Cl | S |
| 21 | —Cl | H | H | H | H | 250°–253° C. | Found:<br>Exact mass calcd. for C13H11Cl2N5O2S:<br>Found:<br>Analysis | 42.24<br>371.0010<br>370.9997 | 2.94 | 18.90 | 18.83 | 8.82 |
| 22 | —Cl | H | H | H | —Cl | 260.5°–262.5° C. | Calcd. for C13H11Cl2N5O2S:<br>Found: | 41.95<br>42.12 | 2.98<br>2.94 | 18.81<br>19.01 | 19.05<br>18.89 | 8.61<br>8.57 |
| 23 | H | —Cl | —Cl | H | H | 240°–242° C. | Calcd. for C13H11Cl2N5O2S:<br>Found: | 41.95<br>42.32 | 2.98<br>2.87 | 18.81<br>18.82 | 19.05<br>18.65 | 8.61<br>8.42 |
| 24 | H | —Cl | H | —Cl | H | 273.5°–275.5° C. | Calcd. for C13H11Cl2N5O2S:<br>Found: | 41.95<br>42.30 | 2.98<br>2.89 | 18.81<br>18.42 | 19.05<br>18.85 | 8.61<br>8.49 |
| 25 | —F | H | H | H | —F | 229.5°–231° C. | Exact mass calcd. for C13H11F2N5O2S:<br>Found:<br>Analysis | 339.0630<br>339.0602<br>C | H | N | Cl | S |
| 26 | —COOMe | H | H | H | F | 181.5°–183.5° C. | Calcd. for C15H14FN5O4S:<br>Found: | 47.49<br>47.65 | 3.72<br>3.60 | 18.46<br>18.19 | | 8.45<br>8.35 |
| 27 | —COOH | H | H | H | F | 228.5°–230° C. | Calcd. for C14H12FN5O4S:<br>Found: | 46.03<br>45.56 | 3.31<br>3.26 | 19.17<br>19.05 | | 8.78<br>8.50 |
| 28 | —SO2NMe2 | H | H | —CF3 | H | 174.5°–176.5° C. | Calcd. for C16H17F3N6O4S2:<br>Found: | 40.16<br>40.16 | 3.58<br>3.49 | 17.56<br>17.39 | | 13.40<br>13.17 |
| 29 | —F | H | —F | H | H | 223°–224.5° C. | Calcd. for C13H11F2N5O2S:<br>Found: | 46.02<br>46.19 | 3.27<br>3.37 | 20.63<br>20.59 | | |
| 30 | —Cl | H | H | H | H | 203°–205° C. | Calcd. for C13H11ClFN5O2S:<br>Found: | 43.89<br>44.02 | 3.12<br>3.12 | 19.68<br>19.89 | | |
| 31 | —Cl | H | H | H | —CH3 | 230°–231.5° C. (decomp.) | Calcd. for C14H14ClN5O2S:<br>Found: | 47.82<br>47.87 | 3.98<br>4.06 | 19.07<br>19.66 | | |
| 32 | —CH3 | H | H | H | —CH3 | 263°–266° C. (decomp.) | Calcd. for C15H17N5O2S:<br>Found: | 54.31<br>53.59 | 5.23<br>5.07 | 21.23<br>20.65 | | |
| 33 | —CH2CH3 | H | H | H | —CH2CH3 | 248°–249.5° C. (decomp.) | Calcd. for C17H21N5O2S:<br>Found: | 56.83<br>57.06 | 5.84<br>5.98 | 19.48<br>19.40 | | |
| 34 | —CF3 | H | —Cl | H | H | 189°–193° C. (decomp.) | Calcd. for C14H11ClF3N5O2S:<br>Found: | 41.41<br>41.78 | 2.71<br>2.73 | 17.25<br>17.23 | | |
| 35 | —Cl | H | —Cl | H | —Cl | >200° C. (decomp.) | Calcd. for C13H10Cl3N5O2S:<br>Found: | 38.40<br>38.36 | 2.48<br>2.48 | 17.22<br>17.14 | | |
| 36 | —COOiPr | H | H | H | H | 130°–132° C. | Calcd. for C17H19N5O4S:<br>Found: | 52.43<br>51.83 | 4.92<br>4.77 | 17.98<br>17.70 | | |
| 37 | —CONH2 | H | H | H | H | 258°–260° C. | Calcd. for C14H14N6O3S:<br>Found: | 48.55<br>48.58 | 4.07<br>4.00 | 24.26<br>24.01 | | |
| 38 | —Br | H | H | H | —Br | 285°–287° C. | Calcd. for C13H11Br2N5O2S:<br>Found: | 33.86<br>33.92 | 2.40<br>2.42 | 15.18<br>15.41 | | |
| 39 | —Br | H | H | H | —Cl | >230° C. (decomp.) | Calcd. for C13H11BrClN5O2S:<br>Found: | 37.47<br>37.50 | 2.66<br>2.64 | 16.80<br>16.87 | | |
| 40 | —Br | H | —Cl | H | H | 177°–179° C. | Calcd. for C13H11BrClN5O2S:<br>Found: | 37.47 | 2.66 | 16.80 | | |

TABLE I-continued

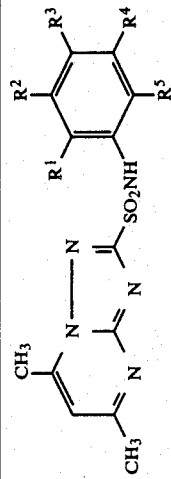

| Compound | R¹ | R² | R³ | R⁴ | R⁵ | Melting Point | Elemental Analysis | | | | | |
|---|---|---|---|---|---|---|---|---|---|---|---|---|
| | | | | | | | | C | H | N | Cl | S |
| 41 | —Br | H | H | H | H | 188°–190° C. | Found: | 37.45 | 2.67 | 16.64 | | |
| | | | | | | | Calcd. for $C_{13}H_{12}BrN_5O_2S$: | 40.85 | 3.16 | 18.32 | | |
| 42 | —CONMe₂ | H | H | H | H | 193°–194° C. | Found: | 41.09 | 3.12 | 18.19 | | |
| | | | | | | | Calcd. for $C_{16}H_{18}N_6O_3S$: | 51.33 | 4.85 | 22.44 | | |
| 43 | —CONMe₂ | H | —Cl | H | H | 194°–195° C. | Found: | 51.08 | 4.65 | 22.12 | | |
| | | | | | | | Calcd. for $C_{16}H_{17}ClN_6O_3S$: | 47.00 | 4.19 | 20.55 | | |
| 44 | —Cl | H | F | H | —Cl | 271°–273° C. (decomp.) | Found: | 47.16 | 4.07 | 20.50 | | |
| | | | | | | | Calcd. for $C_{13}H_{10}Cl_2FN_5O_2S$: | 40.02 | 2.58 | 17.94 | | |
| 45 | —SO₂Me | H | H | H | H | 181°–183° C. | Found: | 40.13 | 2.65 | 18.04 | | |
| | | | | | | | Calcd. for $C_{14}H_{15}N_5O_4S_2$: | 44.09 | 3.96 | 18.35 | | |
| 46 | —Cl | —Me | H | H | —Cl | 280° C. (decomp.) | Found: | 43.64 | 3.84 | 18.16 | | |
| | | | | | | | Calcd. for $C_{14}H_{13}Cl_2N_5O_2S$: | 43.54 | 3.39 | 18.13 | | |
| 47 | —Cl | H | —Me | H | —Cl | 245°–248° C. | Found: | 43.45 | 3.39 | 18.15 | | |
| | | | | | | | Calcd. for $C_{14}H_{13}Cl_2N_5O_2S$: | 43.54 | 3.39 | 18.13 | | |
| 48 | —Cl | H | —Me | H | H | 229°–231° C. | Found: | 43.57 | 3.37 | 18.21 | | |
| | | | | | | | Calcd. for $C_{14}H_{14}ClN_5O_2S$: | 48.00 | 4.01 | 19.90 | | |
| 49 | —NO₂ | H | H | H | —CH₃ | 244°–246° C. | Found: | 48.01 | 3.97 | 20.05 | | |
| | | | | | | | Exact mass calcd. for $C_{14}H_{14}N_6O_4S$: | | | 362.0799 | | |
| | | | | | | | Found: | | | 362.0807 | | |
| | | | | | | | Analysis | | | | | |
| 50 | —COOMe | H | H | H | —CH₃ | 190°–192.5° C. | Calcd. for $C_{16}H_{17}N_5O_4S$: | 51.19 | 4.57 | 18.65 | | |
| | | | | | | | Found: | 51.22 | 4.58 | 18.46 | | |
| 51 | —COO—i-Pr | H | H | H | F | 167°–168° C. | Calcd. for $C_{17}H_{18}FN_5O_4S$: | 50.12 | 4.45 | 17.18 | | |
| | | | | | | | Found: | 50.09 | 4.39 | 17.28 | | |
| 52 | —Cl | H | H | —CF₃ | H | 221.5°–224° C. | Calcd. for $C_{14}H_{10}ClF_3N_5O_2S$: | 41.43 | 2.74 | 17.24 | | |
| | | | | | | | Found: | 41.73 | 2.71 | 17.08 | | |
| 53 | —I | H | H | H | —Cl | >258° C. (decomp.) | Calcd. for $C_{13}H_{11}ClIN_5O_2S$: | 33.68 | 2.39 | 15.10 | | |
| | | | | | | | Found: | 33.66 | 2.38 | 15.03 | | |
| 54* | —Cl | H | H | H | —F | 223°–225.5° C. (decomp.) | Calcd. for $C_{13}H_{11}ClFN_5O_2S$: | 43.89 | 3.12 | 19.68 | | |
| | | | | | | | Found: | 43.20 | 2.89 | 19.41 | | |
| 55 | SCF₃ | H | H | H | H | 175°–178° C. | Calcd. for $C_{14}H_{12}F_3N_5O_2S_2$ | 41.68 | 2.97 | 17.35 | | |
| | | | | | | | Found: | 40.84 | 2.95 | 16.61 | | |
| 56 | COO—t-Bu | H | H | H | F | 151°–153° C. (decomp.) | Calcd. for $C_{18}H_{20}FN_5O_4S$: | 51.30 | 4.78 | 16.61 | | |
| | | | | | | | Found: | 50.90 | 4.69 | 16.49 | | |
| 57 | SO₂CF₃ | H | H | H | H | 68–70° C. | Calcd. for $C_{14}H_{12}F_3N_5O_4S_2$: | 38.62 | 2.75 | 16.09 | | |
| | | | | | | | Found: | 39.10 | 2.71 | 15.87 | | |
| 58 | Br | H | H | H | CH₃ | 225–228° C. | Calcd. for $C_{14}H_{14}BrN_5O_2S$: | 42.44 | 3.56 | 17.67 | | |
| | | | | | | | Found: | 42.56 | 3.55 | 17.66 | | |
| 59 | SCF₂CF₂H | H | H | H | H | 162.5–164° C. | Calcd. for $C_{15}H_{13}F_4N_5O_2S_2$: | 41.38 | 3.01 | 16.08 | | | 14.73 |
| | | | | | | | Found: | 41.54 | 2.88 | 16.06 | | 14.57 |
| 60 | SOCF₂CF₂H | H | H | H | H | 223–224° C. | Calcd. for $C_{15}H_{13}F_4N_5O_3S_2$: | 39.91 | 2.90 | 15.51 | | 14.21 |
| | | | | | | | Found: | 39.88 | 2.83 | 15.37 | | 14.15 |
| 61 | CONH₂ | H | H | H | CH₃ | 231–232° C. | Calcd. for $C_{15}H_{16}N_6O_3S·H_2O$: | 47.61 | 4.80 | 22.20 | | |

TABLE I-continued

Structure:

$$\text{CH}_3-\text{pyrimidine-N=N-C(=N)-NH-SO}_2-\text{phenyl(R}^1,R^2,R^3,R^4,R^5)$$

| Compound | R¹ | R² | R³ | R⁴ | R⁵ | Melting Point | Elemental Analysis | | |
|---|---|---|---|---|---|---|---|---|---|
| 62 | CONMe₂ | H | H | H | CH₃ | 225–257° C. | Found: | 47.74 | 4.71 | 22.04 |
| 63 | Cl | H | H | H | Ph | 256,260° C. (decomp.) | Calcd. for C₁₇H₁₆N₆O₃S: | 52.57 | 5.19 | 21.63 |
|  |  |  |  |  |  |  | Found: | 52.15 | 5.15 | 21.39 |
| 64 | COO-i-Pr | H | H | H | CH₃ | 178–179° C. | Calcd. for C₁₉H₁₆ClN₅O₂S: | 55.14 | 3.90 | 16.92 |
|  |  |  |  |  |  |  | Found: | 54.68 | 3.89 | 16.96 |
| 65 | CH₃ | Cl | H | H | CH₃ | 279–282° C. (decomp.) | Calcd. for C₁₈H₂₁N₅O₄S: | 53.59 | 5.25 | 17.35 |
|  |  |  |  |  |  |  | Found: | 53.32 | 5.18 | 17.15 |
| 66 | SCH₂CH=CH₂ | H | H | H | H | 113–114° C. | Calcd. for C₁₅H₁₆ClN₅O₂S: | 49.25 | 4.41 | 19.14 |
|  |  |  |  |  |  |  | Found: | 49.05 | 4.38 | 19.00 |
| 67 | SCH₂CH₂CH₃ | H | H | H | H | 124° (decomp.) | Calcd. for C₁₆H₁₇N₅O₂S₂: | 51.17 | 4.56 | 18.65 |
|  |  |  |  |  |  |  | Found: | 51.29 | 4.63 | 18.94 |
| 68 | CH₃ | Cl | H | H | H | 223–225° C. | Calcd. for C₁₆H₁₉N₅O₂S₂: | 50.90 | 5.07 | 18.55 |
|  |  |  |  |  |  |  | Found: | 50.41 | 4.76 | 18.79 |
| 69 | SCH₃ | H | H | H | Cl | 171–172° C. | Calcd. for C₁₄H₁₄ClN₅O₂S: | 47.79 | 4.01 | 19.91 |
|  |  |  |  |  |  |  | Found: | 47.52 | 4.31 | 19.84 |
| 70 | SCH₃ | H | H | H | CH₃ | 200–202° C. | Calcd. for C₁₄H₁₄ClN₅O₂S: | 43.80 | 3.68 | 18.24 |
|  |  |  |  |  |  |  | Found: | 44.00 | 3.74 | 17.96 |
| 71 | CH=NOH | H | H | H | OCH₃ | 244–246° C. | Calcd. for C₁₅H₁₇N₅O₂S₂: | 49.56 | 4.71 | 19.27 |
|  |  |  |  |  |  |  | Found: | 49.78 | 4.49 | 18.68 |
| 72 | CO₂CH₂CH₂OEt | H | H | H | CH₃ | 78–80° C. | Calcd. for C₁₅H₁₆N₆O₄S: | 47.86 | 4.29 | 22.33 |
|  |  |  |  |  |  |  | Found: | 47.47 | 4.03 | 23.36 |
| 73 | CO₂CH₂CH₂NMe₂ | H | H | H | CH₃ | 207–208° C. | Calcd. for C₁₉H₂₃N₅O₅S: | 52.65 | 5.35 | 16.16 |
|  |  |  |  |  |  |  | Found: | 51.68 | 5.11 | 16.37 |
| 74 | Cl | Cl | H | H | CH₃ | 287–289° C. (decomp.) | Calcd. for C₁₉H₂₄N₆O₄S: | 52.76 | 5.59 | 19.43 |
|  |  |  |  |  |  |  | Found: | 52.06 | 5.48 | 19.18 |
| 75 | COOPh | H | H | H | CH₃ | 159.5–160.5° C. | Calcd. for C₁₄H₁₃Cl₂N₅O₂S: | 43.54 | 3.39 | 18.13 |
|  |  |  |  |  |  |  | Found: | 43.74 | 3.46 | 18.48 |
| 76 | CO₂CH₂CH=CH₂ | H | H | H | CH₃ | 158–158.5° C. | Calcd. for C₂₁H₁₉N₅O₄S: | 57.66 | 4.38 | 16.01 |
|  |  |  |  |  |  |  | Found: | 57.17 | 4.46 | 15.74 |
| 77 | CO₂CH₂N | H | H | H | CH₃ | 165.5–166° C. | Calcd. for C₁₈H₁₉N₅O₄S: | 53.86 | 4.77 | 17.44 |
|  |  |  |  |  |  |  | Found: | 53.47 | 4.63 | 17.54 |
| 78 | CO₂N=C(CH₃)₂ | H | H | H | CH₃ | 91–94° C. | Calcd. for C₂₁H₂₀N₆O₄S: | 55.74 | 4.46 | 18.57 |
|  |  |  |  |  |  |  | Found: | 55.82 | 4.43 | 18.32 |
| 79 | CH=N-OCH₃ | H | H | H | OCH₃ | 227–229° C. | Calcd. for C₁₈H₂₀N₆O₄S: | 51.91 | 4.84 | 20.18 |
|  |  |  |  |  |  |  | Found: | 51.51 | 4.68 | 19.70 |
| 80 | S–t-Bu | H | H | H | H | 144–146° C. | Calcd. for C₁₆H₁₈N₆O₄S: | 49.22 | 4.65 | 21.53 |
|  |  |  |  |  |  |  | Found: | 49.00 | 4.63 | 21.24 |
| 81 | Cl | H | H | COOMe | H | 175–177° C. | Calcd. for C₁₇H₂₁N₅O₂S₂: | 52.15 | 5.41 | 17.89 |
|  |  |  |  |  |  |  | Found: | 52.31 | 5.34 | 17.92 |
| 82 | Cl | COOMe | H | H | Cl | 217–221° C. (decomp.) | Calcd. for C₁₅H₁₄ClN₅O₄S: | 45.52 | 3.57 | 17.69 |
|  |  |  |  |  |  |  | Found: | 45.42 | 3.45 | 17.66 |
|  |  |  |  |  |  |  | Calcd. for C₁₅H₁₃Cl₂N₅O₄S: | 41.87 | 3.05 | 16.27 |
|  |  |  |  |  |  |  | Found: | 41.96 | 3.10 | 16.22 |

TABLE I-continued

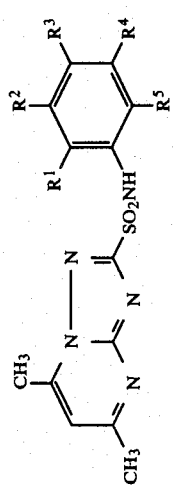

| Compound | R¹ | R² | R³ | R⁴ | R⁵ | Melting Point | Elemental Analysis | | |
|---|---|---|---|---|---|---|---|---|---|
| 83 | Cl | CF₃ | H | H | Cl | 286–290° C. (decomp.) | Calcd. for $C_{14}H_{10}Cl_2F_3N_5O_2S$: Found: | 38.20 38.36 | 2.29 2.29 | 15.90 16.63 |
| 84 | Cl | H | H | CO₂—i-Pr | H | 182–185° C. | Calcd. for $C_{17}H_{18}ClN_5O_4S$: Found: | 48.17 48.31 | 4.28 4.17 | 16.52 16.51 |
| 85 | NO₂ | H | H | CH₃ | CH₃ | 254–257° C. (decomp.) | Calcd. for $C_{15}H_{16}N_6O_4S$: Found: | 47.87 47.52 | 4.29 4.01 | 22.32 22.47 |
| 86 | Br | COOMe | H | H | CH₃ | 229–231° C. | Calcd. for $C_{16}H_{16}BrN_5O_4S$: Found: | 42.30 42.29 | 3.55 3.45 | 15.41 15.68 |
| 87 | Br | COO—i-Pr | H | H | CH₃ | 208–211° C. | Calcd. for $C_{18}H_{20}BrN_5O_4S$: Found: | 44.82 45.09 | 4.18 4.11 | 14.51 14.39 |
| 88 | Br | COO—t-Bu | H | H | CH₃ | 181–183° C. (decomp.) | Calcd. for $C_{19}H_{22}BrN_5O_4S$: Found: | 45.98 45.61 | 4.47 4.17 | 14.10 13.84 |
| 89 | COMe | H | H | H | H | 166–168° C. | Calcd. for $C_{15}H_{15}N_5O_3S$: Found: | 52.16 52.07 | 4.38 4.19 | 20.28 20.37 |
| 90 | F | F | H | F | F | 148–149° C. | Calcd. for $C_{13}H_9F_4N_5O_2S$: Found: | 41.60 42.25 | 2.42 2.50 | 18.66 18.52 |
| 91 | CH₂OCH₃ | H | H | H | Cl | 201–202° C. | Calcd. for $C_{15}H_{16}ClN_5O_3S$: Found: | 47.19 47.07 | 4.22 4.16 | 18.33 18.87 |
| 92 | CH₂OCHPh | H | H | H | Cl | 169–171° C. | Calcd. for $C_{21}H_{20}ClN_5O_3S$: Found: | 55.08 54.99 | 4.40 4.38 | 15.29 15.30 |
| 93 | CH₂OH | H | H | H | Cl | 208–209° C. | Calcd. for $C_{14}H_{14}ClN_5O_3S.H_2O$: Found: | 43.60 43.50 | 4.18 3.75 | 18.14 18.43 |
| 94 | CH₂OAc | H | H | H | Cl | 214–217° C. | Calcd. for $C_{16}H_{16}ClN_5O_4S$: Found: | 46.89 46.60 | 3.94 3.80 | 17.08 17.73 |
| 95 | COPh | H | H | H | H | 169–170° C. | Calcd. for $C_{20}H_{17}N_5O_3S$: Found: | 58.95 58.67 | 4.21 4.14 | 17.19 17.51 |
| 96 | SO₂Ph | H | H | H | H | 152–154° C. | Calcd. for $C_{19}H_{17}N_5O_4S_2$: Found: | 51.46 51.31 | 3.86 3.81 | 15.79 15.81 |
| 97 | ![Cl/CF₃-phenoxy] | H | H | H | H | 176–177° C. | Calcd. for $C_{20}H_{15}ClF_3N_5O_3S$: Found: | 48.24 48.11 | 3.03 3.09 | 14.06 14.49 |
| 98 | ![Cl/CF₃-phenoxy] | H | H | H | F | 211–213° C. | Calcd. for $C_{20}H_{14}ClF_4N_5O_3S$: Found: | 46.56 46.02 | 2.74 2.74 | 13.57 13.40 |

TABLE I-continued

[Structure: R¹ substituted pyridinone linked via N=N to pyrimidine (CH₃, CH₃ substituted) with SO₂NH to phenyl ring bearing R², R³, R⁴, R⁵]

For compound 99: R¹ = 3-chloro-4-(trifluoromethyl)-2-pyridinonyl group

| Compound | R¹ | R² | R³ | R⁴ | R⁵ | Melting Point | Elemental Analysis | | |
|---|---|---|---|---|---|---|---|---|---|
| 99 | [3-Cl-4-CF₃-pyridin-2(1H)-one] | H | H | H | H | 178–180° C. | Calcd. for $C_{19}H_{14}ClF_3N_6O_3S$:<br>Found: | 45.74  2.84<br>45.66  2.81 | 16.85<br>17.02 |
| 100 | Cl | H | H | COOH | H | 276–278° C. | Calcd. for $C_{14}H_{12}ClN_5O_4S$:<br>Found: | 44.04  3.17<br>44.06  3.24 | 18.34<br>18.37 |
| 101 | Br | COOH | H | H | CH₃ | 290° C. (decomp.) | Calcd. for $C_{15}H_{14}BrN_5O_4S$:<br>Found: | 40.92  3.21<br>40.51  3.11 | 15.90<br>16.01 |
| 102 | CO₂Me | H | H | CO₂Me | H | 191–194° C. | Calcd. for $C_{17}H_{17}N_5O_6S$:<br>Found: | 48.68  4.09<br>48.47  4.01 | 16.70<br>16.32 |
| 103 | COOH | H | H | H | CH₃ | 268–271° C. | Calcd. for $C_{15}H_{15}N_5O_4S \cdot \tfrac{1}{2}H_2O$:<br>Found: | 48.64  4.35<br>48.88  4.00 | 18.90<br>19.20 |
| 104 | CF₃ | H | H | H | OCH₃ | 246–249° C. | Calcd. for $C_{15}H_{14}F_3N_5O_3S$:<br>Found: | 44.91  3.49<br>44.77  3.61 | 17.47<br>17.94 |

*This compound contains 15% where $R^1 = R^3 = Cl$ and $R^5 = F$.

TABLE II

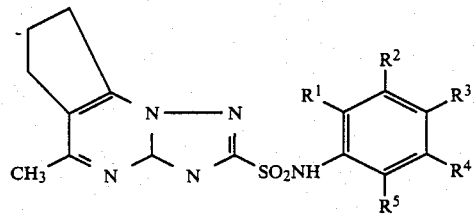

| Compound | R¹ | R² | R³ | R⁴ | R⁵ | Melting Point | Analysis | C | H | N |
|---|---|---|---|---|---|---|---|---|---|---|
| 105 | —NO$_2$ | H | H | H | H | 110°–112° C. (decomp.) | Calcd. for $C_{15}H_{14}N_6O_4S$: Found: | 48.11 46.96 | 3.73 3.54 | 22.43 21.62 |
| 106 | —CF$_3$ | H | H | H | H | ~200° C. | Calcd. for $C_{16}H_{14}F_3N_5O_2S$: Found: | 48.35 48.08 | 3.52 3.40 | 17.61 17.40 |
| 107 | —SO$_2$NMe$_2$ | H | H | H | H | 188°–189° C. (decomp.) | Calcd. for $C_{17}H_{20}N_6O_4S_2$: Found: | 46.78 46.04 | 4.58 4.85 | 19.24 18.90 |
| 108 | —Cl | H | H | H | H | 264°–266° C. | Calcd. for $C_{15}H_{13}Cl_2N_5O_2S$: Found: | 45.24 45.47 | 3.29 3.18 | 17.58 17.41 |
| 109 | —COOMe | H | H | H | H | 180°–182° C. (decomp.) | Calcd. for $C_{17}H_{17}N_5O_4S$: Found: | 52.71 52.19 | 4.42 4.28 | 18.07 18.12 |
| 110 | —COO—i-Pr | H | H | H | H | 170°–172° C. | Calcd. for $C_{19}H_{21}N_5O_4S$: Found: | 54.93 54.82 | 5.10 5.01 | 16.85 16.59 |

TABLE III

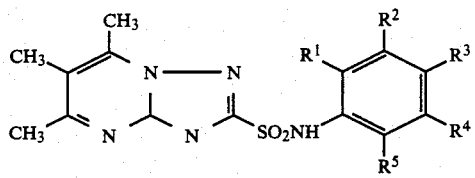

| Compound | R¹ | R² | R³ | R⁴ | R⁵ | Melting Point | Analysis | C | H | N | S | Cl |
|---|---|---|---|---|---|---|---|---|---|---|---|---|
| 111 | Cl | H | H | H | Cl | 296–298° C. | Calcd. for $C_{14}H_{13}Cl_2N_5O_2S$: Found: | 43.53 44.07 | 3.39 3.42 | 18.13 18.16 | 8.30 7.89 | 18.36 17.73 |
| 112 | CF$_3$ | H | H | H | H | 197–199° C. | Calcd. for $C_{15}H_{14}F_3N_5O_2S$: Found: | 46.75 46.54 | 3.66 3.52 | 18.17 18.30 | 8.32 8.59 | |
| 113 | Cl | H | H | H | CH$_3$ | 306–309° C. | Calcd. for $C_{15}H_{16}ClN_5O_2S$: Found: | 49.25 48.70 | 4.41 4.29 | 19.14 19.23 | 8.76 8.82 | 9.69 9.57 |

TABLE IV

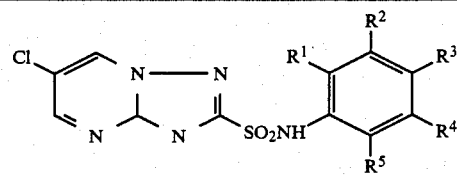

| Compound | R¹ | R² | R³ | R⁴ | R⁵ | Melting Point | Analysis | C | H | N |
|---|---|---|---|---|---|---|---|---|---|---|
| 114 | —Cl | H | H | H | —Cl | 246–248° C. | Calcd. for $C_{11}H_6Cl_3N_5O_2S$: Found: | 34.89 35.02 | 1.60 1.65 | 18.50 18.09 |
| 115 | —SMe | H | H | H | H | 159–162° C. | Calcd. for $C_{12}H_{10}ClN_5O_2S_2$: Found: | 40.50 40.39 | 2.81 2.95 | 19.60 19.90 |
| 116 | F | H | H | H | Cl | 254–257° C. | Calcd. for $C_{11}H_6Cl_2FN_5O_2S$: Found: | 36.48 37.21 | 1.67 1.91 | 19.34 18.74 |
| 117 | F | H | H | H | F | 224–226° C. | Calcd. for $C_{11}H_6ClF_2N_5O_2S$: Found: | 38.21 38.32 | 1.75 1.44 | 20.26 20.18 |
| 118 | CF$_3$ | H | H | H | H | 179–180° C. | Calcd. for $C_{12}H_7ClF_3N_5O_2S$: Found: | 38.15 38.19 | 1.87 1.59 | 18.54 18.00 |
| 119 | Cl | H | H | H | CH$_3$ | 223–226° C. | Calcd. for $C_{12}H_9Cl_2N_5O_2S$: Found: | 40.23 40.44 | 2.53 2.06 | 19.55 19.27 |
| 120 | H | H | H | H | H | 234° C. | Calcd. for $C_{11}H_8ClN_5O_2S$: Found: | 42.65 41.67 | 2.60 2.56 | 22.61 22.01 |
| 121 | Cl | H | H | H | H | 188–189° C. | Calcd. for $C_{11}H_7Cl_2N_5O_2S$: Found: | 38.39 38.26 | 2.05 1.84 | 20.35 19.98 |
| 122 | COOMe | H | H | H | H | 187–188° C. | Calcd. for $C_{13}H_{10}ClN_5O_4S$: Found: | 42.46 42.54 | 2.74 2.79 | 19.04 19.13 |

TABLE IV-continued

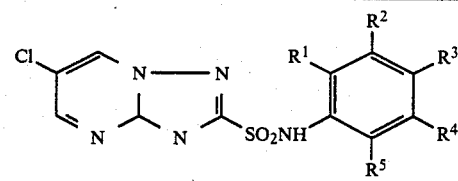

| Compound | R¹ | R² | R³ | R⁴ | R⁵ | Melting Point | Analysis | C | H | N |
|---|---|---|---|---|---|---|---|---|---|---|
| 123 | SO₂NMe₂ | H | H | H | H | 164–165° C. | Calcd. for $C_{13}H_{13}ClN_6O_4S_2$: | 37.46 | 3.14 | 20.16 |
| | | | | | | | Found: | 37.42 | 3.21 | 20.25 |
| 124 | H | Br | H | H | H | 245–247° C. | Calcd. for $C_{11}H_7BrClN_5O_2S$: | 34.00 | 1.82 | 18.02 |
| | | | | | | | Found: | 34.49 | 1.90 | 18.31 |
| 125 | H | H | CF₃ | H | H | 239–241° C. | Calcd. for $C_{12}H_7F_3ClN_5O_2S$: | 38.16 | 1.87 | 18.54 |
| | | | | | | | Found: | 38.54 | 1.83 | 18.83 |
| 126 | CONMe₂ | H | H | H | H | 162–163° C. | Calcd. for $C_{14}H_{13}ClN_6O_3S$: | 44.16 | 3.44 | 22.07 |
| | | | | | | | Found: | 44.57 | 3.47 | 22.43 |
| 127 | COOiPr | H | H | H | H | 158–160° C. | Calcd. for $C_{15}H_{14}ClN_5O_4S$: | 45.52 | 3.57 | 17.69 |
| | | | | | | | Found: | 45.54 | 3.49 | 17.93 |
| 128 | Cl | H | H | H | Ph | 243–245° C. | Calcd. for $C_{17}H_{11}Cl_2N_5O_2S$: | 48.58 | 2.64 | 16.66 |
| | | | | | | | Found: | 49.24 | 2.62 | 16.65 |
| 129 | CH₃ | H | H | H | H | 170–171° C. | Calcd. for $C_{12}H_{10}ClN_5O_2S$: | 44.52 | 3.11 | 21.63 |
| | | | | | | | Found: | 44.66 | 3.04 | 21.96 |
| 130 | H | H | n-Bu | H | H | 233–235° C. | Calcd. for $C_{15}H_{16}ClN_5O_2S$: | 49.25 | 4.41 | 19.14 |
| | | | | | | | Found: | 49.10 | 4.30 | 19.30 |
| 131 | H | OCH₃ | H | H | H | 212–215° C. | Calcd. for $C_{12}H_{10}ClN_5O_3S$: | 42.42 | 2.97 | 20.61 |
| | | | | | | | Found: | 42.33 | 2.97 | 20.65 |
| 132 | SO₂N(Me)Et | H | H | H | H | 155–157° C. | Calcd. for $C_{14}H_{15}ClN_6O_4S_2$: | 39.02 | 3.51 | 19.50 |
| | | | | | | | Found: | 39.17 | 3.47 | 19.54 |
| 133 | F | H | H | H | H | 171–172° C. | Calcd. for $C_{11}H_7ClFN_5O_2S$: | 40.32 | 2.15 | 21.37 |
| | | | | | | | Found: | 41.00 | 2.18 | 21.55 |
| 134 | H | SCH₃ | H | H | H | 210–212° C. | Calcd. for $C_{12}H_{10}ClN_5O_2S_2$: | 40.51 | 2.83 | 19.68 |
| | | | | | | | Found: | 39.29 | 2.77 | 19.70 |

TABLE V

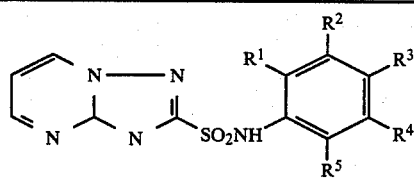

| Compound | R¹ | R² | R³ | R⁴ | R⁵ | Melting Point | Analysis | C | H | N |
|---|---|---|---|---|---|---|---|---|---|---|
| 135 | —SCH₃ | H | H | H | H | 162.5–165° C. (decomp.) | Calcd. for $C_{12}H_{11}N_5O_2S_2$: | 44.85 | 3.43 | 21.78 |
| | | | | | | | Found: | 44.35 | 3.43 | 22.08 |
| 136 | —CF₃ | H | H | H | H | 168.5–171° C. (decomp.) | Calcd. for $C_{12}H_8F_3N_5O_2S$: | 42.11 | 2.33 | 20.45 |
| | | | | | | | Found: | 41.93 | 2.28 | 19.99 |
| 137 | Cl | H | H | H | Cl | 278–280° C. | Calcd. for $C_{11}H_7Cl_2N_5O_2S$: | 38.38 | 2.03 | 20.35 |
| | | | | | | | Found: | 38.28 | 1.70 | 20.75 |
| 138 | F | H | H | H | F | 296–299° C. (decomp.) | Calcd. for $C_{11}H_7F_2N_5O_2S$: | 42.46 | 2.25 | 22.52 |
| | | | | | | | Found: | 42.27 | 2.30 | 22.60 |
| 139 | Cl | CH₃ | H | H | Cl | 252–255° C. (decomp.) | Calcd. for $C_{12}H_9Cl_2N_5O_2S$: | 40.23 | 2.51 | 19.55 |
| | | | | | | | Found: | 40.00 | 2.65 | 19.75 |
| 140 | F | CH₃ | H | H | F | 280–283° C. (decomp.) | Calcd. for $C_{12}H_9F_2N_5O_2S$: | 44.32 | 2.77 | 21.55 |
| | | | | | | | Found: | 44.10 | 2.81 | 21.55 |
| 141 | CF₃ | H | H | H | OCH₃ | 230–232° C. | Calcd. for $C_{13}H_{10}F_3N_5O_3S$: | 41.80 | 2.68 | 18.78 |
| | | | | | | | Found: | 41.40 | 2.77 | 18.69 |

TABLE VI

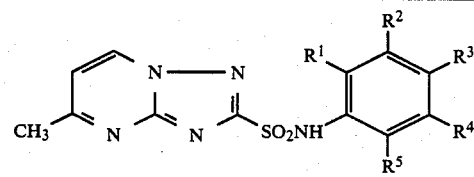

| Compound | R¹ | R² | R³ | R⁴ | R⁵ | Melting Point | Elemental Analysis | | | |
|---|---|---|---|---|---|---|---|---|---|---|
| | | | | | | | Analysis | C | H | N | S |

TABLE VI-continued

Structure: CH₃-substituted pyrimidine linked via N-N to triazole with SO₂NH-aryl group bearing R¹, R², R³, R⁴, R⁵ substituents.

| Compound | R¹ | R² | R³ | R⁴ | R⁵ | Melting Point | Elemental Analysis | C | H | N | S |
|---|---|---|---|---|---|---|---|---|---|---|---|
| 142 | —SCH₃ | H | H | H | H | 166°–169° C. | Calcd. for $C_{13}H_{13}N_5O_2S_2$: | 45.67 | 3.77 | 20.11 | |
| | | | | | | | Found: | 47.34 | 3.90 | 19.86 | |
| 143 | —Cl | H | H | H | —Cl | 228.5°–230° C. | Calcd. for $C_{12}H_9Cl_2N_5O_2S$: | 40.24 | 2.51 | 19.54 | |
| | | | | | | | Found: | 40.34 | 2.52 | 19.09 | |
| 144 | —Cl | H | H | H | —CH₃ | 211–215° C. (decomp.) | Calcd. for $C_{13}H_{12}ClN_5O_2S$: | 46.19 | 3.55 | 20.72 | |
| | | | | | | | Found: | 45.91 | 3.43 | 20.70 | |
| 145 | CF₃ | H | H | H | H | 144–145° C. | Calcd. for $C_{13}H_{10}F_3N_5O_2S$: | 43.67 | 2.79 | 19.59 | |
| | | | | | | | Found: | 43.67 | 2.74 | 19.52 | |
| 146 | COOMe | H | H | H | CH₃ | 184–186° C. | Calcd. for $C_{15}H_{15}N_5O_4S$: | 49.84 | 4.15 | 19.38 | |
| | | | | | | | Found: | 49.65 | 4.13 | 19.45 | |
| 147 | Cl | CH₃ | H | H | Cl | 140° C. (decomp.) | Calcd. for $C_{13}H_{11}Cl_2N_5O_2S$: | 41.91 | 2.95 | 18.80 | |
| | | | | | | | Found: | 41.92 | 2.83 | 18.45 | |
| 148 | Br | H | H | H | CH₃ | 106° C. (decomp.) | Calcd. for $C_{13}H_{12}BrN_5O_2S$: | 40.83 | 3.14 | 18.32 | |
| | | | | | | | Found: | 40.36 | 3.14 | 18.30 | |
| 149 | SOCF₂CF₂H | H | H | H | H | 180° C. (decomp.) | Calcd. for $C_{14}H_{11}F_4N_5O_3S_2$: | 38.40 | 2.52 | 16.03 | |
| | | | | | | | Found: | 36.70 | 2.50 | 14.69 | |
| 150 | SCH₃ | H | H | H | CH₃ | 234° C. (decomp.) | Calcd. for $C_{14}H_{15}N_5O_2S_2$: | 48.12 | 4.33 | 20.04 | |
| | | | | | | | Found: | 47.89 | 4.17 | 20.31 | |
| 151 | NO₂ | H | H | H | CH₃ | 120° C. (decomp.) | Calcd. for $C_{13}H_{12}N_6O_4S$: | 44.82 | 3.47 | 24.13 | |
| | | | | | | | Found: | 45.94 | 3.30 | 23.75 | |
| 152 | Br | H | H | H | Cl | 230–235° C. | Calcd. for $C_{12}H_9BrClN_5O_2S$: | 35.79 | 2.25 | 17.39 | |
| | | | | | | | Found: | 35.50 | 2.19 | 17.97 | |
| 153 | I | H | H | H | Cl | 210–215° C. | Calcd. for $C_{12}H_9ClIN_5O_2S$: | 32.05 | 2.02 | 15.58 | |
| | | | | | | | Found: | 32.36 | 2.29 | 15.31 | |
| 154 | Cl | H | H | H | Ph | 233–234° C. (decomp.) | Calcd. for $C_{18}H_{14}ClN_5O_2S$: | 54.07 | 3.53 | 17.52 | 8.02 |
| | | | | | | | Found: | 53.49 | 3.45 | 17.82 | 8.49 |
| 155 | Cl | Cl | H | H | CH₃ | 256–259° C. (decomp.) | Calcd. for $C_{13}H_{11}Cl_2N_5O_2S$: | 41.95 | 2.98 | 18.81 | 8.61 |
| | | | | | | | Found: | 42.00 | 2.96 | 18.75 | 8.63 |
| 156 | COOCH₃ | H | H | Cl | CH₃ | 75–80° C. | Calcd. for $C_{15}H_{14}ClN_5O_4S$: | 45.52 | 3.57 | 17.69 | 8.10 |
| | | | | | | | Found: | 45.28 | 3.57 | 17.41 | 8.07 |
| 157 | F | H | H | H | F | 245–247° C. | Calcd. for $C_{12}H_9F_2N_5O_2S$: | 44.30 | 2.79 | 21.53 | |
| | | | | | | | Found: | 44.69 | 2.80 | 21.85 | |
| 158 | F | H | H | H | Cl | 243–248° C. | Calcd. for $C_{12}H_9ClFN_5O_2S$: | 42.17 | 2.65 | 20.49 | |
| | | | | | | | Found: | 42.14 | 2.63 | 20.18 | |
| 159 | COOMe | H | H | H | F | 159–163° C. | Calcd. for $C_{14}H_{12}FN_5O_4S$: | 46.03 | 3.31 | 19.16 | |
| | | | | | | | Found: | 45.56 | 3.08 | 19.25 | |
| 160 | NO₂ | H | H | CH₃ | CH₃ | 225–230° C. | Exact mass calcd for $C_{14}H_{14}N_6O_4S$: | | | 262.0799 | |
| | | | | | | | Found: | | | 262.0802 | |
| | | | | | | | Analysis: | C | H | N | S |
| 161 | F | H | H | H | SCH₃ | 190–192° C. | Calcd. for $C_{13}H_{12}FN_5O_2S_2$: | 44.18 | 3.42 | 19.82 | |
| | | | | | | | Found: | 44.02 | 3.41 | 19.51 | |
| 162 | F | H | H | H | CH₃ | 241° C. (decomp.) | Calcd. for $C_{13}H_{12}FN_5O_2S$: | 48.59 | 3.76 | 21.80 | |
| | | | | | | | Found: | 48.31 | 3.51 | 21.62 | |
| 163 | F | F | H | F | F | 209° C. (decomp.) | Calcd. for $C_{12}H_7F_4N_5O_2S$: | 39.89 | 1.95 | 19.39 | |
| | | | | | | | Found: | 38.41 | 2.21 | 19.04 | |
| 164 | CH₂OCH₃ | H | H | H | Cl | 186–191° C. (decomp.) | Calcd. for $C_{14}H_{14}ClN_5O_3S$: | 45.72 | 3.84 | 19.03 | |
| | | | | | | | Found: | 45.46 | 3.88 | 18.97 | |
| 165 | CN | H | H | H | CH₃ | 240–245° C. (decomp.) | Calcd. for $C_{14}H_{12}N_6O_2S$: | 51.22 | 3.68 | 25.59 | 9.77 |
| | | | | | | | Found: | 49.43 | 3.58 | 24.55 | 9.47 |
| 166 | COCH₃ | H | H | H | CH₃ | 204–207° C. | Calcd. for $C_{15}H_{15}N_5O_3S$ | 52.17 | 4.38 | 20.27 | 9.28 |
| | | | | | | | Found: | 51.82 | 4.25 | 20.95 | 9.19 |
| 167 | CN | H | H | H | F | 201–203° C. | Calcd. for $C_{13}H_9FN_6O_2S$: | 46.93 | 2.73 | 25.29 | |
| | | | | | | | Found: | 46.41 | 2.81 | 26.01 | |
| 168 | CF₃ | H | H | H | F | 214–216° C. | Calcd. for $C_{13}H_9F_4N_5O_2S$: | 41.60 | 2.42 | 18.66 | |
| | | | | | | | Found: | 41.33 | 2.61 | 18.74 | |
| 169 | CF₃ | H | Cl | H | H | 170–171° C. | Calcd. for $C_{13}H_9ClF_3N_5O_2S$: | 39.85 | 2.32 | 17.88 | |
| | | | | | | | Found: | 39.96 | 2.29 | 17.30 | |
| 170 | Cl | OCH₃ | H | H | Cl | 229–231° C. (decomp.) | Calcd. for $C_{13}H_{11}Cl_2N_5O_3S$ | 40.21 | 2.86 | 18.04 | |
| | | | | | | | Found: | 40.18 | 2.99 | 17.71 | |
| 171 | F | H | H | H | OCH₃ | 212–214° C. | Calcd. for $C_{13}H_{12}FN_5O_3S$: | 46.28 | 3.58 | 20.76 | |
| | | | | | | | Found: | 46.26 | 3.56 | 20.49 | |
| 172 | F | OCH₃ | H | H | F | 219–221° C. | Calcd. for $C_{13}H_{11}F_2N_5O_3S$: | 43.94 | 3.12 | 19.71 | |
| | | | | | | | Found: | 43.79 | 3.29 | 19.48 | |
| 173 | F | H | H | H | NO₂ | 227° C. (decomp.) | Calcd. for $C_{12}H_9FN_6O_2S$: | 44.99 | 2.83 | 26.24 | |
| | | | | | | | Found: | 44.63 | 2.51 | 26.46 | |
| 174 | F | CH₃ | H | H | F | 219–221° C. | Calcd. for $C_{13}H_{11}F_2N_5O_2S$: | 46.01 | 3.27 | 20.64 | |
| | | | | | | | Found: | 46.27 | 3.47 | 20.27 | |
| 175 | CF₃ | H | H | H | OCH₃ | 209–211° C. | Calcd. for $C_{14}H_{12}F_3N_5O_3S$: | 43.41 | 3.12 | 18.08 | |
| | | | | | | | Found: | 43.31 | 3.07 | 17.97 | |
| 176 | CF₃ | H | H | H | CH₂SCH₃ | 227–229° C. | Calcd. for $C_{15}H_{14}F_3N_5O_2S_2$: | 43.16 | 3.38 | 16.78 | |
| | | | | | | | Found: | 43.24 | 3.71 | 16.37 | |

TABLE VI-continued

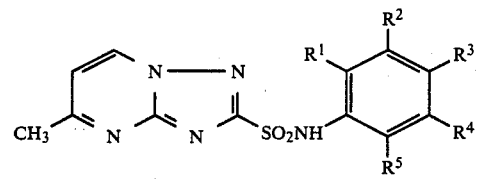

| Compound | R¹ | R² | R³ | R⁴ | R⁵ | Melting Point | Elemental Analysis | | | |
|---|---|---|---|---|---|---|---|---|---|---|
| 177 | CF₃ | H | H | H | CH₃ | 219–220° C. | Calcd. for $C_{14}H_{12}F_3N_5O_2S$: | 48.41 | 3.48 | 20.17 |
| | | | | | | | Found: | 48.14 | 3.71 | 20.34 |

TABLE VII

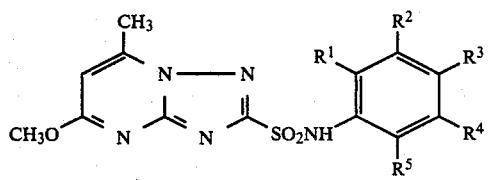

| Compound | R¹ | R² | R³ | R⁴ | R⁵ | Melting Point | Analysis | Elemental Analysis | | |
|---|---|---|---|---|---|---|---|---|---|---|
| | | | | | | | | C | H | N |
| 178 | —Cl | H | H | H | —Cl | 133°–134.5° C. | Calcd. for $C_{13}H_{11}Cl_2N_5O_3S$: | 40.22 | 2.83 | 18.03 |
| 179 | Cl | H | H | H | H | 195–196° C. | Found: | 40.05 | 2.88 | 17.86 |

TABLE VIII

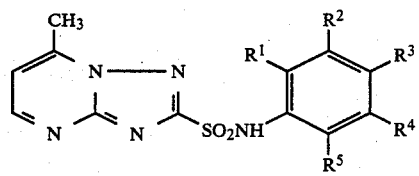

| Compound | R¹ | R² | R³ | R⁴ | R⁵ | Melting Point | Analysis | Elemental Analysis | | |
|---|---|---|---|---|---|---|---|---|---|---|
| | | | | | | | | C | H | N |
| 180 | —Cl | H | H | H | —Cl | 268°–269.5° C. (decomp.) | Calcd. for $C_{12}H_9Cl_2N_5O_2S$: | 40.24 | 2.51 | 19.54 |
| | | | | | | | Found: | 40.19 | 2.68 | 19.06 |
| 181 | F | H | H | H | Cl | 270–273° C. | Calcd. for $C_{12}H_9ClFN_5O_2S$: | 42.17 | 2.65 | 20.49 |
| | | | | | | | Found: | 42.09 | 2.63 | 19.91 |
| 182 | Cl | CH₃ | H | H | Cl | 257–163° C. | Calcd. for $C_{13}H_{11}Cl_2N_5O_2S$: | 41.91 | 2.98 | 18.82 |
| | | | | | | | Found: | 41.88 | 2.86 | 18.30 |
| 183 | CF₃ | H | H | H | H | 171–185° C. | Calcd. for $C_{13}H_{10}F_3N_5O_2S$: | 43.70 | 2.82 | 19.60 |
| | | | | | | | Found: | 42.33 | 2.66 | 19.36 |
| 184 | NO₂ | H | H | H | CH₃ | 200–205° C. | Calcd. for $C_{13}H_{12}N_6O_4S$: | 44.82 | 3.47 | 24.13 |
| | | | | | | | Found: | 44.43 | 3.43 | 23.81 |
| 185 | F | H | H | H | F | 255–257° C. | Calcd. for $C_{12}H_9F_2N_5O_2S$: | 44.30 | 2.79 | 21.53 |
| | | | | | | | Found: | 44.08 | 3.08 | 21.32 |
| 186 | Cl | H | H | H | CH₃ | 229.5–233° C. | Calcd. for $C_{13}H_{12}ClN_5O_2S$: | 46.22 | 3.58 | 20.74 |
| | | | | | | | Found: | 45.56 | 3.93 | 20.27 |
| 187 | COOCH₃ | H | H | H | F | 200–201° C. | Calcd. for $C_{14}H_{12}FN_5O_4S$: | 46.03 | 3.31 | 19.17 |
| | | | | | | | Found: | 45.75 | 3.25 | 19.20 |
| 188 | NO₂ | H | H | CH₃ | CH₃ | 233–236° C. | Calcd. for $C_{14}H_{14}N_6O_4S$: | 46.40 | 3.89 | 23.19 |
| | | | | | | | Found: | 46.29 | 3.67 | 22.84 |
| 189 | COOCH₃ | H | H | H | CH₃ | 167–167.5° C. | Calcd. for $C_{15}H_{15}N_5O_4S$: | 49.86 | 4.18 | 19.38 |
| | | | | | | | Found: | 49.78 | 4.10 | 19.16 |
| 190 | F | CH₃ | H | H | F | 256–258° C. | Calcd. for $C_{13}H_{11}F_2N_5O_2S$: | 46.02 | 3.27 | 20.64 |
| | | | | | | | Found: | 44.95 | 3.00 | 20.00 |
| 191 | CF₃ | H | H | H | OCH₃ | 260–262° C. | Calcd. for $C_{14}H_{12}F_3N_5O_3S$: | 43.41 | 3.12 | 18.08 |
| | | | | | | | Found: | 42.83 | 3.18 | 19.74 |

TABLE IX

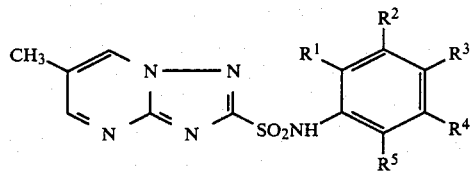

| Compound | R¹ | R² | R³ | R⁴ | R⁵ | Melting Point | Analysis | C | H | N | S |
|---|---|---|---|---|---|---|---|---|---|---|---|
| 192 | Cl | H | H | H | Cl | 249° C. (decomp.) | Calcd. for $C_{12}H_{10}Cl_2N_5O_2S$: Found: | 40.21 39.99 | 2.51 2.66 | 19.56 19.62 | 8.94 8.70 |
| 193 | F | H | H | H | F | 263–265° C. | Calcd. for $C_{12}H_9F_2N_5O_2S$: Found: | 44.30 44.37 | 2.79 2.92 | 21.53 20.98 | 9.86 9.85 |
| 194 | Cl | CH₃ | H | H | Cl | 276–280° C. | Calcd. for $C_{13}H_{11}Cl_2N_5O_2S$: Found: | 41.94 41.59 | 2.98 2.97 | 18.82 19.13 | 8.61 8.46 |
| 195 | Cl | H | H | H | CH₃ | 227–232° C. | Calcd. for $C_{13}H_{12}ClN_5O_2S$: Found: | 46.22 45.73 | 3.58 3.47 | 20.74 20.94 | 9.49 9.49 |
| 196 | NO₂ | H | H | H | CH₃ | 251–253° C. | Calcd. for $C_{13}H_{12}N_6O_4S$: Found: | 44.82 43.84 | 3.47 3.39 | 24.13 24.05 | 9.20 9.28 |
| 197 | COOMe | H | H | H | CH₃ | 208.5–210.5° C. | Calcd. for $C_{15}H_{15}N_5O_4S$: Found: | 49.85 49.96 | 4.18 4.14 | 19.38 19.75 | |

TABLE X

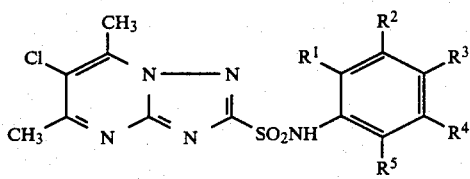

| Compound | R¹ | R² | R³ | R⁴ | R⁵ | Melting Point | Analysis | C | H | N |
|---|---|---|---|---|---|---|---|---|---|---|
| 198 | Cl | H | H | H | H | 174–176° C. | Calcd. for $C_{13}H_{11}Cl_2N_5O_2S$: Found: | 41.95 41.64 | 2.98 2.84 | 18.82 18.54 |
| 199 | Cl | CH₃ | H | H | Cl | 231–233° C. | Calcd. for $C_{14}H_{12}Cl_3N_5O_2S$: Found: | 39.96 39.94 | 2.88 2.88 | 18.65 18.15 |
| 200 | Cl | H | H | H | Cl | 171° C. (decomp.) | Calcd. for $C_{13}H_{10}Cl_3N_5O_2S$: Found: | 38.39 38.47 | 2.48 2.66 | 17.22 17.37 |

TABLE XI

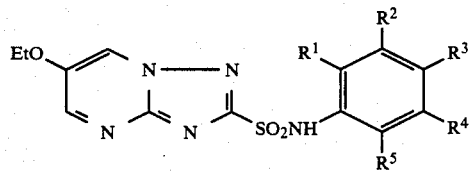

| Compound | R¹ | R² | R³ | R⁴ | R⁵ | Melting Point | Analysis | C | H | N |
|---|---|---|---|---|---|---|---|---|---|---|
| 201 | CF₃ | H | H | H | H | 75–78° C. (decomp.) | Calcd. for $C_{14}H_{12}F_3N_5O_3S$: Found: | 43.36 43.53 | 3.09 3.17 | 18.06 17.50 |
| 202 | Cl | H | H | H | CH₃ | 105–110° C. (decomp.) | Calcd. for $C_{14}H_{14}ClN_5O_3S$: Found: | 45.66 43.74 | 3.80 3.80 | 19.02 18.76 |
| 203 | Cl | H | H | H | Cl | 215–216° C. | Calcd. for $C_{12}H_{12}Cl_2N_5O_2S$: Found: | 40.21 40.13 | 2.83 2.96 | 18.04 17.99 |

TABLE XII

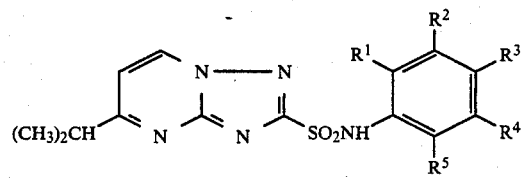

| Compound | $R^1$ | $R^2$ | $R^3$ | $R^4$ | $R^5$ | Melting Point | Elemental Analysis | C | H | N | S |
|---|---|---|---|---|---|---|---|---|---|---|---|
| 204 | Cl | H | H | H | Cl | 214–216° C. | Calcd. for $C_{14}H_{13}Cl_2N_5O_2S$: | 43.51 | 3.37 | 18.13 | 8.30 |
| | | | | | | | Found: | 43.50 | 3.28 | 17.63 | 7.96 |

TABLE XIII

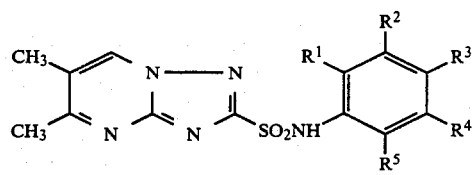

| Compound | $R^1$ | $R^2$ | $R^3$ | $R^4$ | $R^5$ | Melting Point | Elemental Analysis | C | H | N |
|---|---|---|---|---|---|---|---|---|---|---|
| 205 | Cl | H | H | H | Cl | 235–237° C. | Calcd. for $C_{13}H_{11}Cl_2N_5O_2S$: | 41.93 | 2.95 | 18.81 |
| | | | | | | | Found: | 41.80 | 3.08 | 18.65 |

TABLE XIV

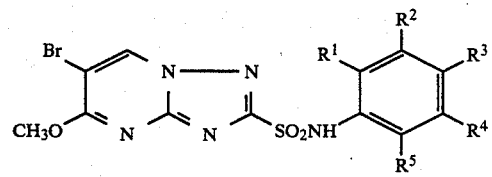

| Compound | $R^1$ | $R^2$ | $R^3$ | $R^4$ | $R^5$ | Melting Point | Elemental Analysis |
|---|---|---|---|---|---|---|---|
| 206 | Cl | H | H | H | Cl | 215–216° C. | Exact mass calcd for $C_{12}H_8BrCl_2N_5O_2S$: 438.8898 |
| | | | | | | | Found: 438.8899 |

TABLE XV

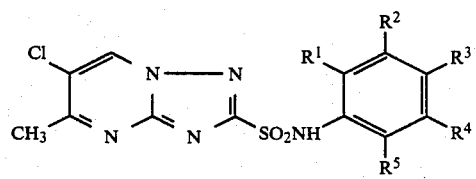

| Compound | $R^1$ | $R^2$ | $R^3$ | $R^4$ | $R^5$ | Melting Point | Elemental Analysis | C | H | N |
|---|---|---|---|---|---|---|---|---|---|---|
| 207 | Cl | H | H | H | Cl | 105–110° C. | Calcd. for $C_{12}H_8Cl_3N_5O_2S$: | 36.69 | 2.04 | 17.80 |
| | | | | | | | Found: | 36.28 | 2.15 | 18.41 |

TABLE XVI

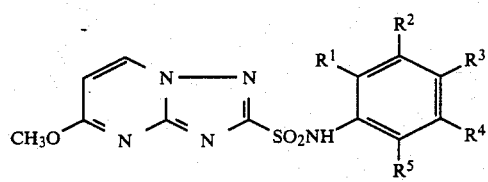

| Compound | R¹ | R² | R³ | R⁴ | R⁵ | Melting Point | Analysis | Elemental Analysis C | N | H |
|---|---|---|---|---|---|---|---|---|---|---|
| 208 | Cl | H | H | H | Cl | 235–237° C. | Calcd. for $C_{12}H_9Cl_2N_5O_3S$: | 38.51 | 2.41 | 18.72 |
|  |  |  |  |  |  |  | Found: | 38.29 | 2.44 | 18.92 |

TABLE XVII

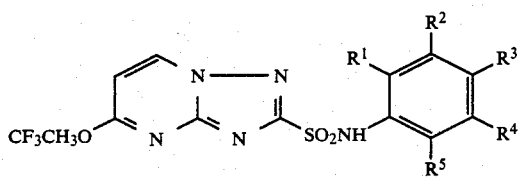

| Compound | R¹ | R² | R³ | R⁴ | R⁵ | Melting Point | Analysis | Elemental Analysis C | H | N |
|---|---|---|---|---|---|---|---|---|---|---|
| 209 | Cl | H | H | H | Cl | 266–269° C. | Calcd. for $C_{13}H_8Cl_2F_3N_5O_3S$: | 35.29 | 1.81 | 15.84 |
|  |  |  |  |  |  |  | Found: | 35.14 | 1.72 | 15.65 |

TABLE XVIII

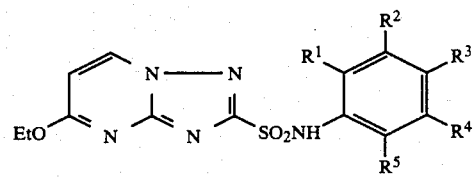

| Compound | R¹ | R² | R³ | R⁴ | R⁵ | Melting Point | Analysis | Elemental Analysis C | H | N |
|---|---|---|---|---|---|---|---|---|---|---|
| 210 | Cl | H | H | H | Cl | 230–233° C. | Calcd. for $C_{13}H_{11}Cl_2N_5O_3S$: | 40.21 | 2.83 | 18.03 |
|  |  |  |  |  |  |  | Found: | 40.10 | 2.76 | 17.87 |

TABLE XIX

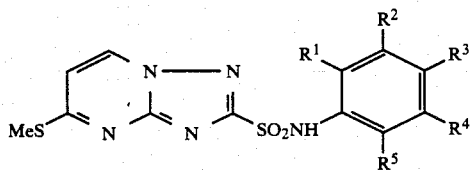

| Compound | R¹ | R² | R³ | R⁴ | R⁵ | Melting Point | Analysis | Elemental Analysis C | H | N |
|---|---|---|---|---|---|---|---|---|---|---|
| 211 | Cl | H | H | H | Cl | 239–243° C. (decomp.) | Calcd. for $C_{12}H_9Cl_2N_5O_2S_2$: Found: | 36.92 36.51 | 2.31 2.41 | 17.95 17.68 |

TABLE XX

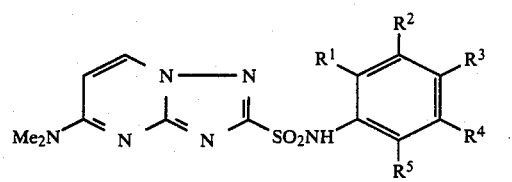

| Compound | R¹ | R² | R³ | R⁴ | R⁵ | Melting Point | Analysis | C | N | H | S |
|---|---|---|---|---|---|---|---|---|---|---|---|
| 212 | Cl | H | H | H | Cl | 310° C. | Calcd. for $C_{13}H_{12}Cl_2N_6O_2S$: | 40.31 | 3.10 | 21.71 | 8.28 |
| | | | | | | | Found: | 40.31 | 3.05 | 22.31 | 7.99 |

TABLE XXI

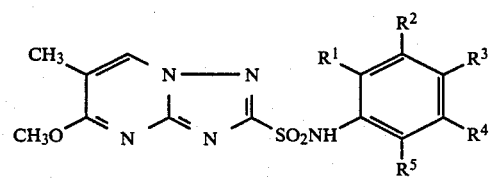

| Compound | R¹ | R² | R³ | R⁴ | R⁵ | Melting Point | Analysis | C | H | N |
|---|---|---|---|---|---|---|---|---|---|---|
| 213 | Cl | H | H | H | Cl | 235-242° C. (decomp.) | Calcd. for $C_{13}H_{11}Cl_2N_5O_3S$: Found: | 40.21 40.37 | 2.84 2.78 | 18.04 18.06 |
| 214 | F | H | H | H | F | 230-232° C. | Calcd. for $C_{13}H_{11}F_2N_5O_3S$: Found: | 43.94 43.80 | 3.12 3.10 | 19.71 20.11 |
| 215 | COOCH₃ | H | H | H | F | 195-197° C. | Calcd. for $C_{15}H_{14}FN_5O_5S$: Found: | 45.57 45.26 | 3.57 3.51 | 17.71 18.12 |
| 216 | COOCH₃ | H | H | H | CH₃ | 197-198° C. | Calcd. for $C_{16}H_{17}N_5O_5S$: Found: | 49.10 48.95 | 4.38 4.28 | 17.89 17.88 |
| 217 | CF₃ | H | H | H | H | 213-215° C. | Calcd. for $C_{14}H_{12}F_3N_5O_3S$: Found: | 43.41 42.90 | 3.12 3.21 | 18.08 18.48 |
| 218 | Cl | CH₃ | H | H | Cl | 240.5-241.5° C. | Calcd. for $C_{14}H_{13}Cl_2N_5O_3S$: Found: | 41.80 41.64 | 3.26 3.28 | 17.41 17.56 |
| 219 | F | CH₃ | H | H | F | 230-231° C. | Calcd. for $C_{14}H_{13}F_2N_5O_3S$: Found: | 45.53 45.16 | 3.55 3.55 | 18.96 19.37 |
| 220 | Cl | H | H | H | CH₃ | 213-214° C. | Calcd. for $C_{14}H_{14}ClN_5O_3S$: Found: | 45.72 45.96 | 3.84 3.90 | 19.04 19.40 |
| 221 | NO₂ | H | H | H | CH₃ | 226-228° C. | Calcd. for $C_{14}H_{14}N_6O_5S$: Found: | 44.44 44.52 | 3.73 3.75 | 22.21 22.50 |
| 222 | NO₂ | H | H | CH₃ | CH₃ | 230-231° C. | Calcd. for $C_{15}H_{16}N_6O_5S$: Found: | 45.91 45.49 | 4.11 4.04 | 21.42 21.64 |
| 223 | CF₃ | H | H | H | OCH₃ | 232-233° C. | Calcd. for $C_{15}H_{14}F_3N_5O_4S$: Found: | 43.17 43.10 | 3.38 3.42 | 16.78 16.92 |

TABLE XXII

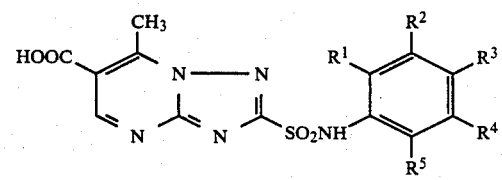

| Compound | R¹ | R² | R³ | R⁴ | R⁵ | Melting Point | Analysis | C | H | N |
|---|---|---|---|---|---|---|---|---|---|---|
| 224 | Cl | H | H | H | Cl | 220° C. (decomp.) | Calcd. for $C_{13}H_9Cl_2N_5O_4S$: Found: | 38.80 39.30 | 2.24 2.66 | 17.41 17.41 |

TABLE XXIII

| Compound | R¹ | R² | R³ | R⁴ | R⁵ | Melting Point | Analysis | C | H | N |
|---|---|---|---|---|---|---|---|---|---|---|
| 225 | Cl | H | H | H | Cl | 310–320° C. (decomp.) | Calcd. for $C_{11}H_7Cl_2N_5O_3S$:<br>Found: | 36.65<br>36.79 | 1.94<br>1.76 | 19.40<br>19.14 |

TABLE XXIV

| Compound | R¹ | R² | R³ | R⁴ | R⁵ | Melting Point | Analysis | C | H | N |
|---|---|---|---|---|---|---|---|---|---|---|
| 225 | Cl | H | H | H | Cl | 285–287° C. | Calcd. for $C_{17}H_{10}Cl_2N_6O_4S$:<br>Found: | 43.84<br>44.12 | 2.15<br>2.43 | 18.00<br>17.45 |

TABLE XXV

| Compound | R¹ | R² | R³ | R⁴ | R⁵ | Melting Point | Analysis | C | H | N |
|---|---|---|---|---|---|---|---|---|---|---|
| 227 | Cl | H | H | H | Cl | 237–239° C. | Calcd. for $C_{13}H_8Cl_2F_3N_5O_2S$:<br>Found: | 36.63<br>36.74 | 1.88<br>1.52 | 16.42<br>16.94 |
| 228 | F | H | H | H | F | 234–237° C. | Calcd. for $C_{13}H_8F_5N_5O_2S$:<br>Found: | 39.74<br>39.49 | 2.04<br>2.08 | 17.83<br>18.11 |
| 229 | Cl | CH₃ | H | H | Cl | 252–254° C. | Calcd. for $C_{14}H_{10}Cl_2F_3N_5O_2S$:<br>Found: | 38.21<br>38.09 | 2.27<br>2.34 | 15.97<br>16.40 |
| 230 | F | CH₃ | H | H | F | 243–245° C. | Calcd. for $C_{14}H_{10}F_5N_5O_2S$:<br>Found: | 41.32<br>41.21 | 2.46<br>2.51 | 17.23<br>17.49 |
| 231 | CF₃ | H | H | H | OCH₃ | 226–229° C. | Calcd. for $C_{15}H_{11}F_6N_5O_3S$:<br>Found: | 39.61<br>39.50 | 2.42<br>2.52 | 15.40<br>15.60 |

TABLE XXVI

| Compound | R¹ | R² | R³ | R⁴ | R⁵ | Melting Point | Analysis | C | H | N |
|---|---|---|---|---|---|---|---|---|---|---|
| 232 | Cl | H | H | H | Cl | >310° C. | Calcd. for $C_{12}H_9Cl_2N_5O_3S$:<br>Found: | 38.51<br>38.28 | 2.41<br>2.44 | 18.72<br>19.03 |

TABLE XXVII

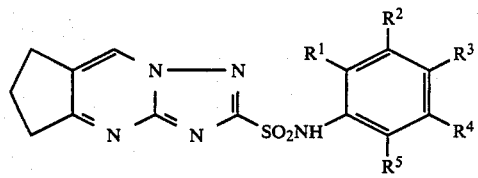

| Compound | R¹ | R² | R³ | R⁴ | R⁵ | Melting Point | Analysis | Elemental Analysis C | H | N |
|---|---|---|---|---|---|---|---|---|---|---|
| 233 | Cl | H | H | H | CH₃ | 221–224° C. (decomp.) | Calcd. for $C_{15}H_{14}ClN_5O_2S$: Found: | 49.52 49.56 | 3.85 3.85 | 19.27 18.90 |

TABLE XXVIII

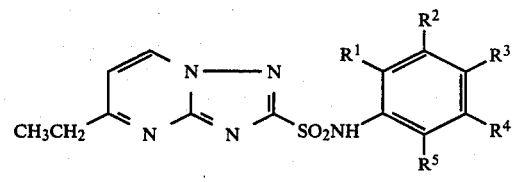

| Compound | R¹ | R² | R³ | R⁴ | R⁵ | Melting Point | Elemental Analysis | |
|---|---|---|---|---|---|---|---|---|
| 234 | Cl | H | H | H | Cl | 80–92° C. (decomp) | Exact mass calcd. for $C_{13}H_{11}Cl_2N_5O_2S$: Found: | 327.9981 327.9994 |

TABLE XXIX

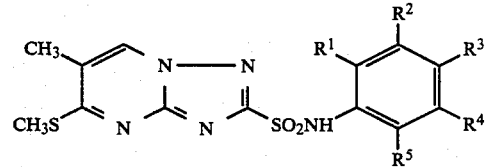

| Compound | R¹ | R² | R³ | R⁴ | R⁵ | Melting Point | Analysis | Elemental Analysis C | H | N |
|---|---|---|---|---|---|---|---|---|---|---|
| 235 | Cl | H | H | H | Cl | 254–258° C. (decomp.) | Calcd. for $C_{13}H_{11}Cl_2N_5O_2S_2$: Found: | 36.96 36.92 | 2.60 2.44 | 16.58 16.57 |

TABLE XXX

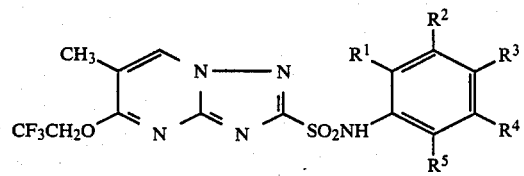

| Compound | R¹ | R² | R³ | R⁴ | R⁵ | Melting Point | Analysis | Elemental Analysis C | H | N |
|---|---|---|---|---|---|---|---|---|---|---|
| 236 | Cl | H | H | H | Cl | 250–253° C. (decomp.) | Calcd. for $C_{14}H_{10}Cl_2F_3N_5O_3S$: Found: | 36.85 36.44 | 2.19 2.07 | 15.35 15.62 |

TABLE XXXI

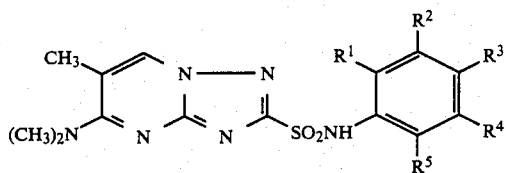

| Compound | R¹ | R² | R³ | R⁴ | R⁵ | Melting Point | Analysis | Elemental Analysis C | H | N |
|---|---|---|---|---|---|---|---|---|---|---|
| 237 | Cl | H | H | H | Cl | 270–274° C. (decomp.) | Calcd. for $C_{14}H_{14}Cl_2N_6O_2S$: Found: | 41.89 41.87 | 3.49 3.49 | 20.95 21.03 |

TABLE XXXII

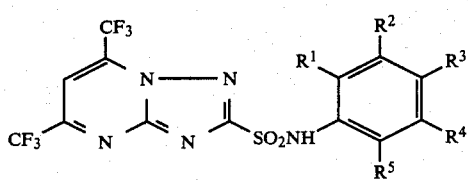

| Compound | R¹ | R² | R³ | R⁴ | R⁵ | Melting Point | Analysis | Elemental Analysis C | H | N |
|---|---|---|---|---|---|---|---|---|---|---|
| 238 | Cl | H | H | H | Cl | 286–287° C. | Calcd. for $C_{13}H_5Cl_2F_6N_5O_2S$: Found: | 32.56 32.98 | 1.04 0.70 | 14.59 14.71 |

TABLE XXXIII

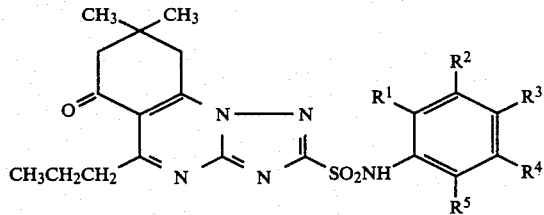

| Compound | R¹ | R² | R³ | R⁴ | R⁵ | Melting Point | Analysis | Elemental Analysis C | H | N |
|---|---|---|---|---|---|---|---|---|---|---|
| 239 | Cl | H | H | H | Cl | 284–286° C. | Calcd. for $C_{20}H_{21}Cl_2N_5O_3S$: Found: | 49.90 49.81 | 4.36 4.22 | 14.52 14.28 |

TABLE XXXIV

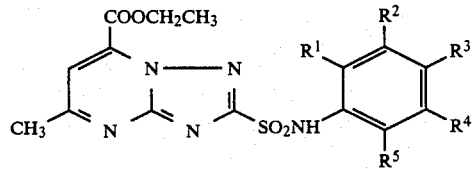

| Compound | R¹ | R² | R³ | R⁴ | R⁵ | Melting Point | Analysis | Elemental Analysis C | H | N |
|---|---|---|---|---|---|---|---|---|---|---|
| 240 | Cl | H | H | H | Cl | 236–239° C. (decomp.) | Calcd. for $C_{15}H_{13}Cl_2N_5O_4S$: Found: | 41.86 41.75 | 3.02 2.79 | 16.28 16.16 |

TABLE XXXV

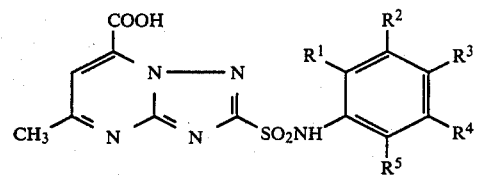

| Compound | R¹ | R² | R³ | R⁴ | R⁵ | Melting Point | Analysis | C | H | N |
|---|---|---|---|---|---|---|---|---|---|---|
| 241 | Cl | H | H | H | Cl | 120–130° C. (decomp.) | Calcd. for $C_{13}H_9Cl_2N_5O_4S\cdot H_2O$ Found: | 37.15 37.03 | 2.38 2.02 | 16.70 17.16 |

TABLE XXXVI

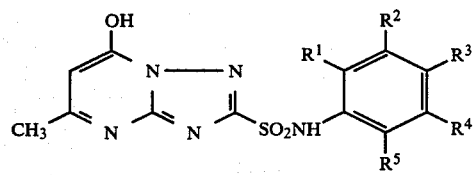

| Compound | R¹ | R² | R³ | R⁴ | R⁵ | Melting Point | Analysis | C | H | N |
|---|---|---|---|---|---|---|---|---|---|---|
| 242 | Cl | H | H | H | Cl | 280–304° C. (decomp.) | Calcd. for $C_{12}H_9Cl_2N_5O_3S$: Found: | 38.51 38.52 | 2.41 2.49 | 18.72 19.03 |

TABLE XXXVII

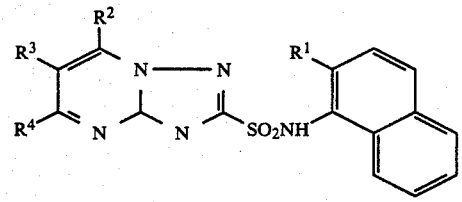

| Compound | R¹ | R² | R³ | R⁴ | Melting Point | Analysis | C | H | N |
|---|---|---|---|---|---|---|---|---|---|
| 243 | Cl | CH₃ | H | CH₃ | 303–306° C. (decomp.) | Calcd. for $C_{17}H_{14}ClN_5O_2S$: Found: | 52.65 52.10 | 3.64 3.65 | 18.05 18.51 |
| 244 | Cl | H | H | CH₃ | 262–265° C. (decomp.) | Calcd. for $C_{16}H_{12}ClN_5O_2S$: Found: | 51.41 50.97 | 3.24 3.29 | 18.73 18.99 |

TABLE XXXVIII

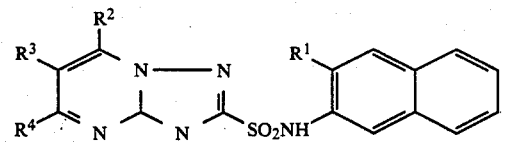

| Compound | R¹ | R² | R³ | R⁴ | Melting Point | Analysis | C | H | N |
|---|---|---|---|---|---|---|---|---|---|
| 245 | COOMe | CH₃ | H | CH₃ | 206–208° C. | Calcd. for $C_{19}H_{17}N_5O_4S\cdot\frac{1}{2}H_2O$: Found: | 54.28 53.98 | 4.32 4.12 | 16.65 16.83 |

TABLE XXXIX

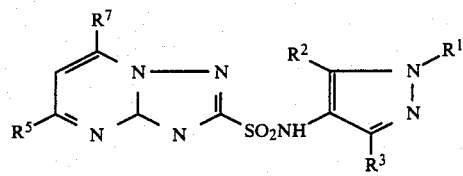

| Compound | $R^1$ | $R^2$ | $R^3$ | $R^4$ | $R^5$ | Melting Point | Analysis | | C | H | N |
|---|---|---|---|---|---|---|---|---|---|---|---|
| 246 | $CH_3$ | $CF_3$ | $CH_3$ | H | $CH_3$ | 273–274° C. (decomp.) | Calcd. for $C_{12}H_{12}F_3N_7O_2S$: Found: | | 38.39 38.73 | 3.22 3.23 | 26.12 25.92 |
| 247 | $CH_3$ | $CF_3$ | $CH_3$ | $CH_3$ | $CH_3$ | 288–288.5° C. (decomp.) | Calcd. for $C_{13}H_{14}F_3N_7O_2S$: Found: | | 40.09 40.22 | 3.62 3.58 | 25.18 25.61 |
| 248 | $CH_3$ | COOMe | $CH_3$ | H | $CH_3$ | 174–175° C. | Calcd. for $C_{13}H_{15}N_7O_4S$: Found: | | 42.73 42.39 | 4.14 4.21 | 26.84 26.91 |
| 249 | $CH_3$ | COOMe | $CH_3$ | $CH_3$ | $CH_3$ | 208–210° C. | Calcd. for $C_{14}H_{17}N_7O_4S$: Found: | | 44.32 44.07 | 4.52 4.31 | 25.85 25.72 |
| 250 | $CH_3$ | $CH_3$ | COOMe | $CH_3$ | $CH_3$ | 228–230° C. | Calcd. for $C_{14}H_{17}N_7O_4S$: Found: | | 44.32 44.06 | 4.52 4.82 | 25.85 25.97 |

TABLE XL

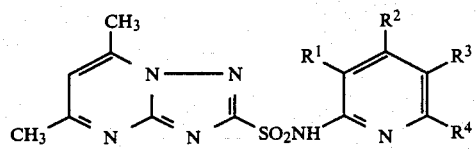

| Compound | $R^1$ | $R^2$ | $R^3$ | $R^4$ | Melting Point | Elemental Analysis | | | |
|---|---|---|---|---|---|---|---|---|---|
| 251 | —Cl | H | —Cl | H | 159°–161° C. | Exact mass calcd. for $C_{12}H_{10}Cl_2N_6O_2S$: Found: Analysis | | 371.9963 371.9973 | |
| | | | | | | | C | H | N |
| 252 | —Cl | H | H | H | >210° C. (decomp) | Calcd. for $C_{12}H_{11}ClN_6O_2S$: Found: | 42.55 42.19 | 3.27 3.28 | 24.80 24.27 |

TABLE XLI

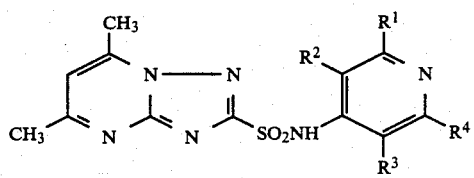

| Compound | $R^1$ | $R^2$ | $R^3$ | $R^4$ | Melting Point | Analysis | C | H | N |
|---|---|---|---|---|---|---|---|---|---|
| 253 | H | H | H | H | >250° C. (decomp) | Calcd. for $C_{12}H_{12}N_6O_2S \cdot H_2O$: Found: | 44.72 44.88 | 4.38 4.19 | 26.06 26.37 |
| 254 | H | —Cl | H | H | >260° C. (decomp) | Calcd. for $C_{12}H_{11}ClN_6O_2S$: Found: | 42.55 42.48 | 3.27 3.40 | 24.80 24.49 |

TABLE XLII

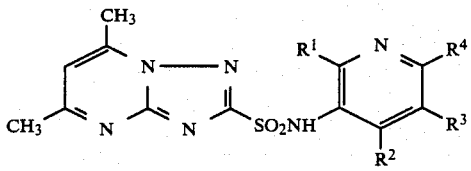

| Compound | $R^1$ | $R^2$ | $R^3$ | $R^4$ | Melting Point | Elemental Analysis | |
|---|---|---|---|---|---|---|---|
| 255 | —Cl | H | H | H | 207.5°–208.5° C. | Exact mass calcd. for $C_{12}H_{11}ClN_6O_2S$: Found: | 338.0352 338.0342 |

TABLE XLIII

Structure: 2,7-dimethyl-pyrazolo-triazine with SO$_2$NHAr substituent (CH$_3$ groups at 2,7 positions; N—N, N=N, and SO$_2$NHAr on the core)

| Compound | Ar | Melting Point | Analysis | C | H | N |
|---|---|---|---|---|---|---|
| 256 | thiazol-2-yl | 120–125° C. | Calcd. for C$_{10}$H$_{10}$N$_6$O$_2$S$_2$:<br>Found: | 38.66<br>38.48 | 3.22<br>3.28 | 27.06<br>26.92 |
| 257 | 3-methyl-2-(methoxycarbonyl)thien-yl | 160–168° C. | Calcd. for C$_{13}$H$_{13}$N$_5$O$_4$S$_2$:<br>Found: | 42.49<br>42.04 | 3.53<br>3.40 | 19.05<br>18.81 |
| 258 | 4-chloro-2-methylbenzothiazolyl | 224–226° C.<br>(decomp) | Calcd. for C$_{14}$H$_{11}$ClN$_6$O$_2$S$_2$:<br>Found: | 42.58<br>43.10 | 2.78<br>2.79 | 21.27<br>20.74 |
| 259 | 1-methylbenzotriazol-yl | 195° C.<br>(decomp.) | Calcd. for C$_{13}$H$_{11}$N$_8$O$_2$S:<br>Found: | 47.41<br>47.01 | 3.37<br>3.31 | 29.78<br>30.78 |

TABLE XLIV

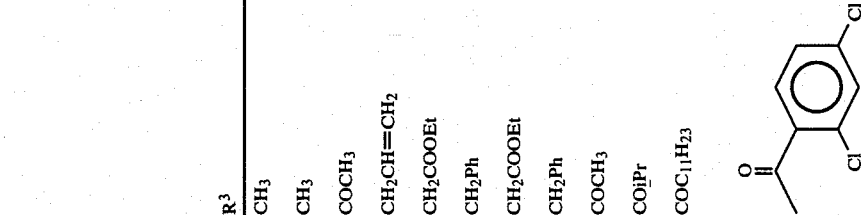

| Compound | R¹ | R² | R³ | R⁴ | R⁵ | Melting Point | Analysis | Elemental Analysis C | H | N | Cl | S |
|---|---|---|---|---|---|---|---|---|---|---|---|---|
| 260 | Cl | Cl | CH₃ | CH₃ | CH₃ | 220–222° C. | Calcd. for C₁₄H₁₃Cl₂N₅O₂S: Found: | 43.54 43.55 | 3.39 3.32 | 18.13 18.03 | | |
| 261 | COOMe | CH₃ | CH₃ | CH₃ | CH₃ | 175.5–177° C. | Calcd. for C₁₇H₁₉N₅O₄S: Found: | 52.43 52.31 | 4.92 4.93 | 17.98 17.94 | | |
| 262 | Cl | Cl | COCH₃ | CH₃ | CH₃ | 214–217° C. | Calcd. for C₁₅H₁₃Cl₂N₅O₃S: Found: | 43.49 43.44 | 3.16 3.16 | 16.90 16.77 | | |
| 263 | Cl | Cl | CH₂CH=CH₂ | CH₃ | CH₃ | 182–184° C. | Calcd. for C₁₆H₁₅Cl₂N₅O₂S: Found: | 46.61 46.74 | 3.67 3.67 | 16.98 16.86 | | |
| 264 | Cl | Cl | CH₂COOEt | CH₃ | CH₃ | 173–176° C. | Calcd. for C₁₇H₁₇Cl₂N₅O₄S: Found: | 44.55 44.74 | 3.74 3.85 | 15.27 15.08 | | |
| 265 | Cl | Cl | CH₂Ph | CH₃ | CH₃ | >240° C. (decomp.) | Calcd. for C₂₀H₁₇Cl₂N₅O₂S.½H₂O: Found: | 50.97 50.93 | 3.85 3.66 | 14.85 14.85 | | |
| 266 | COOMe | CH₃ | CH₂COOEt | CH₃ | CH₃ | 152–155° C. | Calcd. for C₂₀H₂₃N₅O₆S: Found: | 52.05 51.64 | 5.02 4.94 | 15.17 15.39 | | |
| 267 | COOMe | CH₃ | CH₂Ph | CH₃ | CH₃ | 174–176° C. | Calcd. for C₂₃H₂₃N₅O₄S: Found: | 59.34 59.00 | 4.98 4.89 | 15.04 15.18 | | |
| 268 | Cl | Cl | COCH₃ | H | CH₃ | 176–181° C. | Calcd. for C₁₄H₁₁Cl₂N₅O₃S: Found: | 42.02 42.28 | 2.77 2.90 | 17.49 17.16 | | |
| 269 | Cl | Cl | COiPr | H | CH₃ | 193–194.5° C. | Calcd. for C₁₆H₁₅Cl₂N₅O₃S: Found: | 44.87 45.26 | 3.53 3.53 | 16.35 16.39 | | |
| 270 | Cl | Cl | COC₁₁H₂₃ | H | CH₃ | 105.5–106.5° C. | Calcd. for C₂₄H₃₁Cl₂N₅O₃S: Found: | 53.33 53.40 | 5.78 5.77 | 12.96 12.84 | | |
| 271 | Cl | Cl | (2,4-dichlorobenzoyl) | H | CH₃ | 234–235° C. | Calcd. for C₁₉H₁₁Cl₄N₅O₃S: Found: | 42.96 43.31 | 2.09 2.29 | 13.18 13.04 | | |
| 272 | Cl | Cl | CO₂Et | H | CH₃ | 189–191° C. | Calcd. for C₁₅H₁₅Cl₂N₅O₄S: Found: | 41.87 42.51 | 3.05 3.25 | 16.28 16.02 | | |
| 273 | Cl | Cl | CON(CH₃)₂ | H | CH₃ | 225–228° C. (decomp.) | Calcd. for C₁₅H₁₄Cl₂N₆O₃S: Found: | 41.97 42.08 | 3.29 3.27 | 19.58 20.18 | | |
| 274 | Cl | Cl | COPh | H | CH₃ | 187–189° C. | Calcd. for C₁₉H₁₃Cl₂N₅O₃S: Found: | 49.36 48.97 | 2.83 2.84 | 15.15 15.16 | | |
| 275 | F | F | COCH₃ | H | CH₃ | 195–200° C. | Calcd. for C₁₄H₁₁F₂N₅O₃S: Found: | 45.77 45.59 | 3.02 3.12 | 19.07 19.16 | | 8.73 8.91 |
| 276 | F | F | COEt | H | CH₃ | 154–160° C. | Calcd. for C₁₅H₁₃F₂N₅O₃S: Found: | 47.24 47.05 | 3.44 3.44 | 18.37 18.49 | | 8.41 |
| 277 | F | F | COiPr | H | CH₃ | 182–184° C. | Calcd. for C₁₆H₁₅F₂N₅O₃S: Found: | 48.60 48.49 | 3.82 | 17.71 | | 8.27 |

TABLE XLIV-continued

Structure:

$R^4$, $R^5$ substituents on a pyrimidine ring linked via N—N to C(=N) with N—SO₂N(R³) to a phenyl bearing $R^1$ and $R^2$.

| Compound | $R^1$ | $R^2$ | $R^3$ | $R^4$ | $R^5$ | Melting Point | Analysis | Elemental Analysis C | H | N | Cl | S |
|---|---|---|---|---|---|---|---|---|---|---|---|---|
| 278 | F | F | COCH₂tBu | H | CH₃ | 158–162° C. | Found: | 48.41 | 3.93 | 17.43 | | 7.57 |
| | | | | | | | Calcd. for C₁₈H₁₉F₂N₅O₃S: | 51.05 | 4.52 | 16.54 | | 7.83 |
| 279 | F | F | COnBu | H | CH₃ | 131–134° C. | Found: | 51.15 | 4.62 | 16.38 | | |
| | | | | | | | Calcd. for C₁₇H₁₇F₂N₅O₃S: | 49.87 | 4.19 | 17.11 | | |
| 280 | F | F | COiBu | H | CH₃ | 185–186° C. (decomp.) | Found: | 49.10 | 4.04 | 17.05 | | 7.83 |
| | | | | | | | Calcd. for C₁₇H₁₇F₂N₅O₃S: | 49.87 | 4.19 | 17.11 | | 7.10 |
| 281 | F | F | COCH₂Ph | H | CH₃ | 178–185° C. | Found: | 49.93 | 3.89 | 16.82 | | |
| | | | | | | | Calcd. for C₂₀H₁₅F₂N₅O₃S: | 54.17 | 3.41 | 15.80 | | |
| 282 | F | F | COCH₂CH₂Cl | H | CH₃ | 195° C. (decomp.) | Found: | 53.60 | 3.18 | 15.56 | | 7.71 |
| | | | | | | | Calcd. for C₁₅H₁₂ClF₂N₅O₃S: | 43.33 | 2.91 | 16.84 | 8.53 | 7.47 |
| 283 | F | F | COnPr | H | CH₃ | 130–135° C. | Found: | 43.21 | 2.95 | 17.31 | 8.45 | 8.11 |
| | | | | | | | Calcd. for C₁₆H₁₅F₂N₅O₃S: | 48.60 | 3.82 | 17.71 | | 7.98 |
| 284 | F | F | COCH₂iPr | H | CH₃ | 154–159° C. | Found: | 48.42 | 3.81 | 17.91 | | 7.83 |
| | | | | | | | Calcd. for C₁₇H₁₇F₂N₅O₃S: | 49.87 | 4.19 | 17.11 | | 7.68 |
| 285 | F | F | COCH₂Cl | H | CH₃ | 156–158° C. | Found: | 49.45 | 4.04 | 17.15 | | |
| | | | | | | | Calcd. for C₁₄H₁₀ClF₂N₅O₃S: | 41.85 | 2.51 | 17.43 | | |
| 286 | F | F | COCHCH₃=CH₂ | H | CH₃ | 171.5–174° C. | Found: | 42.19 | 2.68 | 17.43 | | 8.15 |
| | | | | | | | Calcd. for C₁₆H₁₃F₂N₅O₃S: | 48.85 | 3.33 | 17.81 | | 7.94 |
| 287 | F | F | COnC₉H₁₉ | H | CH₃ | 97–99° C. | Found: | 48.36 | 3.51 | 17.91 | | 6.69 |
| | | | | | | | Calcd. for C₂₂H₂₇F₂N₅O₃S: | 55.10 | 5.68 | 14.61 | | 6.63 |
| 288 | F | F | COCH=CHCH₃ | H | CH₃ | 154–156° C. | Found: | 55.22 | 5.60 | 14.85 | | |
| | | | | | | | Calcd. for C₁₆H₁₃F₂N₅O₃S: | 48.85 | 3.33 | 17.81 | | 8.15 |
| 289 | F | F | COcycloC₃H₅ | H | CH₃ | 200.5–203° C. | Found: | 48.41 | 3.41 | 17.94 | | 8.34 |
| | | | | | | | Calcd. for C₁₆H₁₃F₂N₅O₃S: | 48.85 | 3.33 | 17.81 | | 7.47 |
| 290 | F | F | COPh | H | CH₃ | 186–189° C. | Found: | 48.32 | 3.34 | 18.03 | | 7.11 |
| | | | | | | | Calcd. for C₁₉H₁₃F₂N₅O₃S: | 53.14 | 3.05 | 16.31 | | 7.36 |
| 291 | F | F | COcycloC₆H₁₁ | H | CH₃ | 178–180° C. | Found: | 53.74 | 3.16 | 16.63 | | 7.78 |
| | | | | | | | Calcd. for C₁₉H₁₉F₂N₅O₃S: | 52.40 | 4.40 | 16.08 | | 6.98 |
| 292 | F | F | COCH₂OPh | H | CH₃ | 141–144° C. | Found: | 51.40 | 4.28 | 16.08 | | 6.76 |
| | | | | | | | Calcd. for C₂₀H₁₅F₂N₅O₄S: | 52.28 | 3.29 | 15.25 | | 7.04 |
| 293 | F | F | COCH=CHPh | H | CH₃ | oil | Found: | 51.77 | 3.38 | 15.28 | | 6.98 |
| | | | | | | | Calcd. for C₂₁H₁₅F₂N₅O₃S: | 55.38 | 3.32 | 15.29 | | 7.07 |
| 294 | F | F | COCH₂CH₂CO₂CH₂CH₃ | H | CH₃ | 157–162° C. | Found: | 55.55 | 3.45 | 15.38 | | 7.03 |
| | | | | | | | Calcd. for C₁₈H₁₇F₂N₅O₅S: | 47.68 | 3.78 | 15.45 | | 7.03 |
| 295 | F | F | CO(2-furyl) | H | CH₃ | 120° C. (decomp.) | Found: | 47.32 | 3.78 | 15.68 | | 7.65 |
| | | | | | | | Calcd. for C₁₇H₁₁F₂N₅O₄S: | 48.69 | 2.64 | 16.70 | | 7.83 |
| 296 | F | F | COcycloC₄H₇ | H | CH₃ | 161–170° C. | Found: | 48.49 | 2.75 | 17.03 | | 7.87 |
| | | | | | | | Calcd. for C₁₇H₁₅F₂N₅O₃S: | 50.12 | 3.71 | 17.19 | | 8.07 |
| 297 | F | F | SO₂CH₃ | H | CH₃ | 193–195° C. | Found: | 49.58 | 3.89 | 17.21 | | 15.90 |
| | | | | | | | Calcd. for C₁₃H₁₁F₂N₅O₄S₂: | 38.71 | 2.75 | 17.36 | | 15.72 |
| | | | | | | | Found: | 38.98 | 2.92 | 17.18 | | |

TABLE XLIV-continued

[Structure: pyrimidine-hydrazone with R⁴, R⁵ on pyrimidine ring, connected via N=N to C(SO₂NR³)=N, with phenyl ring bearing R¹ and R²]

| Compound | R¹ | R² | R³ | R⁴ | R⁵ | Melting Point | Analysis | Elemental Analysis C | H | N | Cl | S |
|---|---|---|---|---|---|---|---|---|---|---|---|---|
| 298 | F | F | SO₂Ph | H | CH₃ | 182–190° C. | Calcd. for $C_{18}H_{13}F_2N_5O_4S_2$: | 46.45 | 2.82 | 15.05 | | 13.78 |
| | | | | | | | Found: | 46.41 | 3.03 | 14.79 | | 14.01 |
| 299 | F | F | CH₂Ph | H | CH₃ | 170–177° C. | Calcd. for $C_9H_{15}F_2N_5O_2S$: | 54.93 | 3.64 | 16.86 | | 7.72 |
| | | | | | | | Found: | 54.45 | 3.73 | 16.63 | | 7.77 |
| 300 | F | F | C=O(SEt) | H | CH₃ | 197–199° C. | Calcd. for $C_{15}H_{13}F_2N_5O_3S_2$: | 43.58 | 3.17 | 16.94 | | 15.51 |
| | | | | | | | Found: | 43.45 | 3.19 | 17.12 | | 15.64 |
| 301 | F | F | CH₂(4-NO₂Ph) | H | CH₃ | 194–200° C. | Calcd. for $C_{19}H_{14}F_2N_6O_4S$: | 49.64 | 3.07 | 18.26 | | 6.96 |
| | | | | | | | Found: | 49.64 | 3.25 | 18.40 | | 6.88 |
| 302 | F | F | CH₂(4-MeOPh) | H | CH₃ | 156–158° C. | Calcd. for $C_{20}H_{17}F_2N_5O_3S$: | 53.92 | 3.85 | 15.72 | | 7.20 |
| | | | | | | | Found: | 53.65 | 3.98 | 15.95 | | 7.46 |
| 303 | F | F | CH₂(2-furyl) | H | CH₃ | 177–180° C. | Calcd. for $C_{17}H_{13}F_2N_5O_3S$: | 50.37 | 3.23 | 17.28 | | 7.91 |
| | | | | | | | Found: | 50.50 | 3.30 | 17.33 | | 7.74 |

TABLE XLV

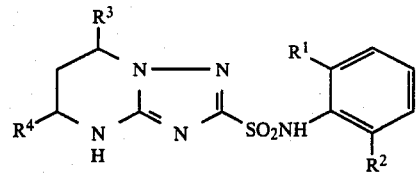

| Compound | R¹ | R² | R³ | R⁴ | Melting Point | Elemental Analysis | | | |
|---|---|---|---|---|---|---|---|---|---|
| | | | | | | | C | H | N |
| 304 | Cl | Cl | Me | Me | 198–205° C. | Analysis | | | |
| | | | | | | Calcd. for $C_{13}H_{15}Cl_2N_5O_2S$: | 41.49 | 3.98 | 18.50 |
| | | | | | | Found: | 41.27 | 3.81 | 18.28 |
| 305 | CF₃ | H | Me | Me | 74.5–84° C. | Exact mass calcd for $C_{14}H_{16}F_3N_5O_2S$: | | 375.0979 | |
| | | | | | | Found: | | 375.0978 | |
| 306 | Cl | Cl | H | Me | 230–235° C. | Analysis | C | H | N |
| | | | | | | Calcd. for $C_{12}H_{13}Cl_2N_5O_2S$: | 39.89 | 3.32 | 19.39 |
| | | | | | | Found: | 39.72 | 3.42 | 19.90 |

The compounds of the present invention are highly effective herbicides when applied to the locus of vegetation, herein defined as encompassing preemergent (soil) applications as well as postmergent (foliar) applications. They have utility for broadspectrum pre- and/or postemergence weed control in areas where complete vegetation control is desired. The subject compounds are also useful for selective pre- and/or post-emergence weed control in crops such as wheat. Certain of these compounds are effective for the control of nutsedge (cyperus spp.) and some compounds may be used for selective weed control in corn, soybeans and rice.

For all such uses, unmodified active ingredients of the present invention can be employed. However, the present invention embraces the use of a herbicidally-effective amount of the active ingredients in composition form with an inert material known in the art as an agricultural adjuvant or carrier in solid or liquid form. Such adjuvants or carriers must not be phytotoxic to valuable crops particularly at the concentration employed in applying the composition in attempting selective weed control in the presence of crops. If weed control is desired in the absence of crops, it is generally sufficient to employ adjuvants or carriers which do not leave a persistent phytotoxic residue.

Thus, for example, an active ingredient can be dispersed on a finely-divided solid and employed therein as a dust. Also, the active ingredients, as liquid concentrates or solid compositions comprising one or more of the active ingredients can be dispersed in water, typically with aid of a wetting agent, and the resulting aqueous dispersion employed as a spray. In other procedures the active ingredients can be employed as a constituent of organic liquid compositions, oil-in-water and water-in-oil emulsions or dispersions, with or without the addition of wetting, dispersing, or emulsifying agents.

Suitable adjuvants of the foregoing type are well known to those skilled in the art. The methods of applying the solid or liquid herbicidal formulations similarly are well known to the skilled artisan.

Organic solvents that can be employed include toluene, xylene, kerosene, diesel fuel, fuel oil, and petroleum naphtha, ketones such as acetone, methylethyl ketone and cyclohexanone, chlorinated hydrocarbons such as trichloroethylene, and perchloroethylene, esters such as ethyl acetate, amyl acetate and butyl acetate, ethers, e.g., ethylene glycol monomethyl ether and diethylene glycol monomethyl ether, alcohols, e.g., methanol, ethanol, isopropanol, amyl alcohol, ethylene glycol, propylene glycol, butylcarbitol acetate and glycerine. Mixtures of water and organic solvents, either as emulsions or solutions, can be employed.

The active ingredients of the present invention can also be applied as aerosols, e.g., by dispersing them by means of a compressed gas such as one of the fluorocarbons or one of its hydrocarbon successors.

The active ingredients of the present invention can also be applied with solid adjuvants or carriers such as talc, pyrophyllite, synthetic fine silica, attapulgus clay, kieselguhr, chalk, diatomaceous earth, lime, calcium carbonate, bentonite, Fuller's earth, cotton seed hulls, wheat flour, soybean flour, pumice, tripoli, wood flour, walnut shell flour, redwood flour and lignin.

As stated, it is frequently desirable to incorporate a surface-active agent in the compositions if the present invention. Such surface-active or wetting agents are advantageously employed in both the solid and liquid compositions. The surface-active agent can be anionic, cationic or nonionic in character.

Typical classes of surface-active agents include alkyl sulfonate salts, alkylaryl sulfonate salts, alkylaryl polyether alcohols, fatty acid esters of polyhydric alcohols and the alkylene oxide addition products of such esters, and addition products of long-chain mercaptans and alkylene oxides. Typical examples of such surface-active agents include the sodium alkylbenzene sulfonates having 10 to 18 carbon atoms in the alkyl group, alkyl phenol ethylene oxide condensation products, e.g., p-isooctylphenol condensed with 20 ethylene oxide units, soaps, e.g., sodium stearate and potassium oleate, sodium salt of propylnaphthalene sulfonic acid, di(2-ethylhexyl)ester of sodium sulfosuccinic acid, sodium lauryl sulfate, sodium decyl sulfonate, sodium salt of the sulfonated monoglyceride of coconut fatty acids, sorbitan sequioleate, lauryl trimethyl ammonium chloride, octadecyl trimethyl ammonium chloride, polyethylene glycol lauryl ether, polyethylene glycol esters of fatty acids and rosin acids, e.g., Ethofat ® 7 and 13, sodium N-methyl-N-oleyl taurate, sodium dibutylnaphthalene sulfonate, sodium lignin sulfonate, polyethylene glycol stearate, sodium dodecyl benzene sulfonate, tertiary dodecyl polyethylene glycol thioether (nonionic 218), long-chain ethylene oxide-propylene oxide condensation products e.g., Pluronic ® 61 (molecular weight about 1000), polyethylene glycol ester of tall oil acids, sodium octophenoxyethoxyethyl sulfate, tris(polyoxyethylene)sorbitan monostearate (Tween ® 60), and sodium dihexylsulfosuccinate.

The herbicidally effective concentration of the active ingredients in solid or liquid compositions generally is from about 0.00003 to about 95 percent by weight or more. Concentrations from about 0.05 to about 50 percent by weight are often employed. In compositions to be employed as concentrates, the active ingredient can be present in a concentration from about 5 to about 98 weight percent, preferably 15–50 weight percent. The active ingredient compositions can also contain other compatible additaments, for example, phytotoxicants, plant growth regulators, pesticides and the like and can be formulated with solid particulate fertilizer carriers such as ammonium nitrate, urea and the like.

In further embodiments, the compounds of the present invention or compositions containing the same, can be advantageously employed in combination with one or more additional pesticidal compounds. Such additional pesticidal compounds may be insecticides, nematocides, miticides, arthropodicides, herbicides, fungicides or bactericides that are compatible with the compounds of the present invention in the medium selected for application. In such embodiments, the pesticidal compound is employed as a supplemental toxicant for the same or for a different pesticidal use or as an additament.

The compounds of the present invention are particularly useful in combination with other herbicides including the substituted urea herbicides such as 3-(3,4-dichlorophenyl)-1,1-dimethylurea, 3-(3,4-dichlorophenyl)-1-methoxy-1methylurea (Lorox ®) and 1,1-dimethyl-3-(α,α,α-trifluoro-m-tolyl)urea (Cotoran ®); the triazines such as 2-chloro-4-(ethylamino)-6-(isopropylamino)-s-triazine and 2-chloro-4-(1-cyano-1-methylethylamino)-6-ethylamino-s-triazine (Bladex ®); the uracils such as 5-bromo-3-sec-butyl-6-methyluracil; N-(phosphonomethyl)glycine; the phenoxys such as 2,4-dichlorophenoxyacetic acid; picolinic acids such as 4-amino-3,5,6-trichloropicolinic acid (Tordon ®) and 3,6-dichloropicolinic acid (Lontrel ®); 4-chloro-2-butynyl-3-chlorophenyl carbamate (Carbyne ®); diisopropylthiocarbamic acid, ester with 2,3-dichloroallyl alcohol (Avadex ®); diisopropylthiocarbamic acid, ester with 2,3,3-trichloroallyl alcohol (Avadex ® BVD); ethyl-N-benzoyl-N-(3,4-dichlorophenyl)-2-aminopropionate (Suffix ®); 1,2-dimethyl-3,5-diphenylpyrazolium methylsulfate (Avenge ®); methyl (2-[4-(2,4-dichlorophenoxy)phenoxy]propanoate) (Hoelon ®); butyl 2-[4-[(5-(trifluoromethyl)-2-pyridinyl)oxy]phenoxy]propanoate (Fusilade ®); esters of 2-[4-[(3-chloro-5-trifluoromethyl)-2-pyridinyl)oxy]phenoxy]propionic acid; 4-amino-6-tert-butyl-3-(methylthio)-1,2,4-triazin-5-(4H)-one (Lexone ®); 3-isopropyl-1H-2,1,3-benzothiadiazin-(4)-3H-one 2,2-dioxide; α,α,α-trifluoro-2,6-dinitro-N,N-dipropyl-p-toluidine; 1,1'-dimethyl-4,4'-bipyridinium ion; 2-chloro-2',6'-diethyl-(methoxymethyl)acetanilide; and 2-[1-(ethoxyimino)-butyl]-5-[(2-ethylthio)propyl]-3-hydroxy-2-cyclohexen-1-one (Poast ®).

The rates of application for compounds of the invention are determined by a number of factors including the active ingredient being applied, the particular action desired (e.g., general or selective control), the plant species to be modified and the stage of growth thereof, the part of the plant to be contacted with the toxic active ingredient, the formulation selected, weather and climate, etc. Thus, it is to be understood that all of the active ingredients of the present invention and compositions containing the same may not be equally effective at similar concentrations or against the same plant species. In non-selective preemergence and foliar treatments, the active ingredients of the invention are usually applied at an approximate rate of from about 0.01 to about 10 pounds/acre. In pre- and postemergence operations for selective uses, a dosage of about 0.01 to about 10 pounds/acre is generally applicable, a rate of 0.01 to 4 pounds/acre being preferred.

The following example illustrates the effect of the compounds of this invention applied postemergently.

Plant species in this and other tests were the following:

|    | Common Name          | Scientific Name        |
| -- | -------------------- | ---------------------- |
| A. | cotton               | Gossypium spp.         |
| B. | rape                 | Brassica napus         |
| C. | soybean              | Glycine max.           |
| D. | sugar beet           | Beta saccharifera      |
| E. | cocklebur            | Xanthium spp.          |
| F. | jimsonweed           | Datura stramonium      |
| G. | annual morning glory | Ipomoea spp.           |
| H. | pigweed              | Amaranthus spp.        |
| I. | velvetleaf           | Abutilon theophrasti   |
| J. | corn                 | Zea mays               |
| K. | rice                 | Oryza sativa           |
| L. | sorghum              | Sorghum vulgare        |
| M. | wheat                | Triticum aestivum      |
| N. | barnyardgrass (watergrass) | Echinochloa crusgalli |
| O. | crabgrass            | Digitaria spp.         |
| P. | yellow foxtail       | Setaria lutescens      |
| Q. | johnson grass        | Sorghum halepense      |
| R. | wild oats            | Avena fatua            |
| S. | sprangletop          | Leptochloa filiformis  |
| T. | yellow nutsedge      | Cyperus esculentus     |

EXAMPLE 94

In representative operations, each compound to be utilized in a series of tests is dissolved in acetone to one-half of the final volume (twice the final concentration) to be used and the acetone solution in each case is admixed with an equal volume of water containing 0.1 percent by weight of surface active material. The compositions, generally in the nature of an emulsion, were employed to spray separate respective plant species which had been grown to a 2–4 leaf stage in soil of good nutrient content in a greenhouse. Sufficient amounts were employed to provide various application rates as listed in the table. The various beds were positioned side by side and exposed to substantially identical conditions of temperature and light. Each bed was maintained so as to prevent any interaction with test compounds in different seed beds. Other plants were left untreated to serve as controls. After treatment, the plants were maintained for about two weeks under greenhouse conditions conducive for good plant growth and watered as necessary. The specific plant species, test compound and dosage and the percent postermergent control obtained are set forth in the table below. Control refers to the reduction in growth compared to the observed results of the same untreated species.

| | | POSTEMERGENT CONTROL OF PLANT SPECIES | | | | | | | | | |
|---|---|---|---|---|---|---|---|---|---|---|---|
| | Dosage | Plant Species | | | | | | | | | |
| Compound | (ppm) | A | B | C | D | E | F | G | H | I | J |
| 1 | 500 | 0 | 60 | 30 | 85 | 0 | 0 | 0 | 60 | 70 | 0 |
| 2 | 1000 | 10 | 50 | 40 | 90 | 80 | 90 | 10 | 0 | 50 | 0 |
| 4 | 500 | 10 | 40 | 40 | 70 | 40 | 60 | 0 | 0 | 60 | 0 |
| 6 | 500 | 60 | 80 | 70 | 90 | 90 | 30 | 80 | 30 | 90 | 0 |
| 7 | 500 | — | 90 | 55 | 100 | 100 | 20 | 90 | 60 | 65 | 0 |
| 8 | 500 | — | 90 | 75 | 95 | 90 | 90 | 70 | 50 | 75 | 20 |
| | 62.5 | — | 60 | 40 | 60 | 70 | 15 | 35 | 40 | 20 | 0 |
| 9 | 1000 | 50 | 60 | 65 | 80 | 90 | 90 | 20 | 80 | 40 | 0 |
| 10 | 2000 | 15 | 30 | 50 | 75 | 90 | 0 | 0 | 100 | 15 | 10 |
| | 500 | 0 | 10 | 20 | 60 | 15 | 0 | 0 | 20 | 0 | 0 |
| 12 | 500 | — | 100 | 80 | 95 | 100 | 70 | 100 | 100 | 95 | 10 |
| | 125 | — | 95 | 80 | 95 | 100 | 20 | 60 | 90 | 75 | 0 |
| | 15.6 | — | 75 | 60 | 65 | 90 | 0 | 20 | 70 | 0 | 0 |
| 13 | 250 | 95 | 100 | 95 | 100 | 100 | 90 | 90 | 100 | 95 | 15 |
| | 62.5 | 95 | 100 | 95 | 95 | 100 | 50 | 90 | 100 | 80 | 0 |
| | 15.6 | 60 | 90 | 85 | 90 | 100 | 30 | 85 | 70 | 70 | 0 |
| 14 | 1000 | 20 | — | 25 | 90 | 80 | 0 | 10 | 60 | 0 | 0 |
| 15 | 1000 | — | 70 | 25 | 40 | 80 | 0 | 70 | 40 | 60 | 0 |
| 17 | 1000 | 20 | 95 | 15 | 15 | 10 | 0 | 0 | 60 | 85 | 30 |
| | 500 | 15 | 70 | 15 | 10 | 10 | 0 | 0 | 50 | 70 | 20 |
| 19 | 1000 | 90 | 90 | 90 | 100 | 90 | 95 | 40 | 100 | 80 | 0 |
| 21 | 1000 | 90 | 100 | 70 | 95 | 95 | 0 | 45 | 80 | 30 | 0 |
| 22 | 250 | 100 | 100 | 95 | 100 | 100 | 100 | 100 | 100 | 95 | 25 |
| | 62.5 | 95 | 100 | 90 | 100 | 100 | 95 | 80 | 100 | 95 | 15 |
| | 15.6 | 85 | 95 | 90 | 90 | 90 | 80 | 75 | 95 | 90 | 0 |
| 24 | 1500 | 40 | 90 | 40 | 70 | 90 | — | 0 | — | 50 | 0 |
| 25 | 250 | 100 | 100 | 90 | 100 | 100 | 100 | 80 | 100 | 95 | 70 |
| | 62.5 | 90 | 100 | 80 | 100 | 100 | 100 | 35 | 100 | 60 | 40 |
| | 15.6 | 30 | — | 70 | 90 | 90 | 80 | 20 | 100 | 40 | 20 |
| 26 | 500 | 100 | 100 | 95 | 100 | 100 | 100 | 90 | 100 | 100 | 80 |
| | 125 | 100 | 100 | 85 | 100 | 100 | 100 | 85 | 100 | 90 | 80 |
| | 31.25 | 90 | 100 | 80 | 95 | 90 | 60 | 75 | 100 | 40 | 20 |
| 30 | 500 | 0 | 40 | 30 | 0 | 40 | 0 | 60 | 0 | 40 | 0 |
| 31 | 125 | 90 | 100 | 95 | 100 | 90 | 100 | 60 | 85 | 90 | 40 |
| | 31.25 | 75 | 95 | 90 | 90 | 75 | 80 | 40 | 80 | 95 | 50 |
| | 7.8 | 60 | 60 | 75 | 100 | 60 | 60 | 0 | 55 | 85 | 30 |
| 32 | 500 | 20 | 0 | 15 | 30 | 15 | 60 | 0 | 0 | 50 | 0 |
| | 250 | 30 | 0 | 15 | 0 | 0 | 30 | 0 | 0 | 40 | 0 |
| 33 | 500 | 50 | 60 | 40 | 40 | 60 | 40 | 60 | 10 | 80 | 25 |
| 34 | 500 | 70 | 100 | 90 | 100 | 100 | 90 | 75 | 100 | 100 | 0 |
| 35 | 500 | 0 | 70 | 70 | 80 | 95 | 30 | 40 | 90 | 0 | 0 |
| 38 | 62.5 | 80 | 98 | 90 | 100 | 98 | 60 | 80 | 98 | 98 | 0 |
| | 15.6 | 10 | 98 | 70 | 98 | 95 | 50 | 50 | 80 | 40 | 0 |
| 39 | 62.5 | 98 | 98 | 98 | 98 | 100 | 90 | 98 | 100 | 98 | 0 |
| | 15.6 | 80 | 98 | 98 | 98 | 95 | 90 | 95 | 95 | 98 | 0 |
| | 3.9 | 40 | 95 | 40 | 98 | 90 | 40 | 70 | 70 | 40 | 0 |
| 40 | 1000 | 25 | 90 | 25 | 90 | 80 | 60 | 20 | 75 | 20 | 0 |
| 41 | 4000 | 30 | — | — | — | — | — | 70 | — | 98 | — |
| 43 | 2000 | 0 | 20 | 15 | 0 | 0 | 0 | 0 | — | 0 | 0 |
| 44 | 250 | 40 | 80 | 75 | 80 | 85 | 20 | 75 | 90 | 80 | 0 |
| 45 | 500 | 0 | 70 | 60 | 70 | 25 | 0 | 10 | — | 50 | 0 |
| 46 | 31.3 | 95 | 98 | 98 | 98 | 98 | 95 | 98 | 100 | 98 | 15 |
| | 7.8 | 80 | 95 | 98 | 98 | 98 | 80 | 98 | 100 | 98 | 15 |
| | 1.9 | 60 | 98 | 95 | 95 | 95 | 30 | 90 | 90 | 95 | 15 |
| 47 | 62.5 | 70 | 90 | 98 | 100 | 98 | 20 | 98 | 90 | 98 | 0 |
| 48 | 500 | 10 | 75 | 55 | 70 | 70 | 30 | 60 | — | 40 | 0 |
| 49 | 250 | 90 | 100 | 95 | 100 | 100 | 100 | 95 | 90 | 100 | 0 |
| | 62.5 | 95 | 100 | 95 | 100 | 100 | 100 | 95 | 80 | 100 | 0 |
| 50 | 62.5 | 98 | 100 | 100 | 100 | 98 | 98 | 98 | 98 | 100 | 93 |
| | 15.6 | 90 | 100 | 98 | 90 | 98 | 90 | 80 | 90 | 100 | 70 |
| 51 | 62.5 | 98 | 98 | 98 | 98 | 100 | 95 | 98 | 90 | 100 | 40 |
| | 7.8 | 30 | 70 | 80 | 95 | 95 | 60 | 90 | 20 | 70 | 0 |
| 52 | 2000 | 70 | 10 | 70 | 50 | 70 | 0 | — | 0 | 0 | 0 |
| 53 | 62.5 | 90 | 100 | 98 | 100 | 100 | 98 | 90 | 100 | 100 | 0 |
| | 15.6 | 60 | 98 | 98 | 98 | 98 | 98 | 90 | 100 | 98 | 0 |
| 54 | 62.5 | 98 | 98 | 98 | 100 | 98 | 90 | 98 | 98 | 98 | 30 |
| | 7.8 | 60 | 98 | 80 | 98 | 98 | 40 | 40 | 90 | 50 | 0 |
| 55 | 125 | 25 | 70 | 15 | 95 | 80 | 25 | 20 | 20 | 20 | 0 |
| 56 | 62.5 | 85 | 95 | 90 | 100 | 99 | 85 | 80 | 95 | 90 | 0 |
| 57 | 125 | 20 | 95 | 10 | 85 | 80 | 0 | 0 | 0 | — | 0 |
| 58 | 125 | 90 | 100 | 95 | 100 | 100 | 95 | 95 | 100 | 100 | 85 |
| | 31.25 | 90 | 100 | 95 | 100 | 100 | 95 | 90 | 100 | 95 | 75 |
| 59 | 250 | 0 | 70 | 10 | 40 | 75 | 50 | 0 | 0 | — | 0 |
| 60 | 2000 | 60 | — | 15 | — | — | 50 | 80 | 100 | 80 | — |
| 61 | 125 | 40 | 75 | 90 | 90 | 30 | 75 | 5 | 60 | 40 | 0 |
| 62 | 125 | 40 | 80 | 90 | 70 | 80 | 75 | 65 | 75 | 80 | 0 |
| 63 | 62.5 | 90 | 90 | 90 | 90 | 95 | 95 | 80 | 90 | 90 | 0 |
| 64 | 125 | 100 | 99 | 90 | 100 | — | 95 | 80 | 100 | 100 | 85 |

-continued

POSTEMERGENT CONTROL OF PLANT SPECIES

| | | | | | | | | | | | |
|---|---|---|---|---|---|---|---|---|---|---|---|
| 65 | 250 | — | 85 | 75 | 60 | — | 10 | 0 | 40 | — | 70 |
| 66 | 1000 | 50 | 80 | 0 | 90 | — | 0 | 0 | 95 | 30 | 0 |
| 67 | 1000 | 40 | 70 | 0 | 30 | — | 0 | 0 | 100 | 30 | 0 |
| 68 | 1000 | 70 | 80 | 60 | 100 | 100 | 75 | 50 | 100 | 90 | 0 |
| | 125 | 80 | 50 | 40 | 40 | 60 | 25 | 0 | 65 | 50 | 0 |
| 69 | 500 | 90 | 90 | 40 | 100 | — | 90 | 80 | 100 | 85 | 90 |
| | 62.5 | 75 | 80 | 5 | 40 | — | 50 | 60 | 100 | 50 | 40 |
| 70 | 250 | 90 | 95 | 70 | 90 | 95 | 95 | 80 | 50 | 85 | 0 |
| 71 | 500 | 75 | 70 | 35 | 70 | 0 | 60 | 0 | 0 | 70 | 0 |
| 72 | 62.5 | 100 | 100 | 85 | 50 | 100 | 90 | 85 | 70 | 100 | 0 |
| 73 | 125 | 0 | 50 | 50 | 30 | 80 | 70 | 20 | 40 | 50 | 0 |
| 74 | 500 | 70 | 100 | 80 | 100 | 100 | 90 | 80 | 70 | 100 | 0 |
| 75 | 125 | 25 | 65 | 40 | 0 | 75 | 40 | 0 | 0 | 100 | 0 |
| 76 | 125 | 80 | 95 | 90 | 90 | 90 | 100 | 90 | 100 | 100 | 40 |
| | 31.25 | 60 | 95 | 80 | 60 | 70 | 50 | 80 | 80 | 98 | 30 |
| 77 | 125 | 80 | 100 | 90 | 80 | 85 | 100 | 95 | 100 | 100 | 10 |
| | 15.6 | 50 | — | 75 | 20 | 50 | 80 | 50 | 20 | 80 | 0 |
| 78 | 125 | 75 | 95 | 90 | 85 | 40 | 0 | 0 | 100 | 90 | 0 |
| 79 | 2000 | 80 | 90 | 70 | 90 | 75 | 85 | 15 | 30 | 75 | 0 |
| 81 | 2000 | 50 | — | 10 | 0 | — | 20 | 0 | 30 | 40 | 0 |
| 82 | 500 | 85 | 100 | 85 | 95 | 85 | 90 | 85 | 100 | 85 | 0 |
| 83 | 62.5 | 50 | 60 | 10 | 60 | 20 | 0 | 0 | 0 | 30 | 0 |
| 84 | 2000 | 30 | 100 | 40 | 100 | — | — | 0 | 100 | 98 | 0 |
| 85 | 62.5 | 70 | — | 80 | 100 | 70 | 70 | 75 | 100 | 80 | 30 |
| | 7.8 | 50 | — | 80 | 100 | 55 | 80 | 55 | 100 | 80 | 0 |
| 86 | 125 | 50 | 80 | 80 | 100 | 60 | — | 0 | 100 | 65 | 0 |
| 87 | 250 | 50 | 80 | 75 | 100 | 40 | 50 | 40 | 70 | 60 | 0 |
| 89 | 2000 | 50 | — | 35 | 80 | 70 | 85 | 20 | 100 | 90 | 0 |
| 90 | 500 | 0 | 70 | 50 | — | 75 | 70 | 30 | 100 | 50 | 0 |
| 91 | 62.5 | 100 | 100 | 90 | 100 | 100 | 100 | 90 | 100 | 100 | 0 |
| 92 | 62.5 | 25 | 50 | 80 | 0 | — | 90 | 80 | 60 | 50 | 40 |
| 93 | 500 | 0 | 70 | 90 | 70 | 80 | 80 | 0 | 70 | 20 | 0 |
| 94 | 2000 | 0 | 60 | 85 | 100 | 80 | 70 | 0 | 70 | 70 | 0 |
| 97 | 1000 | 70 | 90 | 70 | 90 | 90 | 20 | 50 | 100 | 80 | 0 |
| 98 | 4000 | 60 | — | — | — | — | 60 | 100 | 90 | — | — |
| 99 | 2000 | 25 | 80 | 60 | 65 | 0 | 0 | 0 | 50 | 20 | 0 |
| 101 | 2000 | 40 | — | 50 | 100 | 50 | 80 | 0 | 100 | 35 | 0 |
| 103 | 4000 | 0 | — | — | — | — | — | 100 | 100 | 80 | — |
| 104 | 125 | 65 | 95 | 90 | 100 | 85 | 100 | 100 | 100 | 100 | 100 |
| | 3.9 | 35 | 85 | 80 | 100 | 70 | 75 | 90 | 100 | 90 | 85 |
| 105 | 500 | 35 | 40 | 95 | 90 | 100 | 60 | 70 | 60 | 0 | 80 |
| 106 | 500 | 30 | 40 | 90 | 0 | 90 | 0 | 80 | 40 | 0 | 90 |
| | 250 | 0 | 20 | 90 | 0 | 40 | 0 | 80 | 20 | 0 | 50 |
| 107 | 1000 | 0 | 50 | 85 | 15 | 80 | 0 | 0 | 40 | 25 | 0 |
| 108 | 500 | 70 | 40 | 75 | 70 | 80 | 30 | 10 | 0 | 90 | 80 |
| | 125 | 60 | 25 | 75 | 35 | 70 | 15 | 0 | 0 | 20 | 85 |
| 111 | 250 | 25 | 90 | 70 | 90 | 95 | 50 | 80 | 70 | 85 | 0 |
| 112 | 125 | 0 | 90 | 85 | 90 | 95 | 65 | 80 | 60 | 85 | 0 |
| 113 | 250 | 30 | 70 | 15 | 90 | 90 | 50 | 80 | 70 | 75 | 0 |
| 114 | 1000 | 25 | 95 | 40 | 100 | 100 | 100 | 80 | — | 90 | 0 |
| | 62.5 | 0 | 50 | 25 | 0 | 20 | 60 | 0 | 0 | 60 | 0 |
| 116 | 250 | 100 | — | 45 | 100 | 95 | 90 | 25 | 95 | 90 | 0 |
| 117 | 500 | 90 | 100 | 35 | 100 | 100 | 100 | 80 | 75 | 100 | 0 |
| | 62.5 | 60 | 75 | 0 | 80 | 90 | 90 | 50 | 40 | 50 | 0 |
| 118 | 500 | 0 | 80 | 0 | 100 | 100 | 100 | 70 | 70 | 80 | 0 |
| 119 | 500 | 0 | 100 | 0 | 50 | 70 | 90 | 30 | 0 | 70 | 30 |
| 120 | 4000 | 100 | — | — | — | — | — | 98 | 100 | 98 | — |
| 133 | 4000 | 20 | — | — | — | — | — | 40 | 100 | 40 | — |
| 135 | 2000 | 0 | 50 | 40 | 90 | 75 | 75 | 0 | — | 75 | 0 |
| 136 | 500 | 30 | 80 | 30 | 80 | 98 | 30 | 40 | 90 | 70 | 0 |
| 137 | 1000 | — | — | 50 | 100 | 70 | 100 | 100 | 100 | 80 | 0 |
| | 62.5 | 40 | — | 35 | 90 | 30 | 70 | 50 | 100 | 75 | 0 |
| 138 | 125 | 70 | 100 | 40 | 80 | 80 | 80 | 50 | 100 | 85 | 0 |
| | 31.2 | 40 | 98 | 0 | 70 | 70 | 50 | 0 | 100 | 65 | 0 |
| 139 | 125 | 60 | 98 | 50 | 100 | 100 | 85 | 90 | 100 | 100 | 0 |
| 140 | 125 | 90 | 100 | 65 | 100 | 100 | 95 | 100 | 100 | 90 | 0 |
| | 31.2 | 95 | 100 | 50 | 100 | 100 | 80 | 50 | 100 | 85 | 0 |
| 141 | 125 | 60 | 98 | 80 | 100 | 70 | 98 | 90 | 100 | 98 | 0 |
| | 31.2 | 60 | 100 | 75 | 100 | 65 | 80 | 80 | 100 | 95 | 0 |
| 142 | 2000 | 80 | 75 | 50 | 95 | 100 | 80 | 75 | — | 35 | 0 |
| 143 | 62.5 | 98 | 100 | 60 | 100 | 95 | 50 | 100 | 100 | 0 | 70 |
| | 15.6 | 98 | 98 | 20 | 100 | 90 | 20 | 100 | 100 | 0 | 50 |
| | 3.9 | 80 | 70 | 0 | 98 | 40 | 0 | 60 | 90 | 0 | 0 |
| 144 | 62.5 | 80 | 95 | 15 | 100 | 99 | 99 | 80 | 100 | 100 | 0 |
| | 7.8 | 55 | 70 | 0 | 100 | 85 | 70 | 35 | 95 | 95 | 0 |
| 145 | 62.5 | 75 | 90 | 35 | 100 | 100 | 90 | 95 | 100 | 100 | 0 |
| | 7.8 | 50 | 65 | 0 | 95 | 95 | 55 | 65 | 100 | 75 | 0 |
| 146 | 62.5 | 50 | 95 | 85 | 100 | 100 | 95 | 95 | 100 | 100 | 15 |
| | 3.9 | 20 | 50 | 5 | 70 | 90 | 75 | 60 | 75 | 75 | 0 |
| 147 | 15.6 | 80 | 90 | 45 | 100 | — | 90 | 80 | 100 | 100 | 0 |
| | 3.9 | 25 | 70 | 5 | 100 | — | 60 | 60 | 90 | 90 | 0 |

-continued

POSTEMERGENT CONTROL OF PLANT SPECIES

| | | | | | | | | | | | |
|---|---|---|---|---|---|---|---|---|---|---|---|
| 148 | 25 | 75 | — | 0 | — | — | 80 | 0 | 100 | 90 | — |
| 149 | 2000 | 0 | — | 0 | — | — | 0 | 0 | 100 | 10 | — |
| 150 | 125 | 10 | 70 | 0 | 90 | 90 | 90 | 35 | 70 | 80 | 0 |
| 151 | 62.5 | 95 | 100 | 25 | — | 100 | 100 | 95 | 100 | 95 | 0 |
| | 15.6 | 80 | 75 | 0 | — | 100 | 100 | 90 | 100 | 95 | 0 |
| 152 | 125 | 100 | 100 | 45 | 100 | 100 | 100 | 100 | 100 | 100 | 0 |
| | 7.8 | 90 | 90 | 0 | 90 | 80 | 80 | 85 | 90 | 100 | 0 |
| 153 | 125 | 90 | 100 | 35 | 100 | 100 | 100 | 85 | 100 | 100 | 0 |
| | 7.8 | 70 | 100 | 0 | 100 | 60 | 70 | 55 | 40 | 90 | 0 |
| 154 | 62.5 | 40 | 90 | 0 | 80 | 95 | 90 | 50 | 20 | 90 | 0 |
| 155 | 125 | 90 | 100 | 20 | 100 | 100 | 95 | 85 | 100 | 100 | 0 |
| | 15.6 | 75 | 90 | 0 | 95 | 50 | 80 | 15 | 80 | 95 | 0 |
| 156 | 31.25 | 75 | 90 | 0 | 100 | 90 | 100 | 85 | 100 | 100 | 0 |
| 157 | 15.6 | 70 | 90 | 0 | 80 | 50 | 90 | 40 | 70 | 90 | 0 |
| 158 | 31.25 | 75 | 95 | 20 | 100 | 40 | 90 | 60 | 90 | 95 | 0 |
| | 7.8 | 45 | 80 | 10 | 90 | 0 | 80 | 10 | 40 | 65 | 0 |
| 159 | 125 | 100 | 100 | 25 | 100 | 100 | 100 | 100 | 100 | 100 | 0 |
| | 15.6 | 50 | 100 | 0 | 100 | 70 | 100 | 70 | 70 | 95 | 0 |
| 160 | 62.5 | 65 | 80 | 65 | 100 | 75 | — | 60 | 100 | 100 | 0 |
| 161 | 250 | 80 | 85 | 40 | 80 | 65 | 100 | 75 | 100 | 60 | 15 |
| 162 | 62.5 | 40 | 80 | 0 | — | 10 | 70 | 20 | 95 | 80 | 0 |
| 163 | 500 | 0 | 70 | 0 | 0 | 40 | 70 | 0 | 90 | 20 | 0 |
| 164 | 125 | 90 | 95 | 30 | 100 | 80 | 95 | 80 | 100 | 100 | 0 |
| | 31.25 | 60 | 90 | 0 | 100 | 50 | 50 | 10 | 100 | 90 | 0 |
| 165 | 62.5 | 70 | 70 | 30 | 90 | 50 | 50 | 60 | 100 | 80 | 0 |
| | 15.6 | 45 | 40 | 0 | 70 | 20 | 50 | 40 | 80 | 45 | 0 |
| 166 | 62.5 | 60 | 65 | 55 | 70 | 70 | 60 | 75 | 100 | 90 | 80 |
| | 15.6 | 40 | 40 | 40 | 60 | 20 | 50 | 50 | 100 | 80 | 0 |
| 168 | 62.5 | 60 | — | 80 | — | 70 | 70 | 98 | 100 | 90 | 0 |
| | 15.6 | 20 | 90 | 80 | — | 50 | — | 75 | 100 | 60 | 0 |
| 169 | 125 | 50 | 80 | 0 | 80 | 30 | 70 | 0 | 70 | 65 | 0 |
| 170 | 500 | 50 | — | 30 | 95 | 25 | 90 | 70 | 100 | 90 | 25 |
| | 125 | 50 | 100 | 0 | 90 | 15 | 80 | 60 | 100 | 80 | 0 |
| 171 | 2000 | 60 | 30 | — | 90 | 0 | 50 | 0 | 0 | 50 | 0 |
| 172 | 1000 | 40 | 80 | 50 | 80 | 20 | 70 | 20 | 100 | 70 | 0 |
| 173 | 125 | 0 | 80 | 40 | 100 | 0 | — | 0 | 80 | 0 | 0 |
| 174 | 62.5 | 80 | — | 70 | 90 | 80 | 85 | 100 | 100 | 100 | 20 |
| | 7.8 | 100 | 80 | 50 | 90 | 40 | 80 | 70 | 100 | 90 | 0 |
| 175 | 62.5 | 100 | — | 40 | 100 | 100 | 100 | 100 | 100 | 100 | 0 |
| 176 | 250 | 0 | 95 | 65 | 80 | 0 | 80 | 50 | 100 | 80 | 0 |
| 177 | 62.5 | 90 | 98 | 80 | 90 | 98 | 85 | 80 | 100 | 100 | 50 |
| | 7.8 | 50 | 85 | 60 | 80 | 50 | 40 | 80 | 100 | 100 | 0 |
| 178 | 250 | 50 | 90 | 50 | 80 | 90 | 85 | 35 | — | 80 | 0 |
| 179 | 62.5 | 0 | 50 | 10 | 75 | 50 | 15 | 0 | 0 | 0 | 0 |
| 180 | 500 | 100 | 100 | 100 | 100 | 100 | 100 | 90 | — | 100 | 0 |
| | 125 | 95 | 100 | 90 | 100 | 100 | 100 | 90 | — | 100 | 0 |
| 181 | 125 | 90 | 99 | 95 | 90 | 80 | — | 80 | 100 | 95 | 0 |
| 182 | 125 | 90 | 98 | 95 | — | 100 | 98 | 60 | 100 | 98 | 0 |
| 183 | 125 | 65 | 95 | 0 | 98 | 50 | 90 | 0 | 95 | 90 | 0 |
| 184 | 125 | 95 | 100 | 90 | — | 90 | 100 | 85 | 100 | 100 | 0 |
| 185 | 62.5 | 90 | 98 | — | 95 | 90 | 90 | 50 | — | 90 | 0 |
| 186 | 4000 | 100 | — | — | — | — | — | 80 | 100 | 100 | — |
| 187 | 125 | 40 | — | 90 | 85 | 80 | 80 | 80 | 98 | 90 | 0 |
| 188 | 125 | 90 | 80 | 95 | 85 | 60 | 80 | 100 | 100 | 90 | 0 |
| 189 | 125 | 80 | 100 | 85 | 100 | 25 | 80 | 80 | 90 | 90 | 0 |
| 190 | 125 | 98 | 80 | 85 | 100 | 80 | — | 20 | 100 | 85 | 15 |
| 191 | 125 | 60 | 100 | 80 | 95 | 70 | 100 | 80 | 98 | 98 | 0 |
| | 31.2 | 40 | 100 | 80 | 80 | 20 | 80 | 80 | 50 | 70 | 0 |
| 192 | 125 | 80 | 100 | 20 | 100 | — | 90 | 90 | 100 | 90 | 0 |
| | 31.25 | 40 | 90 | 0 | 100 | — | 80 | 40 | 100 | 20 | 0 |
| 193 | 250 | 80 | 100 | 40 | 100 | 30 | 100 | 80 | 100 | 98 | 0 |
| 194 | 250 | 50 | 100 | 60 | 100 | 70 | 100 | 10 | 100 | 95 | 0 |
| 195 | 250 | 80 | 90 | 65 | 100 | 25 | 85 | 80 | 98 | 100 | 0 |
| 196 | 250 | 70 | 100 | 40 | 100 | 90 | 100 | 100 | 100 | 100 | 0 |
| 197 | 250 | 80 | 85 | 40 | 80 | 65 | 100 | 75 | 100 | 60 | 15 |
| 198 | 2000 | 60 | 100 | 0 | 90 | 0 | 0 | 50 | 30 | 90 | 0 |
| 199 | 62.5 | 40 | 100 | 90 | 90 | — | 40 | 10 | 98 | 80 | 0 |
| 200 | 62.5 | 0 | 95 | 35 | 95 | — | 30 | 0 | 40 | 50 | 0 |
| 201 | 500 | 0 | 20 | 0 | 50 | 80 | 70 | 0 | 90 | 60 | 0 |
| 204 | 1000 | 70 | 60 | 15 | 60 | — | 50 | 0 | 0 | 90 | 0 |
| 205 | 250 | — | 75 | 60 | 95 | — | 60 | 40 | 100 | — | 45 |
| 206 | 250 | 40 | 100 | 20 | 100 | 100 | 90 | 98 | 100 | 98 | 0 |
| 207 | 1000 | 90 | 100 | 25 | 100 | 95 | 95 | 50 | 30 | 100 | 0 |
| 208 | 62.5 | 80 | 100 | 65 | 95 | 65 | 95 | 50 | 100 | 90 | 0 |
| 209 | 250 | 0 | 70 | 0 | 40 | 80 | 70 | 0 | 0 | 70 | 0 |
| 210 | 62.5 | 35 | 30 | 20 | 40 | 0 | — | 0 | 0 | 55 | 0 |
| 211 | 1000 | 20 | — | 0 | 40 | 20 | — | 0 | 75 | 60 | 0 |
| 212 | 2000 | 0 | — | 55 | 98 | 50 | — | 0 | 100 | 70 | 0 |
| 213 | 125 | 95 | 100 | 90 | 100 | 70 | 100 | 80 | 100 | 100 | 98 |
| | 31.2 | 90 | 30 | 80 | 100 | 50 | 80 | 70 | 100 | 98 | 98 |
| 214 | 62.5 | 75 | — | 90 | 100 | 70 | — | 50 | 100 | — | 90 |

-continued

POSTEMERGENT CONTROL OF PLANT SPECIES

| | | | | | | | | | | | |
|---|---|---|---|---|---|---|---|---|---|---|---|
| 215 | 62.5 | 80 | — | 90 | 80 | 70 | 80 | 50 | 100 | 98 | 90 |
| 216 | 62.5 | 80 | — | 85 | 100 | 70 | 80 | 95 | 100 | 80 | 90 |
| 217 | 31.2 | 0 | — | 75 | — | 40 | 60 | 70 | 100 | 85 | 80 |
| 218 | 62.5 | 20 | — | 90 | — | 40 | 80 | 80 | 100 | 85 | 0 |
| 219 | 62.5 | 80 | — | 90 | 98 | 60 | — | 80 | 100 | 90 | 90 |
| | 15.6 | 65 | — | 80 | 90 | 35 | — | 40 | 100 | 90 | 0 |
| 220 | 62.5 | — | 50 | 80 | — | 45 | 50 | 50 | 100 | 85 | 90 |
| 221 | 62.5 | — | — | 50 | — | 60 | 80 | 80 | 100 | — | 75 |
| 222 | 62.5 | — | — | 80 | — | 30 | 100 | 80 | 100 | — | 75 |
| 223 | 125 | 65 | 98 | 80 | 100 | 60 | 100 | 100 | 100 | 100 | 100 |
| | 15.6 | 50 | 90 | 80 | 80 | 40 | 100 | 90 | 100 | 90 | 98 |
| 227 | 250 | 0 | — | 0 | — | 80 | 70 | 80 | 100 | 50 | 40 |
| | 31.2 | 0 | — | 0 | 20 | 50 | 50 | 50 | 100 | 0 | 0 |
| 228 | 125 | 0 | 50 | 0 | 80 | 90 | 50 | 0 | 100 | 40 | 20 |
| 229 | 125 | 30 | 100 | 80 | 100 | 100 | 60 | 70 | 100 | 98 | 0 |
| | 31.2 | 0 | 98 | 70 | 75 | 98 | 40 | 50 | 100 | 75 | 0 |
| 230 | 125 | 0 | 70 | 50 | 80 | 70 | 80 | 35 | 100 | 85 | 80 |
| 231 | 125 | 25 | 98 | 65 | 100 | 80 | 100 | 100 | 100 | 85 | 100 |
| | 31.2 | 0 | 90 | 50 | 100 | 70 | 80 | 80 | 100 | 50 | 95 |
| 232 | 4000 | 50 | — | — | — | — | — | 10 | 0 | 50 | — |
| 233 | 250 | 0 | 80 | 40 | 0 | 20 | 30 | — | 50 | 50 | 0 |
| 234 | 4000 | 60 | — | — | — | — | — | 0 | 100 | 0 | — |
| 235 | 1000 | 20 | 70 | 30 | 50 | 70 | 70 | 20 | 100 | — | 90 |
| 236 | 1000 | 0 | — | 60 | 80 | 75 | 80 | 70 | 100 | 70 | 0 |
| 237 | 1000 | 50 | 70 | 80 | 30 | 70 | — | 50 | 100 | 80 | 75 |
| 239 | 4000 | 90 | — | — | — | — | — | 98 | 100 | 90 | — |
| 240 | 2000 | — | — | 50 | 100 | 20 | 60 | 30 | 100 | 80 | 20 |
| 241 | 2000 | 0 | — | 30 | 50 | 0 | 0 | 20 | 98 | 30 | 0 |
| 242 | 2000 | 0 | — | 0 | 70 | 40 | 0 | 0 | 0 | 70 | 0 |
| 243 | 500 | 80 | 100 | 85 | 95 | 100 | 95 | 80 | 80 | 90 | 75 |
| | 31.25 | 70 | 90 | 80 | 90 | 100 | 80 | 70 | 40 | 80 | 0 |
| 244 | 500 | 100 | 100 | 45 | 100 | 100 | 100 | 90 | 100 | 100 | 40 |
| | 125 | 90 | 100 | 30 | 100 | 100 | 90 | 80 | 85 | 100 | 0 |
| 245 | 4000 | 0 | — | — | — | — | — | 50 | 0 | 30 | — |
| 246 | 500 | 80 | 70 | 85 | 100 | 90 | 80 | 50 | 100 | 70 | 0 |
| 247 | 500 | 0 | 70 | 70 | 70 | 20 | 20 | 0 | 70 | 40 | 0 |
| 248 | 500 | 50 | 100 | 40 | 75 | 0 | 0 | 0 | 0 | 100 | 0 |
| 250 | 500 | 0 | 70 | 50 | 30 | 50 | 50 | 25 | 40 | 70 | 0 |
| 255 | 2000 | 20 | 50 | 5 | 80 | 70 | 0 | 10 | 40 | 0 | 0 |
| 257 | 4000 | 0 | — | — | — | — | — | 20 | 100 | 60 | — |
| 258 | 4000 | 0 | — | — | — | — | — | 20 | — | 20 | — |
| 260 | 500 | 80 | 95 | 90 | 100 | — | 95 | 40 | 45 | 90 | 0 |
| 261 | 500 | 60 | 95 | 90 | 90 | — | 95 | 90 | 65 | 95 | 0 |
| 262 | 500 | 100 | 100 | 95 | 100 | — | 100 | 100 | 100 | 100 | 50 |
| | 31.25 | 80 | 100 | 90 | 100 | — | 100 | 90 | 100 | 95 | 0 |
| 263 | 500 | 50 | 100 | 0 | 100 | — | 80 | 80 | 90 | 40 | 0 |
| 264 | 250 | 0 | 50 | 70 | 80 | — | 80 | 80 | 50 | 0 | 0 |
| 265 | 500 | 0 | 60 | 40 | 80 | — | 0 | 60 | 70 | 0 | 0 |
| 266 | 500 | 10 | 75 | 80 | 30 | — | 90 | 85 | 25 | 75 | 0 |
| 267 | 500 | 0 | 80 | 45 | 80 | — | 80 | 90 | 60 | 95 | 0 |
| 268 | 31.25 | 100 | 100 | 10 | — | 95 | 80 | 90 | 100 | 100 | 0 |
| 269 | 62.5 | 80 | 90 | 0 | 100 | 0 | 80 | 90 | 30 | 100 | 0 |
| 270 | 62.5 | 70 | 80 | 10 | 100 | 60 | — | 55 | 100 | 70 | 35 |
| | 3.9 | 45 | 70 | 0 | 55 | 20 | 75 | 20 | 60 | 55 | 0 |
| 271 | 1000 | 65 | 80 | 40 | 100 | 50 | — | 60 | 100 | 80 | 0 |
| | 62.5 | 50 | 70 | 0 | 60 | 0 | — | 0 | 20 | 60 | 0 |
| 272 | 62.5 | 45 | 60 | 0 | 80 | 30 | 50 | 0 | 50 | 70 | 0 |
| 273 | 500 | — | 100 | 40 | 100 | 40 | 100 | 80 | 100 | 50 | 0 |
| 274 | 2000 | 80 | 90 | 46 | 100 | 75 | 80 | 80 | 100 | 100 | 50 |
| 275 | 125 | — | — | 0 | — | 80 | 98 | 60 | 100 | — | 60 |
| 276 | 125 | — | — | 0 | — | 70 | 100 | 65 | 100 | — | 80 |
| 277 | 125 | 0 | — | 50 | — | 60 | 80 | 20 | 100 | — | 75 |
| | 31.2 | 0 | — | 20 | — | 0 | 80 | 0 | 100 | — | 0 |
| 278 | 125 | — | — | 30 | — | 60 | 70 | 60 | 100 | — | 0 |
| 279 | 125 | — | — | 20 | — | 70 | 98 | 60 | 100 | — | 0 |
| 280 | 250 | — | — | 0 | — | 60 | — | 60 | 100 | — | 75 |
| 281 | 125 | — | — | 0 | — | 60 | 100 | 60 | 100 | — | — |
| 282 | 125 | 70 | 80 | 50 | 80 | 70 | 80 | 80 | 100 | 80 | 0 |
| | 31.2 | 60 | 80 | 20 | — | 50 | 70 | 50 | 100 | 85 | 0 |
| 283 | 125 | 50 | 80 | 80 | 80 | 70 | 100 | 80 | 100 | 80 | 0 |
| 284 | 125 | — | — | 0 | — | 70 | 100 | 80 | 100 | — | 20 |
| 285 | 125 | 80 | 90 | 70 | 90 | 70 | 100 | 50 | 100 | 98 | 0 |
| | 7.8 | — | 80 | 0 | 80 | 50 | 100 | 40 | 100 | 80 | 0 |
| 286 | 125 | 30 | 100 | 65 | 80 | 30 | 90 | 80 | 100 | 80 | 0 |
| 287 | 125 | 70 | 80 | 70 | 85 | 40 | 80 | 70 | 100 | 80 | 0 |
| 288 | 125 | 30 | 95 | 70 | 90 | 40 | — | 80 | 100 | 90 | 0 |
| 289 | 1000 | 50 | 98 | 55 | 90 | 70 | 100 | 80 | 100 | 80 | 0 |
| 290 | 125 | 30 | 80 | 50 | 85 | 40 | 100 | 80 | 100 | 80 | 0 |
| 291 | 125 | 40 | 85 | 40 | 85 | 60 | 100 | 30 | 100 | 80 | 0 |
| | 7.8 | 20 | 60 | 0 | 85 | 0 | 50 | 30 | 100 | 60 | 0 |
| 292 | 125 | 60 | 100 | 50 | — | 90 | 80 | 80 | 100 | 100 | 35 |

-continued
POSTEMERGENT CONTROL OF PLANT SPECIES

|  | 31.2 | 40 | 95 | 0 | — | 60 | 70 | 80 | 100 | 95 | 0 |
|---|---|---|---|---|---|---|---|---|---|---|---|
| 293 | 125 | 90 | 100 | 30 | 100 | 90 | 80 | 0 | 100 | 98 | 0 |
|  | 31.2 | 50 | 80 | 10 | 80 | 90 | 50 | 0 | 100 | 85 | 0 |
| 294 | 125 | 60 | 98 | 55 | 85 | 98 | 90 | 70 | 100 | 98 | 0 |
| 297 | 125 | 70 | 100 | 50 | — | 80 | 80 | 0 | 100 | 95 | 0 |
| 298 | 2000 | 35 | 95 | 30 | 80 | 90 | 80 | 50 | 100 | 85 | 0 |
|  | 500 | 35 | 85 | 0 | 80 | 50 | 50 | 50 | 100 | 80 | 0 |
| 299 | 2000 | 0 | 50 | 0 | 80 | 0 | 0 | 40 | 100 | 50 | 0 |
| 300 | 125 | 60 | 98 | 15 | 85 | 70 | 85 | 60 | 100 | 85 | 0 |
|  | 62.5 | 50 | 98 | 0 | 80 | 50 | 85 | 50 | 100 | 85 | 0 |
| 301 | 2000 | 30 | 90 | 15 | 85 | 60 | — | 50 | 100 | 90 | 0 |
| 304 | 62.5 | 90 | 95 | 80 | — | 95 | 95 | 85 | 100 | 90 | 0 |
| 305 | 250 | 90 | 98 | 98 | 98 | 98 | 90 | 70 | 100 | 100 | 0 |
| 306 | 125 | 50 | — | 98 | 90 | — | — | 80 | 100 | 90 | 0 |

| Compound | Dosage (ppm) | K | L | M | N | O | P | Q | R | T |
|---|---|---|---|---|---|---|---|---|---|---|
| 1 | 500 | 0 | 40 | 0 | 15 | 0 | 40 | 60 | 0 | 0 |
| 2 | 1000 | 20 | 0 | 0 | 0 | 0 | 0 | 90 | 0 | 0 |
| 4 | 500 | 40 | 40 | 0 | 0 | 20 | 0 | 80 | 0 | 0 |
| 6 | 500 | 20 | 80 | 0 | 35 | 20 | 0 | 80 | 0 | 90 |
| 7 | 500 | 15 | 65 | 0 | 35 | 0 | 25 | 50 | 0 | 65 |
| 8 | 500 | 40 | 70 | 10 | 70 | 10 | 25 | 90 | 0 | 60 |
|  | 62.5 | 30 | 20 | 0 | 5 | 0 | 10 | 20 | 0 | 0 |
| 9 | 1000 | 30 | 90 | 0 | 20 | 40 | 0 | 30 | 0 | 40 |
| 10 | 2000 | — | 10 | 0 | 0 | 0 | 0 | 0 | 0 | 60 |
|  | 500 | — | 0 | 0 | 0 | 0 | 0 | 0 | 0 | 0 |
| 12 | 500 | 25 | 75 | 0 | 80 | 25 | 20 | 55 | 0 | 90 |
|  | 125 | 10 | 60 | 0 | 10 | 0 | 0 | 25 | 0 | 40 |
|  | 15.6 | 0 | 0 | 0 | 0 | 0 | 0 | 0 | 0 | 0 |
| 13 | 250 | 15 | 90 | 0 | 90 | 20 | 70 | 90 | 0 | 90 |
|  | 62.5 | 0 | 80 | 0 | 100 | 0 | 50 | 85 | 0 | 75 |
|  | 15.6 | 0 | 80 | 0 | 0 | 0 | 0 | 70 | 0 | 0 |
| 14 | 1000 | 30 | 0 | 0 | 0 | 0 | 0 | 0 | 0 | 0 |
| 15 | 1000 | 35 | 40 | 0 | 0 | 0 | 0 | 0 | 0 | 10 |
| 17 | 1000 | 0 | 60 | 10 | 0 | 15 | 10 | 85 | 0 | 0 |
|  | 500 | 0 | 40 | 0 | 0 | 0 | 20 | 60 | 0 | 0 |
| 19 | 1000 | 0 | 50 | 0 | 20 | 20 | 0 | 65 | 0 | 85 |
| 21 | 1000 | 20 | 30 | 0 | 0 | 0 | 0 | 20 | 0 | 80 |
| 22 | 250 | 50 | 90 | 10 | 100 | 90 | 100 | 100 | 20 | 85 |
|  | 62.5 | 20 | 90 | 0 | 100 | 75 | 90 | 100 | 0 | 80 |
|  | 15.6 | 0 | 75 | 0 | 100 | 0 | 95 | 85 | 0 | 40 |
| 24 | 1500 | 20 | 10 | 0 | 0 | — | — | 10 | 0 | 0 |
| 25 | 250 | 60 | 85 | 0 | 90 | 90 | 95 | 100 | 20 | 80 |
|  | 62.5 | 10 | 80 | 0 | 70 | 70 | 90 | 90 | 0 | 60 |
|  | 15.6 | 0 | 60 | 0 | 20 | 0 | 70 | 75 | 0 | 0 |
| 26 | 500 | 80 | 90 | 30 | 100 | 90 | 90 | 100 | 0 | 90 |
|  | 125 | 40 | 85 | 0 | 100 | 80 | 75 | 95 | 0 | 80 |
|  | 31.25 | 0 | 50 | 0 | 100 | 20 | 30 | 60 | 0 | 80 |
| 30 | 500 | 20 | 0 | 0 | 0 | 0 | 0 | 0 | 0 | 0 |
| 31 | 125 | 0 | 90 | 0 | 40 | 80 | 90 | 100 | 0 | 75 |
|  | 31.25 | 0 | 80 | 0 | 20 | 75 | 80 | 100 | 0 | 80 |
|  | 7.8 | 0 | 50 | 0 | 0 | 0 | 60 | 80 | 0 | 50 |
| 32 | 500 | 10 | 0 | 30 | 0 | 10 | 10 | 95 | 0 | 0 |
|  | 250 | 20 | 0 | 0 | 0 | 0 | 0 | 80 | 0 | 0 |
| 33 | 500 | 0 | 80 | 0 | 0 | 0 | 0 | 60 | 0 | 10 |
| 34 | 500 | 0 | 60 | 0 | 0 | 0 | 0 | 20 | 0 | 60 |
| 35 | 500 | 0 | 20 | — | 0 | 0 | 0 | 0 | 0 | 0 |
| 38 | 62.5 | 0 | 20 | 0 | 10 | 10 | 95 | 90 | 0 | 30 |
|  | 15.6 | 0 | 0 | 0 | 0 | 5 | 80 | 50 | 0 | 10 |
| 39 | 62.5 | 0 | 65 | 0 | 50 | 70 | 97 | 90 | 0 | 40 |
|  | 15.6 | 0 | 80 | 0 | 40 | 0 | 90 | 80 | 0 | 20 |
|  | 3.9 | 0 | 5 | 0 | 0 | 0 | 80 | 0 | 0 | 0 |
| 40 | 1000 | 0 | 20 | 0 | 0 | 0 | 0 | 0 | 0 | 20 |
| 41 | 4000 | — | — | — | 80 | 40 | 40 | — | — | 95 |
| 43 | 2000 | 0 | 0 | 0 | 0 | 25 | 0 | 20 | 0 | 0 |
| 44 | 250 | 0 | 20 | 0 | 0 | 0 | 40 | 0 | 0 | 60 |
| 45 | 500 | 50 | 0 | 0 | 0 | 0 | 0 | 0 | 0 | 0 |
| 46 | 31.3 | 0 | 0 | 0 | 0 | 10 | 80 | 50 | 0 | 40 |
|  | 7.8 | 0 | 0 | 0 | 0 | 0 | 0 | 0 | 0 | 20 |
|  | 1.9 | 0 | 0 | 0 | 0 | 0 | 0 | 0 | 0 | 10 |
| 47 | 62.5 | 0 | 0 | 0 | 0 | 0 | 0 | 0 | 0 | 10 |
| 48 | 500 | 0 | 0 | 0 | 0 | 0 | 0 | 0 | 0 | 0 |
| 49 | 250 | 10 | 80 | 0 | 90 | 80 | 95 | 80 | 20 | 90 |
|  | 62.5 | 0 | 70 | 0 | 80 | 60 | 90 | 100 | 0 | 90 |
| 50 | 62.5 | 97 | 90 | 0 | 95 | 95 | 99 | 97 | 90 | 90 |
|  | 15.6 | 97 | 50 | 0 | 80 | 80 | 97 | 95 | 10 | 80 |
| 51 | 62.5 | 40 | 90 | 0 | 20 | 0 | 93 | 95 | 10 | 80 |
|  | 7.8 | 0 | 50 | 0 | 0 | 0 | 0 | 20 | 0 | 70 |
| 52 | 2000 | 0 | 0 | 0 | 0 | 0 | 0 | 0 | 0 | 0 |
| 53 | 62.5 | 10 | 90 | 0 | 70 | 50 | 95 | 97 | 0 | 60 |

-continued

POSTEMERGENT CONTROL OF PLANT SPECIES

|  |  |  |  |  |  |  |  |  |  |  |
|---|---|---|---|---|---|---|---|---|---|---|
|  | 15.6 | 0 | 90 | 0 | 65 | 20 | 97 | 93 | 0 | 80 |
| 54 | 62.5 | 40 | 93 | 20 | 50 | 30 | 95 | 97 | 15 | 30 |
|  | 7.8 | 0 | 25 | 0 | 0 | 0 | 25 | 60 | 0 | 0 |
| 55 | 125 | 0 | 0 | 0 | 0 | 0 | 0 | 0 | 0 | 0 |
| 56 | 62.5 | 0 | 55 | 0 | 0 | 40 | 75 | 95 | 0 | 15 |
| 57 | 125 | 0 | 70 | — | 0 | 0 | 0 | 85 | 0 | 0 |
| 58 | 125 | 60 | 95 | 60 | 95 | 90 | 90 | 100 | — | 90 |
|  | 31.25 | 50 | 90 | 0 | 90 | 95 | 90 | 95 | — | 90 |
| 59 | 250 | 0 | 0 | 0 | 0 | 0 | 0 | 0 | 0 | 0 |
| 60 | 2000 | 0 | 10 | 0 | — | 0 | 0 | — | — | 15 |
| 61 | 125 | 15 | 0 | 0 | 0 | 70 | 25 | 35 | 0 | 5 |
| 62 | 125 | 15 | 45 | 0 | 0 | 10 | 10 | 80 | 0 | 15 |
| 63 | 62.5 | 10 | 60 | 0 | 50 | 40 | 65 | 60 | 0 | 60 |
| 64 | 125 | 70 | 80 | 80 | 0 | 90 | 80 | 90 | 0 | 80 |
| 65 | 250 | 0 | 70 | 0 | 50 | 70 | 90 | 90 | 0 | 15 |
| 66 | 1000 | 0 | 20 | 0 | 0 | 30 | 0 | 80 | 0 | 0 |
| 67 | 1000 | 0 | 0 | 0 | 0 | 20 | 20 | 0 | 0 | 0 |
| 68 | 1000 | 25 | 80 | 0 | 30 | 80 | 95 | 75 | 0 | 75 |
|  | 125 | 0 | 25 | 0 | 0 | 0 | 50 | 60 | 0 | 20 |
| 69 | 500 | 0 | 80 | 0 | 80 | 80 | 90 | 95 | 0 | 80 |
|  | 62.5 | 0 | 40 | 0 | 0 | 0 | 70 | 30 | 0 | 60 |
| 70 | 250 | 0 | 0 | 0 | 0 | 75 | 80 | 80 | 0 | 90 |
| 71 | 500 | 0 | 0 | 0 | 0 | 20 | 0 | 0 | 0 | 0 |
| 72 | 62.5 | 35 | 50 | 0 | 50 | 0 | 40 | 70 | 0 | 85 |
| 73 | 125 | 0 | 0 | 0 | 0 | 0 | 0 | 0 | 0 | 25 |
| 74 | 500 | 0 | 80 | 0 | 70 | 0 | 60 | 50 | 0 | 95 |
| 75 | 125 | 20 | 0 | 0 | 10 | 0 | 0 | 0 | 0 | 5 |
| 76 | 125 | 80 | 40 | 20 | 35 | 65 | 98 | 60 | 10 | 95 |
|  | 31.25 | 70 | 50 | 0 | 30 | 50 | 85 | 30 | 0 | 80 |
| 77 | 125 | 30 | 0 | 0 | 40 | 20 | 98 | 20 | 0 | 15 |
|  | 15.6 | 15 | 0 | 0 | 0 | 0 | 40 | 20 | 0 | 15 |
| 78 | 125 | 50 | 50 | 0 | 10 | 10 | 50 | 0 | 0 | 75 |
| 79 | 2000 | 0 | 75 | 0 | 10 | 0 | 0 | 60 | 25 | 0 |
| 81 | 2000 | 0 | 0 | 0 | 0 | 0 | 0 | 0 | 0 | 40 |
| 82 | 500 | 0 | 0 | 0 | 0 | 0 | 0 | 0 | 0 | 0 |
| 83 | 62.5 | 0 | 0 | 0 | 0 | 0 | 0 | 0 | 0 | 0 |
| 84 | 2000 | 0 | 0 | 0 | 0 | 0 | 0 | 0 | 0 | 30 |
| 85 | 62.5 | 0 | 40 | 0 | 50 | 50 | 75 | 0 | 0 | 60 |
|  | 7.8 | 0 | 20 | 0 | 0 | 0 | 70 | 0 | 0 | 50 |
| 86 | 125 | 0 | 40 | 0 | 30 | 0 | 70 | 0 | 0 | 20 |
| 87 | 250 | 0 | 20 | 0 | 0 | 0 | 0 | 0 | 20 | 30 |
| 89 | 2000 | 10 | 30 | 0 | 0 | 50 | 40 | 0 | 0 | 50 |
| 90 | 500 | 0 | 0 | 0 | 0 | — | 70 | 20 | 0 | 0 |
| 91 | 62.5 | 0 | 0 | 0 | 0 | 0 | 95 | 20 | 0 | 95 |
| 92 | 62.5 | 0 | 0 | 0 | 0 | 0 | 0 | 0 | 0 | 0 |
| 93 | 500 | 0 | 0 | 0 | 0 | 0 | 0 | 0 | 0 | 15 |
| 94 | 2000 | 0 | 25 | 0 | 20 | 0 | 0 | 0 | 0 | 80 |
| 97 | 1000 | 30 | 55 | 0 | 60 | 0 | 70 | 60 | 0 | 0 |
| 98 | 4000 | — | — | — | 0 | 30 | 98 | — | 0 | 0 |
| 99 | 2000 | 20 | 0 | 0 | 0 | 0 | 0 | 0 | 0 | 0 |
| 101 | 2000 | 30 | 0 | 0 | 20 | 0 | 80 | 0 | 0 | 50 |
| 103 | 4000 | — | — | — | 0 | 0 | 0 | — | 0 | — |
| 104 | 125 | 100 | 100 | 80 | 100 | 100 | 100 | 100 | 80 | 80 |
|  | 3.9 | 85 | 95 | 50 | 100 | — | 100 | 95 | 50 | 60 |
| 105 | 500 | 20 | 0 | 0 | 20 | 0 | — | 0 | 0 | 0 |
| 106 | 500 | 30 | 40 | 20 | 30 | 0 | 0 | 90 | 30 | 0 |
|  | 250 | 10 | 30 | 0 | 0 | 0 | 0 | 80 | 20 | 0 |
| 107 | 1000 | 0 | 40 | 0 | 0 | 0 | 0 | 75 | 0 | 0 |
| 108 | 500 | 0 | 80 | 60 | 100 | 0 | 0 | 100 | 0 | 35 |
|  | 125 | 0 | 90 | 0 | 100 | 0 | 0 | 80 | 0 | 5 |
| 111 | 250 | 0 | 10 | 0 | 0 | 0 | 0 | 50 | 0 | 60 |
| 112 | 125 | 0 | 60 | 0 | 0 | 0 | 0 | 15 | 0 | 40 |
| 113 | 250 | 0 | 50 | 0 | 0 | 0 | 0 | 10 | 0 | 60 |
| 114 | 1000 | 0 | 25 | 85 | 90 | 0 | 40 | 30 | 0 | 75 |
|  | 62.5 | 0 | 0 | 0 | 0 | 0 | 0 | 0 | 0 | 0 |
| 116 | 250 | 0 | 0 | 0 | 10 | 0 | 65 | 0 | 0 | 50 |
| 117 | 500 | 0 | 60 | 0 | 0 | 0 | 65 | 75 | 0 | 25 |
|  | 62.5 | 0 | 15 | 0 | 0 | 0 | 40 | 25 | 0 | 0 |
| 118 | 500 | 0 | 0 | — | 0 | 60 | 20 | 0 | 0 | 70 |
| 119 | 500 | 0 | 0 | 0 | 0 | 0 | 0 | 80 | 0 | 40 |
| 120 | 4000 | — | — | — | 90 | 70 | 98 | — | 50 | — |
| 133 | 4000 | — | — | — | 0 | 0 | 0 | — | 0 | 0 |
| 135 | 2000 | 0 | 10 | 0 | 0 | 0 | 0 | 0 | 0 | 0 |
| 136 | 500 | 0 | 0 | 0 | 0 | 0 | 0 | 0 | 0 | 0 |
| 137 | 1000 | 50 | 50 | 25 | 75 | 98 | 80 | 80 | 50 | 50 |
|  | 62.5 | 30 | 0 | 0 | 60 | 20 | 75 | 20 | 0 | 20 |
| 138 | 125 | 80 | 50 | 30 | 80 | 60 | 85 | 70 | 0 | 0 |
|  | 31.2 | 0 | 0 | 0 | 20 | 0 | 85 | 70 | 0 | 0 |
| 139 | 125 | 0 | 65 | 20 | 0 | 20 | 75 | 80 | 0 | 40 |
| 140 | 125 | 100 | 95 | 30 | 80 | 80 | 80 | 100 | 50 | 35 |
|  | 31.2 | 55 | 70 | 0 | 20 | 50 | 98 | 90 | 0 | 0 |

-continued

| POSTEMERGENT CONTROL OF PLANT SPECIES | | | | | | | | | | |
|---|---|---|---|---|---|---|---|---|---|---|
| 141 | 125 | 80 | 65 | 50 | 80 | 95 | 100 | 80 | 70 | 80 |
|  | 31.2 | 80 | 55 | 0 | 75 | 0 | 80 | 80 | 0 | 60 |
| 142 | 2000 | 0 | 75 | 0 | 0 | 50 | 80 | 80 | 0 | 0 |
| 143 | 62.5 | 93 | 0 | 93 | 60 | 97 | 97 | 97 | 0 | 90 |
|  | 15.6 | 30 | 0 | 35 | 50 | 80 | 80 | 80 | 0 | 70 |
|  | 3.9 | 0 | 0 | 0 | 10 | 70 | 70 | 0 | 0 | 0 |
| 144 | 62.5 | 75 | 80 | 0 | 80 | 100 | 95 | 100 | 0 | 85 |
|  | 7.8 | 15 | 25 | 0 | 50 | 40 | 90 | 10 | 0 | 55 |
| 145 | 62.5 | — | 80 | 0 | 15 | 25 | 75 | 75 | 0 | 20 |
|  | 7.8 | — | 45 | 0 | 0 | 0 | 0 | 65 | 0 | 0 |
| 146 | 62.5 | 90 | 75 | 0 | 95 | 95 | 95 | 90 | — | 85 |
|  | 3.9 | 40 | 10 | 0 | 20 | 0 | 75 | 25 | — | 55 |
| 147 | 15.6 | 0 | 0 | 0 | 0 | 20 | 80 | 40 | 0 | 80 |
|  | 3.9 | 0 | 0 | 0 | 0 | 0 | 0 | 0 | 0 | 15 |
| 148 | 25 | — | 70 | 0 | — | 60 | 95 | — | — | 90 |
| 149 | 2000 | — | 0 | 0 | — | 0 | 90 | — | — | 0 |
| 150 | 125 | 0 | 0 | 0 | 10 | 0 | 80 | 25 | 0 | 65 |
| 151 | 62.5 | 25 | 40 | 0 | 80 | 0 | 85 | — | 0 | 95 |
|  | 15.6 | 0 | 0 | 0 | 30 | 0 | 85 | — | 0 | 90 |
| 152 | 125 | 50 | 80 | 0 | 100 | 0 | 100 | 90 | 0 | 95 |
|  | 7.8 | 0 | 40 | 0 | 55 | 0 | 90 | 65 | 0 | 90 |
| 153 | 125 | 50 | 80 | 0 | 90 | 25 | 100 | 80 | 0 | 90 |
|  | 7.8 | 0 | 20 | 0 | 70 | 0 | 55 | 0 | 0 | 80 |
| 154 | 62.5 | 25 | 0 | 0 | 0 | 0 | 0 | 0 | 0 | 30 |
| 155 | 125 | 20 | 75 | 10 | 15 | 0 | 75 | 75 | 0 | 95 |
|  | 15.6 | 0 | 15 | 0 | 0 | 0 | 50 | 10 | 0 | 80 |
| 156 | 31.25 | 40 | 20 | 0 | 0 | 0 | 0 | 10 | 0 | 85 |
| 157 | 15.6 | 0 | 80 | 0 | 0 | 0 | 75 | 80 | 0 | 0 |
| 158 | 31.25 | 0 | 50 | 0 | 10 | 0 | 70 | 50 | 0 | 0 |
|  | 7.8 | 0 | 0 | 0 | 0 | 0 | 25 | 0 | 0 | 0 |
| 159 | 125 | 35 | 75 | — | 100 | 0 | 75 | 100 | 0 | 90 |
|  | 15.6 | 15 | 50 | — | 50 | 0 | 60 | 40 | 0 | 10 |
| 160 | 62.5 | 0 | 50 | 0 | 30 | 50 | 70 | 30 | 0 | 100 |
| 161 | 250 | 0 | 65 | 0 | 15 | 30 | 50 | 10 | 0 | 50 |
| 162 | 62.5 | 40 | 55 | 0 | 15 | 30 | 70 | 0 | 0 | 0 |
| 163 | 500 | 0 | 0 | 0 | 0 | 0 | 50 | 0 | 0 | 0 |
| 164 | 125 | 0 | 85 | 0 | 65 | 0 | 70 | 75 | 0 | 70 |
|  | 31.25 | 0 | 15 | 0 | 0 | 0 | 60 | 0 | 0 | 85 |
| 165 | 62.5 | 0 | 0 | 0 | 50 | 0 | 70 | 20 | 0 | 80 |
|  | 15.6 | 0 | 0 | 0 | 20 | 0 | 50 | 25 | 0 | 60 |
| 166 | 62.5 | 0 | 0 | 0 | 80 | 80 | 85 | 100 | 30 | 70 |
|  | 15.6 | 0 | 0 | 0 | 65 | 0 | 50 | 0 | 0 | 60 |
| 168 | 62.5 | 0 | 0 | 0 | 0 | 90 | 80 | — | 0 | 80 |
|  | 15.6 | 0 | 0 | 0 | 0 | 0 | 75 | — | 0 | — |
| 169 | 125 | 0 | 20 | 0 | 0 | 0 | 0 | 0 | 0 | 0 |
| 170 | 500 | 35 | 25 | 0 | 75 | 60 | 80 | 85 | 80 | 98 |
|  | 125 | 30 | 50 | 0 | 40 | 60 | 70 | 80 | 40 | — |
| 171 | 2000 | — | 0 | 0 | 0 | — | 0 | 0 | 0 | 0 |
| 172 | 1000 | 0 | 0 | 0 | 0 | 0 | 40 | 0 | 0 | 50 |
| 173 | 125 | 25 | 0 | — | 0 | — | 20 | 50 | 0 | 0 |
| 174 | 62.5 | 70 | 70 | 25 | 80 | 98 | 80 | 85 | 85 | 90 |
|  | 7.8 | 30 | 20 | 0 | 40 | 20 | 80 | 40 | 40 | 100 |
| 175 | 62.5 | 30 | 80 | 0 | 100 | 100 | 100 | 80 | 40 | 20 |
| 176 | 250 | 0 | 20 | 0 | 0 | 0 | 20 | 100 | 0 | 0 |
| 177 | 62.5 | 98 | 90 | 50 | 100 | 80 | 98 | 98 | 60 | 65 |
|  | 7.8 | 80 | 50 | 0 | 80 | 50 | 95 | 80 | 20 | 45 |
| 178 | 250 | 75 | 0 | 0 | 0 | 0 | 0 | 0 | 0 | 0 |
| 179 | 62.5 | 0 | 0 | 0 | 0 | 0 | 0 | 0 | 0 | 0 |
| 180 | 500 | 10 | 50 | 0 | 10 | 90 | 75 | 20 | 0 | 90 |
|  | 125 | 0 | 40 | 0 | 0 | 40 | 60 | 0 | 0 | 40 |
| 181 | 125 | 0 | 50 | 0 | 0 | 0 | 95 | 40 | 0 | 0 |
| 182 | 125 | 0 | 0 | 0 | 0 | 20 | 95 | 20 | 30 | 20 |
| 183 | 125 | 0 | 20 | 0 | 0 | 20 | 20 | 20 | 0 | 0 |
| 184 | 125 | 0 | 50 | 0 | 0 | 20 | 80 | 30 | 100 | 50 |
| 185 | 62.5 | — | 50 | 0 | 0 | — | — | 20 | 0 | 0 |
| 186 | 4000 | — | — | — | 50 | 70 | 90 | — | 30 | 90 |
| 187 | 125 | 0 | 0 | 0 | 0 | 0 | 70 | 0 | 0 | 70 |
| 188 | 125 | 50 | 50 | 20 | 70 | 80 | 80 | 60 | 70 | 70 |
| 189 | 125 | 25 | 50 | 0 | 70 | 50 | 70 | 40 | 25 | 70 |
| 190 | 125 | 0 | 40 | 0 | 0 | 20 | 85 | 40 | 0 | 0 |
| 191 | 125 | 80 | 70 | 30 | 100 | 60 | 100 | 90 | 65 | 30 |
|  | 31.2 | 50 | 70 | 0 | 75 | 20 | 100 | 80 | 50 | 30 |
| 192 | 125 | 0 | 0 | 0 | 0 | 0 | 40 | 0 | 0 | 98 |
|  | 31.25 | 0 | 0 | 0 | 0 | 0 | 0 | 0 | 0 | 90 |
| 193 | 250 | 20 | 0 | 0 | 60 | 60 | 90 | 75 | 0 | 65 |
| 194 | 250 | 0 | 10 | 0 | 0 | 30 | 80 | 25 | 0 | 70 |
| 195 | 250 | 0 | 0 | 0 | 20 | 20 | 80 | 30 | 0 | 60 |
| 196 | 250 | 0 | 30 | 10 | 20 | 70 | 80 | 40 | 10 | 70 |
| 197 | 250 | 0 | 65 | 0 | 15 | 30 | 50 | 10 | 0 | 50 |
| 198 | 2000 | 0 | 0 | 0 | 0 | 0 | 0 | 0 | 0 | 0 |
| 199 | 62.5 | 0 | 0 | 0 | 0 | 0 | 0 | 0 | 0 | 0 |

POSTEMERGENT CONTROL OF PLANT SPECIES -continued

| | | | | | | | | | | |
|---|---|---|---|---|---|---|---|---|---|---|
| 200 | 62.5 | 0 | 0 | 0 | 0 | 0 | 0 | 0 | 0 | 35 |
| 201 | 500 | 0 | 0 | 0 | 0 | 0 | 0 | 0 | 0 | 0 |
| 204 | 1000 | 0 | 10 | 0 | 0 | 0 | 0 | 0 | 0 | 10 |
| 205 | 250 | 0 | 80 | 0 | 40 | 95 | 95 | 100 | 0 | 60 |
| 206 | 250 | 0 | 0 | 0 | 0 | 20 | 90 | 80 | 0 | 80 |
| 207 | 1000 | 0 | 0 | 0 | 20 | 0 | 20 | 40 | 0 | 70 |
| 208 | 62.5 | 0 | 15 | 0 | 0 | 0 | 50 | 0 | 0 | 25 |
| 209 | 250 | 0 | 0 | 0 | 0 | 0 | 0 | 0 | 0 | 0 |
| 210 | 62.5 | 0 | 0 | 0 | 0 | 0 | 0 | 0 | 0 | 0 |
| 211 | 1000 | 0 | 10 | 0 | 0 | 0 | 0 | 25 | 0 | 0 |
| 212 | 2000 | 0 | 50 | 0 | 0 | 0 | 0 | 0 | — | 0 |
| 213 | 125 | 20 | 85 | 0 | 70 | 90 | 100 | 100 | 50 | 65 |
|  | 31.2 | 0 | 85 | 0 | 35 | 90 | 100 | 98 | 30 | 50 |
| 214 | 62.5 | 35 | 100 | 70 | 80 | 20 | 100 | 98 | 50 | 80 |
| 215 | 62.5 | 30 | 85 | 20 | 90 | 80 | 85 | 100 | 40 | 65 |
| 216 | 62.5 | 0 | 50 | 40 | 80 | 80 | 80 | 80 | 50 | 70 |
| 217 | 31.2 | 30 | 70 | 0 | 80 | 100 | 60 | 75 | 0 | 35 |
| 218 | 62.5 | 0 | 30 | 0 | 0 | 80 | 25 | 0 | 0 | 0 |
| 219 | 62.5 | 0 | 60 | 25 | 60 | 70 | 85 | 85 | 0 | — |
|  | 15.6 | 0 | 50 | 0 | 0 | 50 | 70 | 70 | 0 | 0 |
| 220 | 62.5 | 55 | 30 | 0 | 80 | 90 | 85 | 60 | 70 | 0 |
| 221 | 62.5 | 0 | — | 0 | 50 | 80 | 75 | 90 | 0 | 70 |
| 222 | 62.5 | 0 | — | 0 | 0 | 0 | 50 | 50 | 0 | 70 |
| 223 | 125 | 70 | 100 | 100 | 100 | 100 | 100 | 100 | 80 | 70 |
|  | 15.6 | 80 | 100 | 80 | 98 | 45 | 100 | 100 | 70 | 55 |
| 227 | 250 | 30 | 25 | 0 | 0 | 0 | 80 | 50 | 40 | 50 |
|  | 31.2 | 0 | 20 | 0 | 0 | 0 | 40 | 30 | 0 | 0 |
| 228 | 125 | 0 | 0 | 0 | 0 | 80 | 0 | 60 | 0 | 0 |
| 229 | 125 | — | 0 | — | 0 | 20 | 70 | 50 | 0 | 20 |
|  | 31.2 | 50 | 0 | 0 | 0 | 0 | 50 | 0 | 0 | 20 |
| 230 | 125 | 0 | 55 | 0 | 0 | 0 | 55 | 70 | 0 | 50 |
| 231 | 125 | 90 | 100 | 90 | 100 | 100 | 100 | 100 | 60 | 75 |
|  | 31.2 | 80 | 75 | 70 | 80 | 50 | 100 | 95 | 40 | 70 |
| 232 | 4000 | — | — | — | 0 | 0 | 0 | — | 0 | 80 |
| 233 | 250 | 20 | 0 | 0 | 0 | 0 | 0 | 0 | 0 | 0 |
| 234 | 4000 | — | — | — | 0 | 0 | 0 | — | — | 20 |
| 235 | 1000 | 20 | 35 | 25 | 75 | 98 | 45 | 75 | 60 | 0 |
| 236 | 1000 | 20 | 0 | 0 | 50 | 70 | 80 | 25 | 50 | 70 |
| 237 | 1000 | 50 | 45 | 40 | 40 | 0 | 80 | 85 | 65 | 0 |
| 239 | 4000 | — | — | — | 20 | 20 | 50 | — | 30 | 90 |
| 240 | 2000 | 0 | 20 | 0 | 25 | 70 | 80 | 50 | 0 | 65 |
| 241 | 2000 | 0 | 0 | 0 | 0 | 75 | 75 | 0 | 0 | 70 |
| 242 | 2000 | 20 | 0 | 0 | 0 | 15 | 0 | 0 | — | 0 |
| 243 | 500 | 45 | 75 | 20 | 70 | 0 | 75 | 80 | 0 | 95 |
|  | 31.25 | 0 | 70 | 0 | 0 | 0 | 0 | 30 | 0 | 95 |
| 244 | 500 | 40 | 90 | 20 | 40 | 40 | 95 | 80 | 0 | 90 |
|  | 125 | 0 | 80 | 0 | 0 | 0 | 80 | 65 | 0 | 80 |
| 245 | 4000 | — | — | — | 0 | 0 | 0 | — | 0 | 0 |
| 246 | 500 | 70 | 95 | 0 | 50 | 75 | 90 | 75 | 0 | 80 |
| 247 | 500 | 0 | 0 | 0 | 0 | 0 | 0 | 0 | 0 | 0 |
| 248 | 500 | 50 | 80 | 0 | 0 | 0 | 0 | 0 | 0 | 0 |
| 250 | 500 | 0 | 0 | 0 | 0 | 0 | 0 | 0 | 0 | 0 |
| 255 | 2000 | 0 | 0 | 0 | 0 | 0 | 0 | 0 | 0 | 0 |
| 257 | 4000 | — | — | — | 0 | 0 | 0 | — | 0 | 0 |
| 258 | 4000 | — | — | — | 0 | 0 | 0 | — | 0 | 0 |
| 260 | 500 | 0 | 25 | 0 | 50 | 0 | 90 | 95 | 0 | 0 |
| 261 | 500 | 0 | 30 | 0 | 20 | 10 | 95 | 100 | 0 | 0 |
| 262 | 500 | 40 | 90 | 10 | 100 | 95 | 100 | 100 | 0 | 80 |
|  | 31.25 | 0 | 75 | 0 | 80 | 65 | 95 | 100 | 0 | 15 |
| 263 | 500 | 85 | 70 | 0 | 40 | 90 | 95 | 100 | 0 | 0 |
| 264 | 250 | 0 | 20 | 0 | 20 | 0 | 60 | 10 | 0 | 0 |
| 265 | 500 | 0 | 0 | 0 | 0 | 0 | 0 | 0 | 0 | 0 |
| 266 | 500 | 40 | 0 | 0 | 75 | 70 | 80 | 0 | 0 | 0 |
| 267 | 500 | 40 | 65 | 0 | 35 | 90 | 70 | 75 | 0 | 40 |
| 268 | 31.25 | 10 | 75 | 0 | 100 | 0 | 85 | 0 | 0 | 95 |
| 269 | 62.5 | 0 | 50 | 0 | 30 | 0 | 0 | 70 | 0 | 0 |
| 270 | 62.5 | 0 | 50 | 0 | 60 | 70 | 70 | 0 | 40 | 50 |
|  | 3.9 | 0 | 10 | 0 | 20 | 0 | 65 | 0 | 0 | 0 |
| 271 | 1000 | 0 | 50 | 0 | 85 | 80 | 90 | 30 | 0 | 50 |
|  | 62.5 | 0 | 35 | 0 | 30 | 0 | 0 | 0 | 0 | 45 |
| 272 | 62.5 | 0 | 0 | 0 | 20 | 20 | 50 | 0 | 0 | 20 |
| 273 | 500 | 20 | 40 | 0 | 20 | 100 | 75 | 30 | 0 | 40 |
| 274 | 2000 | 70 | 100 | 0 | 100 | 98 | 98 | 80 | 0 | 80 |
| 275 | 125 | 0 | — | 0 | 20 | 100 | 90 | 80 | 30 | 60 |
| 276 | 125 | 0 | — | 40 | 90 | 90 | 80 | 90 | 0 | 70 |
| 277 | 125 | 80 | — | 20 | 25 | 70 | 80 | — | 0 | 25 |
|  | 31.2 | 20 | — | 0 | 0 | 0 | 100 | — | 0 | 0 |
| 278 | 125 | 0 | — | 0 | 70 | 100 | 90 | — | 0 | 80 |
| 279 | 125 | 35 | — | 0 | 60 | 90 | 80 | — | 0 | 80 |
| 280 | 250 | 0 | — | — | 70 | 95 | 90 | — | 0 | 50 |
| 281 | 125 | 0 | — | 0 | 70 | 85 | 98 | — | 0 | 70 |

POSTEMERGENT CONTROL OF PLANT SPECIES -continued

| | | | | | | | | | | |
|---|---|---|---|---|---|---|---|---|---|---|
| 282 | 125 | 30 | 70 | 0 | 80 | 100 | 80 | 100 | 0 | 75 |
| | 31.2 | 0 | 50 | 0 | 80 | 70 | 75 | 98 | 0 | 20 |
| 283 | 125 | 50 | 80 | 0 | 80 | 90 | 80 | 90 | 0 | 25 |
| 284 | 125 | 0 | — | 0 | 75 | 80 | 85 | 90 | 30 | 70 |
| 285 | 125 | 60 | 50 | 0 | 80 | 80 | 85 | 100 | 0 | 60 |
| | 7.8 | 0 | 20 | 0 | 0 | 0 | 75 | 70 | 0 | 0 |
| 286 | 125 | 80 | 50 | 0 | 80 | 90 | 85 | 90 | 0 | 60 |
| 287 | 125 | 0 | 35 | 0 | 20 | 80 | 80 | 80 | 0 | 0 |
| 288 | 125 | 30 | 50 | 0 | 70 | 100 | 80 | 80 | 50 | 30 |
| 289 | 1000 | 35 | 80 | 0 | 80 | 90 | 85 | 80 | 0 | 0 |
| 290 | 125 | 50 | 50 | 0 | 80 | 100 | 70 | 80 | 50 | 25 |
| 291 | 125 | 20 | 50 | 0 | 80 | 95 | 80 | 85 | 0 | 20 |
| | 7.8 | 0 | 0 | 0 | 0 | 0 | 20 | 20 | 0 | 0 |
| 292 | 125 | 70 | 50 | 0 | 80 | 65 | 98 | 100 | 50 | 60 |
| | 31.2 | 60 | 40 | 0 | 20 | 20 | 98 | 75 | — | 20 |
| 293 | 125 | 60 | 80 | 0 | 70 | 80 | 100 | 80 | 50 | 0 |
| | 31.2 | 30 | 50 | 0 | 20 | 50 | 95 | 50 | 20 | 0 |
| 294 | 125 | 50 | 50 | 0 | 90 | 85 | 98 | 90 | 0 | 0 |
| 297 | 125 | 50 | 80 | 0 | 50 | 80 | 95 | 100 | 20 | 0 |
| 298 | 2000 | 50 | 60 | 20 | 70 | 65 | 98 | 60 | 40 | 20 |
| | 500 | 40 | 40 | 0 | 65 | 25 | 75 | 50 | — | 0 |
| 299 | 2000 | 0 | 0 | 0 | 0 | 0 | 0 | 50 | 0 | 0 |
| 300 | 125 | 30 | 20 | 0 | 70 | 75 | 85 | 70 | 0 | 0 |
| | 62.5 | 30 | 50 | 0 | 65 | 50 | 50 | 70 | 0 | 0 |
| 301 | 2000 | 0 | 25 | 0 | 30 | 70 | 100 | 50 | 0 | 0 |
| 304 | 62.5 | 40 | 20 | 0 | 50 | 55 | 90 | — | 0 | 60 |
| 305 | 250 | 90 | 95 | 0 | 25 | 15 | 90 | 97 | 0 | 40 |
| 306 | 125 | 60 | 60 | 0 | 30 | 80 | 98 | 50 | 0 | 70 |

So as to clearly illustrate the phytotoxic properties of the various active ingredients of the present invention applied preemergently, a controlled greenhouse experiment is described below.

EXAMPLE 95

The seeds of various species of plants were planted in beds of good agricultural soil in a greenhouse. A number of compositions of the present invention, generally in the nature of an aqueous emulsion, were applied at rates listed in the table so as to deposit a predetermined amount of active ingredients uniformly throughout the surface of the bed. Another seed bed was treated only with water to serve as a control. After treatment the seed beds were maintained for two weeks under greenhouse conditions conducive for good plant growth and watered as necessary. The specific plant species, test compound, and dosage and the percent preemergent control are set forth in the table below. Control refers to the reduction in growth compared to the observed results of the same untreated species.

PREEMERGENT CONTROL OF PLANT SPECIES

| Compound | Dosage (lb/acre) | A | B | C | D | F | G | H | I | J | K | L | M | N | O | Q | R | P | T |
|---|---|---|---|---|---|---|---|---|---|---|---|---|---|---|---|---|---|---|---|
| 1 | 10 | 90 | — | — | — | — | 90 | 100 | 98 | — | — | — | — | 100 | 100 | — | 90 | 100 | — |
| 2 | 0.5 | 0 | 95 | 30 | 70 | 0 | 100 | 30 | 95 | 15 | 20 | 60 | 0 | 80 | 95 | 50 | 30 | 95 | 0 |
| 4 | 10 | 98 | — | — | — | — | 90 | 100 | 90 | — | — | — | — | 100 | 80 | — | 90 | 100 | — |
| 6 | 0.5 | 100 | 100 | 95 | 95 | 0 | 30 | 70 | 60 | 10 | 90 | 50 | 50 | 90 | 70 | 10 | — | 50 | 40 |
| | 0.25 | 70 | 100 | 10 | 95 | 0 | 0 | 100 | 60 | 0 | 80 | 50 | 0 | 80 | 0 | 0 | — | — | 50 |
| 7 | 1.0 | 95 | 98 | 95 | 98 | 100 | 80 | 100 | 95 | 90 | 98 | 95 | 100 | 98 | 80 | 80 | 20 | 70 | 90 |
| | 0.125 | 20 | 98 | 20 | 90 | 0 | 40 | 50 | 40 | 0 | 70 | 70 | 0 | 30 | 0 | 10 | 0 | 20 | 0 |
| 8 | 1.0 | 100 | 100 | 95 | 100 | 100 | 60 | 100 | 90 | 95 | 100 | — | 55 | 95 | 95 | 95 | 70 | 95 | 95 |
| | 0.25 | 90 | 100 | 95 | 90 | 100 | 25 | 95 | 60 | 80 | 90 | — | 0 | 75 | 70 | 80 | 15 | 60 | 75 |
| 9 | 0.5 | 0 | 100 | 40 | 100 | 100 | 0 | 30 | 0 | 0 | 50 | 20 | 0 | 98 | 40 | 0 | — | 20 | 0 |
| 10 | 1.0 | 0 | 98 | 0 | 90 | 0 | 0 | 95 | 75 | 0 | 80 | — | 0 | 0 | 40 | 0 | 0 | 0 | 0 |
| 12 | 0.25 | 95 | 95 | 95 | 98 | 0 | 50 | -60 | 30 | 50 | 10 | — | 0 | 40 | 10 | 80 | 0 | 0 | 50 |
| | 0.125 | 80 | 95 | 40 | 95 | 0 | 0 | 0 | 20 | 0 | 0 | — | 0 | 10 | 0 | 50 | 0 | 0 | 30 |
| 13 | 0.25 | 95 | 98 | 95 | 98 | 70 | 90 | 95 | 95 | 80 | 95 | 98 | 20 | 95 | 80 | 95 | 10 | 90 | 98 |
| | 0.062 | 90 | 98 | 80 | 90 | 50 | 90 | 20 | 95 | 0 | 60 | 95 | 0 | 50 | 0 | 90 | 0 | 50 | 80 |
| 14 | 4.0 | 90 | 95 | 20 | 99 | 10 | 0 | 90 | 10 | 10 | 10 | 15 | 0 | 10 | 95 | 60 | 20 | 0 | 0 |
| 15 | 1.0 | 90 | 95 | 60 | 70 | 0 | 30 | 30 | 80 | 10 | 15 | — | 0 | 10 | 15 | 20 | 0 | 10 | 5 |
| 16 | 1.0 | 100 | 0 | 15 | 0 | 0 | 15 | 35 | 0 | 15 | 20 | — | 0 | 0 | 0 | 0 | 0 | 0 | 0 |
| 17 | 1.0 | 0 | 90 | 0 | 40 | 0 | 0 | 70 | 0 | 10 | 50 | 10 | 0 | 0 | 0 | 0 | 0 | 0 | 0 |
| 19 | 1.0 | 95 | 98 | 95 | 95 | 80 | 80 | 98 | 85 | 35 | 50 | 60 | 0 | 40 | 70 | 30 | 80 | 60 | 90 |
| | 0.25 | 90 | 95 | 20 | 90 | 0 | 50 | 90 | 70 | 0 | 20 | 0 | 0 | 0 | 20 | 0 | 0 | 0 | 40 |
| 21 | 2.0 | 80 | 95 | 70 | 98 | 70 | 60 | 100 | 75 | 50 | 80 | — | 0 | 0 | 60 | 40 | 0 | 0 | 60 |
| 22 | 0.25 | 95 | 100 | 95 | 98 | 100 | 70 | 100 | 98 | 50 | 90 | 95 | 50 | 95 | 95 | 98 | 90 | 98 | 98 |
| | 0.062 | 80 | 100 | 95 | 95 | 100 | 30 | 80 | 80 | 0 | 10 | 60 | 0 | 40 | 90 | 40 | 90 | 95 | 90 |
| 24 | 10 | 95 | — | — | — | — | 80 | 100 | 98 | — | — | — | — | 70 | 70 | — | 10 | 70 | — |
| 25 | 0.25 | 98 | 100 | 98 | 100 | 98 | 80 | 100 | 98 | 100 | 100 | — | 70 | 98 | 100 | 98 | 95 | 100 | 95 |
| | 0.062 | 95 | 98 | 95 | 95 | 70 | 40 | 0 | 70 | 98 | 95 | — | 0 | 60 | 20 | 90 | 0 | 50 | 50 |
| 26 | 0.25 | 95 | 98 | 98 | 100 | 100 | 95 | 100 | 95 | 100 | 100 | — | 0 | 98 | 100 | 98 | 40 | 100 | 100 |
| | 0.062 | 95 | 98 | 95 | 98 | 95 | 80 | 100 | 90 | 95 | 90 | — | 0 | 30 | 95 | 60 | 0 | 60 | 100 |
| 29 | 10 | 90 | — | — | — | — | 0 | 60 | 0 | — | — | — | — | 0 | 20 | 20 | 0 | — | — |
| 30 | 1.0 | 0 | 0 | 95 | 0 | 100 | 0 | 100 | 0 | 0 | 0 | 0 | 0 | 0 | 90 | 0 | 90 | 30 | 0 |

-continued

PREEMERGENT CONTROL OF PLANT SPECIES

| Compound | Dosage (lb/acre) | A | B | C | D | F | G | H | I | J | K | L | M | N | O | Q | R | P | T |
|---|---|---|---|---|---|---|---|---|---|---|---|---|---|---|---|---|---|---|---|
| 31 | 0.25 | 80 | 98 | 95 | 100 | 100 | 65 | 100 | 95 | 95 | 95 | 98 | 50 | 98 | 100 | 100 | 100 | 98 | 100 |
|  | 0.062 | 70 | 60 | 90 | 90 | 100 | 0 | 95 | 90 | 0 | 10 | 50 | 0 | 98 | 95 | 90 | 0 | 98 | 80 |
| 32 | 0.5 | 50 | 100 | 90 | 100 | 100 | 98 | 95 | 100 | 20 | 60 | 40 | 40 | 100 | 98 | 100 | 100 | 98 | 50 |
|  | 0.125 | 20 | 0 | 60 | 50 | 40 | 30 | 95 | 90 | 0 | 0 | 50 | 0 | 30 | 95 | 65 | 0 | 0 | 0 |
| 33 | 1.0 | 90 | 98 | 90 | 50 | 95 | 60 | 95 | 80 | 95 | 95 | 70 | 80 | 98 | 98 | 95 | 40 | 98 | 98 |
|  | 0.25 | 20 | 80 | 10 | 50 | 40 | 0 | 0 | 10 | 0 | 0 | 0 | 0 | 70 | 50 | 10 | 0 | 40 | 0 |
| 34 | 1.0 | 95 | 100 | 95 | 95 | 95 | 80 | 98 | 95 | 60 | 70 | 80 | 0 | 70 | 20 | 95 | 30 | 40 | 90 |
|  | 0.25 | 80 | 95 | 80 | 90 | 0 | 20 | 50 | 80 | 0 | 40 | 90 | 0 | 20 | 0 | 80 | 0 | 0 | 70 |
| 35 | 2.0 | 60 | 80 | 60 | 98 | 0 | 10 | — | 50 | 0 | 0 | 0 | 0 | 0 | 60 | 80 | 0 | 0 | 40 |
| 36 | 1.0 | 0 | 30 | 0 | 50 | 100 | 0 | 0 | 0 | 0 | 0 | 0 | 0 | 0 | 0 | 0 | 0 | 0 | 0 |
| 37 | 0.25 | 95 | 95 | 95 | 97 | 100 | 90 | 100 | 95 | 95 | 97 | 95 | 0 | 97 | 70 | 95 | 0 | 97 | 100 |
|  | 0.062 | 95 | 93 | 35 | 100 | 40 | 30 | 100 | 90 | 20 | 50 | 30 | 0 | 30 | 0 | 50 | 0 | 20 | 97 |
| 39 | 0.25 | 95 | 95 | 95 | 97 | 100 | 90 | 100 | 95 | 95 | 97 | 95 | 0 | 97 | 70 | 95 | 0 | 97 | 100 |
|  | 0.031 | 90 | 93 | 30 | 97 | 0 | 30 | 100 | 50 | 0 | 0 | 0 | 0 | 0 | 0 | 0 | 0 | 0 | 60 |
| 40 | 4 | 20 | 100 | 50 | 60 | 100 | 0 | — | 20 | 0 | 50 | — | 0 | 0 | — | 0 | 0 | 0 | 70 |
| 41 | 0.25 | 40 | 80 | 25 | 80 | 0 | 10 | 0 | 10 | 0 | 0 | 20 | 0 | 80 | 10 | 35 | 0 | 30 | 70 |
| 42 | 16 | 0 | 100 | 100 | 70 | 0 | 0 | — | 30 | 0 | 0 | — | 0 | 0 | — | 0 | 100 | 0 | 0 |
| 43 | 4.0 | 30 | 40 | 20 | 95 | 0 | 60 | 70 | 30 | 0 | 0 | 0 | 0 | 20 | 40 | 40 | 0 | 0 | 0 |
| 44 | 0.25 | 85 | 93 | 80 | 97 | 100 | 20 | 95 | 0 | 10 | 70 | 93 | 70 | 40 | 90 | 80 | 40 | 70 | 90 |
| 46 | 0.125 | 95 | 95 | 97 | 97 | 100 | 90 | 100 | 97 | 60 | 0 | 50 | 60 | 70 | 97 | 10 | 60 | 95 | 99 |
|  | 0.031 | 95 | 95 | 93 | 97 | 100 | 70 | 100 | 80 | 0 | 0 | 0 | 0 | 0 | 70 | 0 | 0 | 30 | 97 |
| 47 | 2.0 | 97 | 97 | 97 | 100 | 97 | 70 | 99 | 99 | 0 | 0 | 0 | 30 | — | 40 | 20 | 30 | — | 97 |
|  | 0.5 | 50 | 90 | 85 | 97 | 90 | 20 | 99 | 90 | 0 | 0 | 0 | 0 | — | 40 | 10 | 0 | — | 90 |
| 49 | 0.062 | 100 | 100 | 100 | 99 | 100 | 99 | — | 90 | 90 | 10 | — | 0 | 85 | — | 50 | 0 | 90 | 100 |
| 48 | 1.0 | 30 | 20 | 0 | 50 | 60 | 60 | 0 | 0 | 0 | 0 | 0 | 20 | 20 | 10 | 0 | 70 | 20 | 0 |
| 50 | 0.25 | 80 | 95 | 95 | 100 | 100 | 80 | 100 | 93 | 99 | 97 | 100 | 100 | 95 | 25 | 95 | 60 | 95 | 99 |
|  | 0.062 | 0 | 93 | 85 | 97 | 75 | 40 | 80 | 90 | 90 | 100 | 80 | 0 | 97 | 0 | 90 | 10 | 93 | 99 |
| 51 | 0.25 | 93 | 95 | 90 | 95 | 95 | 80 | 100 | 95 | 97 | 80 | 97 | 97 | 97 | 95 | 95 | 100 | 97 | 100 |
|  | 0.062 | 50 | 95 | 10 | 93 | 90 | 70 | 70 | 20 | 45 | 10 | 55 | 0 | 0 | 90 | 10 | 0 | 45 | 80 |
| 52 | 2.0 | 30 | 80 | — | 30 | 0 | 50 | 0 | 35 | 0 | 0 | 0 | 0 | 0 | 25 | 0 | 0 | 0 | 10 |
| 53 | 0.125 | 90 | 95 | 90 | 100 | 97 | 85 | 100 | 90 | 97 | 97 | 97 | 30 | 95 | 95 | 93 | 99 | 93 | 100 |
|  | 0.031 | 20 | 93 | 20 | 100 | 85 | 40 | 95 | 0 | 20 | 80 | 15 | 0 | 10 | 80 | 75 | 0 | 60 | 97 |
| 54 | 0.125 | 95 | 93 | 95 | 97 | 99 | 70 | 100 | 90 | 95 | 99 | 97 | 0 | 93 | 95 | 95 | 40 | 95 | 97 |
|  | 0.031 | 85 | 93 | 35 | 97 | 90 | 0 | 100 | 20 | 0 | 93 | 50 | 0 | 15 | 10 | 40 | 0 | 45 | 55 |
| 56 | 0.25 | 0 | 100 | 0 | 100 | 0 | 90 | — | 50 | 30 | 0 | — | 0 | 0 | — | 0 | 0 | 20 | 70 |
| 57 | 4 | 100 | 100 | 100 | 100 | 0 | 0 | — | 0 | 40 | 0 | — | 0 | 20 | — | 80 | 0 | 50 | 0 |
| 58 | 0.062 | 0 | 100 | 0 | 100 | 100 | 80 | — | 100 | 70 | 0 | — | 0 | 30 | — | 80 | 50 | 90 | 100 |
| 59 | 20 | 0 | 100 | 60 | 100 | 90 | 35 | — | 50 | 0 | 0 | — | 0 | 0 | — | 0 | 0 | 0 | 0 |
| 60 | 0.5 | 0 | 50 | 20 | 0 | 0 | 100 | — | 0 | 50 | 0 | — | 0 | 0 | — | 0 | 40 | 0 | 0 |
| 61 | 5 | 100 | 100 | 100 | 100 | 100 | 100 | — | 70 | 85 | 100 | — | 0 | 65 | — | 90 | 0 | 100 | 90 |
| 62 | 0.5 | 0 | 90 | 50 | 50 | 0 | 0 | — | 20 | 0 | 80 | — | 0 | 20 | — | 0 | 0 | 20 | 60 |
| 63 | 0.125 | 100 | 100 | 100 | 100 | 100 | 0 | — | 100 | 30 | 90 | — | 40 | 10 | — | 0 | 0 | 30 | 100 |
| 64 | 0.062 | 50 | 100 | 90 | 100 | 100 | 70 | — | 90 | 60 | 0 | 30 | 0 | 0 | — | 40 | 0 | 90 | 90 |
| 65 | 0.25 | 0 | 20 | 100 | 100 | 90 | 50 | — | 20 | 0 | 30 | — | 0 | 70 | — | 95 | 0 | 95 | 95 |
| 66 | 10 | 100 | — | — | — | — | 100 | 100 | 100 | — | — | — | — | 80 | 100 | — | 50 | 100 | — |
| 67 | 10 | 30 | — | — | — | — | 100 | 30 | 30 | — | — | — | — | 70 | — | — | 40 | — | — |
| 68 | 1 | 100 | 100 | 80 | 90 | 100 | 0 | — | 90 | 80 | 0 | 90 | 20 | 70 | — | 50 | 20 | 80 | 50 |
| 69 | 0.5 | 100 | 100 | 50 | 100 | 0 | 30 | — | 40 | 93 | 0 | 100 | 70 | 0 | — | 20 | 0 | 70 | 100 |
| 70 | 1 | 90 | 100 | 70 | 95 | 100 | 30 | — | 80 | 100 | 40 | 90 | 80 | 40 | — | 90 | 60 | 90 | 95 |
| 71 | 10 | 98 | — | — | — | — | 50 | 100 | 70 | — | — | — | — | 50 | 98 | — | 70 | 100 | — |
| 72 | 0.25 | 40 | 100 | 90 | 90 | 100 | 10 | — | 60 | 90 | 70 | 80 | 90 | 30 | — | 50 | 90 | 50 | 100 |
| 73 | 0.125 | 0 | 30 | 0 | 0 | 0 | 0 | 0 | 0 | 0 | 0 | 0 | 40 | 0 | 0 | 0 | 0 | 0 | 0 |
| 74 | 0.125 | 90 | 100 | 100 | 100 | 100 | 0 | — | 70 | 0 | 0 | 100 | 0 | 30 | — | 70 | 0 | 70 | 100 |
| 75 | 0.5 | 0 | 100 | 0 | 90 | 0 | 20 | — | 90 | 0 | 0 | 0 | — | 20 | — | 0 | 0 | 80 | 0 |
| 76 | 0.25 | 60 | 100 | 95 | 100 | 100 | 90 | — | 100 | 100 | 70 | 90 | 100 | 70 | — | 80 | 90 | 90 | 100 |
| 77 | 0.25 | 0 | 80 | 80 | 50 | 90 | 60 | — | 0 | 70 | 40 | 50 | 0 | 20 | — | 0 | 0 | 80 | 90 |
| 78 | 0.25 | 0 | 100 | 30 | 70 | 0 | 0 | — | 30 | 10 | 40 | 0 | 40 | 20 | — | 0 | 30 | 20 | 50 |
| 79 | 0.5 | 40 | 100 | 40 | 70 | 90 | 10 | — | 30 | 50 | 30 | 10 | 0 | 0 | — | 0 | — | 0 | 0 |
| 80 | 10 | 0 | — | — | — | — | — | 100 | 80 | — | — | — | — | 0 | 0 | — | — | 0 | — |
| 82 | 0.125 | 0 | 90 | 0 | 90 | 0 | 0 | 0 | 0 | 0 | 0 | 0 | 0 | 0 | 0 | 0 | 0 | 0 | 0 |
| 83 | 0.5 | 0 | 98 | 0 | 30 | 50 | 0 | — | 20 | 0 | 0 | 0 | 0 | 0 | 0 | 0 | 0 | 0 | 0 |
| 84 | 10 | 30 | — | — | — | — | 20 | 90 | 98 | — | — | — | — | 0 | 0 | — | 0 | 0 | — |
| 85 | 0.125 | 90 | 100 | 100 | 100 | 100 | 90 | — | 100 | 70 | 0 | 0 | 0 | 20 | — | 30 | 0 | 60 | 100 |
|  | 0.015 | 70 | 100 | 30 | — | 90 | 20 | — | 60 | 0 | 0 | 0 | 0 | 0 | — | 0 | 0 | 0 | 0 |
| 86 | 0.25 | 0 | 100 | 20 | 100 | 100 | 0 | — | 0 | 0 | 0 | 0 | 0 | 0 | — | 0 | 0 | 0 | 0 |
| 87 | 4 | 80 | 90 | 65 | — | 20 | 70 | — | 0 | 0 | 0 | 70 | 0 | 0 | — | 50 | 0 | 40 | 100 |
| 90 | 2 | 100 | 100 | 70 | 100 | 100 | 70 | — | 95 | 80 | 90 | 70 | 20 | 50 | — | 40 | 30 | 80 | 90 |
|  | 1 | 90 | 100 | 50 | 100 | 60 | 30 | — | 30 | 70 | 20 | 40 | 0 | 0 | — | 30 | 0 | 80 | 100 |
| 91 | 0.25 | 100 | 100 | 100 | 100 | 100 | 40 | — | 100 | 60 | 30 | 50 | 0 | 20 | — | 40 | 0 | 70 | 100 |
|  | 0.062 | 20 | 100 | 90 | 90 | 100 | 0 | — | 50 | 0 | 0 | 20 | 0 | 0 | — | 0 | 0 | 20 | 20 |
| 92 | 0.5 | 10 | 100 | 0 | 70 | 0 | 0 | — | 0 | 0 | 0 | 40 | 0 | 0 | — | 0 | 0 | 0 | 0 |
| 93 | 0.5 | 70 | 40 | 20 | 0 | 0 | 0 | — | 0 | 0 | 10 | 0 | — | 0 | — | 0 | 0 | 0 | 0 |
| 94 | 0.25 | 60 | 100 | 50 | 0 | 0 | 0 | — | 0 | 0 | 0 | 0 | — | 0 | — | 0 | 0 | 0 | 0 |
| 97 | 1.0 | 30 | 100 | 0 | 20 | 80 | 0 | — | 0 | 0 | 0 | 10 | 40 | 0 | — | 0 | 0 | 0 | 100 |
| 98 | 10 | 80 | — | — | — | — | 40 | 100 | 98 | — | — | — | — | 90 | 90 | — | 40 | 90 | — |
| 101 | 10 | 40 | — | — | — | — | 0 | 40 | 70 | — | — | — | — | 0 | 60 | — | 20 | 0 | — |
| 104 | 0.25 | 100 | 100 | 100 | 100 | 100 | 100 | — | 100 | 100 | 100 | 100 | 100 | 100 | 100 | 100 | 100 | 100 | 100 |

-continued
PREEMERGENT CONTROL OF PLANT SPECIES

| Compound | Dosage (lb/acre) | A | B | C | D | F | G | H | I | J | K | L | M | N | O | Q | R | P | T |
|---|---|---|---|---|---|---|---|---|---|---|---|---|---|---|---|---|---|---|---|
| | 0.016 | 100 | 100 | 80 | 100 | 80 | 100 | — | 100 | 95 | 95 | 100 | 100 | 100 | — | 100 | 90 | 95 | 100 |
| 106 | 1 | 95 | 95 | 95 | 100 | 100 | 85 | — | 98 | 98 | 70 | 98 | 98 | 70 | 20 | 95 | 98 | 70 | 80 |
| 108 | 0.5 | 95 | 95 | 100 | 80 | 80 | 70 | 80 | 98 | 95 | 100 | 70 | 98 | 85 | 95 | 98 | 50 | 50 | 90 |
| | 0.125 | 40 | 95 | 30 | 70 | 70 | 50 | 40 | 90 | 60 | 80 | 10 | 30 | 0 | 0 | 50 | 0 | 0 | 60 |
| 110 | 2.0 | 0 | 50 | 0 | 0 | 0 | 0 | — | 0 | 90 | 40 | 50 | 0 | 80 | 0 | 0 | 0 | 0 | 0 |
| 111 | 0.25 | 20 | 95 | 10 | 90 | 95 | 20 | 50 | 80 | 35 | 65 | 65 | 0 | 15 | 90 | 75 | 0 | 30 | 93 |
| 112 | 0.25 | 80 | 85 | 0 | 99 | 0 | 80 | 90 | 20 | 50 | 25 | 20 | 0 | 0 | 97 | 30 | 90 | 0 | 90 |
| 113 | 0.25 | 30 | 90 | 0 | 100 | 0 | 0 | 100 | 60 | 0 | 40 | 0 | 0 | 20 | 90 | 50 | 0 | 50 | 50 |
| 114 | 0.5 | 95 | 95 | 15 | 50 | 100 | 50 | 100 | 60 | 0 | 80 | 40 | 0 | 0 | 0 | 10 | 0 | 10 | 80 |
| 116 | 0.5 | 90 | 100 | 10 | 100 | 100 | 20 | — | 60 | 0 | 0 | 0 | — | 0 | — | 0 | 0 | 0 | 30 |
| 117 | 0.5 | 90 | 100 | 20 | 90 | 90 | 20 | — | 90 | 0 | 0 | 0 | 0 | 0 | — | 60 | 0 | 40 | 0 |
| 118 | 0.5 | 30 | 90 | 0 | 60 | 0 | 0 | — | 0 | 0 | 0 | 0 | — | 0 | — | 0 | 0 | 0 | 0 |
| 119 | 0.5 | 90 | 100 | 0 | 90 | 100 | 0 | — | 20 | 0 | 0 | 50 | 0 | 0 | — | 0 | 0 | 0 | 70 |
| 120 | 10 | 100 | — | — | — | — | 60 | 100 | 98 | — | — | — | — | 100 | 90 | — | 60 | 90 | — |
| 128 | 1.0 | 20 | 100 | 0 | 90 | 100 | 0 | — | 30 | 0 | 0 | 50 | 0 | 0 | — | 0 | 0 | 0 | 0 |
| 136 | 1.0 | 30 | 65 | 0 | 0 | 0 | 0 | — | 98 | 0 | 0 | 0 | — | 0 | 0 | 80 | — | 0 | 10 |
| 137 | 0.25 | 80 | — | 0 | 100 | 10 | 70 | — | 80 | 0 | 50 | 30 | 30 | 20 | — | 20 | — | 20 | 100 |
| 138 | 0.25 | 100 | 100 | 50 | 90 | 20 | 20 | — | 90 | 30 | 50 | 50 | 10 | 0 | — | 90 | — | 90 | 80 |
| 139 | 0.25 | 100 | 100 | 50 | 100 | 100 | 90 | — | 100 | 70 | 90 | 100 | 80 | 80 | — | 100 | — | 100 | 100 |
| 140 | 0.125 | 100 | 100 | 50 | 100 | 60 | 80 | — | 90 | 0 | — | 70 | 10 | 70 | — | 70 | 0 | 80 | 100 |
| 141 | 0.25 | 100 | 100 | 100 | 100 | 100 | 100 | — | 100 | 100 | 100 | 100 | 95 | 95 | — | 100 | — | 100 | 75 |
| 142 | 0.5 | 20 | 20 | 0 | 100 | 100 | 0 | 100 | 40 | 0 | 0 | 50 | 0 | 0 | 0 | 0 | 0 | 0 | 25 |
| 143 | 0.25 | 100 | 95 | 70 | 100 | 100 | 90 | 100 | 97 | 95 | 97 | 99 | 50 | 97 | 100 | 100 | 50 | 97 | 100 |
| | 0.062 | 95 | 95 | 25 | 100 | 100 | 80 | 100 | 95 | 60 | 80 | 99 | 0 | 97 | 50 | 85 | 0 | 95 | 100 |
| | 0.016 | 95 | 95 | 25 | 100 | 40 | 0 | 40 | 90 | 0 | 70 | 20 | 0 | 75 | 0 | 75 | 0 | 50 | 75 |
| 144 | 0.25 | 100 | 100 | 60 | 100 | 100 | 95 | — | 100 | 70 | 40 | — | 0 | 80 | — | 100 | 70 | 100 | 100 |
| | 0.062 | 100 | 90 | 70 | 100 | 100 | 0 | — | 60 | 0 | 0 | — | 0 | 60 | — | 60 | 0 | 93 | 80 |
| 145 | 0.125 | 100 | 100 | 40 | 100 | 100 | 60 | — | 100 | 0 | 0 | — | 0 | 0 | — | 50 | 0 | 20 | 80 |
| | 0.062 | 90 | 90 | 0 | 100 | 50 | 100 | — | 90 | 0 | 0 | — | 0 | 0 | — | 20 | 0 | 0 | 40 |
| 146 | 0.125 | 100 | 85 | 0 | 100 | — | 90 | — | 90 | 60 | 60 | — | 0 | 100 | — | 97 | 0 | 95 | 100 |
| | 0.062 | 60 | 30 | 0 | 90 | — | 0 | — | 20 | 0 | 30 | — | 0 | 95 | — | 90 | 0 | 85 | 100 |
| 147 | 0.031 | 70 | 100 | 0 | 100 | 100 | 20 | — | 100 | 20 | 20 | 0 | 30 | 0 | — | 0 | 90 | 0 | 100 |
| 148 | 0.125 | 30 | 90 | 0 | 100 | 100 | 0 | — | 50 | 20 | 0 | — | 0 | 30 | — | 90 | 0 | 70 | 100 |
| 149 | 10 | 30 | — | — | — | — | 40 | 40 | 50 | — | — | — | — | 50 | 50 | — | 20 | 20 | — |
| 150 | 0.5 | 90 | 100 | 30 | 90 | 100 | 80 | — | 20 | 80 | 0 | 95 | 50 | 30 | — | 70 | 50 | 80 | 95 |
| 151 | 0.031 | 100 | 100 | 0 | 100 | 100 | 30 | — | 90 | 30 | 30 | 40 | 50 | 60 | — | 50 | 30 | 60 | 100 |
| 152 | 0.031 | 90 | 100 | 0 | 100 | 100 | 60 | — | 100 | 0 | 0 | 40 | 0 | 40 | — | 30 | 0 | 90 | 100 |
| 153 | 0.031 | 100 | 100 | 0 | 100 | 100 | 20 | — | 100 | 30 | 20 | 20 | 0 | 65 | — | 30 | 0 | 70 | 100 |
| 154 | 0.125 | 30 | 100 | 0 | 90 | 100 | 0 | — | 20 | 0 | 0 | 10 | 0 | 0 | — | 0 | 0 | 0 | 100 |
| 156 | 0.125 | 90 | 100 | 0 | 100 | 100 | 70 | — | 90 | 0 | 50 | 90 | 0 | 60 | — | 20 | 30 | 20 | 95 |
| 157 | 0.031 | 100 | 100 | 0 | 100 | 90 | 50 | — | 100 | 0 | 20 | 50 | 0 | 10 | — | 90 | 0 | 80 | 30 |
| 158 | 0.031 | 90 | 100 | 0 | 100 | 80 | 20 | — | 100 | 0 | 20 | 30 | 0 | 40 | — | 0 | 0 | 30 | 0 |
| 159 | 0.062 | 100 | 100 | 0 | 100 | 100 | 60 | — | 100 | 50 | 90 | 70 | 0 | 80 | — | 80 | 0 | 75 | 70 |
| 160 | 0.62 | 100 | 100 | 0 | 100 | 100 | 80 | — | 100 | 35 | 0 | 60 | 0 | 0 | — | 0 | 0 | 30 | 100 |
| | 0.015 | 90 | 100 | 0 | 100 | 100 | 80 | — | 80 | 0 | 0 | 0 | 0 | 0 | — | 0 | 0 | 0 | 100 |
| 161 | 10 | 100 | — | — | — | — | 100 | 100 | 100 | — | — | — | — | 100 | 100 | — | 100 | 100 | — |
| 162 | 0.125 | 80 | 100 | 10 | 100 | 0 | 0 | — | 90 | 0 | 0 | 50 | 0 | 40 | — | 30 | 30 | 80 | 100 |
| 163 | 2 | 100 | 100 | 0 | 100 | 100 | 0 | — | 60 | 40 | 0 | 0 | 0 | 0 | — | 0 | 0 | 0 | 60 |
| 164 | 0.125 | 90 | 100 | 10 | 100 | 100 | 20 | — | 100 | 0 | 0 | 20 | 0 | 0 | — | 0 | 0 | 60 | 90 |
| | 0.031 | 70 | 100 | 0 | 90 | 70 | 0 | — | 100 | 0 | 0 | 0 | 0 | 0 | — | 0 | 0 | 20 | 90 |
| 165 | 0.25 | 90 | 75 | 10 | 90 | 90 | 60 | — | 30 | 0 | 0 | 60 | 0 | 60 | — | 0 | 0 | 90 | 90 |
| 166 | 0.25 | 100 | 100 | 80 | 100 | 90 | 95 | — | 100 | 10 | 40 | 80 | 20 | 80 | — | 20 | 30 | 80 | 100 |
| | 0.062 | 80 | 90 | 40 | 100 | 70 | 0 | — | 90 | 0 | 0 | 0 | 0 | 70 | — | 0 | 0 | 50 | 100 |
| 169 | 10 | 90 | — | — | — | — | 100 | 100 | 98 | — | — | — | — | 50 | 40 | — | — | 50 | — |
| 170 | 0.25 | 70 | 100 | 0 | 90 | 0 | 30 | — | 85 | 20 | 30 | 80 | 10 | 40 | — | 90 | — | 70 | 0 |
| 171 | 0.25 | 70 | 100 | 20 | 100 | 20 | 50 | — | 90 | 40 | 90 | 100 | 50 | 100 | — | 100 | — | 100 | 80 |
| 172 | 0.25 | 100 | — | 90 | 100 | 100 | 90 | — | 100 | 80 | 100 | 100 | 90 | 100 | — | 90 | — | 100 | 100 |
| | 0.31 | 80 | — | 0 | 100 | 40 | 80 | — | 90 | 20 | 0 | 90 | 60 | 0 | — | 70 | 0 | 0 | 100 |
| 173 | 0.25 | 50 | 80 | 0 | 90 | 0 | 0 | — | 0 | 30 | 70 | 30 | 20 | 30 | — | 70 | — | 50 | 0 |
| 175 | 0.125 | 100 | 100 | 100 | 100 | 100 | 100 | — | 100 | 100 | 100 | 100 | 100 | 100 | — | 100 | — | 100 | 100 |
| | 0.016 | 70 | 100 | 0 | 100 | 60 | 0 | — | 60 | 0 | 0 | 30 | 0 | 50 | — | 50 | 0 | 80 | 70 |
| 178 | 0.25 | 65 | 80 | 0 | 95 | 0 | 10 | 60 | 40 | 0 | 0 | 0 | — | 25 | 0 | 0 | — | 0 | 0 |
| 181 | 0.25 | 98 | 100 | 80 | 98 | 98 | 80 | — | 98 | 0 | 30 | 95 | 0 | 20 | — | 60 | 40 | 80 | 50 |
| 182 | 0.12 | 98 | 98 | 98 | 98 | 99 | 98 | — | 98 | 0 | 0 | 20 | 0 | 0 | — | 70 | 0 | 90 | 100 |
| 183 | 0.5 | 98 | 98 | 0 | 100 | 98 | 0 | — | 100 | 0 | 0 | 90 | 0 | 0 | — | 0 | 0 | 0 | 0 |
| 184 | 0.25 | 100 | 98 | 50 | 100 | 98 | 80 | — | 100 | 0 | 0 | 95 | 0 | 0 | — | 30 | 0 | 80 | 80 |
| 185 | 0.25 | 98 | 100 | 70 | 98 | 90 | 80 | — | 100 | 0 | 20 | 90 | 0 | 20 | — | 90 | 0 | — | 0 |
| 186 | 0.062 | 90 | 98 | 20 | 90 | 90 | 0 | — | 95 | 0 | 0 | 30 | 0 | 30 | — | 40 | 0 | 50 | 30 |
| 187 | 10 | 100 | — | — | — | — | 100 | 100 | 100 | — | — | — | — | 100 | 100 | — | 100 | 100 | — |
| 188 | 10 | 98 | — | — | — | — | 100 | 100 | 100 | — | — | — | — | 100 | 100 | — | 100 | 100 | — |
| 189 | 0.25 | 100 | 100 | 80 | 100 | 80 | 50 | — | 100 | 80 | 90 | 100 | 80 | 80 | — | 70 | — | 80 | 100 |
| | 0.063 | 80 | 100 | 60 | 80 | 0 | 50 | 0 | 70 | 0 | 10 | 10 | 50 | 70 | — | 50 | — | 40 | 100 |
| 190 | 0.25 | 90 | — | 90 | 100 | 90 | 50 | — | 50 | 10 | 20 | 95 | 20 | 30 | — | 30 | — | 70 | 100 |
| 191 | 0.25 | 100 | 100 | 100 | 100 | 100 | 100 | — | 100 | 95 | — | 100 | 100 | 100 | — | 100 | — | 100 | 100 |
| 192 | 0.25 | 95 | 100 | 90 | 100 | 100 | 97 | — | 100 | 10 | 0 | — | 0 | 0 | — | 0 | 0 | 70 | 90 |
| 193 | 0.125 | 90 | 100 | 0 | 100 | 100 | 40 | — | 60 | 0 | 0 | 0 | 0 | 0 | — | 20 | 0 | 0 | 0 |
| 194 | 0.25 | 90 | 100 | 70 | 100 | 95 | 90 | — | 90 | 0 | 0 | 30 | 0 | 0 | — | 0 | 0 | 0 | 95 |

PREEMERGENT CONTROL OF PLANT SPECIES

-continued

| Compound | Dosage (lb/acre) | A | B | C | D | F | G | H | I | J | K | L | M | N | O | Q | R | P | T |
|---|---|---|---|---|---|---|---|---|---|---|---|---|---|---|---|---|---|---|---|
| 195 | 0.125 | 30 | 100 | 0 | 95 | 100 | 60 | — | 70 | 10 | 0 | 0 | 0 | 0 | — | 0 | 0 | 20 | 100 |
| 196 | 0.125 | 95 | 100 | 0 | 95 | 100 | 60 | — | 70 | 0 | 0 | 0 | 0 | 0 | — | 0 | 0 | 0 | 20 |
| 197 | 0.125 | 99 | 99 | 30 | 99 | 99 | 80 | — | 99 | 0 | 40 | 20 | 10 | 50 | — | 80 | 10 | 98 | 90 |
| 198 | 4 | 90 | 100 | 0 | 100 | 0 | 0 | — | 80 | 10 | 70 | 20 | 50 | 0 | — | 0 | 70 | 0 | 30 |
| 199 | 0.25 | 20 | 100 | 70 | 90 | 0 | 20 | — | 70 | 0 | 0 | — | — | — | — | 0 | 0 | 0 | 0 |
| 200 | 0.5 | 100 | 100 | 100 | 100 | 100 | 60 | — | 90 | 50 | 0 | 10 | 0 | 0 | — | 0 | 0 | 0 | 60 |
| 202 | 4 | 0 | 20 | 40 | 100 | 0 | 100 | — | 0 | 0 | 0 | — | 0 | 0 | — | 0 | 0 | 0 | 0 |
| 203 | 1.0 | 40 | 100 | 0 | 80 | 0 | 0 | — | 0 | 0 | 0 | 0 | 0 | 0 | — | 0 | 0 | 0 | 0 |
| 204 | 0.25 | 80 | 40 | 0 | 90 | — | 0 | — | 0 | 40 | 0 | 60 | 0 | 0 | — | 0 | 0 | 0 | 0 |
| 205 | 0.25 | 100 | 100 | 90 | 100 | 100 | 75 | — | 100 | 95 | 50 | — | 0 | 50 | — | 0 | 50 | 0 | 70 |
| 206 | 0.5 | 100 | 100 | 100 | 100 | 50 | 35 | — | 100 | 0 | 0 | — | 0 | 40 | — | 40 | 0 | 60 | 97 |
| 208 | 0.25 | 100 | 100 | 45 | 100 | 90 | 40 | — | 90 | 0 | 0 | 30 | 0 | 0 | — | 0 | 0 | 50 | 60 |
| 209 | 10 | 100 | — | — | — | — | 100 | 100 | 90 | — | — | — | — | 70 | 100 | — | 70 | 50 | — |
| 211 | 10 | 90 | — | — | — | — | 80 | 80 | 95 | — | — | — | — | — | 80 | — | 50 | 90 | — |
| 212 | 1 | 30 | 30 | 70 | 90 | 30 | 0 | — | 40 | 10 | 0 | 0 | 0 | 0 | — | 0 | 0 | 0 | 0 |
| 213 | 0.125 | 100 | — | 70 | 100 | 90 | 80 | — | 100 | 100 | 10 | 100 | 70 | 80 | — | 80 | 50 | 100 | — |
|  | 0.031 | 50 | — | 0 | 60 | 90 | 50 | — | 100 | 10 | 0 | 50 | 0 | 0 | — | 50 | 0 | 0 | — |
| 214 | 0.25 | 100 | 100 | 100 | 100 | 100 | 100 | — | 100 | 100 | 100 | 100 | 100 | 100 | — | 100 | 100 | 100 | 100 |
|  | 0.031 | 100 | 100 | 50 | 100 | 100 | 70 | — | 100 | 90 | 80 | 100 | 100 | 70 | — | 90 | 100 | 100 | 70 |
| 215 | 0.25 | 100 | 100 | 100 | 100 | 100 | 100 | — | 100 | 100 | 100 | 100 | 100 | 100 | — | 100 | 100 | 100 | 100 |
|  | 0.031 | 70 | 100 | 100 | 100 | 100 | 100 | — | 100 | 70 | 60 | 100 | 50 | 10 | — | 90 | 50 | 90 | 95 |
| 216 | 0.25 | 100 | 20 | 70 | 100 | 100 | 90 | — | 100 | 100 | 90 | 100 | 100 | 75 | — | 100 | 100 | 100 | 70 |
|  | 0.063 | 50 | 0 | 10 | 70 | 100 | 50 | — | 70 | 50 | 50 | 50 | 100 | 70 | — | 70 | 90 | 100 | 70 |
| 217 | 0.25 | 100 | 100 | 100 | 100 | 100 | 100 | — | 100 | 50 | 90 | 100 | 100 | 90 | — | 100 | — | 50 | 70 |
|  | 0.125 | 100 | 100 | 100 | 100 | 100 | 100 | — | 100 | 0 | 0 | 100 | 50 | 30 | — | 90 | — | 30 | 70 |
| 218 | 0.25 | 100 | 100 | 100 | 100 | 100 | 100 | — | 100 | 0 | 0 | 95 | 0 | 0 | — | 50 | — | 50 | 50 |
| 219 | 0.25 | 100 | 100 | 100 | 100 | 100 | 100 | — | 100 | 100 | 50 | 100 | 100 | 100 | — | 100 | — | 100 | 100 |
|  | 0.031 | 100 | 100 | 30 | 100 | 100 | 100 | — | 100 | 70 | 10 | 70 | 100 | 0 | — | 100 | — | 70 | 70 |
| 220 | 0.25 | 100 | 100 | 90 | 100 | 100 | 70 | — | 100 | 100 | 50 | 100 | 100 | 90 | — | 100 | — | 100 | 100 |
|  | 0.063 | 50 | 80 | 0 | 100 | 90 | 30 | — | 100 | 50 | 50 | 10 | 100 | 90 | — | 90 | — | 100 | 50 |
| 221 | 0.25 | 100 | 100 | 100 | 100 | 100 | 100 | — | 100 | 90 | 100 | 100 | 90 | 100 | — | 70 | — | 100 | 100 |
|  | 0.031 | 70 | 60 | 0 | 70 | 75 | 90 | — | 100 | 0 | 0 | 30 | 0 | 90 | — | 0 | — | 50 | 70 |
| 222 | 0.25 | 100 | 100 | 100 | 100 | 100 | 90 | — | 100 | 40 | 90 | 50 | 0 | 0 | — | 100 | — | 30 | 50 |
|  | 0.125 | 100 | 100 | 60 | 100 | 100 | 90 | — | 100 | 0 | 100 | 30 | 0 | 0 | — | 70 | — | 30 | 50 |
| 213 | 0.25 | 100 | 100 | 100 | 100 | 100 | 100 | — | 100 | 100 | 95 | 100 | 100 | 100 | — | 100 | 80 | 100 | 100 |
|  | 0.031 | 95 | 100 | 100 | 100 | 100 | 100 | — | 100 | 90 | 100 | 100 | 90 | 100 | — | 100 | 80 | 75 | 75 |
| 227 | 0.25 | 60 | 100 | 0 | 100 | 100 | 70 | — | 30 | 40 | 50 | 100 | 90 | 50 | — | 70 | — | 90 | 100 |
| 228 | 0.25 | 90 | 80 | 20 | 100 | 100 | 70 | — | 90 | 50 | — | 100 | 50 | 90 | — | 90 | — | 50 | 50 |
| 229 | 0.25 | 100 | 100 | 30 | 100 | 90 | 100 | — | 90 | 40 | 10 | 90 | 0 | 0 | — | 0 | — | 0 | 100 |
| 230 | 0.25 | 100 | 90 | 20 | 100 | 100 | 90 | — | 90 | 90 | 50 | 100 | 30 | 100 | — | 90 | — | 80 | 100 |
|  | 0.063 | 80 | 30 | 0 | 100 | 100 | 30 | — | 90 | 40 | 50 | 70 | 30 | 0 | — | 70 | — | 30 | 50 |
| 231 | 0.063 | 100 | 100 | 20 | 100 | 100 | 100 | — | 75 | 100 | — | 100 | 80 | 95 | — | 100 | 50 | 95 | 90 |
| 232 | 10 | 90 | — | — | — | — | 80 | 98 | 98 | — | — | — | — | 40 | 90 | — | 40 | 98 | — |
| 233 | 1 | 80 | 100 | 20 | 80 | 90 | 70 | — | 70 | 0 | 0 | 0 | 0 | 0 | — | 0 | 0 | 0 | 0 |
| 234 | 2 | 80 | 100 | 0 | 0 | 40 | 0 | — | 0 | 10 | 0 | 30 | 0 | 0 | — | 30 | 0 | 0 | 100 |
| 235 | 0.25 | 50 | — | 0 | 50 | 50 | 90 | — | 20 | 50 | 10 | 50 | 50 | — | — | 0 | — | 20 | 0 |
| 236 | 10 | 100 | — | — | — | — | 100 | 100 | 100 | — | — | — | — | 100 | 100 | — | 100 | 100 | — |
| 237 | 0.25 | 50 | — | 40 | 50 | 10 | 20 | — | 0 | 20 | 20 | 20 | 100 | 10 | — | 10 | — | 30 | 30 |
| 238 | 10 | 0 | — | — | — | — | 0 | 80 | 60 | — | — | — | — | 0 | 0 | — | 0 | 0 | — |
| 239 | 10 | 90 | — | — | — | — | 100 | 100 | 100 | — | — | — | — | 95 | 98 | — | 98 | 98 | — |
| 243 | 0.125 | 90 | 100 | 100 | 100 | 100 | 80 | — | 60 | 75 | 0 | 90 | 0 | 70 | — | 80 | 0 | 80 | 100 |
| 244 | 0.125 | 70 | 100 | 20 | 100 | 100 | 0 | — | 100 | 0 | 0 | 0 | 0 | 0 | — | 0 | 0 | 0 | 95 |
| 245 | 10 | 0 | — | — | — | — | 100 | 0 | 60 | — | — | — | — | 0 | 0 | — | 0 | 0 | — |
| 246 | 0.25 | 80 | 80 | 90 | 90 | 0 | 0 | — | 30 | 20 | 20 | 95 | 10 | 0 | — | 20 | 40 | 20 | 20 |
| 247 | 2.0 | 80 | 100 | 100 | 100 | 100 | 0 | — | 80 | 85 | 70 | 80 | 70 | 60 | — | 90 | 90 | 70 | 30 |
| 250 | 0.5 | 0 | 100 | 0 | 30 | 0 | 10 | — | 0 | 0 | 0 | 50 | 40 | 10 | — | 30 | 100 | 0 | 0 |
| 252 | 10 | 0 | 100 | 100 | 100 | 100 | 50 | — | 0 | 80 | 100 | — | 30 | 60 | — | 50 | 50 | 80 | 90 |
| 255 | 4.0 | 60 | 90 | 15 | 80 | 40 | 0 | 95 | 0 | 0 | 10 | 30 | 0 | 0 | 0 | 40 | 60 | 0 | 15 |
| 257 | 10 | 90 | — | — | — | — | 80 | 100 | 90 | — | — | — | — | 0 | 30 | — | 0 | 30 | 0 |
| 258 | 2.0 | 0 | 10 | 20 | 0 | 100 | 0 | 90 | 20 | 0 | 30 | 0 | 0 | 0 | 60 | 0 | 0 | 0 | 0 |
| 260 | 1.0 | 20 | 80 | 0 | 80 | 90 | 50 | — | 70 | 0 | 0 | — | 0 | 0 | — | 40 | 0 | 30 | 70 |
| 261 | 2.0 | 0 | 100 | 100 | 90 | — | 90 | — | 80 | 0 | 0 | — | 0 | 0 | — | 10 | 70 | 50 | 0 |
| 262 | 0.25 | 90 | 100 | 100 | 100 | 100 | 90 | — | 100 | 80 | 95 | — | 0 | 90 | — | 60 | 50 | 95 | 100 |
| 263 | 0.5 | 0 | 40 | 0 | 100 | 0 | 50 | — | 20 | 0 | 0 | — | 0 | 0 | — | 0 | 50 | 50 | 0 |
| 264 | 2.0 | 0 | 60 | 0 | 40 | 100 | 0 | — | 0 | 10 | 0 | — | 0 | 0 | — | 0 | 0 | 0 | 0 |
| 265 | 10 | 0 | — | — | — | — | 60 | 60 | 30 | — | — | — | — | 0 | 0 | — | 0 | 0 | — |
| 266 | 4.0 | 50 | 100 | 50 | 90 | 80 | 0 | — | 0 | 0 | 0 | 30 | 40 | 0 | — | 0 | 50 | 90 | 80 |
| 267 | 4.0 | 0 | 100 | 30 | 80 | 90 | 0 | — | 90 | 70 | 30 | 30 | 50 | 20 | — | 10 | 50 | 90 | 0 |
| 268 | 0.25 | 100 | 100 | 0 | 100 | 100 | 90 | — | 100 | 80 | 100 | 100 | — | 90 | — | 80 | 30 | 100 | 100 |
|  | 0.015 | 70 | 100 | 0 | 90 | 90 | 0 | — | 20 | 0 | 0 | 60 | 0 | 40 | — | 40 | 0 | 60 | 97 |
| 269 | 0.062 | 100 | 100 | 0 | 90 | 90 | 0 | — | 90 | 0 | 0 | 70 | 0 | 20 | — | 10 | 0 | 70 | 90 |
| 270 | 2.0 | 100 | 100 | 0 | 100 | 100 | 95 | — | 98 | 90 | 100 | 98 | 70 | 98 | — | 98 | 80 | 100 | 100 |
|  | 0.125 | 98 | 98 | 0 | 98 | 100 | 90 | — | 98 | 30 | 70 | 90 | 0 | 95 | — | 90 | 20 | 95 | 100 |
| 272 | 0.5 | 90 | 100 | 0 | 100 | 100 | 60 | — | 100 | 50 | 40 | 50 | 0 | 75 | — | 60 | 0 | 95 | 100 |
|  | 0.25 | 80 | 100 | 0 | 100 | 90 | 40 | — | 100 | 0 | 30 | 40 | 0 | 60 | — | 40 | 0 | 90 | 100 |
| 273 | 10 | 98 | — | — | — | — | 98 | 100 | 98 | — | — | — | — | 95 | 98 | — | 90 | 100 | — |
| 274 | 2 | 100 | 100 | 20 | 100 | 100 | 90 | — | 100 | 80 | 95 | 100 | 30 | 90 | — | 80 | 20 | 100 | 100 |

-continued

PREEMERGENT CONTROL OF PLANT SPECIES

| Compound | Dosage (lb/acre) | A | B | C | D | F | G | H | I | J | K | L | M | N | O | Q | R | P | T |
|---|---|---|---|---|---|---|---|---|---|---|---|---|---|---|---|---|---|---|---|
|  | 0.25 | 95 | 100 | 0 | 100 | 90 | 80 | — | 100 | 60 | 80 | 90 | 0 | 80 | — | 70 | 0 | 95 | 100 |
| 275 | 0.25 | 100 | 100 | 20 | 100 | 100 | 90 | — | 100 | 80 | 90 | 100 | 100 | 100 | — | 100 | — | 100 | 100 |
|  | 0.063 | 80 | 100 | 0 | 95 | 50 | 50 | — | 100 | 30 | 0 | 60 | 20 | 50 | — | 90 | — | 90 | 0 |
| 276 | 0.25 | 80 | 100 | 10 | 100 | 100 | 90 | — | 100 | 60 | 90 | 100 | 80 | 100 | — | 90 | — | 100 | 100 |
|  | 0.063 | 70 | 100 | 0 | 100 | 100 | 80 | — | 100 | 0 | 10 | 90 | 50 | 70 | — | 80 | — | 90 | 100 |
| 277 | 0.25 | 50 | 100 | 20 | 100 | 100 | 30 | — | 40 | 80 | 90 | 80 | 90 | — | 100 | — | 100 | 100 |  |
| 278 | 0.25 | 100 | 100 | 70 | 100 | 100 | 100 | — | 100 | 60 | 90 | 100 | 70 | 100 | — | 90 | — | 100 | 100 |
|  | 0.063 | 100 | 100 | 0 | 100 | 60 | 100 | — | 100 | 0 | 50 | 70 | 30 | 50 | — | 90 | — | 80 | 100 |
| 279 | 0.25 | 90 | 100 | 20 | 100 | 100 | 90 | — | 100 | 80 | 100 | 100 | 90 | 100 | — | 100 | — | 100 | 100 |
|  | 0.063 | 100 | 100 | 0 | 100 | 100 | 90 | — | 100 | 0 | 40 | 90 | 60 | 50 | — | 80 | — | 100 | 100 |
| 280 | 0.25 | 80 | 100 | 10 | 100 | 100 | 90 | — | 100 | 50 | 50 | 100 | 60 | 100 | — | 90 | — | 100 | 100 |
|  | 0.063 | 80 | 100 | 0 | 100 | 100 | 70 | — | 100 | 10 | 50 | 50 | 90 | 50 | — | 80 | — | 100 | 100 |
| 282 | 0.25 | 100 | 100 | 50 | 100 | 100 | 80 | — | 100 | 95 | 100 | 100 | 70 | 70 | — | 100 | 100 | 100 | 100 |
|  | 0.063 | 100 | 100 | 10 | 100 | 70 | 80 | — | 100 | 0 | 50 | 90 | 50 | 70 | — | 100 | 100 | 80 | 70 |
| 283 | 0.25 | 100 | 100 | 20 | 100 | 95 | 80 | — | 100 | 40 | 100 | 100 | 100 | 100 | — | 100 | — | 100 | 100 |
|  | 0.063 | 100 | 100 | 0 | 100 | 70 | 70 | — | 100 | 0 | 80 | 90 | 50 | 85 | — | 90 | — | 70 | 90 |
| 284 | 0.25 | 100 | 100 | 20 | 100 | 100 | 80 | — | 100 | 85 | 100 | 100 | 100 | 100 | — | 100 | 90 | 100 | 100 |
|  | 0.063 | 70 | 100 | 0 | 100 | 85 | 70 | — | 100 | 0 | 70 | 90 | 50 | 100 | — | 70 | 10 | 70 | 100 |
| 286 | 0.25 | 100 | 100 | 30 | 100 | 100 | 100 | — | 100 | 50 | 100 | 100 | 70 | 100 | — | 100 | — | 100 | 100 |
|  | 0.063 | 100 | 100 | 0 | 100 | 100 | 100 | — | 100 | 0 | 95 | 30 | 0 | 95 | — | 80 | — | 100 | 85 |
| 287 | 0.25 | 100 | 100 | 30 | 100 | 100 | 100 | — | 100 | 60 | 100 | 100 | 70 | 100 | — | 100 | — | 100 | 100 |
|  | 0.063 | 100 | 100 | 0 | 100 | 100 | 50 | — | 100 | 0 | 80 | 70 | 100 | 100 | — | 80 | — | 100 | 70 |
| 288 | 0.25 | 100 | 100 | 40 | 100 | 100 | 100 | — | 100 | 80 | 100 | 100 | 60 | 100 | — | 100 | 90 | 100 | 100 |
|  | 0.063 | 100 | 100 | 0 | 100 | 50 | 100 | — | 100 | 0 | 100 | 95 | 0 | 75 | — | 100 | 80 | 100 | 60 |
| 289 | 0.25 | 100 | 100 | 50 | 100 | 100 | 100 | — | 100 | 95 | — | 100 | 80 | 100 | — | 100 | 100 | 100 | 100 |
|  | 0.063 | 100 | 100 | 0 | 100 | 80 | 70 | — | 100 | 60 | — | 95 | 50 | 60 | — | 95 | 50 | 100 | 50 |
| 290 | 0.25 | 100 | 100 | 70 | 100 | 100 | 100 | — | 100 | 90 | 100 | 100 | 95 | 100 | — | 100 | 70 | 100 | 80 |
|  | 0.063 | 100 | 100 | 20 | 100 | 100 | 40 | — | 100 | 60 | 50 | 100 | 20 | 70 | — | 100 | 20 | 90 | 50 |
| 291 | 0.25 | 100 | 100 | 20 | 100 | 100 | 90 | — | 100 | 55 | 100 | 100 | 100 | 100 | — | 100 | 70 | 100 | 100 |
|  | 0.063 | 100 | 100 | 0 | 100 | 100 | 0 | — | 100 | 0 | 70 | 100 | 30 | 75 | — | 100 | 70 | 90 | 100 |
| 293 | 0.25 | 100 | 100 | 10 | 100 | 100 | 70 | — | 100 | 60 | 90 | 100 | 60 | 100 | — | 95 | 95 | 100 | 100 |
|  | 0.063 | 100 | 75 | 0 | 100 | 95 | 20 | — | 80 | 0 | 100 | 60 | 0 | 20 | — | 50 | 50 | 65 | 0 |
| 297 | 0.025 | 100 | 100 | 50 | 100 | 100 | 95 | — | 100 | 80 | 100 | 100 | 60 | 100 | — | 100 | 80 | 100 | 100 |
|  | 0.063 | 100 | 100 | 0 | 100 | 90 | 85 | — | 100 | 0 | 50 | 90 | 20 | 65 | — | 70 | 50 | 40 | 90 |
| 298 | 0.25 | 100 | 100 | 0 | 100 | 100 | 70 | — | 100 | 40 | 95 | 95 | 50 | 100 | — | 95 | 50 | 100 | 100 |
|  | 0.063 | 90 | 100 | 0 | 85 | 0 | 0 | — | 70 | 0 | 50 | 60 | 20 | 50 | — | 75 | 20 | 20 | 40 |
| 304 | 0.125 | 100 | 97 | 90 | 100 | 95 | 40 | 100 | 95 | 90 | 95 | 97 | 0 | 55 | 20 | 95 | 0 | 93 | 97 |
|  | 0.031 | 70 | 95 | 40 | 100 | 20 | 0 | 100 | 60 | 0 | 10 | 10 | 0 | 0 | 0 | 10 | 0 | 20 | 35 |
| 305 | 1.0 | 97 | 97 | 95 | 100 | 80 | 90 | 100 | 95 | 90 | 98 | 100 | 0 | 93 | 50 | 95 | 0 | 50 | 100 |
| 306 | 0.125 | 90 | 100 | 70 | 90 | 100 | 40 | — | 100 | 0 | 0 | 40 | 0 | 0 | — | 80 | 0 | 20 | 70 |

Certain of the compounds of this invention have been found to be useful for the control of aquatic weeds and some of these are useful for the selective control of, e.g., barnyardgrass and yellow nutsedge in paddy fields in the presence of rice. The following example illustrate the utility of the compounds of this invention in aquatic weed control.

EXAMPLE 96

In testing for such utility, the plant species to be tested were transplanted into 16 oz. containers into about 2 inches of soil when they were in the 1–2 inch stage and then flooded to a depth of about 1 inch. An acetone concentrate of the chemical to be tested was then injected into the paddy water, the volume injected being varied as desired to provide the desired concentration. Percent control was evaluated nine days after application. The results were as follows:

CONTROL OF AQUATIC PLANT SPECIES

| Compound | Dosage (Kg/Ha) | K | N | S | T |
|---|---|---|---|---|---|
| 1 | 2.0 | 97 | 95 | 90 | 70 |
| 2 | 2.0 | 97 | 97 | 99 | 93 |
| 4 | 2.0 | 90 | 95 | 45 | 80 |
| 6 | 1.0 | 93 | 99 | 20 | 90 |
| 7 | 1.0 | 97 | 99 | 93 | 90 |
| 8 | 1.0 | 97 | 99 | 0 | 93 |
| 9 | 1.0 | 25 | 99 | 97 | 85 |
|  | 0.25 | 0 | 93 | 80 | 30 |
| 10 | 1.0 | 93 | 90 | 50 | 90 |
| 12 | 1.0 | 70 | 97 | 0 | 95 |
| 13 | 0.25 | 97 | 93 | 10 | 93 |
| 15 | 4.0 | 35 | 25 | 0 | 70 |
| 17 | 4.0 | 97 | 40 | 0 | 90 |
| 22 | 0.25 | 97 | 97 | 30 | 97 |
| 25 | 0.25 | 97 | 95 | 0 | 90 |
| 26 | 0.125 | 93 | 90 | 0 | 95 |
| 31 | 0.125 | 90 | 97 | 45 | 97 |
| 32 | 0.5 | 93 | 97 | 95 | 95 |
| 33 | 1.0 | 97 | 97 | 90 | 97 |
| 38 | 0.25 | 97 | 99 | 85 | 97 |
|  | 0.031 | 0 | 80 | 0 | 95 |
| 39 | 0.25 | 75 | 99 | 75 | 99 |
|  | 0.031 | 0 | 20 | 0 | 85 |
| 41 | 1.0 | 97 | 99 | 95 | 80 |
| 49 | 0.5 | 97 | 97 | 97 | 99 |
|  | 0.016 | 0 | 50 | 0 | 95 |
| 50 | 0.125 | 97 | 97 | 97 | 97 |
| 51 | 1.0 | 95 | 97 | 70 | 97 |
|  | 0.031 | 0 | 35 | 0 | 93 |
| 53 | 0.5 | 99 | 99 | 97 | 99 |
|  | 0.031 | 0 | 80 | 10 | 95 |
| 54 | 0.5 | 97 | 97 | 0 | 95 |
| 108 | 1.0 | 97 | 97 | 97 | 90 |
| 111 | 4.0 | 93 | 99 | 80 | 99 |
| 114 | 1.0 | 70 | 95 | 0 | 90 |
|  | 0.25 | 0 | 80 | 0 | 65 |

-continued

CONTROL OF AQUATIC PLANT SPECIES

| Compound | Dosage (Kg/Ha) | Plant Species | | | |
|---|---|---|---|---|---|
| | | K | N | S | T |
| 143 | 0.5 | 95 | 99 | 97 | 97 |
| | 0.031 | 0 | 95 | 0 | 93 |

It has further been found that soil nitrogen may be conserved and plant nutrition improved by treating plant growth media with the novel compounds of this invention.

By the practice of the embodiment of the invention, the nitrification of ammonium nitrogen in the soil to nitrate nitrogen is suppressed, thereby preventing the rapid loss of ammonium nitrogen from the soil. Furthermore, by proper distribution of the novel compounds, this action of inhibiting the transformation of ammonium nitrogen to nitrate nitrogen is effective over a prolonged period of time including those situations where treated fertilizer is stored for some time before use. The ammonium nitrogen may arise from added ammonium nitrogen fertilizers or be formed in the soil by conversion of the organic nitrogen constituents found in soil or added thereto as components of organic fertilizers.

The provision of an effective but sublethal dosage of the active ingredient in the soil or growth medium is essential for the practice of the present invention. In general, good results are obtained when the growth medium is impregnated with the active ingredient in the amount of from 0.01 part to 100 parts or more by weight per million parts by weight of growth medium. (Hereinafter, the abbreviation ppm when employed is meant to designate parts by weight of active ingredient per million parts by weight of soil or growth medium.) The preferred amounts to be employed are dependent upon the particular situation. Thus, in determining the amount to be employed, consideration is made not only of the treatment need, i.e., soil pH, temperature, soil type, etc., but also of the mode of application to the soil. When the active ingredient is to be applied in a broadcast application, the concentration may frequently be less than in row or band application where for a substantial depth and width within the vicinity of application there may be a very high concentration of the active ingredient. When application is made near the root zone of growing plants or when application is made immediately prior to seeding or transplanting, the amounts supplied are frequently at a lower rate than when application is made at the end of the growing season to prepare the soil for the following season. By dispersing very large dosages in growth media, a prolonged inhibition of nitrification may be obtained over a period of many months. The concentration of the active ingredient is eventually reduced to a minimum by decomposition in the soil.

In one method for carrying out this embodiment of the invention, the active ingredient is distributed throughout the growth media in a broadcast application such as by spraying, dusting, distributing in irrigation water, etc. In such application, the active ingredient is supplied in amounts sufficient to permeate the growing area of soil with an amount of from 0.05 to 1000 ppm. In field administration, the active ingredient may be distributed in the soil in the amount of at least 0.05 pound per acre (0.056 kg/hectare) and through such cross-section of the soil as to provide for the presence therein of an effective concentration of the agent. It is usually preferred that the active ingredient be distributed to a depth of at least two inches (5.08 cm) below the soil surface and at a dosage of at least 0.1 pound per acre (0.112 kg/hectare).

In another method for carrying out the present invention, the active ingredient is administered to the growth medium in a band or row application. In such application, administration is made with or without carrier in an amount sufficient to supply to soil or growth medium a concentration of the active ingredient which may be as high as 4000 ppm or more. After administration with or without discing or dragging, subsequent irrigation or rainfall distributes the active ingredient throughout the growth medium.

In one embodiment of the present invention, the active ingredient is distributed throughout the growth media prior to seeding or transplanting the desired crop plant.

In another embodiment, the soil in the root zone of growing plants is treated with the active ingredient in an amount effective to inhibit nitrification. Oftentimes, it is desirable to treat the soil adjacent to plants, and this procedure may be carried out conveniently in side-dressing operations.

In a further embodiment, soil may be treated with the compounds following harvest or after fallowing to prevent rapid loss of ammonium nitrogen and to build up the ammonium nitrogen formed by conversion of organic nitrogen compounds. Such practice conserves the soil nitrogen for the following growing season. In such application, the upper limit is primarily an economic consideration.

In an additional embodiment, the soil is treated with the active ingredient in conjunction with the application of reduced nitrogen fertilizers. The treatment with the active ingredient may be carried out prior to, subsequent to or simultaneously with the application of fertilizers. Such practice prevents the rapid loss of the ammonium nitrogen added as fertilizer and of the ammonium nitrogen formed from organic nitrogen in fertilizers by the action of soil microorganisms. The administration to the soil of the active ingredient in an ammonium nitrogen or ammonium nitrogen forming fertilizer composition constitutes a preferred embodiment of the present invention.

The present invention may be carried out by distributing the active ingredient in an unmodified form through growth medium. The present method also embraces distributing the active ingredient as a constituent in liquid or finely divided solid compositions. In such practice, the active ingredient may be modified with one or more additaments or soil treating adjuvants including water, petroleum distillates or other liquid carriers, surface-active dispersing agents, finely divided inert solids and nitrogen fertilizers. Depending upon the concentration of the active ingredient, such augmented composition may be distributed in the soil without further modification or be considered a concentrate and subsequently diluted with additional inert carrier to produce the ultimate treating composition. The required amount of the active ingredient may be supplied to growth media in an organic solvent carrier, in an aqueous carrier or in a solid carrier. When an organic solvent carrier is employed, it may be further dispersed in an aqueous liquid carrier.

The concentration of the active ingredient in compositions to be employed for the treatment of growth mediais not critical and may vary considerably provided the required dosage of effective agent is supplied to the growth media. The concentration of the active ingredient may vary from 0.00001 percent by weight to 95 percent by weight of the composition, depending on whether the composition is a treating composition or a concentrate composition and whether it is in the form of a solid or a liquid. In aqueous liquid treating compositions, concentrations of from 0.00001 percent to 0.25 percent by weight of the active ingredient is considered the preferred composition. The concentration of the active ingredient in organic solvents may be from 2 to 95 percent by weight. Concentrate liquid compositions generally contain from 2.5 to 95 percent by weight of the active ingredient. Treating compositions generally contain from 0.0001 percent to 10 percent by weight of the active ingredient while concentrate compositions contain from 2.5 to 95 percent.

Liquid compositions containing the desired amount of the active ingredient may be prepared by dispersing the latter in one or more liquid carriers such as water or an organic solvent, with or without the aid of a suitable surface-active dispersing agent or emulsifying agent. Suitable organic solvents include acetone, diisobutylketone, methanol, ethanol, isopropyl alcohol, toluene, methylene chloride, chlorobenzene and the petroleum distillates. The preferred organic solvents are those which are of such volatility that they leave little permanent residue in the soil. When the solutions of the active ingredient in organic solvents are to be further diluted to produce aqueous dispersions, the preferred solvents include acetone and the alcohols. When the liquid carrier is entirely organic in nature, particularly desirable carriers are the petroleum distillates boiling almost entirely under 400° F. (204° C.) at atmospheric pressure and having a flash point above 100° F. (38° C.). Dispersing and emulsifying agents which may be employed in liquid compositions include condensation products of alkylene oxides with phenols and organic acids, alkyl aryl sulfonates, polyoxyalkylene derivatives of sorbitan esters, complex ether alcohols, mahogany soaps and the like. The surface-active agents are generally employed in the amount of from 1 to 20 percent by weight of the active ingredient.

Solid compositions containing the active ingredient may be prepared by dispersing the latter in finely divided inert solid carriers such as talc, chalk, gypsum, vermiculite, bentonite and the like, fuller's earth, attapulgite and other clays, various solid detergent dispersing agents and solid fertilizer compositions. In preparing such compositions, the carrier is mechanically ground with the active ingredient or wet with a solution or dispersion thereof in a volatile organic solvent. Depending upon the proportions of ingredients, these compositions may be employed without further modification or be considered concentrates and subsequently further diluted with solid surface-active dispersing agent, talc, chalk, gypsum or the like to obtain the desired treating composition. Furthermore, such concentrate compositions have the properties of wettable powders and may be dispersed in water with or without added dispersing agent or agents to prepare aqueous soil treating compositions.

Soil treatment compositions may be prepared by dispersing the active ingredient in fertilizers such as ammonium fertilizer or organic nitrogen fertilizer. The resulting fertilizer composition may be employed as such or may be modified as by dilution with additional nitrogen fertilizer or with inert solid carrier to obtain a composition containing the desired amount of active agent for the treatment of soil. Further, an aqueous dispersion of the active ingredient-fertilizer composition may be prepared and administered to the growth medium. Fertilizer compositions comprising the active ingredient in intimate admixture with ammonium fertilizers constitute preferred embodiments of the present invention.

In fertilizer compositions comprising a reduced nitrogen fertilizer, it is desirable that the active ingredient be present in an amount of at least 0.05 percent by weight based on the weight of the nitrogen present in the fertilizer as reduced nitrogen and may be present in amounts as high as 95 percent by weight of the reduced nitrogen in the fertilizer. Thus, when a fertilizer composition contains both reduced nitrogen and other forms of nitrogen such as in the case of ammonium nitrate fertilizer compositions, the amount of the active ingredient is based on the weight of nitrogen present in the ammonium component.

In operations carried out in accordance with the present invention, the soil may be treated in any convenient fashion with the active compound or a composition containing the latter. For example, these modified or unmodified compositions may be mechanically mixed with soil; applied to the surface of soil and thereafter dragged or disced into the soil to a desired depth; or transported into the soil with a liquid carrier wuch as by injection, spraying or irrigation. When the distribution is carried out by introducing the compound in the water employed to irrigate the soil, the amount of water is varied in accordance with the moisture content of the soil in order to obtain a distribution of the compound to the desired depth. The compound may be readily and conveniently distributed to a depth of a few inches to four feet by irrigation methods. The preferred methods embrace procedures using any of these steps or combination of steps wherein the compound is distributed in the soil substantially simultaneously with a reduced nitrogen fertilizer.

A number of the compounds of this invention were tested for their ability to reduce the rate of nitrification of ammonium nitrogen, applied as ammonium phosphate to the soil. The activity is reported in the following table.

EXAMPLE 97

The test method comprised selecting a soil which had a low nitrate concentration and good nitrification activity. A sufficient volume of water was added to 20 g of the soil in a wide-mouth, screw-cap, 4-ounce, glass bottle, such that the moisture content of the mixture was made equal to the $\frac{1}{3}$ bar tension value for that soil. The mixture was thoroughly mixed before sealing. The added water contained 5 mg (250 ppm) of nitrogen in the form of $(NH_4)_2HPO_4$ (23.6 mg of ammonium phosphate) and the desired quantity of test chemical (i.e., 20 mg for a 1 ppm concentration based on dry weight of soil). When the test chemical had a low water solubility, it was compounded in acetone (or other suitable solvent) in such a way that the final mixture in the soil contained no more than 10 $\mu$l of acetone. Acetone slows the rate of soil nitrification and its concentration must be carefully controlled. Single samples of each test chemical were incubated for two weeks at 27° C.

The experiment comprised the following types of samples:

1. Nitrate blank containing soil, water and solvent only. (BLANK)
2. Test chemicals containing soil, water, ammonium phosphate, solvent, and test chemical. Single samples. (SAMPLE)
3. Nitrate control containing soil, water and ammonium phosphate only. (CONTROL)

The soil samples were analyzed as follows: Sufficient ammonium sulfate extracting solution was added to the sample, such that the total volume of added water was 50 ml (included water added during sample preparation). The capped mixture was shaken 10 minutes to solubilize nitrate and the soil particulates were allowed to settle. The nitrate concentration in the water phase was determined with a nitrate-specific ion electrode such as Orion Model 93-07.

The non-nitrate nitrogen remaining (% $NH_4$—N remaining) in the soil after two weeks (performance value) was calculated as follows:

$$\% \ NH_4\text{---N remaining} = \frac{\text{Control} - \text{Sample}}{\text{Control} - \text{blank}} \times 100$$

| Compound | \multicolumn{13}{c}{% $NH_4$—N Remaining After 2 Weeks Incubation at Indicated Concentration (ppm)} | | | | | | | | | | | | |
|---|---|---|---|---|---|---|---|---|---|---|---|---|---|
| | 10 | 5 | 4 | 2.5 | 1.25 | 1 | 0.6 | 0.5 | 0.25 | 0.125 | 0.1 | 0.06 | 0.01 |
| 1 | 75 | — | — | — | — | 35 | — | — | — | — | 0 | — | 0 |
| 2 | 78 | — | — | — | — | 39 | — | — | — | — | 0 | — | 0 |
| 3 | 25 | — | — | — | — | 0 | — | — | — | — | 0 | — | 0 |
| 4 | 71 | — | — | — | — | 38 | — | — | — | — | 0 | — | 0 |
| 5 | 28 | — | — | — | — | 1 | — | — | — | — | 0 | — | 0 |
| 6 | 87 | — | — | — | — | 78 | — | — | — | — | 55 | — | 15 |
| 7 | — | — | — | — | — | 80 | — | 73 | 62 | 30 | — | 17 | — |
| 8 | — | — | — | — | — | 67 | — | 59 | 44 | 23 | — | 4 | — |
| 9 | 88 | — | — | — | — | 59 | — | — | — | — | 14 | — | 0 |
| 10 | 70 | — | — | — | — | 27 | — | — | — | — | 0 | — | 0 |
| 11 | 5 | — | — | — | — | 0 | — | — | — | — | 0 | — | 0 |
| 12 | — | — | — | — | — | 87 | — | 83 | 74 | 70 | — | 40 | — |
| 13 | — | — | — | — | — | 89 | — | 85 | 81 | 78 | — | 73 | — |
| 14 | 77 | — | — | — | — | 52 | — | — | — | — | 10 | — | 0 |
| 15 | — | — | — | — | — | 54 | — | 42 | 23 | 0 | — | 1 | — |
| 16 | 67 | — | — | — | — | 26 | — | — | — | 0 | — | — | 0 |
| 17 | 80 | — | — | — | — | 38 | — | — | — | — | 1 | — | 0 |
| 18 | 50 | — | — | — | — | 5 | — | — | — | — | 0 | — | 0 |
| 20 | — | — | — | — | — | 8 | — | 5 | 0 | 0 | — | 0 | — |
| 21 | 86 | — | — | — | — | 68 | — | — | — | — | 42 | — | 8 |
| 22 | — | — | — | — | — | 86 | — | 86 | 82 | 77 | — | 69 | — |
| 24 | 83 | — | — | — | — | 65 | — | — | — | — | 28 | — | 0 |
| 25 | — | — | — | — | — | 79 | — | 73 | 48 | 46 | — | 31 | — |
| 26 | — | — | — | — | — | 79 | — | 73 | 65 | 45 | — | 37 | — |
| 27 | 35 | — | — | — | — | 0 | — | — | — | — | 0 | — | 0 |
| 28 | 66 | — | — | — | — | 42 | — | — | — | — | 5 | — | 0 |
| 29 | 51 | — | — | — | — | 1 | — | — | — | — | 0 | — | 0 |
| 30 | 81 | — | — | — | — | 54 | — | — | — | — | 6 | — | 0 |
| 31 | 91 | — | — | — | — | 86 | — | — | — | — | 66 | — | 0 |
| 32 | 100 | — | — | — | — | 82 | — | — | — | — | 33 | — | 0 |
| 33 | 88 | — | — | — | — | 77 | — | — | — | — | 42 | — | 8 |
| 34 | 90 | — | — | — | — | 78 | — | — | — | — | 51 | — | 11 |
| 35 | 78 | — | — | — | — | 50 | — | — | — | — | 3 | — | 0 |
| 36 | 60 | — | — | — | — | 17 | — | — | — | — | 0 | — | 0 |
| 37 | 44 | — | — | — | — | 7 | — | — | — | — | 0 | — | 0 |
| 38 | 94 | — | — | — | — | 84 | — | — | — | — | 68 | — | 46 |
| 39 | 100 | — | — | — | — | 91 | — | — | — | — | 78 | — | 49 |
| 40 | 66 | 17 | — | 40 | 0 | — | 0 | — | — | — | — | — | — |
| 41 | 100 | — | — | — | — | 87 | — | — | — | — | 54 | — | 23 |
| 42 | 68 | — | — | — | — | 8 | — | — | — | — | 0 | — | 0 |
| 43 | 91 | — | — | — | — | 44 | — | — | — | — | 0 | — | 0 |
| 44 | 95 | — | — | — | — | 71 | — | — | — | — | 42 | — | 0 |
| 45 | 94 | — | — | — | — | 45 | — | — | — | — | 3 | — | 0 |
| 46 | 94 | — | — | — | — | 88 | — | — | — | — | 71 | — | 50 |
| 47 | 92 | — | — | — | — | 73 | — | — | — | — | 40 | — | 0 |
| 48 | 93 | — | — | — | — | 56 | — | — | — | — | 3 | — | 0 |
| 49 | 99 | — | — | — | — | 90 | — | — | — | — | 77 | — | 42 |
| 50 | 92 | — | — | — | — | 73 | — | — | — | — | 38 | — | 40 |
| 51 | — | — | 87 | — | — | 78 | — | — | 58 | — | — | 33 | — |
| 52 | 91 | — | — | — | — | 74 | — | — | — | — | 39 | — | 0 |
| 53 | 93 | — | — | — | — | 85 | — | — | — | — | 71 | — | 47 |
| 54 | — | — | 76 | — | — | 66 | — | — | 51 | — | — | 20 | — |
| 55 | — | — | 84 | — | — | 65 | — | — | 91 | — | — | 19 | — |
| 56 | — | — | 78 | — | — | 59 | — | — | 37 | — | — | 0 | — |
| 57 | — | — | 69 | — | — | 45 | — | — | 17 | — | — | 2 | — |
| 58 | — | — | 80 | — | — | 58 | — | — | 48 | — | — | 92 | — |
| 59 | — | — | 66 | — | — | 51 | — | — | 33 | — | — | 11 | — |
| 60 | 58 | 41 | — | 8 | 0 | — | 0 | — | — | — | — | — | — |
| 61 | 100 | 89 | — | 65 | 34 | — | 20 | — | — | — | — | — | — |
| 62 | 75 | 55 | — | — | 13 | — | 0 | — | — | — | — | — | — |
| 63 | — | — | 61 | — | — | 36 | — | — | 6 | — | — | 6 | — |
| 64 | — | — | 81 | — | — | 62 | — | — | 43 | — | — | 19 | — |
| 65 | — | — | 85 | — | — | 65 | — | — | 52 | — | — | 5 | — |

-continued

| | % NH₄—N Remaining After 2 Weeks Incubation at Indicated Concentration (ppm) | | | | | | | | | | | | |
|---|---|---|---|---|---|---|---|---|---|---|---|---|---|
| Compound | 10 | 5 | 4 | 2.5 | 1.25 | 1 | 0.6 | 0.5 | 0.25 | 0.125 | 0.1 | 0.06 | 0.01 |
| 66 | — | — | 78 | — | — | 66 | — | — | 41 | — | — | 0 | — |
| 67 | — | — | 69 | — | — | 41 | — | — | 0 | — | — | 0 | — |
| 68 | — | — | 57 | — | — | 16 | — | — | 20 | — | — | 0 | — |
| 70 | — | — | 87 | — | — | 69 | — | — | 29 | — | — | 0 | — |
| 71 | — | — | 90 | — | — | 84 | — | — | 49 | — | — | 35 | — |
| 73 | — | — | 62 | — | — | 41 | — | — | 47 | — | — | 26 | — |
| 75 | — | — | 86 | — | — | 67 | — | — | 61 | — | — | 25 | — |
| 76 | — | — | 86 | — | — | 74 | — | — | 52 | — | — | 34 | — |
| 77 | — | — | 71 | — | — | 34 | — | — | 80 | — | — | 17 | — |
| 78 | — | — | 72 | — | — | 53 | — | — | 32 | — | — | 74 | — |
| 80 | — | — | 43 | — | — | 20 | — | — | 0 | — | — | 0 | — |
| 91 | — | — | 80 | — | — | 55 | — | — | 46 | — | — | 15 | — |
| 92 | — | — | 25 | — | — | 0 | — | — | 4 | — | — | 0 | — |
| 93 | — | — | 89 | — | — | 64 | — | — | 57 | — | — | 79 | — |
| 94 | — | — | 84 | — | — | 56 | — | — | 48 | — | — | 28 | — |
| 95 | — | — | 67 | — | — | 53 | — | — | 36 | — | — | 26 | — |
| 96 | 100 | 42 | — | 7 | 0 | — | 0 | — | — | — | — | — | — |
| 97 | — | — | 19 | — | — | 3 | — | — | 0 | — | — | 67 | — |
| 98 | — | — | 37 | — | — | 0 | — | — | 25 | — | — | 0 | — |
| 99 | — | — | 57 | — | — | 0 | — | — | 0 | — | — | 0 | — |
| 102 | 44 | 24 | — | 0 | 0 | — | 0 | — | — | — | — | — | — |
| 103 | — | — | 53 | — | — | 43 | — | — | 15 | — | — | 0 | — |
| 106 | 96 | — | — | — | — | 88 | — | — | — | — | 56 | — | 29 |
| 108 | 90 | — | — | — | — | 84 | — | — | — | — | 69 | — | 43 |
| 109 | 92 | — | — | — | — | 41 | — | — | — | — | 0 | — | 0 |
| 110 | 59 | — | — | — | — | 13 | — | — | — | — | 0 | — | 0 |
| 111 | — | — | 92 | — | — | 69 | — | — | 60 | — | — | 22 | — |
| 112 | — | — | 72 | — | — | 65 | — | — | 53 | — | — | 31 | — |
| 113 | — | — | 86 | — | — | 69 | — | — | 39 | — | — | 16 | — |
| 115 | — | — | 86 | — | — | 64 | — | — | 41 | — | — | 37 | — |
| 116 | — | — | 81 | — | — | 57 | — | — | 50 | — | — | 27 | — |
| 117 | — | — | 72 | — | — | 41 | — | — | 24 | — | — | 32 | — |
| 118 | — | — | 85 | — | — | 61 | — | — | 37 | — | — | 30 | — |
| 119 | — | — | 88 | — | — | 69 | — | — | 33 | — | — | 23 | — |
| 120 | — | — | 87 | — | — | 63 | — | — | 46 | — | — | 71 | — |
| 135 | 100 | — | — | — | — | 12 | — | — | — | — | 0 | — | 0 |
| 136 | 98 | — | — | — | — | 67 | — | — | — | — | 10 | — | 0 |
| 142 | 98 | — | — | — | — | 62 | — | — | — | — | 5 | — | 0 |
| 143 | 100 | — | — | — | — | 91 | — | — | — | — | 78 | — | 50 |
| 144 | — | — | 92 | — | — | 63 | — | — | 43 | — | — | 16 | — |
| 146 | — | — | 79 | — | — | 60 | — | — | 48 | — | — | 19 | — |
| 147 | — | — | 87 | — | — | 72 | — | — | 55 | — | — | 41 | — |
| 148 | 93 | 89 | — | 81 | 75 | — | 69 | — | — | — | — | — | — |
| 149 | 62 | 26 | — | 5 | 0 | — | 0 | — | — | — | — | — | — |
| 150 | — | — | 93 | — | — | 91 | — | — | 74 | — | — | 83 | — |
| 159 | — | — | 94 | — | — | 80 | — | — | 56 | — | — | 49 | — |
| 178 | 91 | — | — | — | — | 43 | — | — | — | — | 0 | — | — |
| 192 | — | — | 86 | — | — | 74 | — | — | 48 | — | — | 21 | — |
| 198 | — | — | 74 | — | — | 53 | — | — | 37 | — | — | 22 | — |
| 199 | — | — | 88 | — | — | 78 | — | — | 63 | — | — | 40 | — |
| 200 | — | — | 60 | — | — | 50 | — | — | 31 | — | — | 0 | — |
| 201 | — | — | 67 | — | — | 56 | — | — | 11 | — | — | 0 | — |
| 202 | — | — | 32 | — | — | 0 | — | — | 0 | — | — | 0 | — |
| 204 | 66 | 56 | — | 34 | 0 | — | 0 | — | — | — | — | — | — |
| 205 | — | — | 81 | — | — | 76 | — | — | 38 | — | — | 32 | — |
| 208 | — | — | 37 | — | — | 42 | — | — | 38 | — | — | 38 | — |
| 224 | — | — | 63 | — | — | 27 | — | — | 0 | — | — | 1 | — |
| 226 | — | — | 69 | — | — | 42 | — | — | 17 | — | — | 2 | — |
| 245 | — | — | 30 | — | — | 0 | — | — | 0 | — | — | 0 | — |
| 247 | — | — | 82 | — | — | 58 | — | — | 47 | — | — | 58 | — |
| 251 | 29 | — | — | — | — | 0 | — | — | — | — | 0 | — | 0 |
| 252 | 82 | — | — | — | — | 38 | — | — | — | — | 0 | — | 0 |
| 253 | 17 | — | — | — | — | 0 | — | — | — | — | 5 | — | 0 |
| 255 | 72 | — | — | — | — | 37 | — | — | — | — | 0 | — | 0 |
| 256 | 48 | — | — | — | — | 10 | — | — | — | — | 13 | — | 20 |
| 257 | 58 | — | — | — | — | 0 | — | — | — | — | 0 | — | 0 |
| 258 | 78 | — | — | — | — | 23 | — | — | — | — | 0 | — | 0 |
| 259 | — | — | 40 | — | — | 0 | — | — | 0 | — | — | 0 | — |
| 260 | — | — | 45 | — | — | 37 | — | — | 14 | — | — | 0 | — |
| 261 | — | — | 18 | — | — | 21 | — | — | 0 | — | — | 0 | — |
| 262 | — | — | 89 | — | — | 75 | — | — | 49 | — | — | 28 | — |
| 263 | — | — | 11 | — | — | 87 | — | — | 0 | — | — | 0 | — |
| 264 | — | — | 37 | — | — | 26 | — | — | 1 | — | — | 0 | — |
| 265 | — | — | 17 | — | — | 0 | — | — | 0 | — | — | 0 | — |
| 266 | — | — | 13 | — | — | 2 | — | — | 0 | — | — | 0 | — |
| 267 | — | — | 11 | — | — | 0 | — | — | 0 | — | — | 0 | — |

| Compound | 10 | 5 | 4 | 2.5 | 1.25 | 1 | 0.6 | 0.5 | 0.25 | 0.125 | 0.1 | 0.06 | 0.01 |
|---|---|---|---|---|---|---|---|---|---|---|---|---|---|
| | | | | | | % NH$_4$—N Remaining After 2 Weeks Incubation at Indicated Concentration (ppm) | | | | | | | |
| 268 | — | — | 92 | — | — | 80 | — | — | 71 | — | — | 53 | — |

Additionally, certain compounds of the present invention may be used to modify plant growth benefically such as the inhibition of bolting in sugarbeets. Other compounds of the present invention alter the normal growth of sugarbeets by stunting the plant. Both of the effects described above are not accompanied by any phytotoxic symptoms.

Sugar beet flowering is controlled by a cold weather treatment of the plants (vernalization) followed by long days. As the days lengthen, the beets produce bolters—elongated stems bearing flowers—and ultimately seeds on indeterminate, multibranced racemes. In Europe where a large acreage of sugar beet is grown, cold spring weather following sowing is often enough to induce bolting of the beets. This bolting causes various problems to the farmer who grows the beet for the sugar content of the beet root. The problems are numerous:

1. Bolting reduces both the size and the sugar content of the beet root since the products of photosynthesis are diverted to flower production.
2. Bolting causes processing difficulties due to lignification of the root. Lignification uses up stored sugars as well, thus reducing the efficiency of the extraction process.
3. Bolters physically interfere with mechanical harvesting by becoming entangled in harvesting machinery.
4. Bolted plants cause a large amount of competition by shading of adjacent plants, thereby reducing their root size.
5. With time, the seed from early bolters have produced a weed beet with an annual habit requiring little or no vernalization. This weed beet, besides causing severe competition, prevents "beet-free periods" which are necessary for the control of beet yellowing virus.

If bolting could be completely prevented, this would be a possible means of realizing the potential physiological advantages of autumn sowing. Greater utilization of the season would be achieved by the capturing or radiation which normally falls on bare ground. Yield increases of up to 25% have been predicted from autumn as opposed to spring sowing. Even an earlier spring sowing promises an increase in yield. The following example illustrates the plant growth regulator effects of the compounds of this invention.

EXAMPLE 98

Using a regular biennial variety, even a bolting-susceptible variety would require a cold treatment of around 10–16 weeks plus a hormone treatement in conjunction with specific light intensities. Thus, for a screening organism, we selected one which would consistently produce bolting on a regular schedule. The screen is run with an annual sugar beet variety (SLC03) provided by Dr. Richard J. Hecker, Fort Collins, Colo. This variety is an inbred which bolts in the 6- to 8-leaf stage without any need for vernalization. This allows the screen to be run entirely in the greenhouse with all 110 chemical compounds tested on one tray. The sugarbeets are grown in 3×3 inch square pots in a greenhouse sandy loam potting mix. The sugarbeets are sprayed with test compounds when they are 2 to 3 weeks old (2 true leaves). The compounds are dissolved in acetone and diluted with water containing Tween 20 as a wetting agent. The concentration of acetone in the final spray is 20% and the concentration of Tween 20 is 0.05 percent. The plants are examined for the appearance of a bolt 4 weeks after spraying.

Preemergence tests are conducted by spraying formulated chemical on seeds placed on potting soil. The sprayed seeds are then covered with ¼ inch of potting soil and the pots are watered. Bolting is evaluated 6–7 weeks after the initiation of the test. At this time untreated plants have a vigorous bolting stem with visible flowers.

| | Plant Growth Regulator Activity Observed Effect at Concentration Indicated | |
|---|---|---|
| Compound | Bolting Inhibition (postemergence) | Bolting Inhibition (preemergence) |
| 8 | 50 ppm | |
| 14 | | 400 ppm |
| 16 | | 400 ppm |
| 52 | | 100 ppm |
| 63 | 5 ppm | |
| 65 | 12 ppm | |
| 66 | | 400 ppm |
| 71 | | 400 ppm |
| 77 | 12 ppm | |
| 95 | | 400 ppm |
| 98 | 400 ppm | |
| 119 | 400 ppm (stunting) | |
| 129 | 400 ppm | 400 ppm |
| 132 | | 400 ppm |
| 133 | | 400 ppm (stunting) |
| 134 | | 400 ppm (stunting) |
| 198 | | 400 ppm (stunting) |
| 204 | 400 ppm | |
| | 200 ppm | |
| 267 | 400 ppm (stunting) | |

EXAMPLE 99

The compounds of this invention are also plant gametocides depending on the dosage and timing of application and the species of plant to which the compounds are applied. For example, certain of the compounds were sprayed on corn seedlings at the three leaf stage of growth, and the seedlings were returned to the greenhouse for subsequent growth and observation. The corn variety was "First In". The chemicals were dissolved in acetone, and the acetone solution was diluted with water containing Tween 20 wetting agent such that the final spray solution contained 50% acetone and 0.1% Tween 20 in water. At the time of tassel formation the anthers appeared normal, but they did not contain pollen. Tabulated below are data which illustrate the use of the compounds of this invention as plant gametocides in corn.

| Gametocidal Activity in Corn (Postemergent Application) | |
|---|---|
| Compound | Concentration (ppm)* |
| 275 | 400 |
| 277 | 200 |
| 279 | 50 |

*concentration required to produce 100% control.

We claim:

1. Method for inhibiting pollen formation in corn which comprises the application of a pollen inhibiting amount of a compound having the formula:

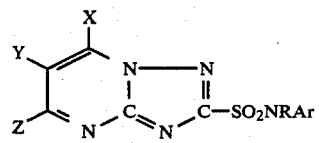

wherein Ar represents an aromatic or heteroaromatic ring chosen from among phenyl; 1- or 2-naphthyl; 2-, 3- or 4-pyridyl; 2- or 3-thienyl; 2- or 3-furyl; 2-, 4- or 5-thiazoyl; 2-, 4- or 5-imidazoyl; 2-, 4- or 5-oxazoyl; 3-, 4- or 5-isothiazoyl; 3-, 4- or 5-isoxazoyl; 3-, 4- or 5-pyrazoyl; 2-benzthiazoyl; 2-benzoxazoyl; 2-benzimidazoyl or 1-benztriazoyl; and Ar is unsubstituted or Ar is substituted with one to five substituents chosen from among (except in the cases of thio, sulfinyl and sulfonyl substituents where if one of these substituents is present the other one to four Ar substituents may not be chosen from among the other two); oxycarbonyl substituents where the other one to four Ar substituents may not be chosen from among different oxycarbonyl; or aminocarbonyl substituents; where the other one to four Ar substituents may not be chosen from among different aminocarbonyl substituents; $C_1$–$C_6$ alkyl; halo; $C_1$–$C_6$ mono- or polyhaloalkyl; phenyl; hydroxy; $C_1$–$C_6$ alkoxy; $C_1$–$C_6$ mono- or polyhaloalkoxy; phenoxy; phenoxy substituted with one or more of groups chosen from halo, $C_1$–$C_6$ alkyl or $C_1$–$C_6$ haloalkyl; 2-pyridyloxy; 2-pyridyloxy substituted with one or more of groups chosen from halo, $C_1$–$C_6$ alkyl or $C_1$–$C_6$ haloalkyl; $C_1$–$C_6$ alkylamino; $C_1$–$C_6$ dialkylamino; nitro; $C_1$–$C_6$ alkylthio; $C_1$–$C_6$ polyhaloalkylthio; $C_1$–$C_6$ alkylsulfinyl; $C_1$–$C_6$ polyhaloalkylsulfinyl; $C_1$–$C_6$ alkylsulfonyl; $C_1$–$C_6$ polyhaloalkylsulfonyl; phenylthio; phenylthio substituted with one or more of groups chosen from halo, $C_1$–$C_6$ alkyl or $C_1$–$C_6$ haloalkyl; phenylsulfinyl; phenylsulfinyl substituted with one or more of groups chosen from halo, $C_1$–$C_6$ alkyl or $C_1$–$C_6$ haloalkyl; phenylsulfonyl; phenylsulfonyl substituted with one or more of groups chosen from halo, $C_1$–$C_6$ alkyl or $C_1$–$C_6$ haloalkyl; cyano; carboxyl; $C_1$–$C_{10}$ alkoxycarbonyl; phenoxycarbonyl; phenoxycarbonyl substituted with one or more of groups chosen from halo, $C_1$–$C_6$ alkyl or $C_1$–$C_6$ haloalkyl; alkoxyalkoxycarbonyl wherein the number of carbons in the alkoxyalkoxy fragment ranges from 2-10 and the number of oxygens in the alkoxyalkoxy fragment ranges from 2-4; 2-pyridylmethoxycarbonyl; dialkylaminoalkoxycarbonyl wherein the number of carbons in the dialkyl aminoalkoxy fragment ranges from 3-10 and the number of oxygens in the dialkylaminoalkoxy fragment is one; $C_1$–$C_6$ alkenyloxycarbonyl; COON=C($R^1$)($R^2$) wherein $R^1$ and $R^2$ independently represent hydrogen, $C_1$–$C_6$ alkyl or phenyl; unsubstituted, N—$C_1$–$C_6$ alkyl or N,N-di-$C_1$–$C_6$ alkylaminocarbonyl; $C_1$–$C_{10}$ dialkylaminosulfonyl; formyl; $C_1$–$C_6$ alkylcarbonyl; $C_1$–$C_6$ mono- or polyhaloalkylcarbonyl; phenylcarbonyl; phenylcarbonyl substituted with one or more of groups chosen from halo, $C_1$–$C_6$ alkyl or $C_1$–$C_6$ haloalkyl; or C($R^3$)($R^4$)O$R^5$ wherein $R^3$ and $R^4$ independently represent hydrogen or $C_1$–$C_6$ alkyl and $R^5$ represents hydrogen, $C_1$–$C_6$ alkyl, benzyl, phenylcarbonyl or $C_1$–$C_6$ alkylcarbonyl; X, Y and Z independently represent hydroxyl, carboxyl, hydrogen, $C_1$–$C_6$ alkyl, $C_1$–$C_6$ mono- or polyhaloalkyl, $C_1$–$C_6$ alkoxy, $C_1$–$C_6$ mono- or polyhaloalkoxy, phenyl, phenyl substituted with one or more groups chosen from halo, nitro, $C_1$–$C_6$ alkyl or $C_1$–$C_6$ mono- or polyhaloalkyl, $C_1$–$C_6$ alkylthio, halogen, or two adjacent substituents (i.e. X and Y or Y and Z) are joined together to form a saturated five, six or seven-membered saturated cyclic structure of carbon atoms or one carbon atom of X,Y or Y,Z is replaced by a heteroatom chosen from among nitrogen, oxygen or sulfur (i.e. X,Y or Y,Z is —(CH$_2$)$_n$— wherein n is 3, 4 or 5; or X,Y or Y,Z is —(CH$_2$)$_n$—A—(CH$_2$)$_m$ wherein n is 0-4, the value of m is equal to the ring size minus (n+3) and A is NH, O or S) and R represents alkyl, alkenyl, alkynyl, phenylalkyl, acyl, alkoxycarbonyl, phenoxycarbonyl, dialkylaminocarbonyl, alkylsulfonyl, phenylsulfonyl, alkylthiocarbonyl or phenylthiocarbonyl wherein alkyl, alkenyl, alkynyl and alkoxy in each instance have from 1 to 10 carbon atoms.

2. Method of claim 1 which comprises the application of a pollen inhibiting amount of a compound wherein Ar represents substituted or unsubstituted phenyl; 1- or 2-naphthyl; 2-, 3- or 4-pyridyl; 2- or 3-thienyl; or 3-, 4- or 5-pyrazolyl.

3. Method of claim 1 which comprises the application of a pollen inhibiting amount of a compound wherein Ar represents substituted phenyl, substituted 1-naphthyl or substituted 4-pyrazolyl.

4. Method of claim 1 which comprises the application of a pollen inhibiting amount of a compound wherein Ar is

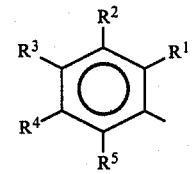

wherein $R^1$, $R^2$, $R^3$, $R^4$ and $R^5$ independently represent (except in the case of thio, sulfinyl or sulfonyl substituents where if one of these substituents is present the other one to four Ar substituents may not be chosen from among the other two; oxycarbonyl substituents where the other one to four Ar substituents may not be chosen from among different oxycarbonyl substituents; or aminocarbonyl substituents where the other one to four Ar substituents may not be chosen from among different aminocarbonyl substituents) H; $C_1$–$C_6$ alkyl; halo; $C_1$–$C_6$ mono- or polyhaloalkyl; phenyl; hydroxy; $C_1$–$C_6$ alkoxy; $C_1$–$C_6$ mono- or polyhaloalkoxy; phenoxy; phenoxy substituted with one or more of groups chosen from halo, $C_1$–$C_6$ alkyl or $C_1$–$C_6$ haloalkyl; 2-pyridyloxy; 2-pyridyloxy substituted with one or more of groups chosen from halo, $C_1$–$C_6$ alkyl or $C_1$–$C_6$ haloalkyl; $C_1$–$C_6$ alkylamino; $C_1$–$C_6$ dialkylamino; nitro; $C_1$–$C_6$ alkylthio; $C_1$–$C_6$ polyhaloalkylthio; $C_1$–$C_6$ alkylsulfinyl; $C_1$–$C_6$ polyhaloalkylsulfinyl; $C_1$–$C_6$ alkylsulfonyl; $C_1$–$C_6$ polyhaloalkylsulfonyl; phenylthio; phenylthio substituted with one or more of groups chosen from halo, $C_1$–$C_6$ alkyl or $C_1$–$C_6$ haloalkyl; phenylsulfinyl; phenylsulfinyl substituted with one or more of groups chosen from halo, $C_1$–$C_6$ alkyl or $C_1$–$C_6$ haloalkyl; phenylsulfonyl; phenylsulfonyl substituted with one or more of groups chosen from halo, $C_1$–$C_6$ alkyl or $C_1$–$C_6$ haloalkyl; cyano; carboxyl; $C_1$–$C_{10}$ alkoxycarbonyl; phenoxycarbonyl; phenoxycarbonyl substituted with one or more of groups chosen from halo, $C_1$–$C_6$ alkyl or $C_1$–$C_6$ haloalkyl; alkoxyalkoxycarbonyl wherein the number of carbons in the alkoxyalkoxy fragment ranges from 2–10 and the number of oxygens in the alkoxyalkoxy fragment ranges from 2–4; 2-pyridylmethoxycarbonyl; dialkylaminoalkoxycarbonyl wherein the number of carbons in the dialkylaminoalkoxy fragment ranges from 3–10 and the number of oxygens in the dialkylaminoalkoxy fragment is one; $C_1$–$C_6$ alkenyloxycarbonyl; COON=C($R^6$)($R^7$) wherein $R^6$ and $R^7$ independently represent hydrogen, $C_1$–$C_6$ alkyl or phenyl; unsubstituted, N—$C_1$–$C_6$ alkyl or N,N-di-$C_1$–$C_6$ alkylaminocarbonyl; $C_1$–$C_{10}$ dialkylaminosulfonyl; formyl; $C_1$–$C_6$ alkylcarbonyl; $C_1$–$C_6$ mono- or polyhaloalkylcarbonyl; phenylcarbonyl; phenylcarbonyl substituted with one or more of groups chosen from halo, $C_1$–$C_6$ alkyl or $C_1$–$C_6$ haloalkyl; or C($R^8$)($R^9$)O$R^{10}$ wherein $R^8$ and $R^9$ independently represent hydrogen or $C_1$–$C_6$ alkyl and $R^{10}$ represents hydrogen, $C_1$–$C_6$ alkyl, benzyl, phenylcarbonyl or $C_1$–$C_6$ alkylcarbonyl.

* * * * *